(12) United States Patent
Greenlee et al.

(10) Patent No.: US 8,623,818 B2
(45) Date of Patent: Jan. 7, 2014

(54) GLUCAGON RECEPTOR ANTAGONISTS, COMPOSITIONS, AND METHODS FOR THEIR USE

(75) Inventors: William J. Greenlee, Teaneck, NJ (US); Andrew Stamford, Chatham Township, NJ (US); Michael W. Miller, Scotch Plains, NJ (US); Duane Eugene DeMong, Somerset, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 511 days.

(21) Appl. No.: 12/992,771

(22) PCT Filed: May 13, 2009

(86) PCT No.: PCT/US2009/043722
§ 371 (c)(1),
(2), (4) Date: Nov. 24, 2010

(87) PCT Pub. No.: WO2009/140342
PCT Pub. Date: Nov. 19, 2009

(65) Prior Publication Data
US 2011/0065634 A1     Mar. 17, 2011

Related U.S. Application Data

(60) Provisional application No. 61/053,764, filed on May 16, 2008.

(51) Int. Cl.
*A61K 38/28* (2006.01)
*A61K 38/00* (2006.01)

(52) U.S. Cl.
USPC ............ 514/6.5; 514/6.8; 514/6.9; 514/224.2

(58) Field of Classification Search
None
See application file for complete search history.

(56) References Cited

U.S. PATENT DOCUMENTS

| | | | |
|---|---|---|---|
| 7,301,036 B2 | 11/2007 | Parmee et al. | |
| 7,563,815 B2 | 7/2009 | Parmee et al. | |
| 7,625,938 B2 | 12/2009 | Brockunier et al. | |
| 7,803,951 B2 | 9/2010 | Liang et al. | |
| 7,935,713 B2 | 5/2011 | Kim et al. | |
| 7,989,472 B2 | 8/2011 | Kim et al. | |
| 8,318,667 B2 | 11/2012 | Lin et al. | |
| 8,318,760 B2 | 11/2012 | Stelmach et al. | |
| 2005/0272794 A1 | 12/2005 | Parmee et al. | |
| 2007/0088070 A1 | 4/2007 | Parmee et al. | |
| 2011/0251248 A1 | 10/2011 | Lin et al. | |
| 2011/0281795 A1 | 11/2011 | Lin et al. | |
| 2011/0312911 A1 | 12/2011 | Kats-Kagen et al. | |

FOREIGN PATENT DOCUMENTS

| | | |
|---|---|---|
| WO | 02/00612 | 1/2002 |
| WO | 02/40444 | 5/2002 |
| WO | 03/048109 | 6/2003 |
| WO | 2004/002480 | 1/2004 |
| WO | 2004/069158 | 8/2004 |
| WO | 2004/098528 | 11/2004 |
| WO | 2005/121097 A2 | 12/2005 |
| WO | 2006/014618 A2 | 2/2006 |
| WO | 2006/017055 A2 | 2/2006 |
| WO | 2006/102067 | 9/2006 |
| WO | 2007/015999 A2 | 2/2007 |
| WO | 2007/091396 | 8/2007 |
| WO | 2008/042223 A1 | 4/2008 |
| WO | 2009/035558 A1 | 3/2009 |

*Primary Examiner* — Cecilia J Tsang
*Assistant Examiner* — Li Lee
(74) *Attorney, Agent, or Firm* — Anna L. Cocuzzo; Catherine D. Fitch

(57) ABSTRACT

The present invention relates to compounds of general formula (I), wherein ring A, ring B, $R^1$, $R^2$, $R^3$, Z, and $L^1$ are selected independently of each other and are as defined herein, to compositions comprising the compounds, and methods of using the compounds as glucagon receptor antagonists and for the treatment or prevention of type 2 diabetes and conditions related thereto.

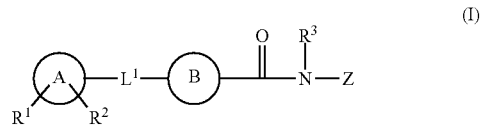

(I)

12 Claims, No Drawings

GLUCAGON RECEPTOR ANTAGONISTS, COMPOSITIONS, AND METHODS FOR THEIR USE

RELATED APPLICATIONS

This application claims priority to provisional application U.S. Ser. No. 61/053,764, filed on May 16, 2008, herein incorporated by reference.

FIELD OF THE INVENTION

The present invention relates to certain novel compounds as glucagon receptor antagonists, compositions comprising these compounds, and methods for their use in treating, preventing, or delaying the onset of type 2 diabetes and related conditions.

BACKGROUND OF THE INVENTION

Diabetes refers to a disease state or process derived from multiple causative factors and is characterized by elevated levels of plasma glucose (hyperglycemia) in the fasting state or after administration of glucose during a glucose tolerance test. Persistent or uncontrolled hyperglycemia is associated with a wide range of pathologies. Frank diabetes mellitus (e.g., fasting blood glucose levels above about 126 mg/dL) is associated with increased and premature cardiovascular disease and premature mortality, and is related directly and indirectly to various metabolic conditions, including alterations of lipid, lipoprotein, apolipoprotein metabolism and other metabolic and hemodynamic diseases. As such, the diabetic patient is at increased risk of macrovascular and microvascular complications. Such complications can lead to diseases and conditions such as coronary heart disease, stroke, peripheral vascular disease, hypertension, nephropathy, neuropathy, and retinopathy. Accordingly, therapeutic control and correction of glucose homeostasis is regarded as important in the clinical management and treatment of diabetes mellitus.

There are two generally recognized forms of diabetes. In type 1 diabetes, or insulin-dependent diabetes mellitus (IDDM), the diabetic patient's pancreas is incapable of producing adequate amounts of insulin, the hormone which regulates glucose uptake and utilization by cells. In type 2 diabetes, or noninsulin dependent diabetes mellitus (NIDDM), patients often produce plasma insulin levels comparable to those of nondiabetic subjects; however, the cells of patients suffering from type 2 diabetes develop a resistance to the effect of insulin, even in normal or elevated plasma levels, on glucose and lipid metabolism, especially in the main insulin-sensitive tissues (muscle, liver and adipose tissue).

Insulin resistance is not associated with a diminished number of cellular insulin receptors but rather with a post-insulin receptor binding defect that is not well understood. This cellular resistance to insulin results in insufficient insulin activation of cellular glucose uptake, oxidation, and storage in muscle, and inadequate insulin repression of lipolysis in adipose tissue, and of glucose production and secretion in the liver. A net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

The available treatments for type 2 diabetes, some of which have not changed substantially in many years, are used alone and in combination. Many of these treatments have recognized limitations, however. For example, while physical exercise and reductions in dietary intake of fat, high glycemic carbohydrates, and calories can dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic beta-cells to secrete more insulin, and/or by injection of insulin when sulfonylureas or meglitinide become ineffective, can result in insulin concentrations high enough to stimulate insulin-resistance in tissues. However, dangerously low levels of plasma glucose can result from administration of insulin or insulin secretagogues (sulfonylureas or meglitinide), and an increased level of insulin resistance due to the even higher plasma insulin levels can occur. The biguanides are a separate class of agents that can increase insulin sensitivity and bring about some degree of correction of hyperglycemia. These agents, however, can induce lactic acidosis, nausea and diarrhea.

The glitazones (i.e. 5-benzylthiazolidine-2,4-diones) are another class of compounds that have proven useful for the treatment of type 2 diabetes. These agents increase insulin sensitivity in muscle, liver and adipose tissue in several animal models of type 2 diabetes, resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type II diabetes are agonists of the alpha, gamma or delta subtype, or a combination thereof, and in many cases are chemically different from the glitazones (i.e., they are not thiazolidinediones). Serious side effects (e.g. liver toxicity) have been noted in some patients treated with glitazone drugs, such as troglitazone.

Compounds that are inhibitors of the dipeptidyl peptidase-IV (DPP-IV) enzyme are also under investigation or available as drugs for the treatment of diabetes, and particularly type 2 diabetes. Examples include alogliptin (Takeda), saxagliptin (Brystol-Myers Squibb), sitagliptin (Januvia™, Merck), vildagliptin (Galvus™, Novartis), denagliptin (GlaxoSmithKline), ABT-279 and ABT-341 (Abbott), ALS-2-0426 (Alantos), ARI-2243 (Arisaph), BI-A and BI-B (Boehringer Ingelheim), SYR-322 (Takeda), compounds disclosed in U.S. Pat. No. 6,699,871, MP-513 (Mitsubishi), DP-893 (Pfizer), RO-0730699 (Roche) and combinations thereof.

Additional methods of treating hyperglycemia and diabetes are currently under investigation. New biochemical approaches include treatment with alpha-glucosidase inhibitors (e.g. acarbose) and protein tyrosine phosphatase-1B (PTP-1B) inhibitors.

Other approaches to treating hyperglycemia, diabetes, and indications attendant thereto have focused on the glucagon hormone receptor. Glucagon and insulin are the two primary hormones regulating plasma glucose levels. Insulin, released in response to a meal, increases the uptake of glucose into insulin-sensitive tissues such as skeletal muscle and fat. Glucagon, which is secreted by alpha cells in pancreatic islets in response to decreased postprandial glucose levels or during fasting, signals the production and release of glucose from the liver. Glucagon binds to specific receptors in liver cells that trigger glycogenolysis and an increase in gluconeogenesis through cAMP-mediated events. These responses generate increases in plasma glucose levels (e.g., hepatic glucose production), which help to regulate glucose homeostasis.

Type 2 diabetic patients typically have fasting hyperglycemia that is associated with elevated rates of hepatic glucose production. This is due to increased gluconeogenesis coupled with hepatic insulin resistance. Such patients typically have a relative deficiency in their fasting and postprandial insulin-to-glucagon ratio that contributes to their hyperglycemic state. Several studies have demonstrated that hepatic glucose production correlates with fasting plasma glucose levels, suggesting that chronic hepatic glucagon receptor antagonism should improve this condition. In addition, defects in rapid postprandial insulin secretion, as well as ineffective suppression of glucagon secretion, lead to increased glucagon levels that elevate hepatic glucose production and contribute to hyperglycemia. Suppression of elevated postprandial glucagon levels in type 2 diabetics with somatostatin has been shown to lower blood glucose concentrations. This indicates that acute postprandial glucagon receptor antagonism would also be beneficial. Based on these and other data, glucagon receptor antagonism holds promise as a potential treatment of type 2 diabetes by reducing hyperglycemia. There is thus a need in the art for small-molecule glucagon receptor antagonists with good safety profiles and efficacy that are useful for the treatment of hyperglycemia, diabetes, and related metabolic diseases and indications. The present invention addresses that need.

SUMMARY OF THE INVENTION

In one embodiment, the present invention provides a compound, or a pharmaceutically acceptable salt, solvate, ester, prodrug, tautomer, or isomer of said compound, said compound having the general structure shown in Formula (A):

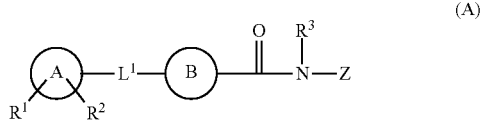

(A)

wherein ring A, ring B, $R^1$, $R^2$, $R^3$, Z, and $L^1$ are selected independently of each other and are as defined below. These and other embodiments are described in more detail below.

DETAILED DESCRIPTION OF THE INVENTION

In one embodiment, the present invention provides a compound, or a pharmaceutically acceptable salt, solvate, ester, prodrug, tautomer, or isomer of said compound, said compound having the general structure shown in Formula (A):

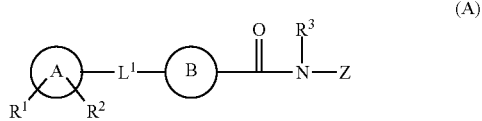

(A)

wherein ring A, ring B, $R^1$, $R^2$, $R^3$, Z, and C are selected independently of each other and wherein:

ring A is a 5-membered heteroaryl ring having from 1 to 3 ring nitrogen atoms, with the proviso that ring A is not an imidazole;

ring B is a phenyl ring wherein the -$L^1$- and the —C(O)N($R^3$)Z moieties shown in the formula are bound to said phenyl ring in a 1,4-relationship, and wherein said phenyl ring is (in addition to the -$L^1$- and —C(O)N($R^3$)—Z moieties shown) optionally further substituted with one or more substituents, each substituent (when present) being independently selected from the group consisting of halo, alkyl, and haloalkyl, or ring B is a 5-membered heteroaromatic ring containing from 1 to 3 ring heteroatoms independently selected from the group consisting of N, O, and S, wherein the -$L^1$- and the —C(O)N($R^3$)—Z moieties shown in the formula are bound to said 5-membered ring in a 1,3-relationship, and wherein said 5-membered heteroaromatic ring is (in addition to the -$L^1$- and —C(O)N($R^3$)—Z moieties shown) optionally further substituted with one or more substituents, each substituent (when present) being independently selected from the group consisting of halo, alkyl, and haloalkyl, or ring B is a 6-membered heteroaromatic ring containing from 1 to 3 ring nitrogen atoms, wherein the -$L^1$- and the —C(O)N($R^3$)—Z moieties shown in the formula are bound to said 6-membered ring in a 1,4-relationship, and wherein said 6-membered heteroaromatic ring is (in addition to -$L^1$- and —C(O)N($R^3$)Z moieties shown) optionally further substituted with one or more substituents, each substituent (when present) being independently selected from the group consisting of halo, alkyl, and haloalkyl;

r is an integer from 0 to 2;
s is an integer from 0 to 2;
t, when present, is an integer from 1-2;
$R^1$ is selected from the group consisting of:

(a) —$CO_2R^6$, —C(O)$R^6$, —$SR^7$, —S(O)$R^7$, —$SO_2R^7$, —C(O)$NR^8R^9$, and —$NR^8R^9$;

(b) alkyl, -heteroalkyl, —C(O)alkyl, —C(O)-heteroalkyl, —O-alkyl, —O-heteroalkyl, -alkenyl, -heteroalkenyl, —C(O)alkenyl, —C(O)-heteroalkenyl, —O-alkenyl, —O-heteroalkenyl, -alkynyl, -heteroalkynyl, —C(O)alkynyl, —C(O)-heteroalkynyl, —O-alkynyl, and —O-heteroalkynyl, wherein each of the alkyl, alkenyl and alkynyl portions of said alkyl, -heteroalkyl, —C(O)alkyl, —C(O)-heteroalkyl, —O-alkyl, —O-heteroalkyl, -alkenyl, -heteroalkenyl, —C(O)alkenyl, —C(O)-heteroalkenyl, —O-alkenyl, —O-heteroalkenyl, -alkynyl, -heteroalkynyl, —C(O)alkynyl, —C(O)-heteroalkynyl, —O-alkynyl, and —O-heteroalkynyl are unsubstituted or optionally independently substituted with one or more groups each independently selected from the group consisting of:

halo, OH, —$CO_2R^6$, —C(O)$R^6$, —$SR^7$, —S(O)$R^7$, —$SO_2R^7$, CN, $NO_2$, —C(O)$NR^8R^9$, —$NR^8R^9$, haloalkoxy, —$NR^{10}$—C(O)—$NR^8R^9$, —$NR^{10}$—$CO_2R^6$, —$NR^{10}$—C(O)$R^6$, —$NR^{10}$—$SO_2R^6$, —$SO_2$—$NR^8R^9$, —C(O)$NR^8R^9$, —OC(O)$NR^8R^9$, unsubstituted alkoxy, and alkoxy substituted with one or more groups independently selected from the group consisting of halo, perhaloalkoxy, OH, and —$CO_2R^6$;

(c) —O-aryl, —S-aryl, arylalkyl-, —O-heteroaryl, —S-heteroaryl, heteroarylalkyl-, cycloalkyl, aryl-fused cycloalkyl, cycloalkylalkyl-, —O-cycloalkyl, —S-cycloalkyl, heterocycloalkyl, aryl-fused heterocycloalkyl, heterocycloalkylalkyl-, —O-heterocycloalkyl, —S-heterocycloalkyl, cycloalkenyl, —O-cycloalkenyl, —S-cycloalkenyl, heterocycloalkenyl, —O-heterocycloalkenyl, and —S-heterocycloalkenyl, wherein the aryl, heteroaryl, cycloalkyl, heterocycloalkyl, cycloalkenyl, and heterocycloalkenyl portions of said —O-aryl, —S-aryl, arylalkyl-, —O-heteroaryl, —S-heteroaryl, heteroarylalkyl-, cycloalkyl, aryl-fused cycloalkyl, cycloalkylalkyl-, —O-cycloalkyl, —S-cycloalkyl, heterocycloalkyl, aryl-fused heterocycloalkyl, heterocycloalkylalkyl-, —O-heterocycloalkyl, —S-heterocycloalkyl, cycloalkenyl, —O-cycloalkenyl, —S-cycloalkenyl, heterocycloalkenyl, —O-heterocycloalkenyl, and —S-heterocycloalkenyl, and the alkyl portions of said arylalkyl-, said heteroarylalkyl-, said cycloalkylalkyl-, and said heterocycloalkylalkyl-, are each independently unsubstituted or optionally independently substituted with 1 or more groups each independently selected from the group consisting of:

(i) halo, OH, —CO$_2$R$^6$, —C(O)R$^6$, —SR$^7$, —S(O)R$^7$, —SO$_2$R$^7$, CN, NO$_2$, —C(O)NR$^8$R$^9$, —NR$^8$R$^9$, haloalkoxy, —NR$^8$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, and —OC(O)NR$^8$R$^9$, (ii) -alkyl, -heteroalkyl, —C(O)alkyl, —C(O)-heteroalkyl, —O-alkyl, —O-heteroalkyl, -alkenyl, -heteroalkenyl, —C(O)alkenyl, —C(O)-heteroalkenyl, —O-alkenyl, —O-heteroalkenyl, -alkynyl, -heteroalkynyl, —C(O)alkynyl, —C(O)-heteroalkynyl, —O-alkynyl, and —O-heteroalkynyl, wherein the alkyl, alkenyl and alkynyl portions of said -alkyl, -heteroalkyl, —C(O)alkyl, —C(O)-heteroalkyl, —O-alkyl, -heteroalkyl, -alkenyl, -heteroalkenyl, —C(O)alkenyl, —C(O)-heteroalkenyl, —O-alkenyl, —O-heteroalkenyl, -alkynyl, -heteroalkynyl, —C(O)alkynyl, —C(O)-heteroalkynyl, —O-alkynyl, and —O-heteroalkynyl are unsubstituted or optionally independently substituted with one or more groups each independently selected from the group consisting of:

halo, OH, —CO$_2$R$^6$, —C(O)R$^6$, —SR$^7$, —S(O)R$^7$, —SO$_2$R$^7$, CN, NO$_2$, —C(O)NR$^8$R$^9$, —NR$^8$R$^9$, haloalkoxy, —NR$^{10}$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, and —OC(O)NR$^8$R$^9$, and (iii) aryl, —O-aryl, —C(O)-aryl, heteroaryl, —O-heteroaryl, —C(O)-heteroaryl, cycloalkyl, —O-cycloalkyl, —C(O)-cycloalkyl, heterocycloalkyl, —O-heterocycloalkyl, —C(O)-heterocycloalkyl, cycloalkenyl, —O-cycloalkenyl, —C(O)-cycloalkenyl, and heterocycloalkenyl, —O-heterocycloalkenyl, —C(O)-heterocycloalkenyl, each of which is unsubstituted or optionally independently substituted with from 1 to 2 groups each independently selected from (i) and (ii) above;

and (d) aryl and heteroaryl, wherein said aryl and said heteroaryl are substituted with at least one group each independently selected from the group consisting of:

(1) halo, OH, —CO$_2$R$^6$, —C(O)R$^6$, —SR$^7$, —S(O)R$^7$, —SO$_2$R$^7$, —SF$_5$, —Si(R$^7$)$_3$, CN, NO$_2$, —C(O)NR$^8$R$^9$, —NR$^8$R$^9$, haloalkoxy, —NR$^{10}$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, and —OC(O)NR$^8$R$^9$, (2) -alkyl, -heteroalkyl, —C(O)alkyl, —C(O)-heteroalkyl, —O-alkyl, —O-heteroalkyl, -alkenyl, -heteroalkenyl, —C(O)alkenyl, —C(O)-heteroalkenyl, —O-alkenyl, —O-heteroalkenyl, -alkynyl, -heteroalkynyl, —C(O)alkynyl, —C(O)-heteroalkynyl, —O-alkynyl, and —O-heteroalkynyl, wherein each of the alkyl, alkenyl and alkynyl portions of said -alkyl, -heteroalkyl, —C(O)alkyl, —C(O)-heteroalkyl, —O-alkyl, —O-heteroalkyl, -alkenyl, -heteroalkenyl, —C(O)alkenyl, —C(O)-heteroalkenyl, —O-alkenyl, —O-heteroalkenyl, -alkynyl, -heteroalkynyl, —C(O)alkynyl, —C(O)-heteroalkynyl, —O-alkynyl, and —O-heteroalkynyl are unsubstituted or optionally independently substituted with one or more groups each independently selected from the group consisting of:

halo, OH, —CO$_2$R$^6$, —C(O)R$^6$, —SR$^7$, —S(O)R$^7$, —SO$_2$R$^7$, CN, NO$_2$, —C(O)NR$^8$R$^9$, —NR$^8$R$^9$, haloalkoxy, —NR$^{10}$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, and —OC(O)NR$^8$R$^9$, and (3) aryl, —O-aryl, —C(O)-aryl, heteroaryl, —O-heteroaryl, —C(O)-heteroaryl, cycloalkyl, —O-cycloalkyl, —C(O)-cycloalkyl, heterocycloalkyl, —O-heterocycloalkyl, —C(O)-heterocycloalkyl, cycloalkenyl, —O-cycloalkenyl, —C(O)-cycloalkenyl, and heterocycloalkenyl, —O-heterocycloalkenyl, —C(O)-heterocycloalkenyl, each of which is unsubstituted or optionally independently substituted with from 1 to 2 groups each independently selected from (1) and (2) above;

R$^2$ is selected from the group consisting of aryl, arylalkyl-, heteroaryl, and heteroarylalkyl-, wherein the aryl and heteroaryl, and the aryl and heteroaryl portions of said arylalkyl- and said heteroarylalkyl-, are substituted with 1 or more groups each independently selected from the group consisting of:

(A) halo, OH, —CO$_2$R$^6$, —C(O)R$^6$, —SR$^7$, —S(O)R$^7$, —SO$_2$R$^7$, —SF$_5$, —Si(R$^7$)$_3$, CN, NO$_2$, —C(O)NR$^8$R$^9$, —NR$^8$R$^9$, haloalkoxy, —NR$^{10}$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, and —OC(O)NR$^8$R$^9$, (B) -alkyl, -heteroalkyl, —C(O)alkyl, —C(O)-heteroalkyl, —O-alkyl, —O-heteroalkyl, -alkenyl, -heteroalkenyl, —C(O)alkenyl, —C(O)-heteroalkenyl, —O-alkenyl, —O-heteroalkenyl, -alkynyl, -heteroalkynyl, —C(O)alkynyl, —C(O)-heteroalkynyl, —O-alkynyl, and —O-heteroalkynyl, wherein each of the alkyl, alkenyl and alkynyl portions of said -alkyl, -heteroalkyl, —C(O)alkyl, —C(O)-heteroalkyl, —O-alkyl, —O-heteroalkyl, -alkenyl, -heteroalkenyl, —C(O)alkenyl, —C(O)-heteroalkenyl, —O-alkenyl, —O-heteroalkenyl, -alkynyl, -heteroalkynyl, —C(O)alkynyl, —C(O)-heteroalkynyl, —O-alkynyl, and —O-heteroalkynyl are unsubstituted or optionally independently substituted with one or more groups each independently selected from the group consisting of:

halo, OH, —CO$_2$R$^6$, —C(O)R$^6$, —SR$^7$, —S(O)R$^7$, —SO$_2$R$^7$, CN, NO$_2$, —C(O)NR$^8$R$^9$, —NR$^8$R$^9$, haloalkoxy, —NR$^{10}$—C(O)—NR$^6$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, and —OC(O)NR$^8$R$^9$, and (C) aryl, —O-aryl, —C(O)-aryl, heteroaryl, —O-heteroaryl, —C(O)-heteroaryl, cycloalkyl, —O-cycloalkyl, —C(O)-cycloalkyl, heterocycloalkyl, —O-heterocycloalkyl, —C(O)-heterocycloalkyl, cycloalkenyl, —O-cycloalkenyl, —C(O)-cycloalkenyl, and heterocycloalkenyl, —O-heterocycloalkenyl, —C(O)-heterocycloalkenyl, each of which is unsubstituted or optionally independently substituted with from 1 to 2 groups each independently selected from (A) and (B) above;

$R^3$ is selected from the group consisting of H and lower alkyl;

Z is a moiety selected from the group consisting of —(C($R^{11}$)$_2$)—(C($R^{12}R^{13}$))$_m$—C(O)OH, —(C($R^{11}$)$_2$)—(C($R^{14}$)$_2$)$_n$—C(O)OH,

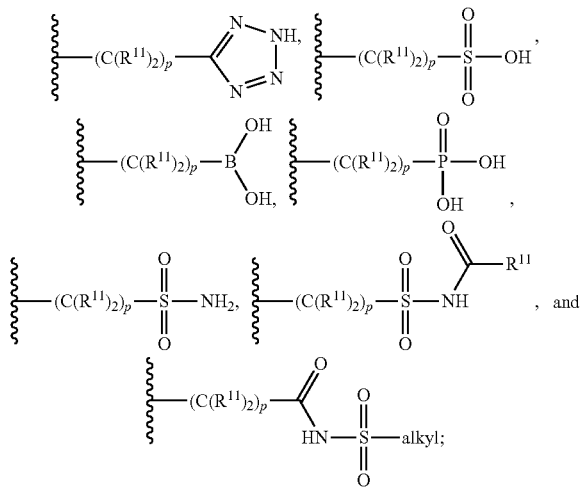

m is an integer from 0 to 5;
n is an integer from 0 to 5;
p is an integer from 0 to 5;
each $R^4$ is independently selected from the group consisting of H, lower alkyl, cycloalkyl, heterocycloalkyl, heteroalkyl, and haloalkyl;
each $R^5$ is independently selected from the group consisting of H, lower alkyl, hydroxy-substituted lower alkyl;
each $R^6$ is independently selected from the group consisting of H and alkyl;
each $R^7$ is independently selected from the group consisting of H, alkyl, aryl, arylalkyl-;
each $R^8$ is independently selected from the group consisting of H and alkyl;
each $R^9$ is independently selected from the group consisting of H and alkyl,
or alternatively $R^8$ and $R^9$ are taken together with the nitrogen to which they are attached to form a 5-, 6-, or 7-membered saturated heterocyclic ring, or a 5-, 6-, or 7-membered unsaturated heterocyclic ring, which ring contains (including said nitrogen) from 1 to 2 ring heteroatoms each independently selected from the group consisting of N, N-oxide, O, S, S(O), or S(O)$_2$,
or alternatively $R^8$ and $R^9$ are taken together with the nitrogen to which they are attached to form a 5-membered heteroaromatic ring containing (including the nitrogen to which $R^8$ and $R^9$ are attached) from 1 to 3 ring nitrogens;
each $R^{10}$ is independently selected from the group consisting of H and alkyl;
each $R^{11}$ is independently selected from the group consisting of H and lower alkyl;
each $R^{12}$ is independently selected from the group consisting of H, lower alkyl, —OH, hydroxy-substituted lower alkyl;

each $R^{13}$ is independently selected from the group consisting of H, unsubstituted lower alkyl, lower alkyl substituted with one or more groups each independently selected from the group consisting of hydroxyl and alkoxy, or $R^{12}$ and $R^{13}$ are taken together to form an oxo;

each $R^{14}$ is independently selected from the group consisting of H and fluoro; and $L^1$ is selected from the group consisting of —N($R^4$)—(C($R^8$)$_2$)$_r$—, —O—(C($R^8$)$_2$)$_s$—, —(C($R^5$)$_2$)$_r$—N($R^4$)—, and —(C($R^5$)$_2$)$_s$—O—, with provisos that:

(i) when ring A contains three ring nitrogens, then $L^1$ is selected from the group consisting of —N($R^4$)—(C($R^8$)$_2$)$_r$—, —O—(C($R^8$)$_2$)$_s$—, —(C($R^8$)$_2$)$_r$—N($R^4$)—, —(C($R^8$)$_2$)$_s$—O—, and —(C($R^5$)$_2$)$_r$, and (ii) with the further proviso that when ring A is a 1,2,3-triazole, then $L^1$ is —(C($R^8$)$_2$)$_r$— and $L^1$ is attached to ring A via a ring nitrogen of said triazole.

In one embodiment, in formula (A), ring B is phenyl.

In one embodiment, in formula (A), ring B is phenyl which, in addition to the moieties -$L^1$- and —C(O)N($R^3$)—Z shown in the formula, is further substituted with one or more substituents.

In one embodiment, in formula (A), ring B is a phenyl which, in addition to the moieties -$L^1$- and —C(O)N($R^3$)—Z shown in the formula, is further substituted with from 1 to 2 substituents, each independently selected from the group consisting of halo, alkyl, and haloalkyl.

In one embodiment, in formula (A), ring B is a 5-membered heteroaromatic ring having from 1 to 3 ring heteroatoms independently selected from the group consisting of N, O, and S, wherein said ring B is not further substituted.

In one embodiment, in formula (A), ring B is a 6-membered heteroaromatic ring having from 1 to 3 ring nitrogen atoms, wherein said ring B is not further substituted.

In one embodiment, in formula (A), ring B is a 5-membered heteroaromatic ring having from 1 to 3 ring heteroatoms independently selected from the group consisting of N, O, and S, wherein said ring B is further substituted with one or more substituents. Said further substituents in such embodiments may be bound to one or more available ring carbon atoms and/or ring nitrogen atoms.

In one embodiment, in formula (A), ring B is a 6-membered heteroaromatic ring having from 1 to 3 ring nitrogen atoms wherein said ring B is further substituted with one or more substituents. Said further substituents in such embodiments may be bound to one or more available ring carbon atoms and/or ring nitrogen atoms.

In one embodiment, in formula (A), ring B is a 5-membered heteroaromatic ring having from 1 to 3 ring heteroatoms independently selected from the group consisting of N, O, and S, wherein said 5-membered heteroaromatic ring is further substituted with from 1 to 2 substituents, each substituent being independently selected from the group consisting of halo, alkyl, and haloalkyl. In one such embodiment, ring B contains two said substituents. In another such embodiment, ring B contains one said substitutent.

When, in Formula (A), ring B is a 5-membered heteroaromatic ring, non-limiting examples of such rings include, but are not limited to: furan, thiophene, pyrrole, imidazole, pyrazole, 1,2,3-triazole, 1,2,4-triazole, thiazole, thiadiazole, oxazole, oxadiazole, and isoxazole, each of which may be optionally further substituted as described herein. Non-limiting examples of ring B (shown connected to moieties $L^1$ and —C(O)—N($R^3$)—Z) include:

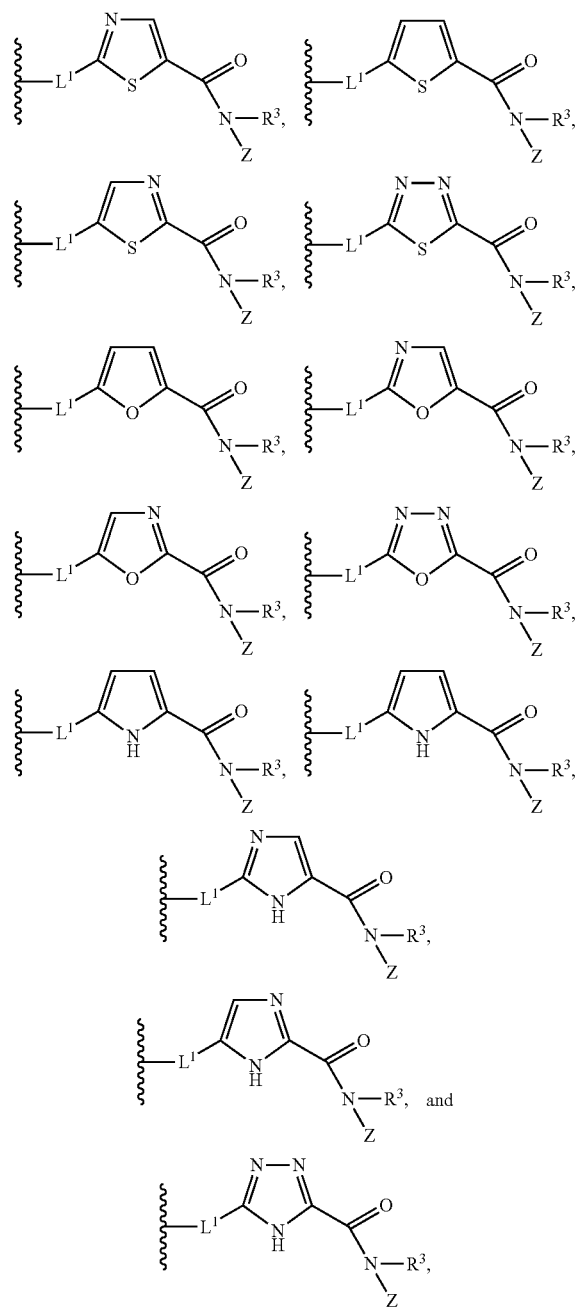

wherein each ring B shown is optionally further substituted on an available ring carbon atom or ring nitrogen atom with one or more groups $R^a$, wherein each $R^a$ group is independently selected from the group consisting of halo, alkyl, and haloalkyl. Those of ordinary skill in the art will appreciate that, for all embodiments wherein a group $R^a$ is attached to ring B via an available ring nitrogen atom, $R^a$ will not include halo. In such embodiments, $R^a$ is selected from the group consisting of alkyl and haloalkyl. For all such embodiments wherein a group $R^a$ is bound to ring B via an available ring carbon atom, $R^a$ is optionally halo, alkyl, and haloalkyl. Non-limiting examples of such groups substituted on an available ring nitrogen atom include:

In one embodiment, in formula (A), ring B is a 6-membered heteroaromatic ring having from 1 to 3 ring nitrogen atoms, wherein said ring B is further substituted with from 1 to 3 substituents, each substituent being independently selected from the group consisting of halo, alkyl, and haloalkyl. In one such embodiment, ring B contains three said substituents. In one such embodiment, ring B contains two said substituents. In another such embodiment, ring B contains one said substitutent.

When, in Formula (A), ring B is a 6-membered heteroaromatic ring, non-limiting examples of such rings include: pyridine, pyrimidine, pyrazine, pyridazine, and triazine, each of which may be optionally further substituted as described herein. Non-limiting examples of ring B (shown connected to moieties $L^1$ and —C(O)—N($R^3$)—Z) include:

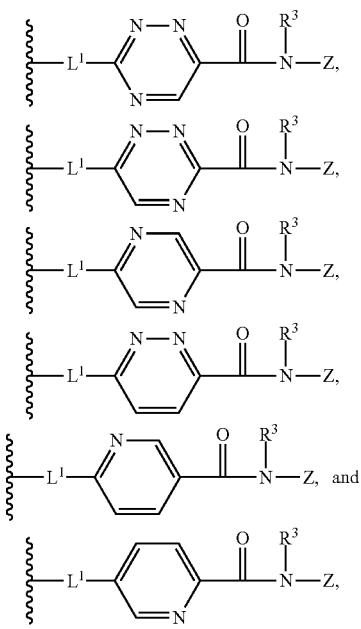

wherein any of such moieties may be optionally further substituted with one or more groups $R^a$, wherein each $R^a$ is independently selected from the group consisting of halo, alkyl, and haloalkyl.

In one embodiment, the present invention provides a compound, or a pharmaceutically acceptable salt, solvate, ester, prodrug, tautomer, or isomer of said compound, said compound having the general structure shown in Formula (I):

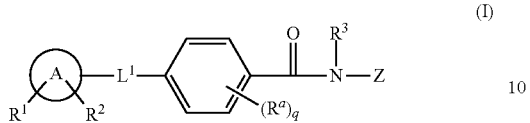

wherein ring A, $R^1$, $R^2$, $R^3$, Z, and $L^1$ are selected independently of each other and wherein:

ring A is a 5-membered heteroaryl ring having from 1 to 3 ring nitrogen atoms other than imidazole;

r is an integer from 0 to 2;

s is an integer from 0 to 2;

t, when present, is an integer from 1-2;

each $R^a$ (when present) is independently selected from the group consisting of halo, alkyl, and haloalkyl;

q is 0 to 2;

$R^1$ is selected from the group consisting of:

(a) —$CO_2R^6$, —$C(O)R^6$, —$SR^7$, —$S(O)R^7$, —$SO_2R^7$, —$C(O)NR^8R^9$, and —$NR^8R^9$;

(b) alkyl, -heteroalkyl, —C(O)alkyl, —C(O)-heteroalkyl, —O-alkyl, —O-heteroalkyl, -alkenyl, -heteroalkenyl, —C(O)alkenyl, —C(O)-heteroalkenyl, -alkenyl, —O-heteroalkenyl, -alkynyl, -heteroalkynyl, —C(O)alkynyl, —C(O)-heteroalkynyl, —O-alkynyl, and —O-heteroalkynyl, wherein each of the alkyl, alkenyl and alkynyl portions of said alkyl, -heteroalkyl, —C(O)alkyl, —C(O)-heteroalkyl, —O-alkyl, —O-heteroalkyl, -alkenyl, -heteroalkenyl, —C(O)alkenyl, —C(O)-heteroalkenyl, —O-alkenyl, —O-heteroalkenyl, -alkynyl, -heteroalkynyl, —C(O)alkynyl, —C(O)-heteroalkynyl, —O-alkynyl, and —O-heteroalkynyl are unsubstituted or optionally independently substituted with one or more groups each independently selected from the group consisting of:

halo, OH, —$CO_2R^6$, —$C(O)R^6$, —$SR^7$, —$S(O)R^7$, —$SO_2R^7$, CN, $NO_2$, —$C(O)NR^8R^9$, —$NR^8R^9$, haloalkoxy, —$NR^{10}$—C(O)—$NR^8R^9$, —$NR^{10}$—$CO_2R^6$, —$NR^{10}$—$C(O)R^6$, —$NR^{10}$—$SO_2R^6$, —$SO_2$—$NR^8R^9$, —$C(O)NR^8R^9$, —$OC(O)NR^8R^9$, unsubstituted alkoxy, and alkoxy substituted with one or more groups independently selected from the group consisting of halo, perhaloalkoxy, OH, and —$CO_2R^6$;

(c) —O-aryl, —S-aryl, arylalkyl-, —O-heteroaryl, —S-heteroaryl, heteroarylalkyl-, cycloalkyl, aryl-fused cycloalkyl, cycloalkylalkyl-, —O-cycloalkyl, —S-cycloalkyl, heterocycloalkyl, aryl-fused heterocycloalkyl, heterocycloalkylalkyl-, —O-heterocycloalkyl, —S-heterocycloalkyl, cycloalkenyl, —O-cycloalkenyl, —S-cycloalkenyl, heterocycloalkenyl, —O-heterocycloalkenyl, and —S-heterocycloalkenyl, wherein the aryl, heteroaryl, cycloalkyl, heterocycloalkyl, cycloalkenyl, and heterocycloalkenyl portions of said —O-aryl, —S-aryl, arylalkyl-, —O-heteroaryl, —S-heteroaryl, heteroarylalkyl-, cycloalkyl, aryl-fused cycloalkyl, cycloalkylalkyl-, —O-cycloalkyl, —S-cycloalkyl, heterocycloalkyl, aryl-fused heterocycloalkyl, heterocycloalkylalkyl-, —O-heterocycloalkyl, —S-heterocycloalkyl, cycloalkenyl, —O-cycloalkenyl, —S-cycloalkenyl, heterocycloalkenyl, —O-heterocycloalkenyl, and —S-heterocycloalkenyl, and the alkyl portions of said arylalkyl-, said heteroarylalkyl-, said cycloalkylalkyl-, and said heterocycloalkylalkyl-, are each independently unsubstituted or optionally independently substituted with 1 or more groups each independently selected from the group consisting of:

(i) halo, OH, —$CO_2R^6$, —$C(O)R^6$, —$SR^7$, —$S(O)R^7$, —$SO_2R^7$, CN, $NO_2$, —$C(O)NR^8R^9$, —$NR^8R^9$, haloalkoxy, —$NR^8$—C(O)—$NR^8R^9$, —$NR^{10}$—$CO_2R^6$, —$NR^{10}$—$C(O)R^6$, —$NR^{10}$—$SO_2R^6$, —$SO_2$—$NR^8R^9$, —$C(O)NR^8R^9$, and —$OC(O)NR^8R^9$, (ii) -alkyl, -heteroalkyl, —C(O)alkyl, —C(O)-heteroalkyl, —O-alkyl, —O-heteroalkyl, -alkenyl, -heteroalkenyl, —C(O)alkenyl, —C(O)-heteroalkenyl, —O-alkenyl, —O-heteroalkenyl, -alkynyl, -heteroalkynyl, —C(O)alkynyl, —C(O)-heteroalkynyl, —O-alkynyl, and —O-heteroalkynyl, wherein each of the alkyl, alkenyl and alkynyl portions of said -alkyl, -heteroalkyl, —C(O)alkyl, —C(O)-heteroalkyl, —O-alkyl, —O-heteroalkyl, -alkenyl, -heteroalkenyl, —C(O)alkenyl, —C(O)-heteroalkenyl, —O-alkenyl, —O-heteroalkenyl, -alkynyl, -heteroalkynyl, —C(O)alkynyl, —C(O)-heteroakynyl, —O-alkynyl, and —O-heteroalkynyl are unsubstituted or optionally independently substituted with one or more groups each independently selected from the group consisting of:

halo, OH, —$CO_2R^6$, —$C(O)R^6$, —$SR^7$, —$S(O)R^7$, —$SO_2R^7$, CN, $NO_2$, —$C(O)NR^8R^9$, —$NR^8R^9$, haloalkoxy, —$NR^{10}$—C(O)—$NR^8R^9$, —$NR^{10}$—$CO_2R^6$, —$NR^{10}$—$C(O)R^6$, —$NR^{10}$—$SO_2R^6$, —$SO_2$—$NR^8R^9$, —$C(O)NR^8R^9$, and —$OC(O)NR^8R^9$, and (iii) aryl, —O-aryl, —C(O)-aryl, heteroaryl, —O-heteroaryl, —C(O)-heteroaryl, cycloalkyl, —O-cycloalkyl, —C(O)-cycloalkyl, heterocycloalkyl, —O-heterocycloalkyl, —C(O)-heterocycloalkyl, cycloalkenyl, —O-cycloalkenyl, —C(O)-cycloalkenyl, and heterocycloalkenyl, —O-heterocycloalkenyl, —O(O)-heterocycloalkenyl, each of which is unsubstituted or optionally independently substituted with from 1 to 2 groups each independently selected from the group consisting of (i) and (ii) above;

and (d) aryl and heteroaryl, wherein each of said aryl and said heteroaryl are substituted with at least one group each independently selected from the group consisting of:

(1) halo, OH, —$CO_2R^6$, —$C(O)R^6$, —$SR^7$, —$S(O)R^7$, —$SO_2R^7$, —$SF_5$, —$Si(R^7)_3$, CN, $NO_2$, —$C(O)NR^8R^9$, —$NR^8R^9$, haloalkoxy, —$NR^{10}$—C(O)—$NR^8R^9$, —$NR^{10}$—$CO_2R^6$, —$NR^{10}$—$C(O)R^6$, —$NR^{10}$—$SO_2R^6$, —$SO_2$—$NR^8R^9$, —$C(O)NR^8R^9$, and —$OC(O)NR^8R^9$, (2) -alkyl, -heteroalkyl, —C(O)alkyl, —C(O)-heteroalkyl, —O-alkyl, —O-heteroalkyl, -alkenyl, -heteroalkenyl, —C(O)alkenyl, —C(O)-heteroalkenyl, —O-alkenyl, —O-heteroalkenyl, -alkynyl, -heteroalkynyl, —C(O)alkynyl, —C(O)-heteroalkynyl, —O-alkynyl, and —O-heteroalkynyl, wherein the alkyl, alkenyl and alkynyl portions of said -alkyl, -heteroalkyl, —C(O)alkyl, —C(O)-heteroalkyl, —O-alkyl, —O-heteroalkyl, -alkenyl, -heteroalkenyl, —C(O)alkenyl, —C(O)-heteroalkenyl, —O-alkenyl, —O-heteroalkenyl, -alkynyl, -heteroalkynyl, —C(O)

alkynyl, —C(O)-heteroalkynyl, —O-alkynyl, and —O-heteroalkynyl are unsubstituted or optionally independently substituted with one or more groups each independently selected from the group consisting of:
halo, OH, —CO$_2$R$^6$, —C(O)R$^6$, —SR$^7$, —S(O)R$^7$, —SO$_2$R$^7$, CN, NO$_2$, —C(O)NR$^8$R$^9$, —NR$^8$R$^9$, haloalkoxy, —NR$^{10}$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, and —OC(O)NR$^8$R$^9$, and (3) aryl, —O-aryl, —C(O)-aryl, heteroaryl, —O-heteroaryl, —C(O)-heteroaryl, cycloalkyl, —O-cycloalkyl, —C(O)-cycloalkyl, heterocycloalkyl, —O-heterocycloalkyl, —C(O)-heterocycloalkyl, cycloalkenyl, —O-cycloalkenyl, —C(O)-cycloalkenyl, and heterocycloalkenyl, —O-heterocycloalkenyl, —C(O)-heterocycloalkenyl, each of which is unsubstituted or optionally independently substituted with from 1 to 2 groups each independently selected from (1) and (2) above;

R$^2$ is selected from the group consisting of aryl, arylalkyl-, heteroaryl, and heteroarylalkyl-,
wherein the aryl and heteroaryl, and the aryl and heteroaryl portions of said arylalkyl- and heteroarylalkyl-, are substituted with 1 or more groups each independently selected from the group consisting of:

(A) halo, OH, —CO$_2$R$^6$, —C(O)R$^6$, —SR$^7$, —S(O)R$^7$, —SO$_2$R$^7$, —SF$_5$, —Si(R$^7$)$_3$, CN, NO$_2$, —C(O)NR$^8$R$^9$, —NR$^8$R$^9$, haloalkoxy, —NR$^{10}$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, and —OC(O)NR$^8$R$^9$, (B)-alkyl, -heteroalkyl, —C(O)alkyl, —C(O)-heteroalkyl, —O-alkyl, —O-heteroalkyl, -alkenyl, -heteroalkenyl, —C(O)alkenyl, —C(O)-heteroalkenyl, —O-alkenyl, —O-heteroalkenyl, -alkynyl, -heteroalkynyl, —C(O)alkynyl, —C(O)-heteroalkynyl, —O-alkynyl, and —O-heteroalkynyl,
wherein each of the alkyl, alkenyl and alkynyl portions of said -alkyl, -heteroalkyl, —C(O)alkyl, —C(O)-heteroalkyl, —O-alkyl, —O-heteroalkyl, -alkenyl, -heteroalkenyl, —C(O)alkenyl, —C(O)-heteroalkenyl, —O-alkenyl, —O-heteroalkenyl, -alkynyl, -heteroalkynyl, —C(O)alkynyl, —C(O)-heteroalkynyl, —O-alkynyl, and —O-heteroalkynyl are unsubstituted or optionally independently substituted with one or more groups each independently selected from the group consisting of:
halo, OH, —CO$_2$R$^6$, —C(O)R$^6$, —SR$^7$, —S(O)R$^7$, —SO$_2$R$^7$, CN, NO$_2$, —C(O)NR$^8$R$^9$, —NR$^8$R$^9$, haloalkoxy, —NR$^{10}$—C(O)—NR$^8$R$^9$, —NR$^{10}$—CO$_2$R$^6$, —NR$^{10}$—C(O)R$^6$, —NR$^{18}$—SO$_2$R$^6$, —SO$_2$—NR$^8$R$^9$, —C(O)NR$^8$R$^9$, and —OC(O)NR$^8$R$^9$, and (C) aryl, —O-aryl, —C(O)-aryl, heteroaryl, —O-heteroaryl, —C(O)-heteroaryl, cycloalkyl, —O-cycloalkyl, —O(O)— cycloalkyl, heterocycloalkyl, —O-heterocycloalkyl, —C(O)-heterocycloalkyl, cycloalkenyl, —O-cycloalkenyl, —C(O)-cycloalkenyl, and heterocycloalkenyl, —O-heterocycloalkenyl, —C(O)-heterocycloalkenyl, each of which is unsubstituted or optionally independently substituted with from 1 to 2 groups each independently selected from (A) and (B) above;

R$^3$ is selected from the group consisting of H and lower alkyl;

Z is a moiety selected from the group consisting of —(C(R$^{11}$)$_2$)—(C(R$^{12}$R$^{13}$))$_m$—C(O)OH, —(C(R$^{11}$)$_2$)—(C(R$^{14}$)$_2$)$_n$—C(O)OH, and

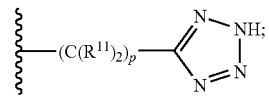

m is an integer from 0 to 5;
n is an integer from 0 to 5;
p is an integer from 0 to 5;

each R$^4$ is independently selected from the group consisting of H, lower alkyl, cycloalkyl, heterocycloalkyl, heteroalkyl, and haloalkyl;

each R$^5$ is independently selected from the group consisting of H, lower alkyl, hydroxy-substituted lower alkyl;

each R$^6$ is independently selected from the group consisting of H and alkyl;

each R$^7$ is independently selected from the group consisting of H, alkyl, aryl, arylalkyl-;

each R$^8$ is independently selected from the group consisting of H and alkyl;

each R$^9$ is independently selected from the group consisting of H and alkyl,
or alternatively R$^8$ and R$^9$ are taken together with the nitrogen to which they are attached to form a 5-, 6-, or 7-membered saturated heterocyclic ring, or a 5-, 6-, or 7-membered unsaturated heterocyclic ring, which ring contains (including said nitrogen) from 1 to 2 ring heteroatoms each independently selected from the group consisting of N,N-oxide, O, S, S(O), or S(O)$_2$,
or alternatively R$^8$ and R$^9$ are taken together with the nitrogen to which they are attached to form a 5-membered heteroaromatic ring containing (including the nitrogen to which R$^8$ and R$^9$ are attached) from 1 to 3 ring nitrogens;

each R$^{10}$ is independently selected from the group consisting of H and alkyl;

each R$^{11}$ is independently selected from the group consisting of H and lower alkyl;

each R$^{12}$ is independently selected from the group consisting of H, lower alkyl, —OH, hydroxy-substituted lower alkyl;

each R$^{13}$ is independently selected from the group consisting of H, unsubstituted lower alkyl, lower alkyl substituted with one or more groups each independently selected from the group consisting of hydroxyl and alkoxy, or R$^{12}$ and R$^{13}$ are taken together to form an oxo;

each R$^{14}$ is independently selected from the group consisting of H and fluoro; and L$^1$ is selected from the group consisting of —N(R$^4$)—(C(R$^5$)$_2$)$_r$, —O—(C(R$^5$)$_2$)$_s$—, —(C(R$^5$)$_2$)$_r$—N(R$^4$)—, and —(C(R$^5$)$_2$)$_s$—O—, with provisos that:

(i) when ring A contains three ring nitrogens, then L$^1$ is selected from the group consisting of —N(R$^4$)—(C(R$^5$)$_2$)$_r$—, —O—(C(R$^5$)$_2$)$_s$—, —(C(R$^5$)$_2$)$_r$—N(R$^4$)—, —(C(R$^5$)$_2$)$_s$—O—, and —(C(R$^5$)$_2$)$_r$, and (ii) with the further proviso that when ring A is a 1,2,3-triazole, then L$^1$ is —(C(R$^5$)$_2$)$_r$, and L$^1$ is attached to ring A via a ring nitrogen of said triazole.

As indicated above, tautomers of the compounds of the various formulas of the invention described herein are embraced by the present invention. For example, it shall be understood that tetrazoles (such as those described in variable "Z") written as:

also embrace

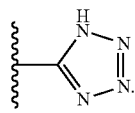

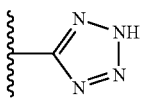

In one embodiment, the present invention provides a compound, or a pharmaceutically acceptable salt, solvate, ester, prodrug, tautomer, or isomer of said compound, said compound having the general structure shown in Formula (II):

(II)

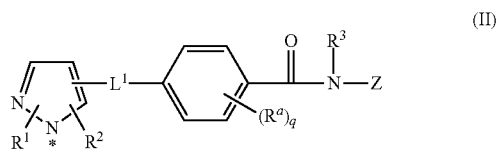

wherein $R^1$, $R^2$, $R^3$, $R^a$, q, $L^1$, and Z are selected independently of each other, and wherein:

$L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—;

and $R^1$, $R^2$, $R^3$, $R^4$, $R^5$, $R^a$, q, r, s, and Z are as defined in Formula (I).

It shall be noted that the moiety,

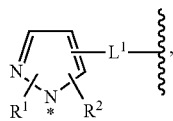

as shown in the general structures herein, e.g., in Formula (II) above, and in Formulas (III), (IV), (V), and (VI) below, represents each of the various possible structural isomers. Non-limiting examples of such structural isomers include:

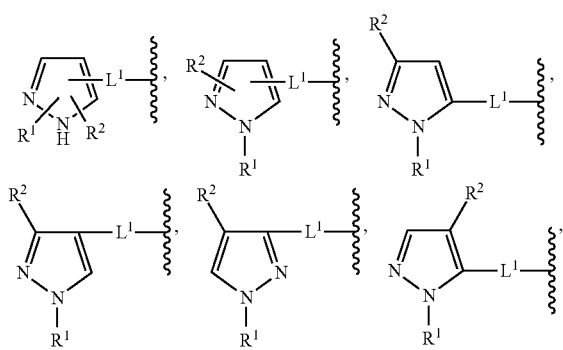

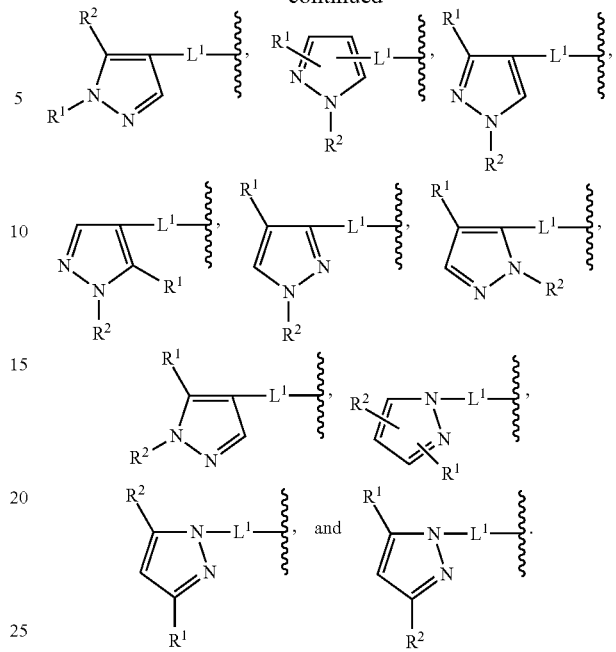

In one embodiment, the present invention provides a compound, or a pharmaceutically acceptable salt, solvate, ester, prodrug, tautomer, or isomer of said compound, said compound having the general structure shown in Formula (II-A):

(II-A)

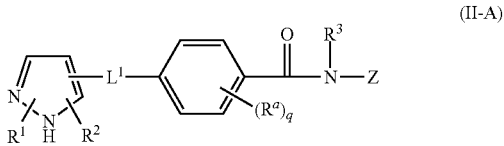

wherein $R^1$, $R^2$, $R^3$, $R^a$, q, $L^1$, and Z are selected independently of each other, and wherein:

$L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—;

and $R^1$, $R^2$, $R^3$, $R^4$, $R^5$, $R^a$, q, r, s, and Z are as defined in Formula (I).

In one embodiment, the present invention provides a compound, or a pharmaceutically acceptable salt, solvate, ester, prodrug, tautomer, or isomer of said compound, said compound having the general structure shown in Formula (II-B):

(II-B)

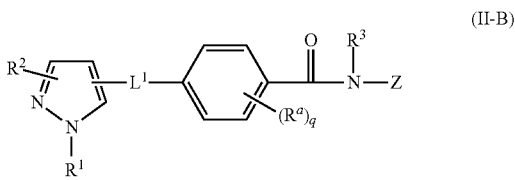

wherein $R^1$, $R^2$, $R^3$, $R^a$, q, $L^1$, and Z are selected independently of each other, and wherein:

$L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—;

and $R^1$, $R^2$, $R^3$, $R^4$, $R^5$, $R^a$, q, r, s, and Z are as defined in Formula (I).

In one embodiment, the present invention provides a compound, or a pharmaceutically acceptable salt, solvate, ester, prodrug, tautomer, or isomer of said compound, said compound having the general structure shown in Formula (II-B1):

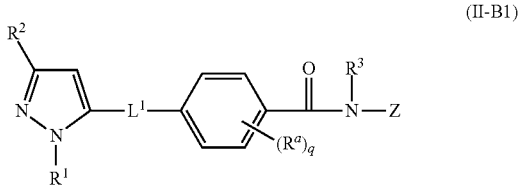

(II-B1)

wherein $R^1$, $R^2$, $R^3$, $R^a$, q, $L^1$, and Z are selected independently of each other, and wherein:

$L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—;

and $R^1$, $R^2$, $R^3$, $R^4$, $R^5$, $R^a$, q, r, s, and Z are as defined in Formula (I).

In one embodiment, the present invention provides a compound, or a pharmaceutically acceptable salt, solvate, ester, prodrug, tautomer, or isomer of said compound, said compound having the general structure shown in Formula (II-B2):

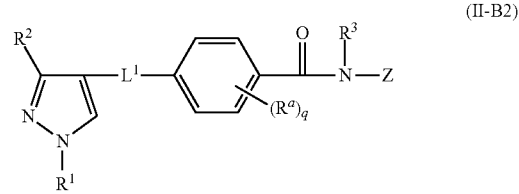

(II-B2)

wherein $R^1$, $R^2$, $R^3$, $R^a$, q, $L^1$, and Z are selected independently of each other, and wherein:

$L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—;

and $R^1$, $R^2$, $R^3$, $R^4$, $R^5$, $R^a$, q, r, s, and Z are as defined in Formula (I).

In one embodiment, the present invention provides a compound, or a pharmaceutically acceptable salt, solvate, ester, prodrug, tautomer, or isomer of said compound, said compound having the general structure shown in Formula (II-B3):

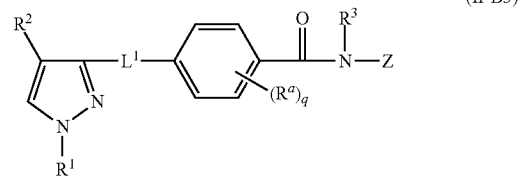

(II-B3)

wherein $R^1$, $R^2$, $R^3$, $R^a$, q, $L^1$, and Z are selected independently of each other, and wherein:

$L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—; and $R^1$, $R^2$, $R^3$, $R^4$, $R^5$, $R^a$, q, r, s, and Z are as defined in Formula (I).

In one embodiment, the present invention provides a compound, or a pharmaceutically acceptable salt, solvate, ester, prodrug, tautomer, or isomer of said compound, said compound having the general structure shown in Formula (II-B4):

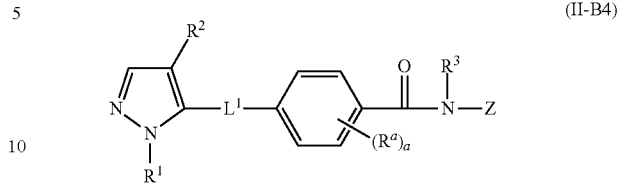

(II-B4)

wherein $R^1$, $R^2$, $R^3$, $R^a$, q, $L^1$, and Z are selected independently of each other, and wherein:

$L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—;

and $R^1$, $R^2$, $R^3$, $R^4$, $R^5$, $R^a$, q, r, s, and Z are as defined in Formula (I).

In one embodiment, the present invention provides a compound, or a pharmaceutically acceptable salt, solvate, ester, prodrug, tautomer, or isomer of said compound, said compound having the general structure shown in Formula (II-B5):

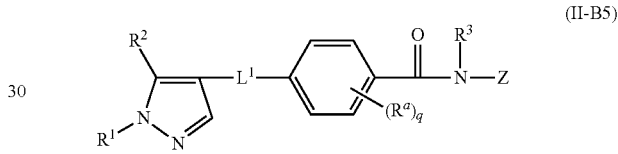

(II-B5)

wherein $R^1$, $R^2$, $R^3$, $R^a$, q, $L^1$, and Z are selected independently of each other, and wherein:

$L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—;

and $R^1$, $R^2$, $R^3$, $R^4$, $R^5$, $R^a$, q, r, s, and Z are as defined in Formula (I).

In one embodiment, the present invention provides a compound, or a pharmaceutically acceptable salt, solvate, ester, prodrug, tautomer, or isomer of said compound, said compound having the general structure shown in Formula (II-C):

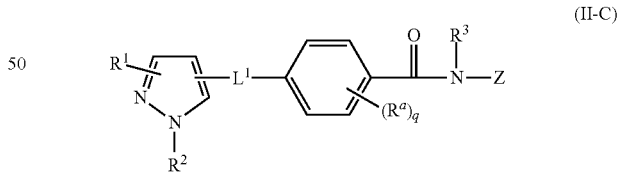

(II-C)

wherein $R^1$, $R^2$, $R^3$, $R^a$, q, $L^1$, and Z are selected independently of each other, and wherein:

$L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—;

and $R^1$, $R^2$, $R^3$, $R^4$, $R^5$, $R^a$, q, r, s, and Z are as defined in Formula (I).

In one embodiment, the present invention provides a compound, or a pharmaceutically acceptable salt, solvate, ester, prodrug, tautomer, or isomer of said compound, said compound having the general structure shown in Formula (II-C1):

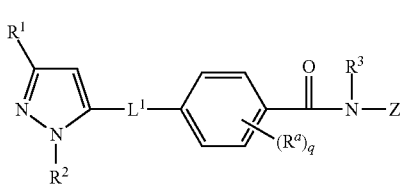
(II-C1)

wherein $R^1$, $R^2$, $R^3$, $R^a$, q, $L^1$, and Z are selected independently of each other, and wherein:

$L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—;

and $R^1$, $R^2$, $R^3$, $R^4$, $R^5$, $R^a$, q, r, s, and Z are as defined in Formula (I).

In one embodiment, the present invention provides a compound, or a pharmaceutically acceptable salt, solvate, ester, prodrug, tautomer, or isomer of said compound, said compound having the general structure shown in Formula (II-C2):

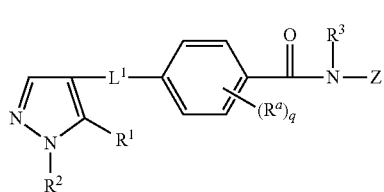
(II-C2)

wherein $R^1$, $R^2$, $R^3$, $R^a$, q, $L^1$, and Z are selected independently of each other, and wherein:

$L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—;

and $R^1$, $R^2$, $R^3$, $R^4$, $R^5$, $R^a$, q, r, s, and Z are as defined in Formula (I).

In one embodiment, the present invention provides a compound, or a pharmaceutically acceptable salt, solvate, ester, prodrug, tautomer, or isomer of said compound, said compound having the general structure shown in Formula (II-C3):

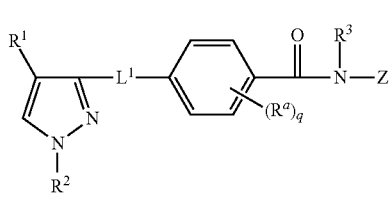
(II-C3)

wherein $R^1$, $R^2$, $R^3$, $R^a$, q, $L^1$, and Z are selected independently of each other, and wherein:

$L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—;

and $R^1$, $R^2$, $R^3$, $R^4$, $R^5$, $R^a$, q, r, s, and Z are as defined in Formula (I).

In one embodiment, the present invention provides a compound, or a pharmaceutically acceptable salt, solvate, ester, prodrug, tautomer, or isomer of said compound, said compound having the general structure shown in Formula (II-C4):

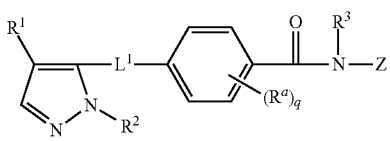
(II-C4)

wherein $R^1$, $R^2$, $R^3$, $R^a$, q, $L^1$, and Z are selected independently of each other, and wherein:

$L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—;

and $R^1$, $R^2$, $R^3$, $R^4$, $R^5$, $R^a$, q, r, s, and Z are as defined in Formula (I).

In one embodiment, the present invention provides a compound, or a pharmaceutically acceptable salt, solvate, ester, prodrug, tautomer, or isomer of said compound, said compound having the general structure shown in Formula (II-05):

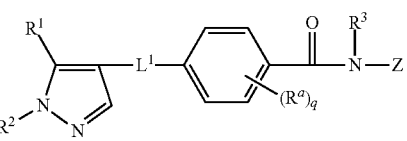
(II-C5)

wherein $R^1$, $R^2$, $R^3$, $R^a$, q, $L^1$, and Z are selected independently of each other, and wherein:

$L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—;

and $R^1$, $R^2$, $R^3$, $R^4$, $R^5$, $R^a$, q, r, s, and Z are as defined in Formula (I).

In one embodiment, the present invention provides a compound, or a pharmaceutically acceptable salt, solvate, ester, prodrug, tautomer, or isomer of said compound, said compound having the general structure shown in Formula (II-D):

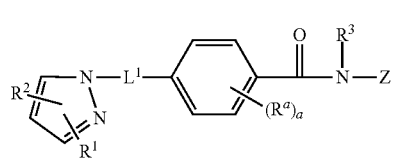
(II-D)

wherein $R^1$, $R^2$, $R^3$, $R^a$, q, $L^1$, and Z are selected independently of each other, and wherein:

$L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—;

and $R^1$, $R^2$, $R^3$, $R^4$, $R^5$, $R^a$, q, r, s, and Z are as defined in Formula (I).

In one embodiment, the present invention provides a compound, or a pharmaceutically acceptable salt, solvate, ester, prodrug, tautomer, or isomer of said compound, said compound having the general structure shown in Formula (II-D1):

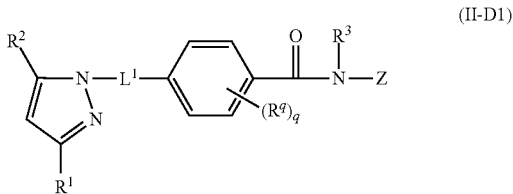

(II-D1)

wherein $R^1$, $R^2$, $R^3$, $R^a$, q, $L^1$, and Z are selected independently of each other, and wherein:

$L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—;

and $R^1$, $R^2$, $R^3$, $R^4$, $R^5$, $R^a$, q, r, s, and Z are as defined in Formula (I).

In one embodiment, the present invention provides a compound, or a pharmaceutically acceptable salt, solvate, ester, prodrug, tautomer, or isomer of said compound, said compound having the general structure shown in Formula (II-D2):

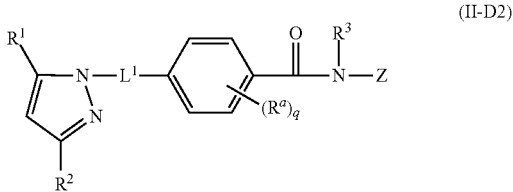

(II-D2)

wherein $R^1$, $R^2$, $R^3$, $R^a$, q, $L^1$, and Z are selected independently of each other, and wherein:

$L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—;

and $R^1$, $R^2$, $R^3$, $R^4$, $R^5$, $R^a$, q, r, s, and Z are as defined in Formula (I).

In one embodiment, in Formula (I), q is 0.
In one embodiment, in Formula (I), q is 1.
In one embodiment, in Formula (I), q is 2.
In one embodiment, in Formula (I), ring A is a pyrazole.
In one embodiment, in Formula (I), and/or Formula (II), $L^1$ is selected from the group consisting of —N($R^4$)—(C($R^5$)$_2$)$_r$—, —O—(C($R^5$)$_2$)$_s$—, —(C($R^5$)$_2$)$_r$—N($R^4$)—, and —(C($R^5$)$_2$)$_s$—O—.

In one embodiment, in Formula (I), and/or Formula (II), $L^1$ is selected from the group consisting of —NH—$CH_2$—, —O—$CH_2$—, —($CH_2$)—NH—, —$CH_2$—O—, —O—, —NH—, and —N($CH_3$)—.

In one embodiment, in Formula (I), and/or Formula (II), $L^1$ is selected from the group consisting of —NH—, —N($CH_3$)—, —O—, and —O$CH_2$—.

In one embodiment, in Formula (I), and/or Formula (II), $R^1$ is selected from the group consisting of:

(a) —$CO_2R^6$, —C(O)$R^6$, —S$R^7$, —C(O)N$R^8R^9$, and —N$R^8R^9$, (b) —($C_{4-6}$)alkyl, -heteroalkyl, —C(O)alkyl, —C(O)-heteroalkyl, —O-alkyl, -alkenyl, —C(O)alkenyl, —C(O)-heteroalkenyl, -alkynyl, —C(O)alkynyl, and —C(O)-heteroalkynyl, wherein each of the alkyl, alkenyl and alkynyl portions of said —($C_{4-6}$)alkyl, -heteroalkyl, —C(O)alkyl, —C(O)-heteroalkyl, —O-alkyl, -alkenyl, —C(O)alkenyl, —C(O)-heteroalkenyl, -alkynyl, —C(O)alkynyl, and —C(O)-heteroalkynyl, are unsubstituted or optionally independently substituted with one or more groups each independently selected from the group consisting of:
halo, OH, —$CO_2R^6$, —C(O)$R^6$, —S$R^7$, —S(O)$R^7$, —$SO_2R^7$, CN, $NO_2$, —C(O)N$R^8R^9$, —N$R^8R^9$, haloalkoxy, —N$R^{10}$—C(O)—N$R^8R^9$, —N$R^{10}$—$CO_2R^6$, —N$R^{10}$—C(O)$R^6$, —N$R^{10}$—$SO_2R^8$, —$SO_2$—N$R^8R^9$, —C(O)N$R^8R^9$, —OC(O)N$R^8R^9$, unsubstituted alkoxy, and alkoxy substituted with one or more groups independently selected from the group consisting of halo, perhaloalkoxy, OH, and —$CO_2R^6$, (c) arylalkyl-, cycloalkylalkyl-, heteroarylalkyl-, heterocycloalkyl, heterocycloalkylalkyl-, cycloalkenyl, and heterocycloalkenyl, wherein each of said arylalkyl-, said cycloalkylalkyl-, said heteroarylalkyl-, said heterocycloalkyl, said heterocycloalkylalkyl-, said cycloalkenyl, and said heterocycloalkenyl, and the alkyl portions of said arylalkyl-, said cycloalkylalkyl-, said heteroarylalkyl-, and said heterocycloalkylalkyl-, are each unsubstituted or optionally independently substituted with one or more groups each independently selected from the group consisting of:

(i) halo, OH, —$CO_2R^8$, —C(O)$R^6$, —S$R^7$, —S(O)$R^7$, —$SO_2R^7$, CN, —C(O)N$R^8R^9$, —N$R^8R^9$, haloalkoxy, —N$R^{10}$—C(O)—N$R^8R^9$, —N$R^{10}$—$CO_2R^8$, —N$R^{10}$—C(O)$R^8$, —N$R^{10}$—$SO_2R^6$, —$SO_2$—N$R^8R^9$, —C(O)N$R^8R^9$, and —OC(O)N$R^8R^9$, (ii) -alkyl, -heteroalkyl, —O-alkyl, —O-heteroalkyl, -alkenyl, -heteroalkenyl, —O-alkenyl, —O-heteroalkenyl, -alkynyl, -heteroalkynyl, —O-alkynyl, and —O-heteroalkynyl, wherein each of the alkyl, alkenyl and alkynyl portions of said -alkyl, -heteroalkyl, —O-alkyl, —O-heteroalkyl, -alkenyl, -heteroalkenyl, —O-alkenyl, —O-heteroalkenyl, -alkynyl, -heteroalkynyl, —O-alkynyl, and —O-heteroalkynyl are unsubstituted or optionally independently substituted with one or more groups each independently selected from the group consisting of:
halo, OH, —$CO_2R^6$, —C(O)$R^6$, —S$R^7$, —S(O)$R^7$, —$SO_2R^7$, CN, $NO_2$, —C(O)N$R^8R^9$, —N$R^8R^9$, haloalkoxy, —N$R^{10}$—C(O)—N$R^8R^9$, —N$R^{10}$—$CO_2R^6$, —N$R^{10}$—C(O)$R^6$, —N$R^{10}$—$SO_2R^6$, —$SO_2$—N$R^8R^9$, —C(O)N$R^8R^9$, and —OC(O)N$R^8R^9$, and (iii) aryl, —O-aryl, heteroaryl, —O-heteroaryl, cycloalkyl, —O-cycloalkyl, heterocycloalkyl, —O-heterocycloalkyl, cycloalkenyl, —O-cycloalkenyl, and heterocycloalkenyl, —O-heterocycloalkenyl, —C(O)-heterocycloalkenyl, each of which is unsubstituted or optionally independently substituted with from 1 to 2 groups each independently selected from (i) and (ii) above, and (d) aryl and heteroaryl,
wherein said aryl and said heteroaryl are substituted with at least one group each independently selected from the group consisting of:

(1) halo, —C(O)$R^6$, CN, —C(O)N$R^8R^9$, haloalkoxy, and —C(O)N$R^8R^9$, (2) -alkyl, —C(O)alkyl, —C(O)-heteroalkyl, —O-alkyl, -alkenyl, —C(O)alkenyl, —C(O)-heteroalkenyl, —C(O)alkynyl, and —C(O)-heteroalkynyl, wherein each of the alkyl, alkenyl and alkynyl portions of said -alkyl, —C(O)alkyl, —C(O)-heteroalkyl, —O-alkyl, -alkenyl, —C(O)alkenyl, —C(O)-heteroalkenyl, —C(O)alkynyl, and —C(O)-heteroalkynyl, are unsubstituted or optionally independently substituted with one or more groups each independently selected from the group consisting of:
halo, OH, —$CO_2R^6$, —$C(O)R^6$, —$SR^7$, —$S(O)R^7$, —$SO_2R^7$, CN, —$C(O)NR^8R^9$, —$NR^8R^9$, haloalkoxy, —$NR^{10}$—$C(O)$—$NR^8R^9$, —$NR^{10}$—$CO_2R^6$, —$NR^{10}$—$C(O)R^6$, —$NR^{10}$—$SO_2R^6$, —$SO_2$—$NR^8R^9$, —$C(O)NR^8R^9$, and —$OC(O)NR^8R^9$, and (3) aryl, —O-aryl, —C(O)-aryl, heteroaryl, —O-heteroaryl, —C(O)-heteroaryl, cycloalkyl, —O-cycloalkyl, —C(O)-cycloalkyl, heterocycloalkyl, —O-heterocycloalkyl, —C(O)-heterocycloalkyl, cycloalkenyl, —O-cycloalkenyl, —C(O)-cycloalkenyl, and heterocycloalkenyl, —O-heterocycloalkenyl, —C(O)-heterocycloalkenyl, each of which is unsubstituted or optionally independently substituted with from 1 to 2 groups each independently selected from (1) and (2) above.

In one embodiment, in Formula (I), and/or Formula (II), $R^1$ is selected from the group consisting of:
(a) —$SR^7$, —$C(O)NR^8R^9$, and —$NR^8R^9$,
(b) -alkenyl, and -alkynyl,
wherein each of said alkenyl and said alkynyl are unsubstituted or optionally independently substituted with one or more groups each independently selected from the group consisting of:
halo, OH, —$CO_2R^6$, —$C(O)R^6$, —$SR^7$, —$S(O)R^7$, —$SO_2R^7$, CN, $NO_2$, —$C(O)NR^8R^9$, —$NR^8R^9$, haloalkoxy, —$NR^{10}$—$C(O)$—$NR^8R^9$, —$NR^{10}$—$CO_2R^6$, —$NR^{10}$—$C(O)R^6$, —$NR^{10}$—$SO_2R^6$, —$SO_2$—$NR^8R^9$, —$C(O)NR^8R^9$, —$OC(O)NR^8R^9$, unsubstituted alkoxy, and alkoxy substituted with one or more groups independently selected from the group consisting of halo, perhaloalkoxy, OH, and —$CO_2R^6$,
(c) cycloalkenyl and heterocycloalkenyl,
wherein each of said cycloalkenyl and said heterocycloalkenyl are unsubstituted or optionally independently substituted with one or more groups each independently selected from the group consisting of:
(i) halo, OH, —$CO_2R^6$, —$C(O)R^6$, —$SR^7$, —$S(O)R^7$, —$SO_2R^7$, CN, —$C(O)NR^8R^9$, —$NR^8R^9$, haloalkoxy, —$NR^{10}$—$C(O)$—$NR^8R^9$, —$NR^{10}$—$CO_2R^6$, —$NR^{10}$—$C(O)R^6$, —$NR^{10}$—$SO_2R^6$, —$SO_2$—$NR^8R^9$, —$C(O)NR^8R^9$, and —$OC(O)NR^8R^9$,
(ii) -alkyl, -heteroalkyl, —O-alkyl, —O-heteroalkyl, -alkenyl, -heteroalkenyl, —O-alkenyl, —O-heteroalkenyl, -alkynyl, -heteroalkynyl, —O-alkynyl, and —O-heteroalkynyl,
wherein each of the alkyl, alkenyl and alkynyl portions of said -alkyl, -heteroalkyl, —O-alkyl, —O-heteroalkyl, -alkenyl, -heteroalkenyl, —O-alkenyl, —O-heteroalkenyl, -alkynyl, -heteroalkynyl, —O-alkynyl, and —O-heteroalkynyl are unsubstituted or optionally independently substituted with one or more groups each independently selected from the group consisting of:
halo, OH, —$CO_2R^6$, —$C(O)R^6$, —$SR^7$, —$S(O)R^7$, —$SO_2R^7$, CN, $NO_2$, —$C(O)NR^8R^9$, —$NR^8R^9$, haloalkoxy, —$NR^{10}$—$C(O)$—$NR^8R^9$, —$NR^{10}$—$CO_2R^6$, —$NR^{10}$—$C(O)R^6$, —$NR^{10}$—$SO_2R^6$, —$SO_2$—$NR^8R^9$, —$C(O)NR^8R^9$, and —$OC(O)NR^8R^9$, and
(iii) aryl, —O-aryl, heteroaryl, —O-heteroaryl, cycloalkyl, —O-cycloalkyl, heterocycloalkyl, —O-heterocycloalkyl, cycloalkenyl, —O-cycloalkenyl, and heterocycloalkenyl, —O-heterocycloalkenyl, —C(O)-heterocycloalkenyl, each of which is unsubstituted or optionally independently substituted with from 1 to 2 groups each independently selected from (i) and (ii) above, and (d) aryl and heteroaryl,
wherein said aryl and said heteroaryl are substituted with at least one group each independently selected from the group consisting of:
(1) halo, CN, —$C(O)NR^8R^9$, haloalkoxy, and —$C(O)NR^8R^9$,
(2) -alkyl, —O-alkyl, and -alkenyl,
wherein each of the alkyl, alkenyl and alkynyl portions of said -alkyl, —O-alkyl, and -alkenyl, are unsubstituted or optionally independently substituted with one or more groups each independently selected from the group consisting of:
halo, OH, —$CO_2R^6$, —$SR^7$, —$S(O)R^7$, —$SO_2R^7$, CN, —$C(O)NR^8R^9$, —$NR^8R^9$, haloalkoxy, —$NR^{10}$—$C(O)$—$NR^8R^9$, —$NR^{10}$—$CO_2R^8$, —$NR^{10}$—$C(O)R^6$, —$NR^{10}$—$SO_2R^6$, —$SO_2$—$NR^8R^9$, —$C(O)NR^8R^9$, and —$OC(O)NR^8R^9$, and
(3) aryl, —O-aryl, heteroaryl, —O-heteroaryl, cycloalkyl, heterocycloalkyl, —O-heterocycloalkyl, cycloalkenyl, —O-cycloalkenyl, heterocycloalkenyl, and —O-heterocycloalkenyl, each of which is unsubstituted or optionally independently substituted with from 1 to 2 groups each independently selected from (1) and (2) above.

In one embodiment, in Formula (I), and/or Formula (II), $R^1$ is selected from the group consisting of:
aryl and heteroaryl,
wherein each of said aryl and said heteroaryl are substituted with at least one group each independently selected from the group consisting of:
halo, alkyl, haloalkyl, heteroalkyl, alkenyl, alkoxy, haloalkoxy, cycloalkyl, cycloalkenyl, —O-cycloalkyl, and —O-cycloalkenyl.

In one embodiment, in Formula (I), and/or Formula (II), $R^1$ is selected from the group consisting of:
phenyl and naphthyl,
wherein said phenyl and said naphthyl are substituted with at least one group each independently selected from the group consisting of:
halo, alkyl, cycloalkyl, haloalkyl, alkoxy, and haloalkoxy.

In one embodiment, in Formula (I), and/or Formula (II), $R^2$ is selected from the group consisting of:
aryl and heteroaryl,
wherein said aryl and said heteroaryl are substituted with at least one group each independently selected from the group consisting of:
(1) halo, —$C(O)R^6$, CN, —$C(O)NR^8R^9$, haloalkoxy, and —$C(O)NR^8R^9$,
(2) -alkyl, —C(O)alkyl, —C(O)-heteroalkyl, —O-alkyl, -alkenyl, —C(O)alkenyl, —C(O)-heteroalkenyl, —C(O)alkynyl, and —C(O)-heteroalkynyl,
wherein the alkyl, alkenyl and alkynyl portions of said -alkyl, —C(O)alkyl, —C(O)-heteroalkyl, —O-alkyl, -alkenyl, —C(O)alkenyl, —C(O)-heteroalkenyl, —C(O)alkynyl, and —C(O)-heteroalkynyl, are unsubstituted or optionally independently substituted with one or more groups each independently selected from the group consisting of:
halo, OH, —$CO_2R^6$, —$C(O)R^6$, —$SR^7$, —$S(O)R^7$, —$SO_2R^7$, CN, —$C(O)NR^8R^9$, —$NR^8R^9$, haloalkoxy, —$NR^{10}$—$C(O)$—$NR^8R^9$, —$NR^{10}$—

$CO_2R^6$, $-NR^{10}-C(O)R^6$, $-NR^{10}-SO_2R^6$, $-SO_2-NR^8N^9$, $-C(O)NR^8N^9$, and $-OC(O)NR^8R^9$, and (3) aryl, —O-aryl, —C(O)-aryl, heteroaryl, —O-heteroaryl, —C(O)-heteroaryl, cycloalkyl, —O-cycloalkyl, —C(O)-cycloalkyl, heterocycloalkyl, —O-heterocycloalkyl, —C(O)-heterocycloalkyl, cycloalkenyl, —O-cycloalkenyl, —C(O)-cycloalkenyl, and heterocycloalkenyl, —O-heterocycloalkenyl, —C(O)-heterocycloalkenyl, each of which is unsubstituted or optionally independently substituted with from 1 to 2 groups each independently selected from (1) and (2) above.

In one embodiment, in Formula (I), and/or Formula (II), $R^2$ is selected from the group consisting of the group consisting of:
aryl, arylalkyl-, heteroaryl, and heteroarylalkyl-,
wherein said aryl and said heteroaryl, and the aryl and heteroaryl portions of said arylalkyl- and said heteroarylalkyl-, are substituted with at least one group each independently selected from the group consisting of:
(1) halo, CN, $-C(O)NR^8R^9$, haloalkoxy, and $-C(O)NR^8R^9$,
(2) -alkyl, —O-alkyl, and -alkenyl,
wherein the alkyl, alkenyl and alkynyl portions of said -alkyl, —O-alkyl, and -alkenyl, are unsubstituted or optionally independently substituted with one or more groups each independently selected from the group consisting of:
halo, OH, $-CO_2R^6$, $-SR^7$, $-S(O)R^7$, $-SO_2R^7$, CN, $-C(O)NR^8R^9$, $-NR^8R^9$, haloalkoxy, $-NR^{10}-C(O)-NR^8R^9$, $-NR^{10}-CO_2R^6$, $-NR^{10}-C(O)R^6$, $-NR^{10}-SO_2R^6$, $-SO_2-NR^8R^9$, $-C(O)NR^8R^9$, and $-OC(O)NR^8R^9$, and
(3) aryl, —O-aryl, heteroaryl, —O-heteroaryl, cycloalkyl, —O-cycloalkyl, heterocycloalkyl, —O-heterocycloalkyl, cycloalkenyl, —O-cycloalkenyl, heterocycloalkenyl, and —O-heterocycloalkenyl, each of which is unsubstituted or optionally independently substituted with from 1 to 2 groups each independently selected from (1) and (2) above.

In one embodiment, in Formula (I), and/or Formula (II), $R^2$ is selected from the group consisting of:
aryl, arylalkyl-, heteroaryl, and heteroarylalkyl-,
wherein said aryl and said heteroaryl, and the aryl and heteroaryl portions of said arylalkyl- and said heteroarylalkyl-, are substituted with at least one group each independently selected from the group consisting of:
halo, alkyl, haloalkyl, heteroalkyl, alkenyl, alkoxy, haloalkoxy, cycloalkyl, cycloalkenyl, —O-cycloalkyl, and —O-cycloalkenyl.

In one embodiment, in Formula (I), and/or Formula (II), $R^2$ is selected from the group consisting of: aryl and heteroaryl,
wherein said aryl and said heteroaryl are substituted with at least one group each independently selected from the group consisting of:
halo, alkyl, haloalkyl, heteroalkyl, alkenyl, alkoxy, haloalkoxy, cycloalkyl, cycloalkenyl, —O-cycloalkyl, and —O-cycloalkenyl.

In one embodiment, in Formula (I), and/or Formula (II), $R^2$ is selected from the group consisting of:
phenyl and naphthyl,
wherein said phenyl and said naphthyl are substituted with at least one group each independently selected from the group consisting of:
halo, alkyl, cycloalkyl, haloalkyl, alkoxy, and haloalkoxy.

In one embodiment, in Formula (I), and/or Formula (II), $R^3$ is H.

In one embodiment, in Formula (I), and/or Formula (II), $R^3$ is selected from the group consisting of methyl, ethyl, n-propyl, and isopropyl.

In one embodiment, in Formula (I), and/or Formula (II), each $R^8$ is independently selected from the group consisting of H and alkyl.

In one embodiment, in Formula (I), and/or Formula (II), each $R^9$ is independently selected from the group consisting of H and alkyl.

In one embodiment, in Formula (I), and/or Formula (II), $R^8$ and $R^9$ are taken together with the nitrogen to which they are attached to form a 5-, 6-, or 7-membered heteroaromatic ring, which ring contains (including said nitrogen to which $R^8$ and $R^9$ are attached) from 1 to 2 ring heteroatoms.

In one embodiment, in Formula (I), and/or Formula (II), $R^8$ and $R^9$ are taken together with the nitrogen to which they are attached to form a 5-, 6-, or 7-membered saturated heterocyclic ring, which ring contains (including said nitrogen to which $R^8$ and $R^9$ are attached) from 1 to 2 ring heteroatoms.

In one embodiment, in Formula (I), and/or Formula (II), $R^8$ and $R^9$ are taken together with the nitrogen to which they are attached to form a 5-, 6-, or 7-membered partially or fully unsaturated heterocyclic ring, which ring contains (including said nitrogen to which $R^8$ and $R^9$ are attached) form 1 to 2 ring heteroatoms.

In one embodiment, in Formula (I), and/or Formula (II), $R^8$ and $R^9$ are taken together with the nitrogen to which they are attached to form a 5-, or 6-membered saturated, or partially or fully unsaturated, heterocyclic ring, which ring contains (including said nitrogen to which $R^8$ and $R^9$ are attached) form 1 to 2 ring heteroatoms.

In one embodiment, in Formula (I), and/or Formula (II), $R^8$ and $R^9$ are taken together with the nitrogen to which they are attached to form a 5-, 6-, or 7-membered ring moiety, non-limiting examples of such moieties include pyrrolidine, imidazolidine, piperazine, morpholine, thiomorpholine, oxazolidine, and thiazolidine.

In one embodiment, in Formula (I), and/or Formula (II), Z is a moiety selected from the group consisting of —(C($R^{11}$)$_2$)—(C($R^{12}R^{13}$))$_m$—C(O)OH, —(C($R^{11}$)$_2$)—(C($R^{14}$)$_2$)$_n$—C(O)OH, and

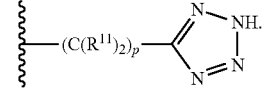

In one embodiment, in Formula (I), and/or Formula (II), Z is —(C($R^{11}$)$_2$)—(C($R^{12}$)($R^{13}$))$_m$—C(O)OH.

In one embodiment, in Formula (I), and/or Formula (II), Z is —($CH_2$)—(CH($CH_3$))—C(O)OH.

In one embodiment, in Formula (I), and/or Formula (II), Z is —($CH_2$)—($CH_2$)—($CH_2$)—C(O)OH.

In one embodiment, in Formula (I), and/or Formula (II), Z is —($CH_2$)—C($CH_3$)$_2$—C(O)OH.

In one embodiment, in Formula (I), and/or Formula (II), Z is —($CH_2$)—C($CH_3$)(OH)—C(O)OH.

In one embodiment, in Formula (I), and/or Formula (II), Z is —$CH_2$—$CH_2$—C(O)OH.

In one embodiment, in Formula (I), and/or Formula (II), Z is —$CH_2$—CH(OH)—C(O)OH.

In one embodiment, in Formula (I), and/or Formula (II), Z is —CH($CH_3$)—$CH_2$—C(O)OH.

In one embodiment, in Formula (I), and/or Formula (II), Z is —C(CH$_3$)$_2$—CH$_2$—C(O)OH.

In one embodiment, in Formula (I), and/or Formula (II), Z is —(C(R$^{11}$)$_2$)—(C(R$^{14}$)$_2$)$_n$—C(O)OH.

In one embodiment, in Formula (I), and/or Formula (II), Z is —CH$_2$—CH(F)—C(O)OH.

In one embodiment, in Formula (I), and/or Formula (II), Z is —CH$_2$—CF$_2$—C(O)OH.

In one embodiment, in Formula (I), and/or Formula (II), Z is —CH(CH$_3$)—CF$_2$—C(O)OH.

In one embodiment, in Formula (I), and/or Formula (II), Z is —CH$_2$—CH$_2$—CF$_2$—C(O)OH.

In one embodiment, in Formula (I), and/or Formula (II), Z is

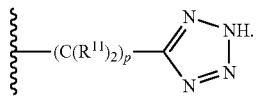

In one embodiment, in Formula (I), and/or Formula (II), Z is

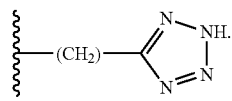

In one embodiment, in Formula (I), and/or Formula (II), Z is

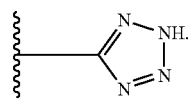

In one embodiment, in Formula (I), and/or Formula (II), Z is selected from the group consisting of:

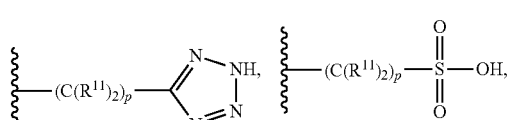

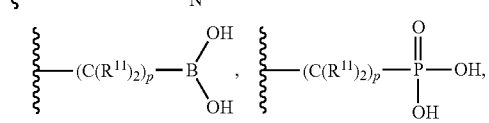

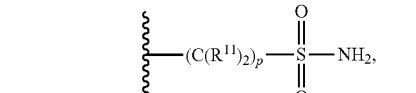

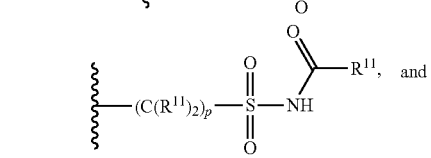

In one embodiment, the present invention provides a compound, or a pharmaceutically acceptable salt, solvate, ester, prodrug, tautomer, or isomer of said compound, said compound having the general structure shown in Formula (III):

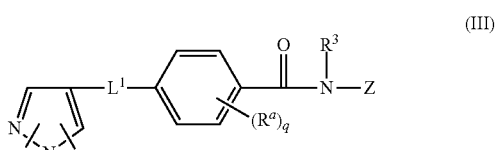

wherein R$^1$, R$^2$, R$^3$, L$^1$, and Z are selected independently of each other and wherein:

L$^1$ is selected from the group consisting of —N(R$^4$)—(C(R$^5$)$_2$)$_r$—, —O—(C(R$^5$)$_2$)$_s$—, —(C(R$^5$)$_2$)$_r$—N(R$^4$)—, and —(C(R$^5$)$_2$)$_s$—O—;

r is 0 to 2;

s is 0 to 2;

q is 0 to 1;

R$^1$ is selected from the group consisting of:

(a) —CO$_2$R$^6$, —C(O)R$^6$, —SR$^7$, —C(O)NR$^8$R$^9$, and —NR$^8$R$^9$, (b) —(C$_{4-6}$)alkyl, -heteroalkyl, —C(O)alkyl, —C(O)-heteroalkyl, —O-alkyl, -alkenyl, —C(O)alkenyl, —C(O)-heteroalkenyl, -alkynyl, —C(O)alkynyl, and —C(O)-heteroalkynyl, wherein each of the alkyl, alkenyl and alkynyl portions of said —(C$_{4-6}$)alkyl, -heteroalkyl, —C(O)alkyl, —C(O)-heteroalkyl, —O-alkyl, -alkenyl, —C(O)alkenyl, —C(O)-heteroalkenyl, -alkynyl, —C(O)alkynyl, and —C(O)-heteroalkynyl, are unsubstituted or optionally independently substituted with one or more groups each independently selected from:

halo, OH, —CO$_2$R$^8$, —C(O)R$^6$, —SR$^7$, —S(O)R$^7$, —SO$_2$R$^7$, CN, NO$_2$, —C(O)NR$^8$R$^9$, —NR$^8$R$^9$, haloalkoxy, —NR$^{10}$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, —OC(O)NR$^8$R$^9$, unsubstituted alkoxy, and alkoxy substituted with one or more groups independently selected from halo, perhaloalkoxy, OH, and —CO$_2$R$^6$, (c) arylalkyl-, cycloalkylalkyl-, heteroarylalkyl-, heterocycloalkyl, heterocycloalkylalkyl-, cycloalkenyl, and heterocycloalkenyl, wherein said arylalkyl-, said cycloalkylalkyl-, said heteroarylalkyl-, said heterocycloalkyl, said heterocycloalkylalkyl-, said cycloalkenyl, and said heterocycloalkenyl, and the alkyl portions of said arylalkyl-, said cycloalkylalkyl-, said heteroarylalkyl-, and said heterocycloalkylalkyl-, are each unsubstituted or optionally independently substituted with one or more groups each independently selected from the group consisting of:

(i) halo, OH, —CO$_2$R$^8$, —C(O)R$^6$, —SR$^7$, —S(O)R$^7$, —SO$_2$R$^7$, CN, —C(O)NR$^8$R$^9$, —NR$^8$R$^9$, haloalkoxy, —NR$^{10}$—C(O)—NR$^8$R$^9$, —NR$^{10}$—

$CO_2R^8$, $-NR^{10}-C(O)R^8$, $-NR^{10}-SO_2R^8$, $-SO_2-NR^8R^9$, $-C(O)NR^8R^9$, and $-OC(O)NR^8R^9$, (ii) -alkyl, -heteroalkyl, —O-alkyl, —O-heteroalkyl, -alkenyl, -heteroalkenyl, —O-alkenyl, —O-heteroalkenyl, -alkynyl, -heteroalkynyl, —O-alkynyl, and —O-heteroalkynyl, wherein each of the alkyl, alkenyl and alkynyl portions of said -alkyl, -heteroalkyl, —O-alkyl, —O-heteroalkyl, -alkenyl, -heteroalkenyl, —O-alkenyl, —O-heteroalkenyl, -alkynyl, -heteroalkynyl, —O-alkynyl, and —O-heteroalkynyl are unsubstituted or optionally independently substituted with one or more groups each independently selected from the group consisting of:

halo, OH, $-CO_2R^6$, $-C(O)R^6$, $-SR^7$, $-S(O)R^7$, $-SO_2R^7$, CN, $NO_2$, $-C(O)NR^8R^9$, $-NR^8R^9$, haloalkoxy, $-NR^{10}-C(O)-NR^8R^9$, $-NR^{10}-CO_2R^6$, $-NR^{10}-C(O)R^6$, $-NR^{10}-SO_2R^6$, $-SO_2-NR^8R^9$, $-C(O)NR^8R^9$, and $-OC(O)NR^8R^9$, and (iii) aryl, —O-aryl, heteroaryl, —O-heteroaryl, cycloalkyl, —O-cycloalkyl, heterocycloalkyl, —O-heterocycloalkyl, cycloalkenyl, —O-cycloalkenyl, and heterocycloalkenyl, —O-heterocycloalkenyl, —C(O)-heterocycloalkenyl, each of which is unsubstituted or optionally independently substituted with from 1 to 2 groups each independently selected from (i) and (ii) above, and (d) aryl and heteroaryl, wherein said aryl and said heteroaryl are substituted with at least one group each independently selected from the group consisting of:

(1) halo, $-C(O)R^6$, CN, $-C(O)NR^8R^9$, haloalkoxy, and $-C(O)NR^8R^9$, (2) -alkyl, $-C(O)$alkyl, $-C(O)$-heteroalkyl, —O-alkyl, -alkenyl, $-C(O)$alkenyl, $-C(O)$-heteroalkenyl, $-C(O)$alkynyl, and $-C(O)$-heteroalkynyl, wherein each of the alkyl, alkenyl and alkynyl portions of said -alkyl, $-C(O)$alkyl, $-C(O)$-heteroalkyl, —O-alkyl, -alkenyl, $-C(O)$alkenyl, $-C(O)$-heteroalkenyl, $-C(O)$alkynyl, and $-C(O)$-heteroalkynyl, are unsubstituted or optionally independently substituted with one or more groups each independently selected from the group consisting of:

halo, OH, $-CO_2R^6$, $-C(O)R^6$, $-SR^7$, $-S(O)R^7$, $-SO_2R^7$, CN, $-C(O)NR^8R^9$, $-NR^8R^9$, haloalkoxy, $-NR^{10}-C(O)-NR^8R^9$, $-NR^{10}-CO_2R^6$, $-NR^{10}-C(O)R^6$, $-NR^{10}-SO_2R^6$, $-SO_2-NR^8R^9$, $-C(O)NR^8R^9$, and $-OC(O)NR^8R^9$, and (3) aryl, —O-aryl, —C(O)-aryl, heteroaryl, —O-heteroaryl, —C(O)-heteroaryl, cycloalkyl, —O-cycloalkyl, —C(O)-cycloalkyl, heterocycloalkyl, —O-heterocycloalkyl, —C(O)-heterocycloalkyl, cycloalkenyl, —O-cycloalkenyl, —C(O)-cycloalkenyl, and heterocycloalkenyl, —O-heterocycloalkenyl, —C(O)-heterocycloalkenyl, each of which is unsubstituted or optionally independently substituted with from 1 to 2 groups each independently selected from (1) and (2) above;

$R^2$ is selected from the group consisting of:
aryl, arylalkyl-, heteroaryl, and heteroarylalkyl-,
wherein each of said aryl, said arylalkyl-, said heteroaryl, and said heteroarylalkyl- is substituted with at least one group each independently selected from the group consisting of:

(1) halo, $-C(O)R^6$, CN, $-C(O)NR^8R^9$, haloalkoxy, and $-C(O)NR^8R^9$, (2) -alkyl, $-C(O)$alkyl, $-C(O)$-heteroalkyl, —O-alkyl, -alkenyl, $-C(O)$alkenyl, $-C(O)$-heteroalkenyl, $-C(O)$alkynyl, and $-C(O)$-heteroalkynyl, wherein each of the alkyl, alkenyl and alkynyl portions of said -alkyl, $-C(O)$alkyl, $-C(O)$-heteroalkyl, —O-alkyl, -alkenyl, $-C(O)$alkenyl, $-C(O)$-heteroalkenyl, $-C(O)$alkynyl, and $-C(O)$-heteroalkynyl, are unsubstituted or optionally independently substituted with one or more groups each independently selected from the group consisting of:

halo, OH, $-CO_2R^6$, $-C(O)R^6$, $-SR^7$, $-S(O)R^7$, $-SO_2R^7$, CN, $-C(O)NR^8R^9$, $-NR^8R^9$, haloalkoxy, $-NR^{10}-C(O)-N^8R^9$, $-NR^{10}-CO_2R^6$, $-NR^{10}-C(O)R^6$, $-NR^{10}-SO_2R^6$, $-SO_2-NR^8R^9$, $-C(O)NR^8R^9$, and $-OC(O)NR^8R^9$, and (3) aryl, —O-aryl, —C(O)-aryl, heteroaryl, —O-heteroaryl, —C(O)-heteroaryl, cycloalkyl, —O-cycloalkyl, —C(O)-cycloalkyl, heterocycloalkyl, —O-heterocycloalkyl, —C(O)-heterocycloalkyl, cycloalkenyl, —O-cycloalkenyl, —C(O)-cycloalkenyl, and heterocycloalkenyl, —O-heterocycloalkenyl, —C(O)-heterocycloalkenyl, each of which is unsubstituted or optionally independently substituted with from 1 to 2 groups each independently selected from (1) and (2) above;

Z is selected from the group consisting of $-(CH_2)-(CH(CH_3))-C(O)OH$, $-(CH_2)-(CH_2)-(CH_2)-C(O)OH$, $-(CH_2)-C(CH_3)_2-C(O)OH$, $-(CH_2)-C(CH_3)(OH)-C(O)OH$, $-CH_2-CH_2-C(O)OH$, $-CH_2-CH(OH)-C(O)OH$, $-CH(CH_3)-CH_2-C(O)OH$, $-CH_2-CH(F)-C(O)OH$, $-CH_2-CF_2-C(O)OH$, $-CH(CH_3)-CF_2-C(O)OH$, $-CH_2-CH_2-CF_2-C(O)OH$,

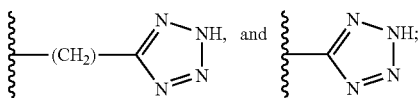

and $R^3$, each $R^4$, each $R^5$, each $R^6$, each $R^7$, each $R^8$, each $R^9$, each $R^{19}$ is independently as defined in Formula (I).

In one embodiment, in Formula (III), Z is selected from the group consisting of $-(CH_2)-(CH(CH_3))-C(O)OH$, $-(CH_2)-(CH_2)-(CH_2)-C(O)OH$, $-(CH_2)-C(CH_3)_2-C(O)OH$, $-(CH_2)-C(CH_3)(OH)-C(O)OH$, $-CH_2-CH_2-C(O)OH$, $-CH_2-CH(OH)-C(O)OH$, $-CH(CH_3)-CH_2-C(O)OH$, $-CH_2-CH(F)-C(O)OH$, $-CH_2-CF_2-C(O)OH$, $-CH(CH_3)-CF_2-C(O)OH$, and $-CH_2-CH_2-CF_2-C(O)OH$.

In one embodiment, in Formula (III), Z is

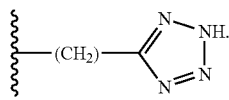

In one embodiment, in Formula (III-A), Z is

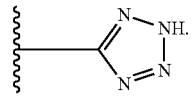

In one embodiment, the present invention provides a compound, or a pharmaceutically acceptable salt, solvate, ester, prodrug, tautomer, or isomer of said compound, said compound having the general structure shown in Formula (IV):

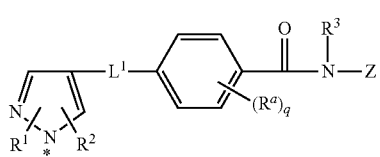

(IV)

wherein $R^1$, $R^2$, $R^3$, $L^1$, and Z are selected independently of each other and wherein:

q is 0 to 1;

$L^1$ is selected from the group consisting of —NH—CH$_2$—, —O—CH$_2$—, —(CH$_2$)—NH—, —CH$_2$—O—, —O—, —NH—, and —N(CH$_3$)—;

$R^1$ is selected from the group consisting of:
(a) —SR$^7$, —C(O)NR$^8$R$^9$, and —NR$^8$R$^9$,
(b) -alkenyl, and -alkynyl,
  wherein each of said alkenyl and said alkynyl are unsubstituted or optionally independently substituted with one or more groups each independently selected from the group consisting of:
    halo, OH, —CO$_2$R$^6$, —C(O)R$^6$, —SR$^7$, —S(O)R$^7$, —SO$_2$R$^7$, CN, NO$_2$, —C(O)NR$^8$R$^9$, —NR$^8$R$^9$, haloalkoxy, —NR$^{10}$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, —OC(O)NR$^8$R$^9$, unsubstituted alkoxy, and alkoxy substituted with one or more groups independently selected from the group consisting of halo, perhaloalkoxy, OH, and —CO$_2$R$^6$,
(c) cycloalkenyl and heterocycloalkenyl,
  wherein each of said cycloalkenyl and said heterocycloalkenyl are unsubstituted or optionally independently substituted with one or more groups each independently selected from the group consisting of:
    (i) halo, OH, —CO$_2$R$^6$, —C(O)R$^6$, —SR$^7$, —S(O)R$^7$, —SO$_2$R$^7$, CN, —C(O)NR$^8$R$^9$, —NR$^8$R$^9$, haloalkoxy, —NR$^{10}$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, and —OC(O)NR$^8$R$^9$,
    (ii) -alkyl, -heteroalkyl, —O-alkyl, —O-heteroalkyl, -alkenyl, -heteroalkenyl, —O-alkenyl, —O-heteroalkenyl, -alkynyl, -heteroalkynyl, —O-alkynyl, and —O-heteroalkynyl,
      wherein each of the alkyl, alkenyl and alkynyl portions of said -alkyl, -heteroalkyl, —O-alkyl, —O-heteroalkyl, -alkenyl, -heteroalkenyl, —O-alkenyl, —O-heteroalkenyl, -alkynyl, -heteroalkynyl, —O-alkynyl, and —O-heteroalkynyl are unsubstituted or optionally independently substituted with one or more groups each independently selected from the group consisting of:
        halo, OH, —CO$_2$R$^6$, —C(O)R$^6$, —SR$^7$, —S(O)R$^7$, —SO$_2$R$^7$, CN, NO$_2$, —C(O)NR$^8$R$^9$, —NR$^8$R$^9$, haloalkoxy, —NR$^{10}$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, and —OC(O)NR$^8$R$^9$, and
    (iii) aryl, —O-aryl, heteroaryl, —O-heteroaryl, cycloalkyl, —O-cycloalkyl, heterocycloalkyl, —O-heterocycloalkyl, cycloalkenyl, —O-cycloalkenyl, and heterocycloalkenyl, —O-heterocycloalkenyl, —C(O)-heterocycloalkenyl, each of which is unsubstituted or optionally independently substituted with from 1 to 2 groups each independently selected from (i) and (ii) above, and
(d) aryl and heteroaryl,
  wherein said aryl and said heteroaryl are substituted with at least one group each independently selected from the group consisting of:
    (1) halo, CN, —C(O)NR$^8$R$^9$, haloalkoxy, and —C(O)NR$^8$R$^9$,
    (2) -alkyl, —O-alkyl, and -alkenyl,
      wherein the alkyl, alkenyl and alkynyl portions of said -alkyl, —O-alkyl, and -alkenyl, are unsubstituted or optionally independently substituted with one or more groups each independently selected from the group consisting of:
        halo, OH, —CO$_2$R$^6$, —SR$^7$, —S(O)R$^7$, —SO$_2$R$^7$, CN, —C(O)NR$^8$R$^9$, —NR$^8$R$^9$, haloalkoxy, —NR$^{10}$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, and —OC(O)NR$^8$R$^9$, and
    (3) aryl, —O-aryl, heteroaryl, —O-heteroaryl, cycloalkyl, —O-cycloalkyl, heterocycloalkyl, —O-heterocycloalkyl, cycloalkenyl, —O-cycloalkenyl, heterocycloalkenyl, and —O-heterocycloalkenyl, each of which is unsubstituted or optionally independently substituted with from 1 to 2 groups each independently selected from (1) and (2) above;

$R^2$ is selected from the group consisting of:
aryl and heteroaryl,
wherein said aryl and said heteroaryl are substituted with at least one group each independently selected from the group consisting of:
(1) halo, CN, —C(O)NR$^8$R$^9$, haloalkoxy, and —C(O)NR$^8$R$^9$,
(2) -alkyl, —O-alkyl, and -alkenyl,
  wherein each of the alkyl, alkenyl and alkynyl portions of said -alkyl, —O-alkyl, and -alkenyl, are unsubstituted or optionally independently substituted with one or more groups each independently selected from the group consisting of:
    halo, OH, —CO$_2$R$^6$, —SR$^7$, —S(O)R$^7$, —SO$_2$R$^7$, CN, —C(O)NR$^8$R$^9$, —NR$^8$R$^9$, haloalkoxy, —NR$^{10}$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, and —OC(O)NR$^8$R$^9$, and
(3) aryl, —O-aryl, heteroaryl, —O-heteroaryl, cycloalkyl, —O-cycloalkyl, heterocycloalkyl, —O-heterocycloalkyl, cycloalkenyl, —O-cycloalkenyl, heterocycloalkenyl, and —O-heterocycloalkenyl, each of which is unsubstituted or optionally independently substituted with from 1 to 2 groups each independently selected from (1) and (2) above;

Z is selected from the group consisting of —(CH$_2$)—(CH(CH$_3$))—C(O)OH, —(CH$_2$)—(CH$_2$)—(CH$_2$)—C(O)OH, —(CH$_2$)—C(CH$_3$)$_2$—C(O)OH, —(CH$_2$)—C(CH$_3$)(OH)—C(O)OH, —CH$_2$—CH$_2$—C(O)OH, —CH$_2$—CH(OH)—C (O)OH, —CH(CH₃)—CH₂—C(O)OH, —CH₂—CH(F)—C(O)OH, —CH₂—CF₂—C(O)OH, —CH(CH₃)—CF₂—C(O)OH, —CH₂—CH₂—CF₂—C(O)OH,

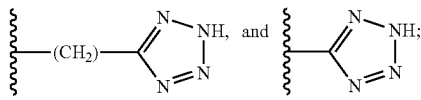

and R³, each R⁴, each R⁵, each R⁶, each R⁷, each R⁸, each R⁹, each R¹⁰ is independently as defined in Formula (I).

In one embodiment, in Formula (IV), Z is selected from the group consisting of —(CH₂)—(CH(CH₃))—C(O)OH, —(CH₂)—(CH₂)—(CH₂)—C(O)OH, —(CH₂)—C(CH₃)₂—C(O)OH, —(CH₂)—C(CH₃)(OH)—C(O)OH, —CH₂—CH₂—C(O)OH, —CF₁₂—CH(OH)—C(O)OH, —CH(CH₃)—CH₂—C(O)OH, —CH₂—CH(F)—C(O)OH, —CH₂—CF₂—C(O)OH, —CH(CH₃)—CF₂—C(O)OH, and —CH₂—CH₂—CF₂—C(O)OH.

In one embodiment, in Formula (IV), Z is

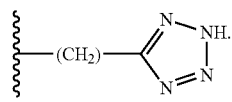

In one embodiment, in Formula (IV), Z is

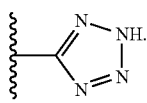

In one embodiment, the present invention provides a compound, or a pharmaceutically acceptable salt, solvate, ester, prodrug, tautomer, or isomer of said compound, said compound having the general structure shown in Formula (V):

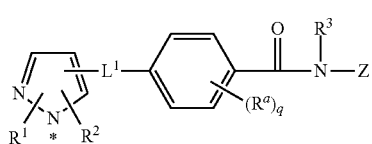

(V)

wherein R¹, R², R³, L¹, and Z are selected independently of each other and wherein:
q is 0 to 1;
L¹ is selected from the group consisting of —NH—, —N(CH₃)—, —O—, and —OCH₂—;
R¹ is selected from the group consisting of:
aryl and heteroaryl,
wherein said aryl and said heteroaryl are substituted with at least one group each independently selected from:
halo, alkyl, haloalkyl, heteroalkyl, alkenyl, alkoxy, haloalkoxy, cycloalkyl, cycloalkenyl, —O-cycloalkyl, and —O-cycloalkenyl;
R² is selected from the group consisting of:
aryl and heteroaryl,
wherein said aryl and said heteroaryl are substituted with at least one group each independently selected from:
halo, alkyl, haloalkyl, heteroalkyl, alkenyl, alkoxy, haloalkoxy, cycloalkyl, cycloalkenyl, —O-cycloalkyl, and —O-cycloalkenyl;
Z is selected from the group consisting of —(CH₂)—(CH(CH₃))—C(O)OH, —(CH₂)—(CH₂)—(CH₂)—C(O)OH, —(CH₂)—C(CH₃)₂—C(O)OH, —(CH₂)—C(CH₃)(OH)—C(O)OH, —CH₂—CH₂—C(O)OH, —CH₂—CH(OH)—C(O)OH, —CH(CH₃)—CH₂—C(O)OH, —CH₂—CH(F)—C(O)OH, —CH₂—CF₂—C(O)OH, —CH(CH₃)—CF₂—C(O)OH, —CH₂—CH₂—CF₂—C(O)OH,

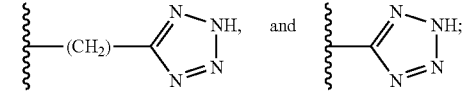

and R³ is as defined in Formula (I).

In one embodiment, in Formula (V), Z is selected from the group consisting of —(CH₂)—(CH(CH₃))—C(O)OH, —(CH₂)—(CH₂)—(CH₂)—C(O)OH, —(CH₂)—C(CH₃)₂—C(O)OH, —(CH₂)—C(CH₃)(OH)—C(O)OH, —CH₂—CH₂—C(O)OH, —CH₂—CH(OH)—C(O)OH, —CH(CH₃)—CH₂—C(O)OH, —CH₂—CH(F)—C(O)OH, —CH₂—CF₂—C(O)OH, —CH(CH₃)—CF₂—C(O)OH, and —CH₂—CH₂—CF₂—C(O)OH.

In one embodiment, in Formula (V), Z is

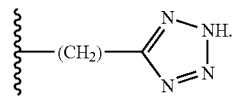

In one embodiment, in Formula (V), Z is

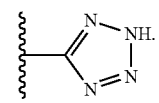

In one embodiment, the present invention provides a compound, or a pharmaceutically acceptable salt, solvate, ester, prodrug, tautomer, or isomer of said compound, said compound having the general structure shown in Formula (VI):

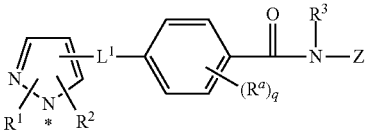

(VI)

wherein R¹, R², R³, L¹, and Z are selected independently of each other and wherein:
q is 0 to 1;
L¹ is selected from the group consisting of —NH—, —N(CH₃)—, —O—, and —OCH₂—;
R¹ is selected from the group consisting of:
phenyl and naphthyl,
wherein said phenyl and said naphthyl are substituted with from 1 to 3 groups each independently selected from:
halo, alkyl, haloalkyl, alkoxy, haloalkoxy, and cycloalkyl;

R² is selected from the group consisting of:
phenyl and naphthyl,
wherein said phenyl and said naphthyl are substituted with from 1 to 3 groups each independently selected from:
halo, alkyl, haloalkyl, alkoxy, haloalkoxy, and cycloalkyl;
Z is selected from the group consisting of —(CH₂)—(CH(CH₃))—C(O)OH, —(CH₂)—(CH₂)—(CH₂)—C(O)OH, —(CH₂)—C(CH₃)₂—C(O)OH, —(CH₂)—C(CH₃)(OH)—C(O)OH, —CH₂—CH₂—C(O)OH, —CH₂—CH(OH)—C(O)OH, —CH(CH₃)—CH₂—C(O)OH, —CH₂—CH(F)—C(O)OH, —CH₂—CF₂—C(O)OH, —CH(CH₃)—CF₂—C(O)OH, —CH₂—CH₂—CF₂—C(O)OH,

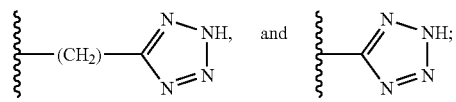

and R³ is as defined in Formula (I).
In one embodiment, in Formula (VI), q is 0.
In one embodiment, in Formula (VI), q is 1.
In one embodiment, in Formula (VI):
R¹ is selected from phenyl and naphthyl,
wherein said phenyl and said naphthyl are substituted with from 1 to 2 groups each independently selected from:
halo, alkyl, haloalkyl, alkoxy, haloalkoxy, and cycloalkyl; and
R² is selected from the group consisting of:
phenyl and naphthyl,
wherein said phenyl and said naphthyl are substituted with from 1 to 2 groups each independently selected from:
halo, alkyl, haloalkyl, alkoxy, haloalkoxy, and cycloalkyl.
In one embodiment, in Formula (VI):
one of R¹ and R² is phenyl and the other is naphthyl,
wherein each of said phenyl and said naphthyl is substituted with from 1 to 2 groups each independently selected from:
halo, alkyl, haloalkyl, alkoxy, haloalkoxy, and cycloalkyl.
In one embodiment, in Formula (VI):
R¹ is phenyl,
wherein said phenyl is substituted with from 1 to 2 groups each independently selected from:
halo, alkyl, haloalkyl, alkoxy, haloalkoxy, and cycloalkyl; and
R² is naphthyl,
wherein said naphthyl is substituted with from 1 to 2 groups each independently selected from:
halo, alkyl, haloalkyl, alkoxy, haloalkoxy, and cycloalkyl.
In one embodiment, in Formula (VI):
R¹ is naphthyl,
wherein said naphthyl is substituted with from 1 to 2 groups each independently selected from:
halo, alkyl, haloalkyl, alkoxy, haloalkoxy, and cycloalkyl; and
R² is phenyl,
wherein said phenyl is substituted with from 1 to 2 groups each independently selected from:
halo, alkyl, haloalkyl, alkoxy, haloalkoxy, and cycloalkyl;
and R² is phenyl,
wherein said phenyl is substituted with from 1 to 2 groups each independently selected from:
halo, alkyl, haloalkyl, alkoxy, haloalkoxy, and cycloalkyl.
In one embodiment, in Formula (VI), R³ is H.
In one embodiment, in Formula (VI), R³ is alkyl.
In one embodiment, in Formula (VI), R³ is methyl.
In one embodiment, in Formula (VI), Z is selected from the group consisting of —(CH₂)—(CH(CH₃))—C(O)OH, —(CH₂)—(CH₂)—(CH₂)—C(O)OH, —(CH₂)—C(CH₃)₂—C(O)OH, —(CH₂)—C(CH₃)(OH)—C(O)OH, —CH₂—CH₂—C(O)OH, —CH₂—CH(OH)—C(O)OH, —CH(CH₃)—CH₂—C(O)OH, —CH₂—CH(F)—C(O)OH, —CH₂—CF₂—C(O)OH, —CH(CH₃)—CF₂—C(O)OH, and —CH₂—CH₂—CF₂—C(O)OH.
In one embodiment, in Formula (VI), R³ is H and Z is selected from the group consisting of —(CH₂)—(CH(CH₃))—C(O)OH, —(CH₂)—(CH₂)—(CH₂)—C(O)OH, —(CH₂)—C(CH₃)₂—C(O)OH, —(CH₂)—C(CH₃)(OH)—C(O)OH, —CH₂—CH₂—C(O)OH, —CH₂—CH(OH)—C(O)OH, —CH(CH₃)—CH₂—C(O)OH, —CH₂—CH(F)—C(O)OH, —CH₂—CF₂—C(O)OH, —CH(CH₃)—CF₂—C(O)OH, and —CH₂—CH₂—CF₂—C(O)OH.
In one embodiment, in Formula (VI), Z is

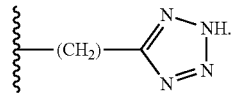

In one embodiment, in Formula (VI), Z is

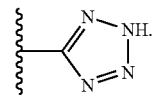

In the various embodiments described herein, variables of each of the general formulas not explicitly defined in the context of the respective formula are as defined in Formula (A).
In one embodiment, a compound or compounds of the invention is/are in isolated or purified form.
The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.
"Mammal" means humans and other mammalian animals.
A "patient" is a human or non-human mammal. In one embodiment, a patient is a human. In another embodiment, a patient is a non-human mammal, including, but not limited to, a monkey, baboon, mouse, rat, horse, dog, cat or rabbit. In another embodiment, a patient is a companion animal, including but not limited to a dog, cat, rabbit, horse or ferret. In one embodiment, a patient is a dog. In another embodiment, a patient is a cat.

The term "obesity" as used herein, refers to a patient being overweight and having a body mass index (BMI) of 25 or greater. In one embodiment, an obese patient has a BMI of 25 or greater. In another embodiment, an obese patient has a BMI from 25 to 30. In another embodiment, an obese patient has a BMI greater than 30. In still another embodiment, an obese patient has a BMI greater than 40.

The term "impaired glucose tolerance" (IGT) as used herein, is defined as a two-hour glucose level of 140 to 199 mg per dL (7.8 to 11.0 mmol) as measured using the 75-g oral glucose tolerance test. A patient is said to be under the condition of impaired glucose tolerance when he/she has an intermediately raised glucose level after 2 hours, wherein the level is less than would qualify for type 2 diabetes mellitus.

The term "impaired fasting glucose" (IFG) as used herein, is defined as a fasting plasma glucose level of 100 to 125 mg/dL; normal fasting glucose values are below 100 mg per dL.

The term "effective amount" as used herein, refers to an amount of Compound of Formula (I) and/or an additional therapeutic agent, or a composition thereof that is effective in producing the desired therapeutic, ameliorative, inhibitory or preventative effect when administered to a patient suffering from a Condition. In the combination therapies of the present invention, an effective amount can refer to each individual agent or to the combination as a whole, wherein the amounts of all agents administered are together effective, but wherein the component agent of the combination may not be present individually in an effective amount.

"Halogen" means fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being as described herein or independently selected from the group consisting of halo, alkyl, haloalkyl, spirocycloalkyl, aryl, cycloalkyl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

The term "haloalkyl" as used herein, refers to an alkyl group, as defined above, wherein one or more of the alkyl group's hydrogen atoms have been independently replaced with —F, —Cl, —Br or —I. Non-limiting illustrative examples of haloalkyl groups include —CH$_2$F, —CHF$_2$, —CF$_3$, —CH$_2$CHF$_2$, —CH$_2$CF$_3$, —CCl$_3$, —CHCl$_2$, —CH$_2$Cl, and —CH$_2$CHCl$_2$.

"Heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, S(O), S(O)$_2$, and —NH—, —N(alkyl)-. Non-limiting examples include ethers, thioethers, amines, hydroxymethyl, 3-hydroxypropyl, 1,2-dihydroxyethyl, 2-methoxyethyl, 2-aminoethyl, 2-dimethylaminoethyl, and the like. The bond to the parent moiety may be through either an available carbon or heteroatom.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. Further non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$— and —CH$_2$CH(CH$_3$)CH$_2$—. In one embodiment, an alkylene group has from 1 to about 6 carbon atoms. In another embodiment, an alkylene group is branched. In another embodiment, an alkylene group is linear. More generally, the suffix "ene" on alkyl, aryl, heterocycloalkyl, etc. indicates a divalent moiety, e.g., —CH$_2$CH$_2$— is ethylene, and

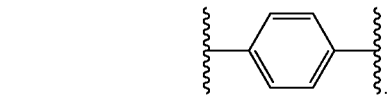

is para-phenylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Alkenylene" means a difunctional group obtained by removal of a hydrogen from an alkenyl group that is defined above. Non-limiting examples of alkenylene include —CH═CH—, —C(CH$_3$)═CH—, and —CH═CHCH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The bond to the parent moiety may be through an available carbon or nitrogen atom.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like. Further non-limiting examples of cycloalkyl include the following:

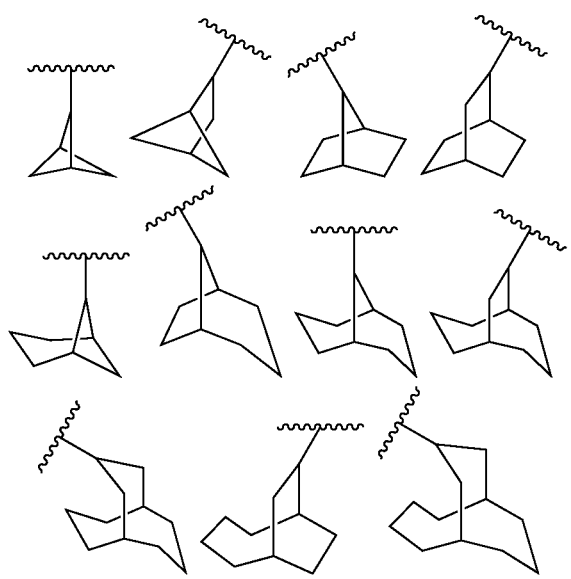

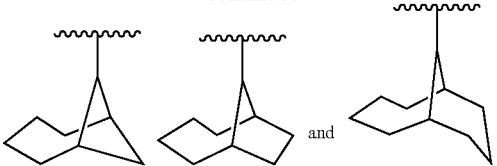

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH— in a heterocyclyl ring may exist protected such as, for example, as an —N(Boc)-, —N(CBz)-, —N(Tos)-group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. Non-limiting examples of suitable monocyclic heterocyclyl rings include piperidinyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes rings wherein =O replaces two available hydrogens on the same carbon atom (i.e., heterocyclyl includes rings having a carbonyl group in the ring). Such =O groups may be referred to herein as "oxo." Example of such moiety is pyrrolidinone (or pyrrolidone):

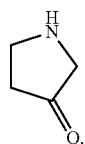

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined herein. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidenone (or pyrrolone):

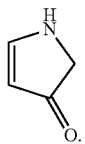

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

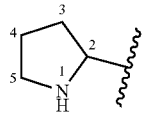

there is no —OH attached directly to carbons marked 2 and 5.

It should also be noted that tautomeric forms such as, for example, the moieties:

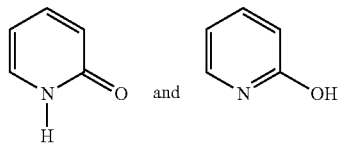 [SMILES: O=c1cccc[nH]1 ; Oc1ccccn1]

are considered equivalent in certain embodiments of this invention.

It should be understood that for hetero-containing functional groups described herein, e.g., heterocycloalkyl, heterocycloalkenyl, heteroalkyl, heteroaryl, and arylheterocycloalkyl (e.g., benzo-fused heterocycloalkyl), the bond to the parent moiety can be through an available carbon or heteroatom (e.g., nitrogen atom).

"Arylcycloalkyl" (or "arylfused cycloalkyl") means a group derived from a fused aryl and cycloalkyl as defined herein. Preferred arylcycloalkyls are those wherein aryl is phenyl (which may be referred to as "benzofused") and cycloalkyl consists of about 5 to about 6 ring atoms. The arylcycloalkyl can be optionally substituted as described herein. Non-limiting examples of suitable arylcycloalkyls include indanyl (a benzofused cycloalkyl) and 1,2,3,4-tetrahydronaphthyl and the like. The bond to the parent moiety is through a non-aromatic carbon atom.

"Arylheterocycloalkyl" (or "arylfused heterocycloalkyl") means a group derived from a fused aryl and heterocycloalkyl as defined herein. Preferred arylheterocycloalkyls are those wherein aryl is phenyl (which may be referred to as "benzofused") and heterocycloalkyl consists of about 5 to about 6 ring atoms. The arylheterocycloalkyl can be optionally substituted, and/or contain the oxide or oxo, as described herein. Non-limiting examples of suitable arylfused heterocycloalkyls include:

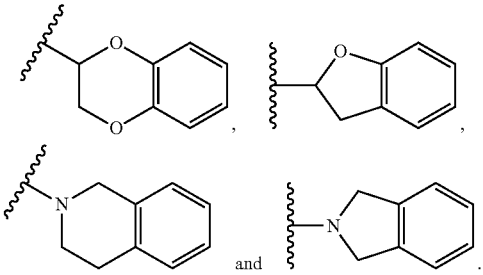

The bond to the parent moiety is through a non-aromatic carbon or nitrogen atom atom.

It is also understood that the terms "arylfused aryl", "arylfused cycloalkyl", "arylfused cycloalkenyl", "arylfused heterocycloalkyl", "arylfused heterocycloalkenyl", "arylfused heteroaryl", "cycloalkylfused aryl", "cycloalkylfused cycloalkyl", "cycloalkylfused cycloalkenyl", "cycloalkylfused heterocycloalkyl", "cycloalkylfused heterocycloalkenyl", "cycloalkylfused heteroaryl, "cycloalkenylfused aryl", "cycloalkenylfused cycloalkyl", "cycloalkenylfused cycloalkenyl", "cycloalkenylfused heterocycloalkyl", "cycloalkenylfused heterocycloalkenyl", "cycloalkenylfused heteroaryl", "heterocycloalkylfused aryl", "heterocycloalkylfused cycloalkyl", "heterocycloalkylfused cycloalkenyl", "heterocycloalkylfused heterocycloalkyl", "heterocycloalkylfused heterocycloalkenyl", "heterocycloalkylfused heteroaryl", "heterocycloalkenylfused aryl", "heterocycloalkenylfused cycloalkyl", "heterocycloalkenylfused cycloalkenyl", "heterocycloalkenylfused heterocycloalkyl", "heterocycloalkenylfused heterocycloalkenyl", "heterocycloalkenylfused heteroaryl", "heteroarylfused aryl", "heteroarylfused cycloalkyl", "heteroarylfused cycloalkenyl", "heteroarylfused heterocycloalkyl", "heteroarylfused heterocycloalkenyl", and "heteroarylfused heteroaryl" are similarly represented by the combination of the groups aryl, cycloalkyl, cycloalkenyl, heterocycloalkyl, heterocycloalkenyl, and heteroaryl, as previously described. Any such groups may be unsubstituted or substituted with one or more ring system substituents at any available position as described herein.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl. The term (and similar terms) may be written as "arylalkyl-" to indicate the point of attachment to the parent moiety.

Similarly, "heteroarylalkyl", "cycloalkylalkyl", "cycloalkenylalkyl", "heterocycloalkylalkyl", "heterocycloalkenylalkyl", etc., mean a heteroaryl, cycloalkyl, cycloalkenyl, heterocycloalkyl, heterocycloalkenyl, etc. as described herein bound to a parent moiety through an alkyl group. Preferred groups contain a lower alkyl group. Such alkyl groups may be straight or branched, unsubstituted and/or substituted as described herein.

Similarly, "arylfused arylalkyl-", arylfused cycloalkylalkyl-, etc., means an arylfused aryl group, arylfused cycloalkyl group, etc. linked to a parent moiety through an alkyl group. Preferred groups contain a lower alkyl group. Such alkyl groups may be straight or branched, unsubstituted and/or substituted as described herein.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl, adamantylpropyl, and the like.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenylalkyl" means a heterocyclenyl moiety as defined above linked via an alkyl moiety (defined above) to a parent core.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Cyanoalkyl" means a NC-alkyl-group in which alkyl is as previously defined. Preferred cyanoalkyls contain lower alkyl. Non-limiting examples of suitable cyanoalkyl groups include cyanomethyl and 2-cyanoethyl.

"Acyl" means an H—C(O)—, alkyl-C(O)— or cycloalkyl-C(O)—, group in which the various groups are as previously described. The bond to the parent moiety is through the carbonyl carbon. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl carbon. Non-limiting examples of suitable groups include benzoyl and 1-naphthoyl.

"Heteroaroyl" means an heteroaryl-C(O)— group in which the heteroaryl group is as previously described. The bond to the parent moiety is through the carbonyl carbon. Non-limiting examples of suitable groups include pyridoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkyoxyalkyl" means a group derived from an alkoxy and alkyl as defined herein. The bond to the parent moiety is through the alkyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" (or "arylalkyloxy") means an aralkyl-O— group (an arylaklyl-β-group) in which the aralkyl group is as previously described. Non-limiting examples of suitable aralkyloxy groups include benzyloxy and 1- or 2-naphthalenemethoxy. The bond to the parent moiety is through the ether oxygen.

"Arylalkenyl" means a group derived from an aryl and alkenyl as defined herein. Preferred arylalkenyls are those wherein aryl is phenyl and the alkenyl consists of about 3 to about 6 atoms. The arylalkenyl can be optionally substituted by one or more substituents. The bond to the parent moiety is through a non-aromatic carbon atom.

"Arylalkynyl" means a group derived from a aryl and alkenyl as defined herein. Preferred arylalkynyls are those wherein aryl is phenyl and the alkynyl consists of about 3 to about 6 atoms. The arylalkynyl can be optionally substituted by one or more substituents. The bond to the parent moiety is through a non-aromatic carbon atom.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl carbon.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl carbon.

"Aralkoxycarbonyl" means an aralkyl-O—C(O)— group. Non-limiting example of a suitable aralkoxycarbonyl group is benzyloxycarbonyl. The bond to the parent moiety is through the carbonyl carbon.

"Alkylsulfonyl" means an alkyl-S(O$_2$)— group. Preferred groups are those in which the alkyl group is lower alkyl. The bond to the parent moiety is through the sulfur atom of the sulfonyl.

"Arylsulfonyl" means an aryl-S(O$_2$)— group. The bond to the parent moiety is through the sulfur atom of the sulfonyl.

"Spirocycloalkyl" means a cycloalkyl group attached to a parent moiety at a single carbon atom. Non-limiting examples of spirocycloalkyl wherein the parent moiety is a cycloalkyl include spiro[2.5]octane, spiro[2.4]heptane, etc. Non-limiting examples of spirocycloalkyl wherein the parent moiety is an The alkyl moiety linking fused ring systems (such as the alkyl moiety in heteroarylfused heteroarylalkyl-) may optionally be substituted with spirocycloalkyl or other groups as described herein. Non-limiting spirocycloalkyl groups include spirocyclopropyl, spriorcyclobutyl, spirocycloheptyl, and spirocyclohexyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., R$^8$ in —N(R$^8$)$_2$, or a variable appears more than once in a structure presented herein such as Formula (I), the variables can be the same or different.

The term, "compound(s) of the invention," as used herein, refers, collectively or independently, to any of the compounds embraced by the general formulas described herein, e.g., Formula (A), Formula (I), Formula (II-A), Formula (II-B), Formula (II-B1), Formula (II-B2), Formula (II-B3), Formula (II-B4), Formula (II-B5), Formula (II-C), Formula (II-C1), Formula (II-C2), Formula (II-C3), Formula (II-C4), Formula (II-C5), Formula (II-D), Formula (II-D1), Formula (II-D2), Formula (III), Formula (IV), Formula (IV), Formula (V), and Formula (VI), and the example compounds thereof.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods comprising the use of "at least one compound of the invention, e.g., of Formula (I)," one to three compounds of the invention, e.g., of Formula (I) can be administered at the same time, preferably one.

Compounds of the invention may contain one or more rings having one or more ring system substituents. "Ring system substituent" means a substituent attached to an aromatic or non-aromatic ring system which, for example, replaces an available hydrogen on the ring system. Ring system substituents may be the same or different, each being as described herein or independently selected from the group consisting of alkyl, alkenyl, alkynyl, haloalkyl, heteroalkyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moieties are rings such as heteroaryl, cycloalkyl, cycloalkenyl, heterocycloalkyl, and heterocycloalkenyl rings. Additional non-limiting examples include methylene dioxy, ethylenedioxy, —C(CH$_3$)$_2$— and the like which form moieties such as, for example:

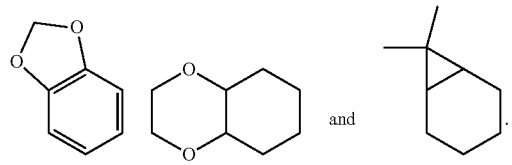

As used herein, the term "composition" is intended to encompass a product comprising the specified ingredients in the specified amounts, as well as any product which results, directly or indirectly, from combination of the specified ingredients in the specified amounts.

The line ----, as a bond generally indicates a mixture of, or either of, the possible isomers, e.g., containing (R)- and (S)- stereochemistry. For example:

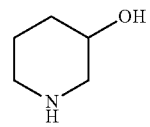

means containing both

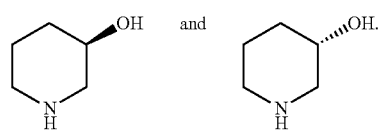

The wavy line ～ as used herein, indicates a point of attachment to the rest of the compound. For example, each wavy line in the following structure:

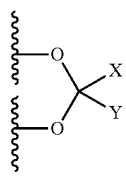

indicates a point of attachment to the core structure, as described herein.

Lines drawn into the ring systems, such as, for example:

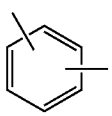

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

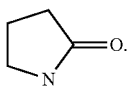

In this specification, where there are multiple oxygen and/or sulfur atoms in a ring system, there cannot be any adjacent oxygen and/or sulfur present in said ring system.

It is noted that the carbon atoms for compounds of the invention may be replaced with 1 to 3 silicon atoms so long as all valency requirements are satisfied.

As well known in the art, a bond drawn from a particular atom wherein no moiety is depicted at the terminal end of the bond indicates a methyl group bound through that bond to the atom, unless stated otherwise. For example:

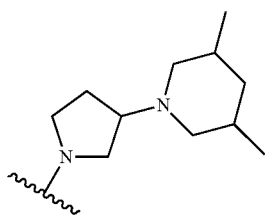 [SMILES: *N1CCC(N2CC(C)CC(C)C2)C1]

represents

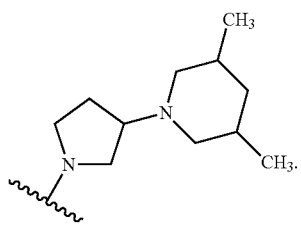 [SMILES: *N1CCC(N2CC(C)CC(C)C2)C1]

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1999), Wiley, New York.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$ alkyl, and the like.

Similarly, if a compound of the invention contains an alcohol functional group, a prodrug can be formed by the replacement of the hydrogen atom of the alcohol group with a group such as, for example, $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_8)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of the invention incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino$(C_1-C_4)$alkyl or mono-N- or di-N,N—$(C_1-C_6)$alkylaminoalkyl, —C(Y$^4$)Y$^5$ wherein Y$^4$ is H or methyl and Y$^5$ is mono-N- or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of the invention can form salts which are also within the scope of this invention. Reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di $(C_{6-24})$acyl glycerol.

Compounds of the invention, and salts, solvates, esters and prodrugs thereof, may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of the invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of the invention can generally be prepared by following procedures analogous to those disclosed in the Schemes and/or in the Examples hereinbelow, by substituting an appropriate isotopically labelled reagent for a non-isotopically labelled reagent.

Bioisosters of the compounds of the invention are also contemplated as being within the scope of the invention. Non-limiting examples of suitable bioisosteres include those described in Lima, et al., "Bioisosterism: A Useful Strategy for Molecular Modification and Drug Design", *Current Medicinal Chemistry*, 2005, 12, 23-29. Accordingly, the moiety represented by Z in Formula (A) includes the moieties

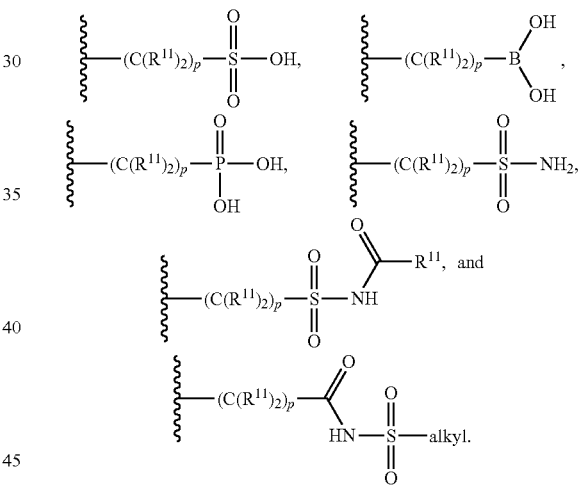

Compounds of the invention which comprise such moieties can be prepared by methods known to those skilled in the art, e.g., by reference to Schemes H and/or I below and substituting suitable starting materials.

Polymorphic forms of the compounds of the invention, and of the salts, solvates, esters and prodrugs of the compounds of the invention, are intended to be included in the present invention.

EXAMPLES

A general approach to the synthesis of substituted phenoxypyrazoles is outlined in Scheme A. Hydroxybenzoate a is combined with a bromoketone b and a base such as potassium carbonate in a solvent such as DMF and the like to afford the phenoxy ketone c. The ketone c can then be heated in DM-DMA under microwave conditions or treated with tert-butoxy(bis-dimethylamino)-methane in a solvent such as THF and the like at room temperature or an elevated temperature to afford the enaminoketone d. The enaminoketone d can then be combined with a hydrazine hydrochloride e in a solvent such as EtOH and the like and heated to afford a phenoxypyrazole f. Hydrolysis of the alkyl ester contained in phenoxypyrazole f affords the phenoxypyrazole carboxylate g.

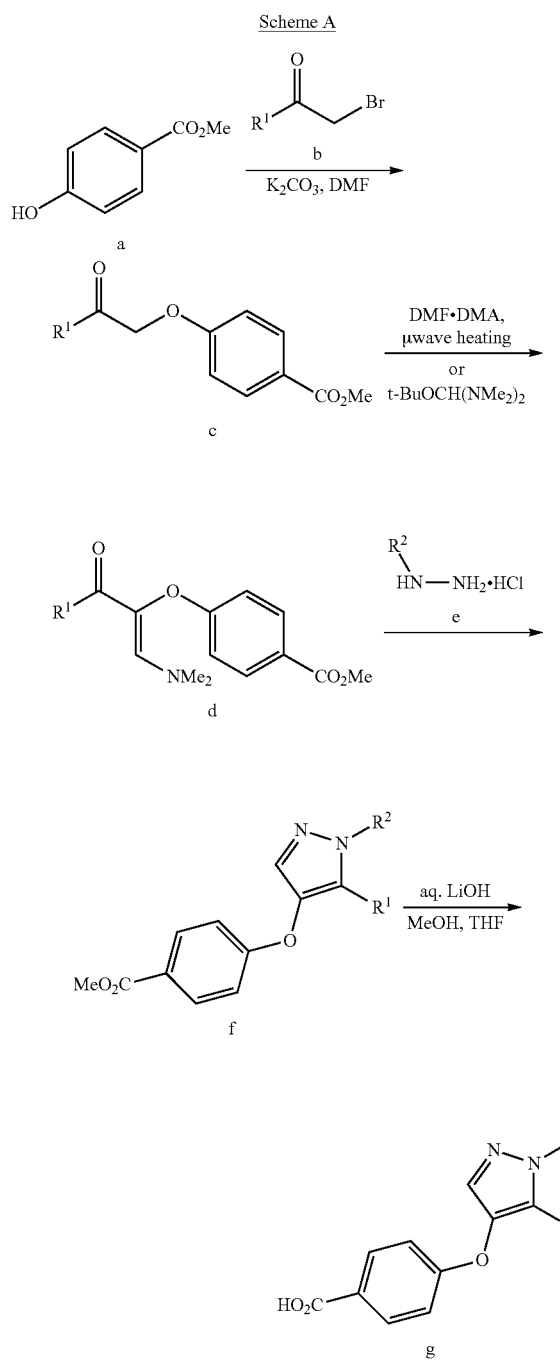

A second method for the preparation of substituted phenoxypyrazoles is outlined in Scheme B. The enaminoketone d prepared in Scheme A can be treated with hydrazine hydrate in a solvent such as methanol and the like to afford the phenoxypyrazole h. Phenoxypyrazoles i can be can be accessed via copper-mediated oxidative coupling of h and a requisite boronic acid. Hydrolysis of the benzoate ester will provide benzoic acids j.

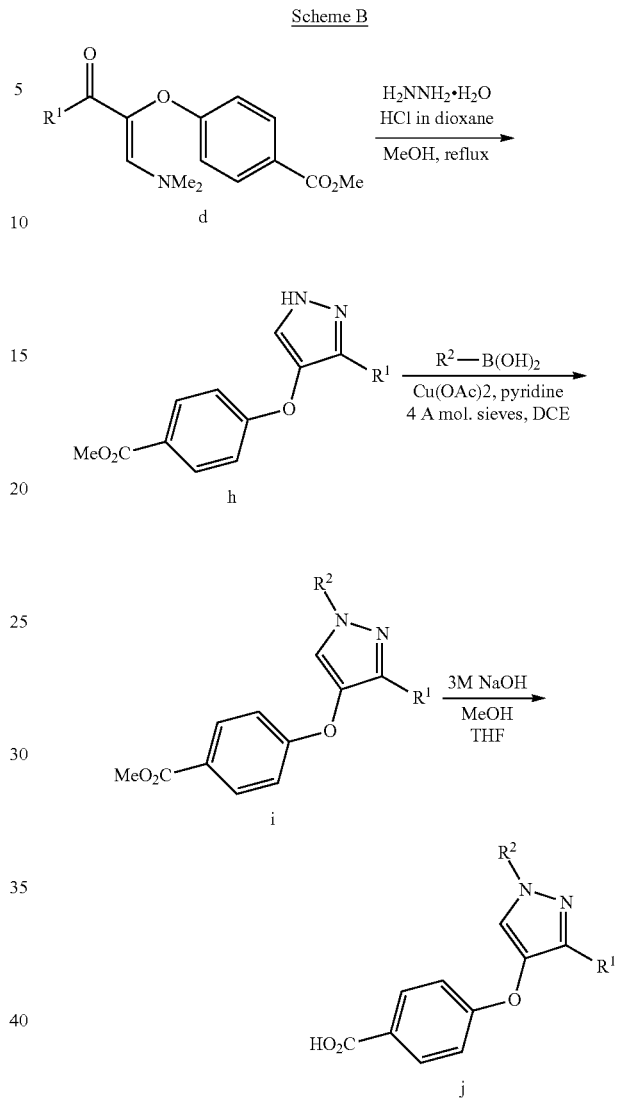

A third method for the preparation of substituted phenoxypyrazoles is outlined in Scheme C. Condensation of a ketoester k with hydrazine in a solvent such as ethanol and the like will afford a pyrazolone l. Phenoxypyrazole n can be prepared via heating a pyrazolone l and a fluorobenzoate m in the presence of a base such as potassium carbonate and the like in a solvent such as DMF and the like. Phenoxypyrazoles o can be can be accessed via copper-mediated oxidative coupling of n and a requisite boronic acid in a solvent such as DCE and the like. Cleavage of the benzoate ester present in compound o will provide benzoic acids p.

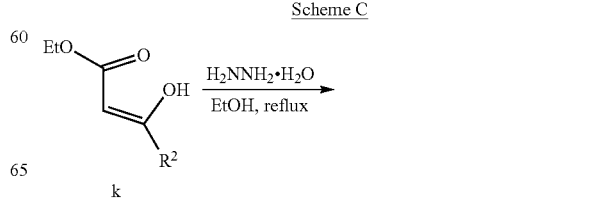

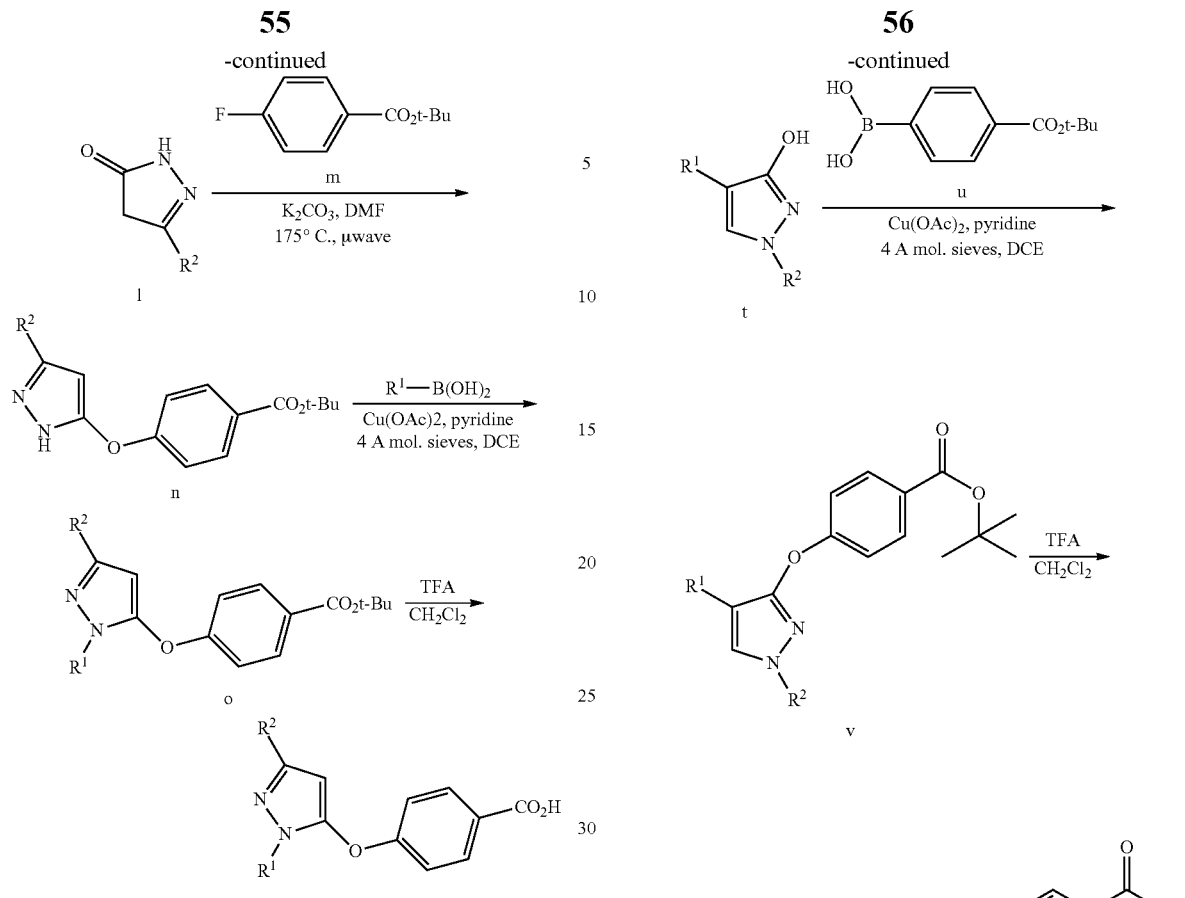

A fourth method for the preparation of substituted phenoxypyrazoles is outlined in Scheme D. A substituted acetic acid q can be coupled with a hydrazine r using a coupling reagent such as EDCI and the like in a solvent such as MeCN and the like to afford the hydrazide s. Formylation of the hydrazide s with a formylating reagent such as tert-butoxy bis(dimethylamino)methane and the like in a solvent such as THF and the like and subsequent cyclization with an acid such as HCl and the like in a solvent such as EtOH will provide the pyrazolone t. Phenoxypyrazoles v can be can be accessed via copper-mediated oxidative coupling of t and a boronic acid such as u in a solvent such as DCE and the like. Cleavage of the benzoate ester present in compound v will provide benzoic acids w.

An approach to the synthesis of substituted phenyl aminopyrazoles is outlined in Scheme E. Ketoamides x can be condensed with hydrazines in a solvent such as MeOH and the like to afford aminopyrazoles y. Palladium-mediated coupling of y with a 4-bromobenzoate will provide a substituted phenyl aminopyrazole z. Cleavage of the benzoate ester present in compound z will provide benzoic acid aa.

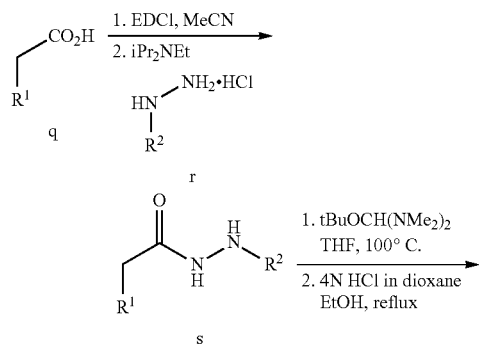

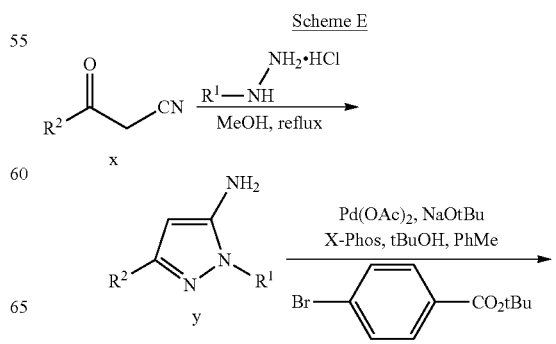

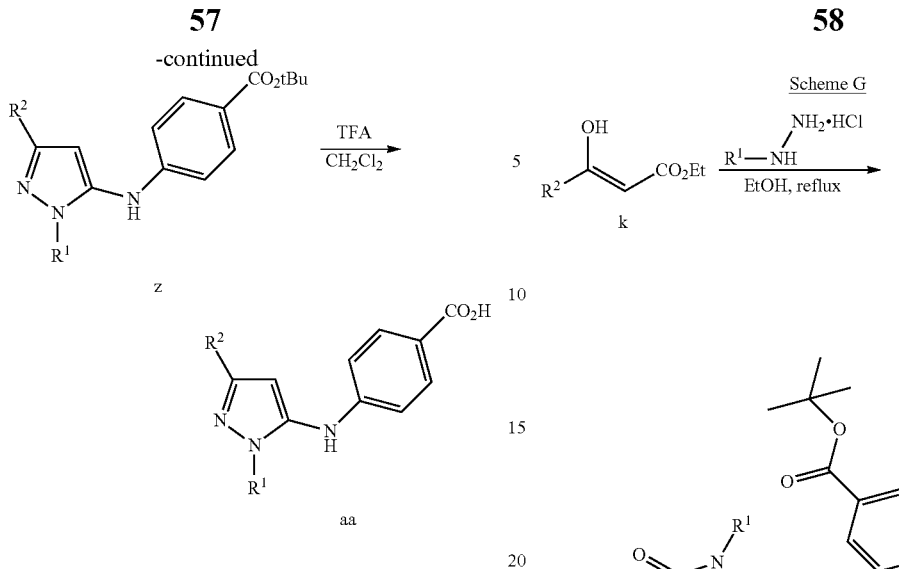

Further elaboration of z via treatment with an R⁴—X (wherein X is a halide such as iodine and the like) and a suitable base such as potassium carbonate and the like in a solvent such as acetone and the like at an elevated temperature will provide compound ab. Cleavage of the tert-butyl ester in compound ab will provide the benzoic acid ac.

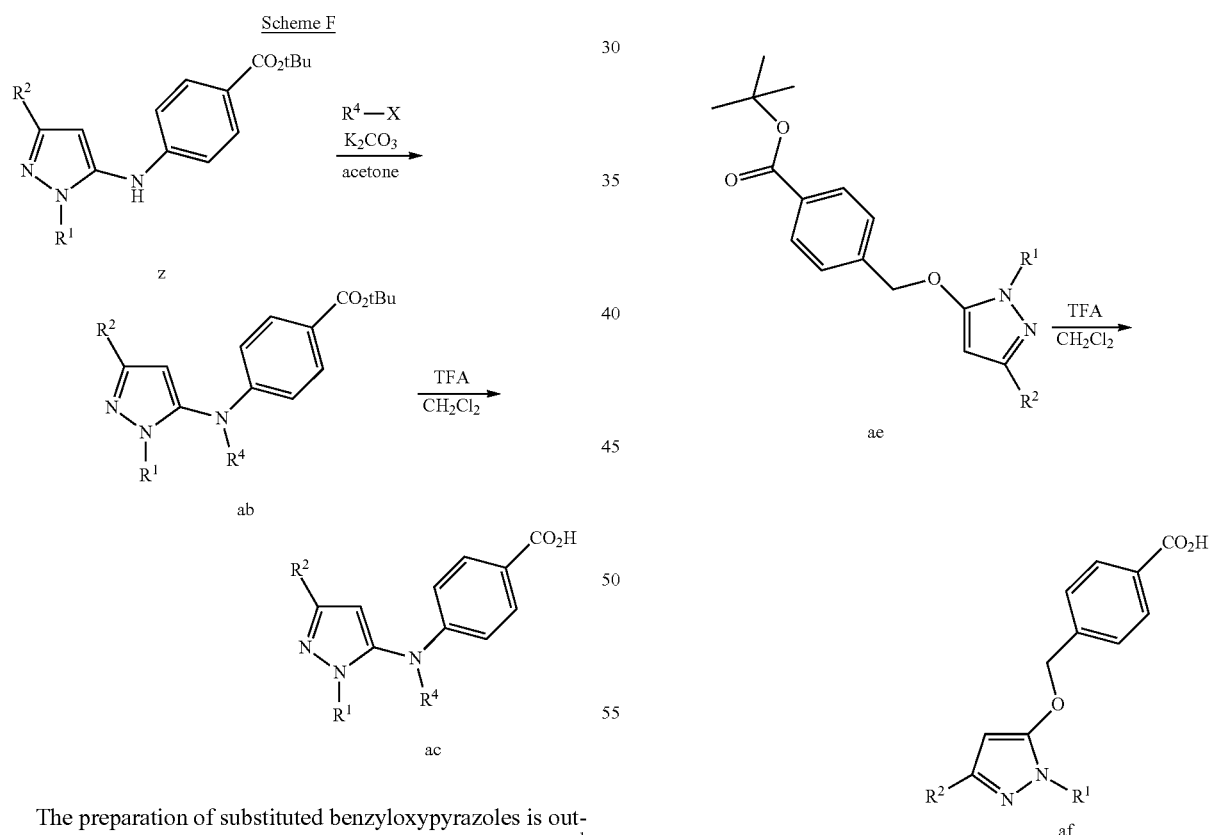

The preparation of substituted benzyloxypyrazoles is outlined in Scheme G. Condensation of a ketoester k with an R¹ substituted hydrazine in a solvent such as ethanol and the like will afford a pyrazolone ad. Benzyloxypyrazole ae can be prepared via treating a mixture of pyrazolone ad and a 4-(bromomethyl)benzoate in a solvent such as DMF and the like with a base such as potassium carbonate and the like. Cleavage of the benzoate ester present in compound ae will provide benzoic acids af.

A general experimental procedure for the synthesis of benzamide ah from a benzoic acid ag is described in Scheme H below. Treatment of a suitable amino tetrazole and a benzoic acid ag with a coupling reagent such as PyBOP and the like in a solvent such as DMF and the like will provide a desired compound ah.

Scheme H

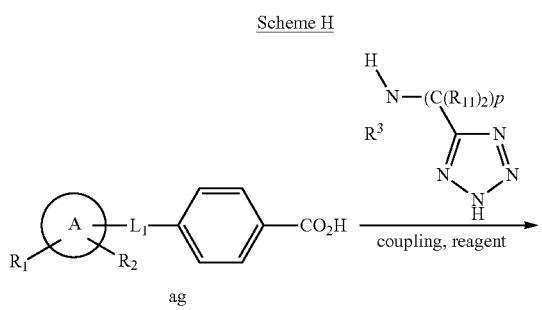

A general experimental procedure for the syntheses of benzamides ak and al from a benzoic acid ag is described in Scheme I below. Treatment of a suitable primary or secondary amine and a benzoic acid ag with a coupling reagent such as PyBOP and the like in a solvent such as DMF and the like will provide compounds ai or aj. Cleavage of the tert-butyl ester present in compound ai with an acid such as trifluoroacetic acid or hydrochloric acid and the like will afford compound ak. Cleavage of the tert-butyl ester present in compound aj with an acid such as trifluoroacetic acid or hydrochloric acid and the like will afford compound al.

Scheme I

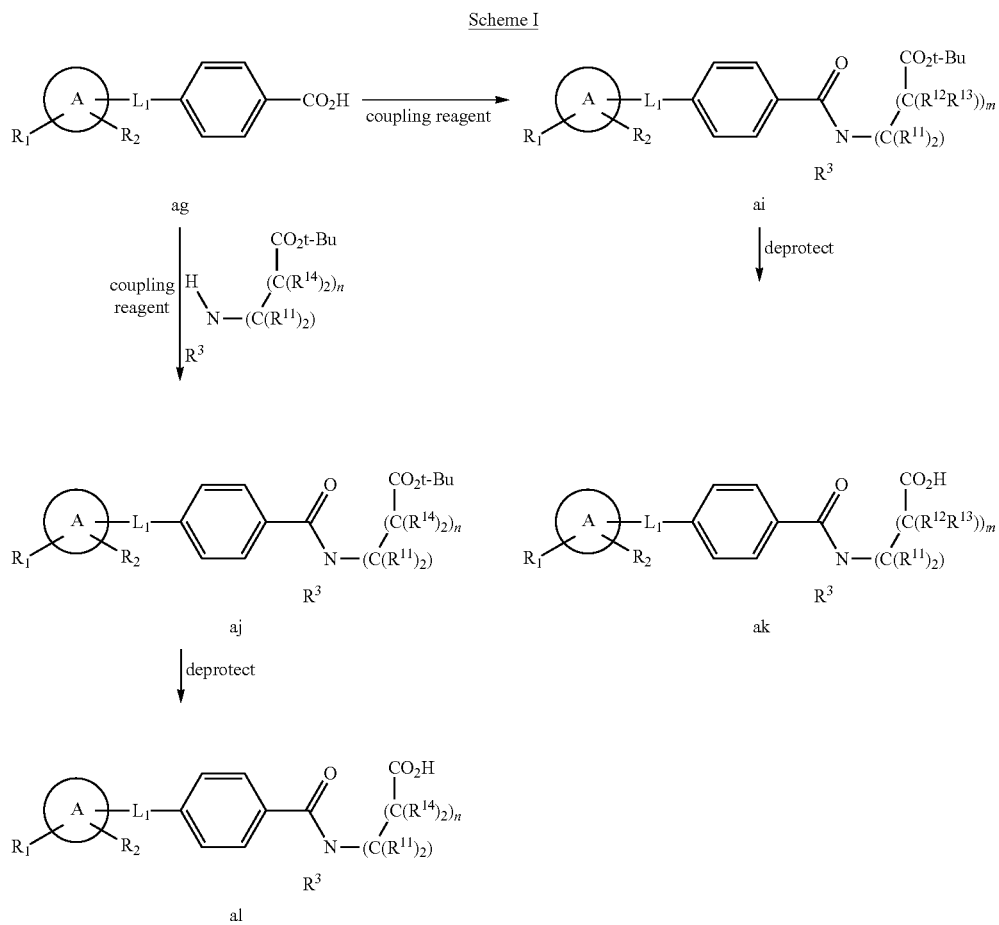

The general synthesis of N-benzyloxy pyrazoles is presented in Scheme J. Methyl ketone am is condensed with O-benzyl hydroxylamine to afford the oxime an. Treatment of an with a base such as LDA and the like in a solvent such as THF and the like is followed by addition of $R^2CN$ to afford the product ao. Oxidative cyclization of ao with copper (II) acetate and the like provides the desired pyrazole ap. Cleavage of the benzyl ether present in ap via hydrogenation in the presence of palladium on barium sulfate will afford the N-hydroxypyrazole aq. Benzylation of the hydroxyl group will afford compound ar. Hydrolysis of the benzoate ester will afford the desired benzoic acid as.

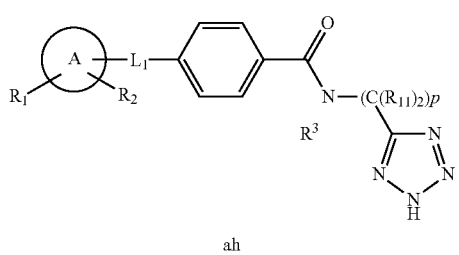

Scheme J

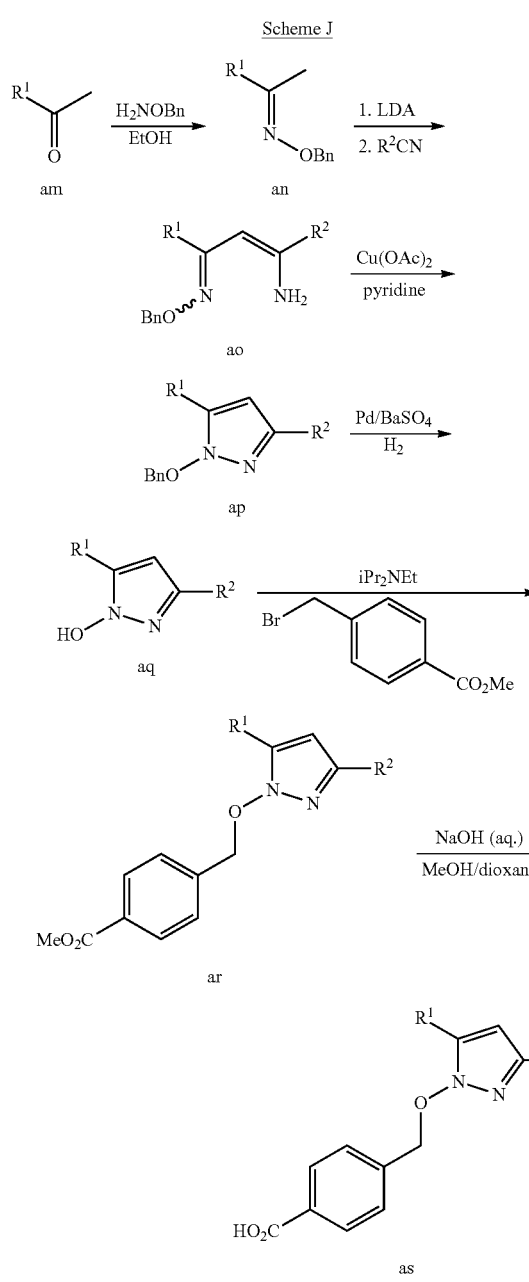

Scheme K

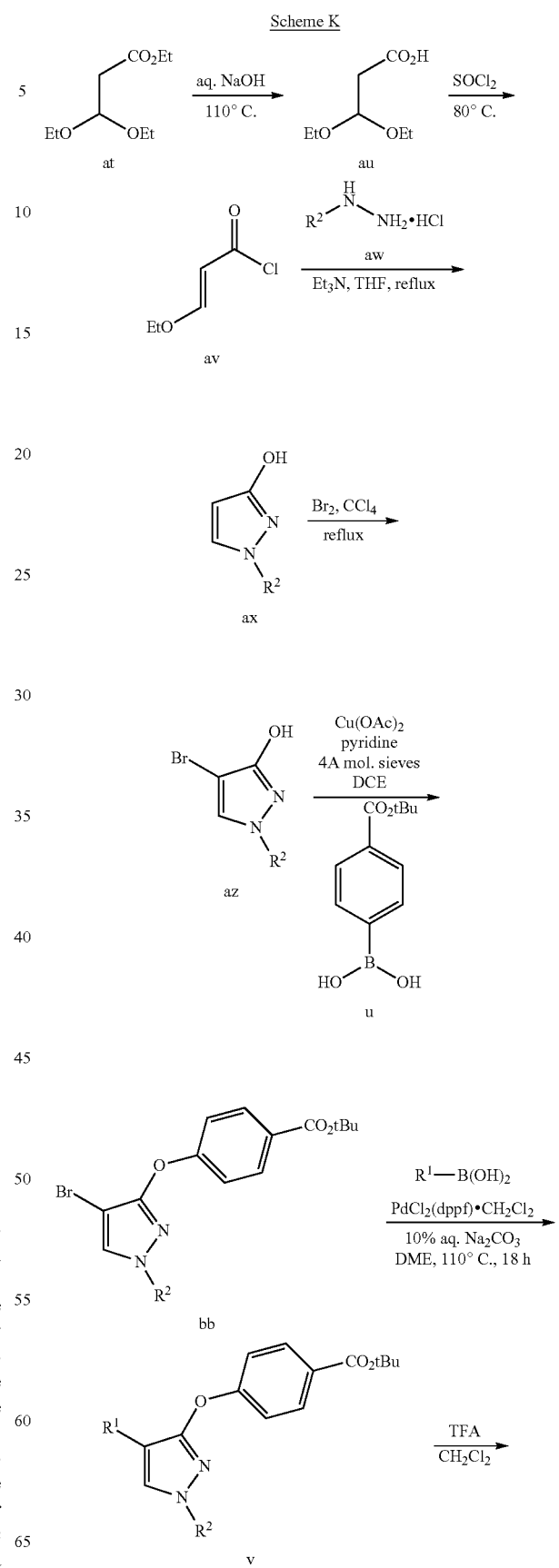

An additional method for the synthesis of substituted pyrazoles such as w is outlined in Scheme K. Hydrolysis of a dialkoxy propanoate such as at affords the desired acid au. Treatment of au with thionyl chloride and the like affords the alkoxyacryloyl chloride ay. Condensation of intermediate av with a hydrazine aw, provides the pyrazolone ax. Bromination of ax with bromine in carbon tetrachloride and the like yields the pyrazolyl bromide az. Copper-mediated oxidative coupling between az and u accesses compounds such as bb. Palladium-mediated coupling between bb and a suitable coupling partner such as $R^1$—$B(OH)_2$ and the like will provide the desired compound v. Cleavage of the tert-butyl ester present in compound v with an acid such as trifluoroacetic acid or hydrochloric acid and the like will afford compound w.

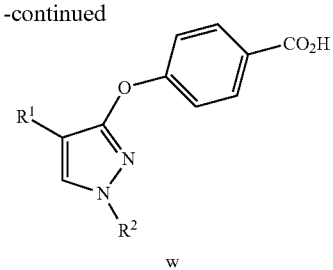

Another method for preparing substituted pyrazoles such as w is shown in Scheme L. An $R^1$-substituted alkyl acetate such as bc can be prepared via esterification of an $R^1$-substituted acetic acid or by palladium-mediated coupling of an $R^1$—$B(OH)_2$ with an alkyl bromoacetate. Bis(dimethylamino)methylation affords compound bd. Condensation of bd with hydrazine hydrate can yield the $R^1$-substituted pyrazolone be. A mitsunobu reaction between compounds be and benzyl alcohol affords the benzyloxy-substituted pyrazole bf. Copper-mediated oxidative coupling between bf and an $R^2$—$B(OH)_2$ can access the desired compound bg. Cleavage of the benzyl ether with hydrogen and a poisoned catalyst such as palladium on barium sulfate and the like results in the formation of pyrazolone t which can be further elaborated using the methods described in Scheme D to afford pyrazoles w.

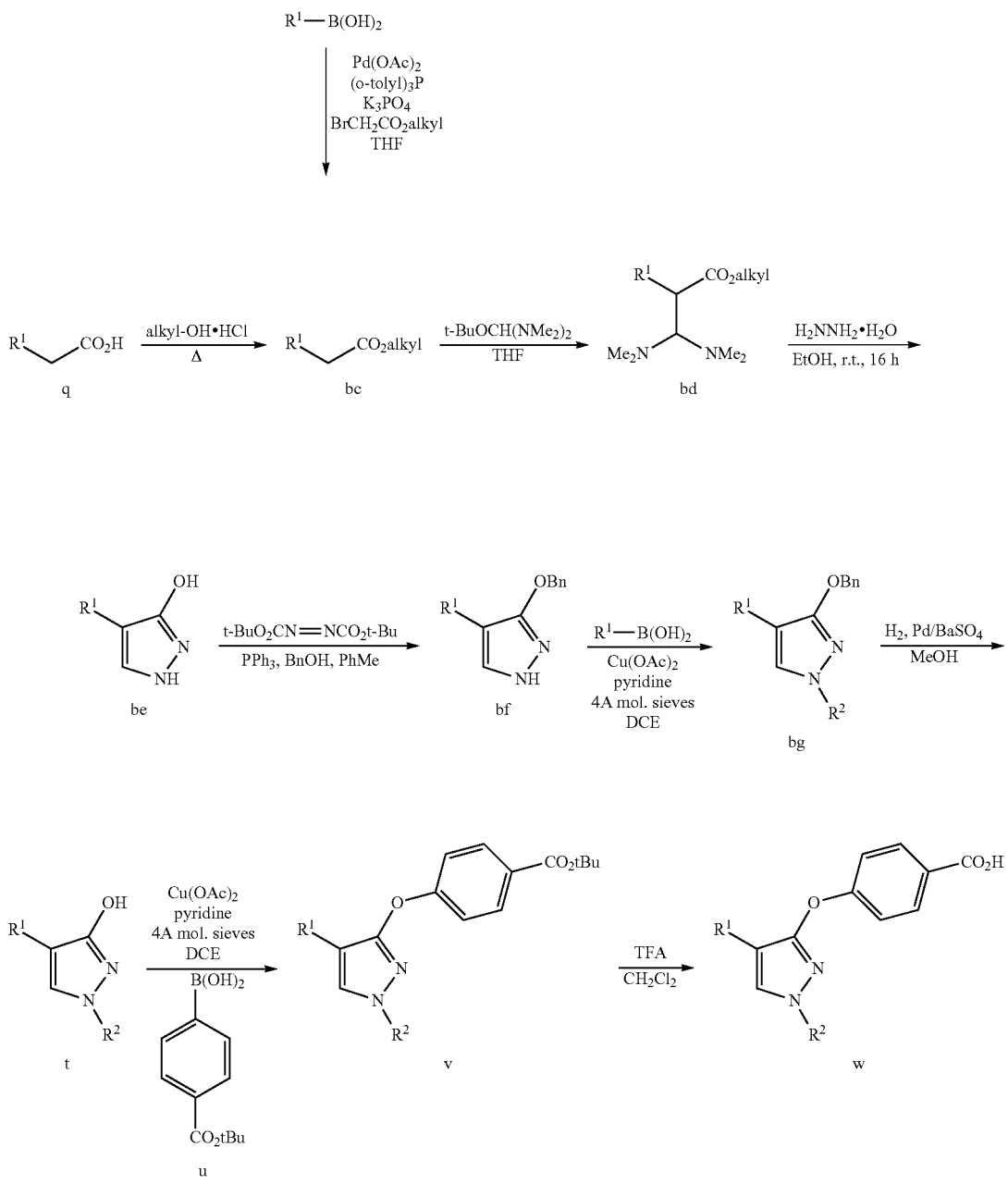

Scheme M
Compounds t and az can alternatively be oxidatively coupled with boronic acids bh to afford intermediates bi and bj respectively. Deprotection of bi leads to bk. Palladium-mediated coupling of an $R^1$—$B(OH)_2$ and bj, followed by deprotection will afford compound bk as well.
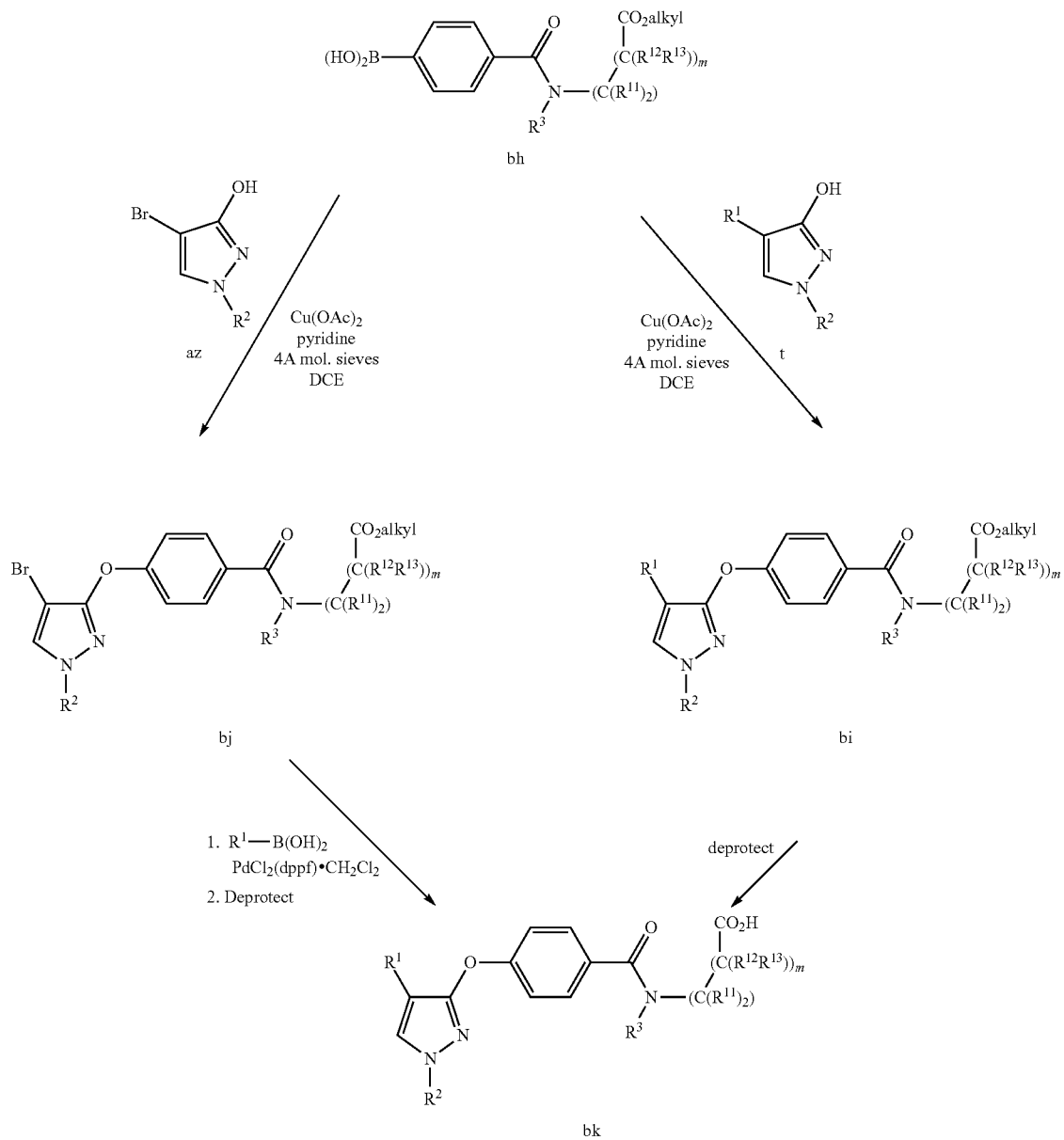
Examples
Scheme 1
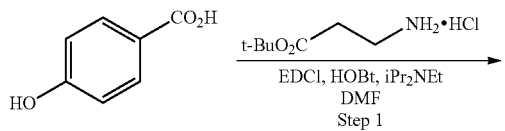

-continued
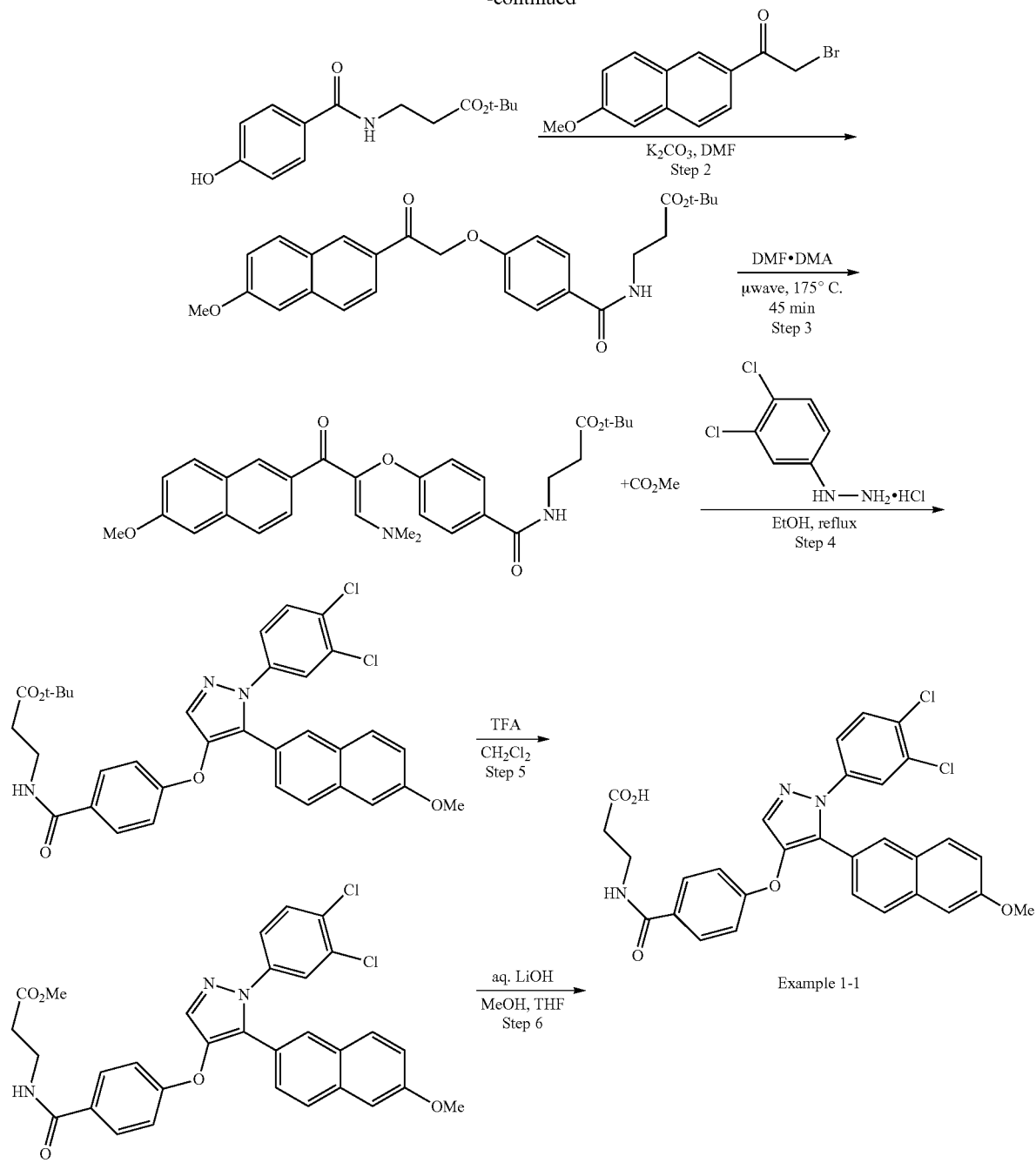
Step 1:
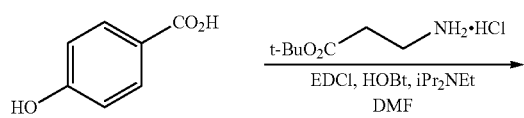
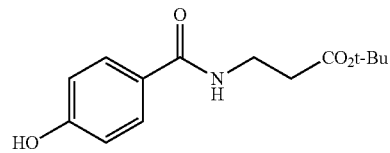
EDCI (3.3 g, 17.4 mmol, 1.2 eq), HOBt (1 g, 7.3 mmol, 0.5 eq), and i-Pr$_2$NEt (3 mL, 17.4 mmol, 1.2 eq) were added to a solution of 4-hydroxybenzoic acid (2 g, 14.5 mmol, 1 eq) and tert-butyl 3-aminopropanoate, hydrochloride salt (2.6 g, 14.5 mmol, 1 eq) in DMF (10 mL). The resulting solution was stirred 20 h at room temperature. The reaction was partitioned between dilute brine and 2:1 EtOAc:hexanes. Upon discarding the aqueous layer, the organic layer was washed once with dilute aqueous HCl and twice with brine. The organic layer was evaporated to afford and off-white solid which was triturated with EtOAc, filtered, washed with EtOAc and dried to afford the desired benzamide (3.4 g, 89%) as a white solid.
Step 2:

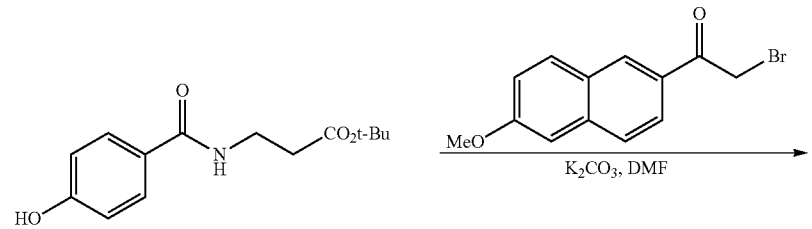

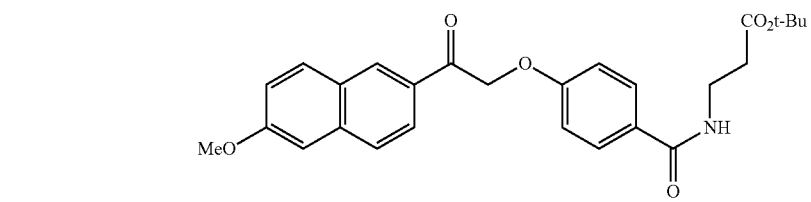

Potassium carbonate (622 mg, 4.50 mmol, 1.5 eq) was added to a solution of the benzamide prepared in Step 1 (796 mg, 3.00 mmol, 1 eq)) and 2-bromo-1-(6-methoxynaphthalen-2-yl)ethanone (*Organic Syntheses, Coll*. Vol. 6, p. 175 (1988); *Organic Syntheses*, Vol. 53, p. 111 (1973), 837 mg, 3.00 mmol, 1 eq) in DMF (10 mL). After stirring the reaction mixture for 90 h, the reaction was partitioned between dilute brine and 2:1 EtOAc:hexanes. The aqueous layer was discarded and the organic layer was washed with aqueous 0.5M NaOH and brine twice. The organic layer was dried over MgSO$_4$, filtered and evaporated to afford a crude yellow solid which was purified via silica gel chromatography (gradient elution: 0% to 100% EtOAc in hexanes) to afford the desired product as an off-white solid (930 mg).
Step 3:

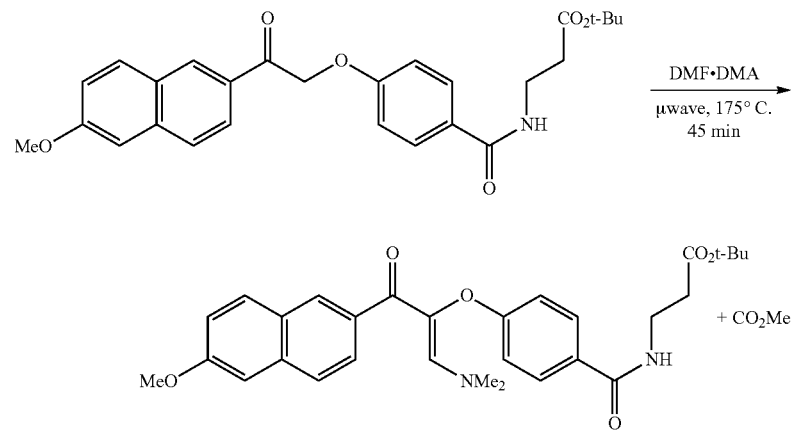

The product from Step 2 (480 mg, 1.04 mmol) was dissolved in dimethylformamide dimethyl acetal (12 mL), transferred to a 10-20 mL Biotage microwave vial, purged with nitrogen, and sealed. The vessel was heated at 175° C. for 45 min (Biotage microwave, high absorption) then cooled to room temperature. The reaction mixture was transferred to a 250 mL round-bottomed flask, and the solvents were removed under high vacuum to afford a crude orange solid, which was determined to be the desired product as a mixture of t-butyl and methyl esters. This crude material was used in the next step without further purification.

Step 4:

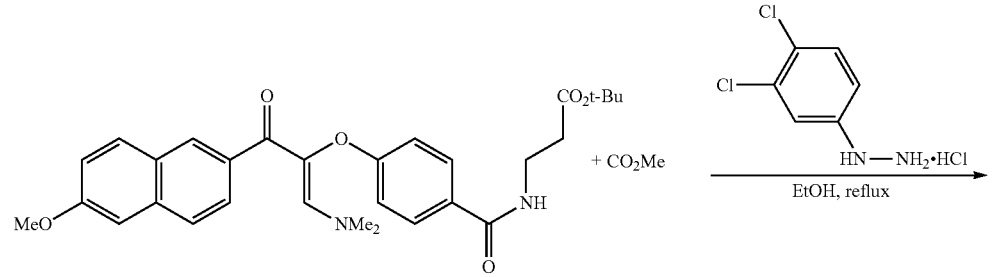

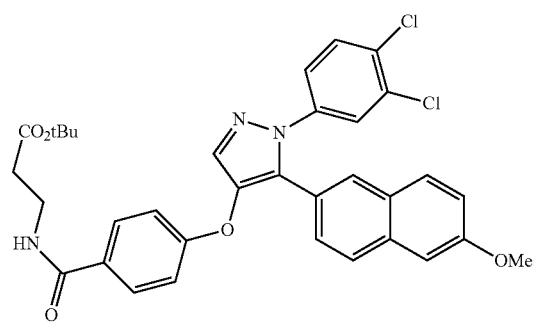

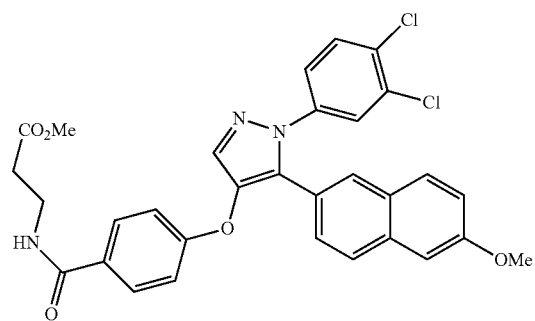

The crude product from Step 3 (100 mg, 0.19 mmol, 1 eq) and 3,4-dichloro-phenylhydrazine hydrochloride (41 mg, 0.19 mmol, 1 eq) were combined in absolute ethanol (2 mL). The resulting mixture was heated 1 h at 50° C. and 1 h at 90° C., after which the reaction was cooled to room temperature and stirred 16 h. After removal of the solvent in vacuo, the resulting residue was purified via silica gel chromatography (gradient elution, 0% to 40% EtOAc in hexanes) to afford the desired t-butyl ester product (45 mg) and methyl ester product (46 mg).

Step 5:

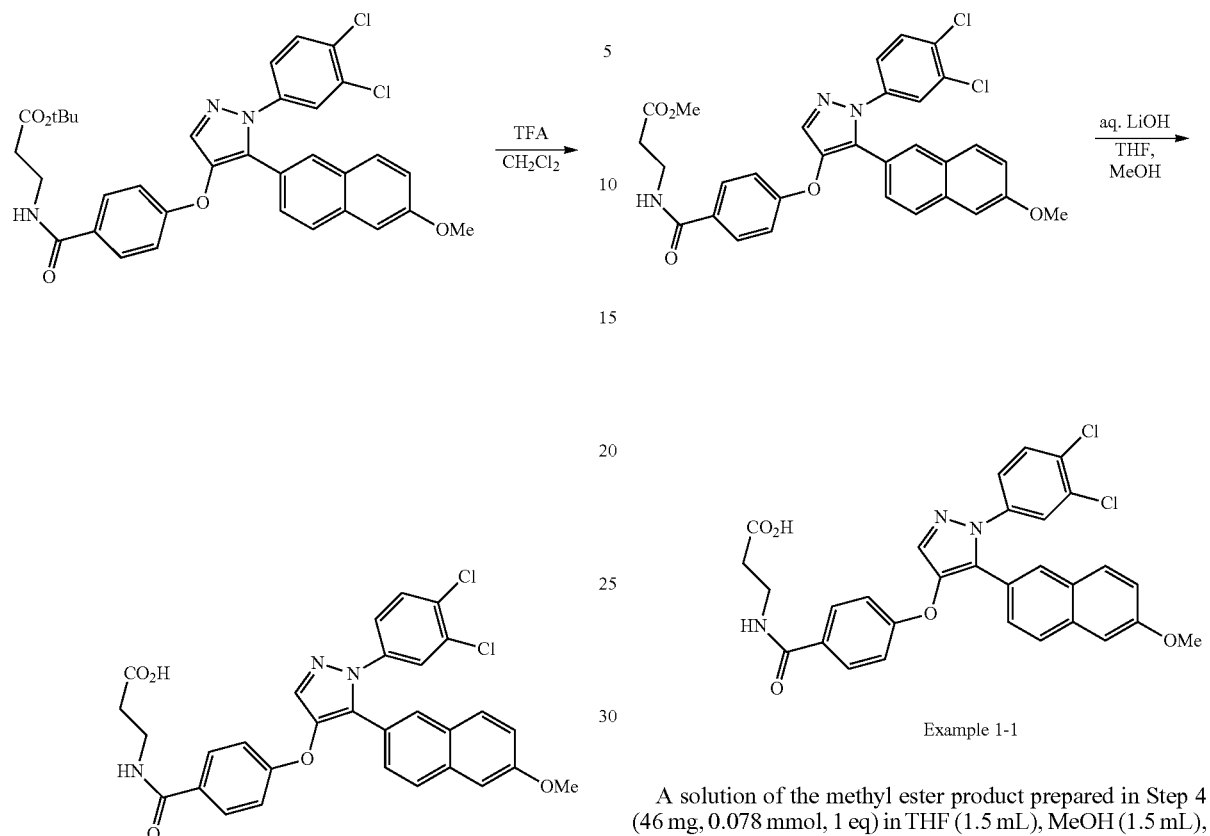

To a room temperature solution of the t-butyl ester product prepared in Step 4 (45 mg, 0.071 mmol) in CH$_2$Cl$_2$ (3 mL) was added TFA (1.5 mL) with stirring. After 3 h, the volatiles were removed in vacuo, and the crude product was combined with the crude product from Step 6 for purification.

Step 6:

Example 1-1

A solution of the methyl ester product prepared in Step 4 (46 mg, 0.078 mmol, 1 eq) in THF (1.5 mL), MeOH (1.5 mL), and water (0.2 mL) was treated with aqueous LiOH (2M, 0.2 mL) with stirring. After 3 h, aqueous HCl (2M, 0.2 mL) was added, and the quenched reaction combined with the crude product from Step 5 and evaporated in vacuo. The residue was purified via reversed-phase C18 HPLC using the method described below to afford Example 1-1 (25 mg) as a white solid.

The compounds in Table 1 were prepared in a manner similar to the preparation of Example 1-1 in Scheme 1.

TABLE 1

Using the conditions described in Scheme 1, and the requisite phenyl hydrazine hydrochloride salt, the following compound was prepared:

| Phenyl Hydrazine Hydrochloride | Example Number | Structure |
|---|---|---|
| (3-chlorophenyl hydrazine·HCl) | 1-2 | (structure shown) |

TABLE 1-continued
Using the conditions described in Scheme 1, and the requisite phenyl hydrazine hydrochloride salt, the following compound was prepared:
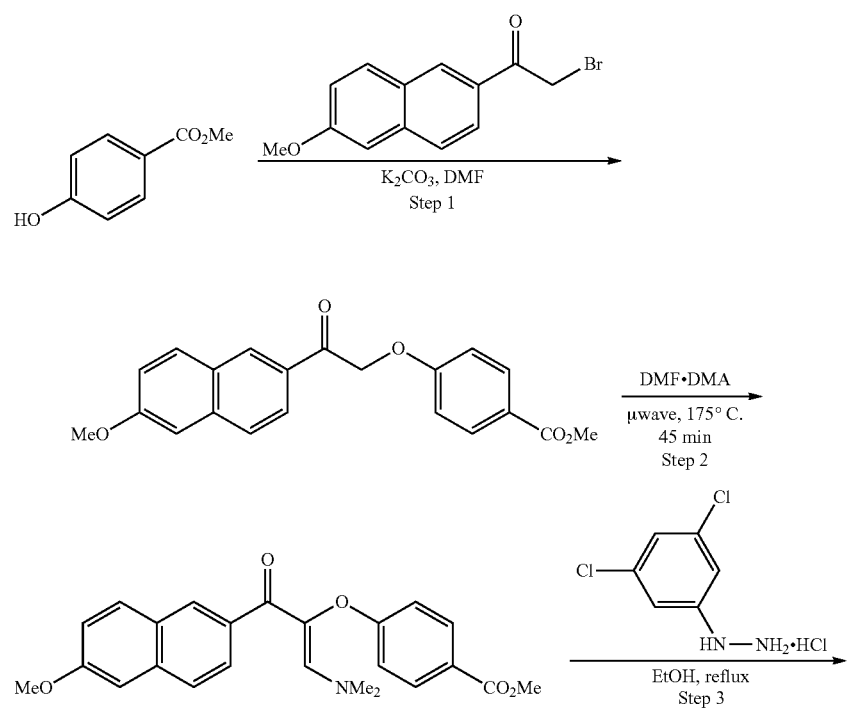

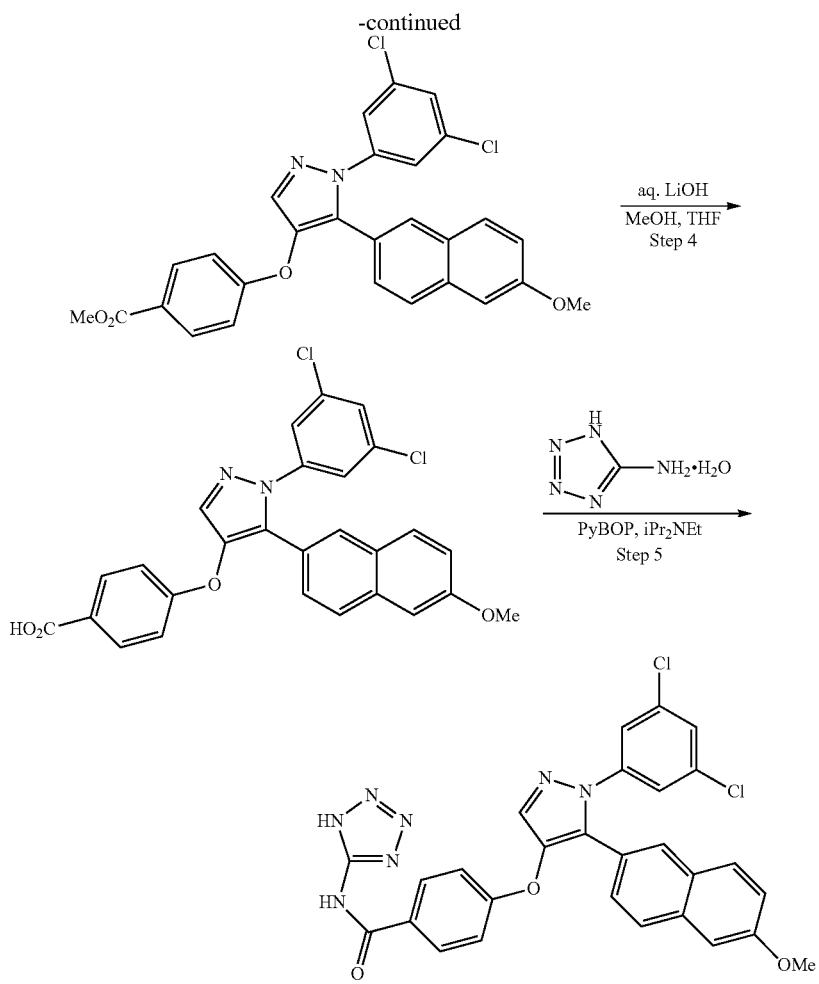

Example 2-1

Step 1:

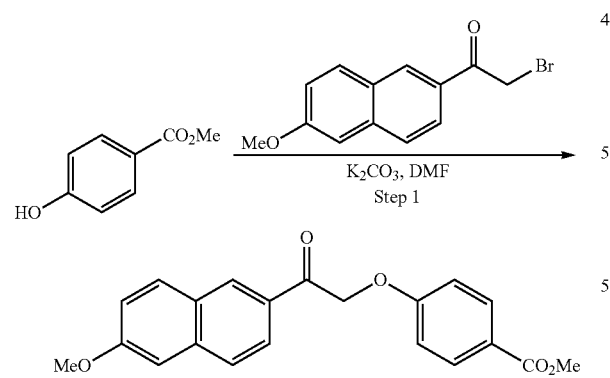

Potassium carbonate (265 mg, 1.92 mmol, 3 eq) was added to a solution of methyl 4-hydroxy-benzoate (170 mg, 0.64 mmol, 1 eq)) and 2-bromo-1-(6-methoxynaphthalen-2-yl) ethanone (97 mg, 0.64 mmol, 1. eq) in DMF (2 mL) at room temperature. After stirring the reaction mixture for 1.5 h, one half of the reaction mixture was partitioned between dilute aqueous HCl and 2:1 EtOAc:hexanes. The aqueous layer was discarded and the organic layer was washed twice with brine. The organic layer was dried over anhydrous MgSO₄, filtered and evaporated to afford the desired product (128 mg) as a crude yellow solid which was used in the next step without further purification.

Step 2:

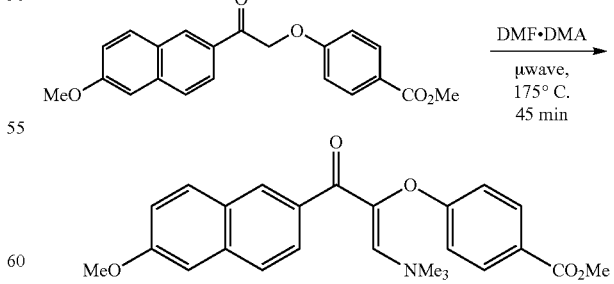

The material prepared in Step 1 (300 mg, 1.04 mmol) was dissolved in dimethylformamide dimethyl acetal (3 mL), transferred to a 2-5 mL Biotage microwave vial, purged with nitrogen, and sealed. The vessel was heated at 170° C. for 40 min, then 175° C. for 45 min (Biotage microwave, high absorption). After cooling the reaction to room temperature, the solvent was removed in vacuo to afford a crude orange oil. Absolute ethanol was added to the residue and sonicated to afford a pale yellow solid which was collected via filtration, washed with ethanol and dried to afford 200 mg of the desired product.

Step 3:

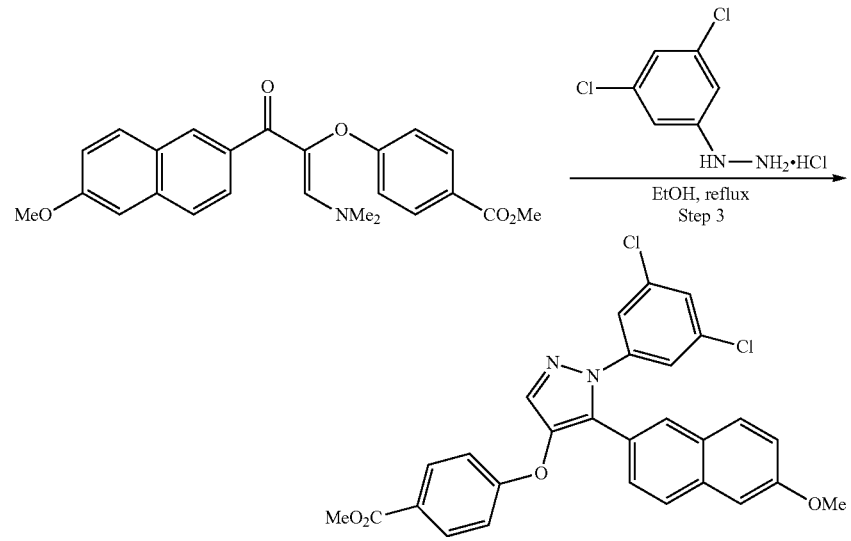

The product from Step 2 (313 mg, 0.77 mmol, 1 eq) and 3,4-dichloro-phenylhydrazine hydrochloride (164 mg, 0.77 mmol, 1 eq) were combined in absolute ethanol (7 mL). The resulting mixture was heated 4 h at reflux, after which the reaction was cooled to room temperature and stirred 16 h. After removal of the solvent in vacuo, the resulting residue was purified via silica gel chromatography (gradient elution, 0% to 50% EtOAc in hexanes) to afford the desired pyrazole (130 mg).

Step 4:

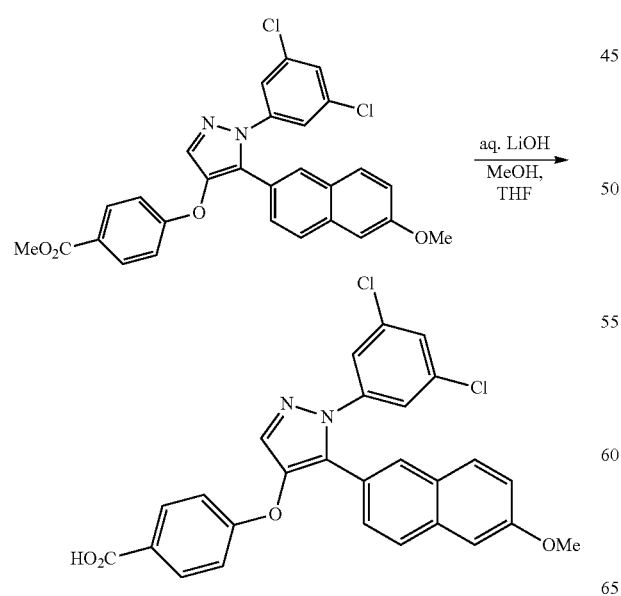

The pyrazole prepared in Step 3 (121 mg, 0.23 mmol, 1 eq) was dissolved in a mixture of THF (1.5 mL), MeOH (2 mL), and water (0.2 mL). Aqueous LiOH (2M, 0.2 mL, 0.4 mmol, 1.7 eq) was added and the reaction stirred. Additional amounts of 2M LiOH (0.9 mL), THF (3 mL), and MeOH (3 mL) were added, and the reaction stirred 16 h. The reaction mixture was partitioned between $CH_2Cl_2$ and dilute aqueous HCl, and the organic layer saved. The aqueous layer was extracted with $CH_2Cl_2$. Evaporation of the combined organic layers afforded an orange residue which was subjected to silica gel chromatography (gradient elution: 0% to 30% MeOH in $CH_2Cl_2$) resulting in the isolation of the desired benzoic acid (49 mg).

Step 5:

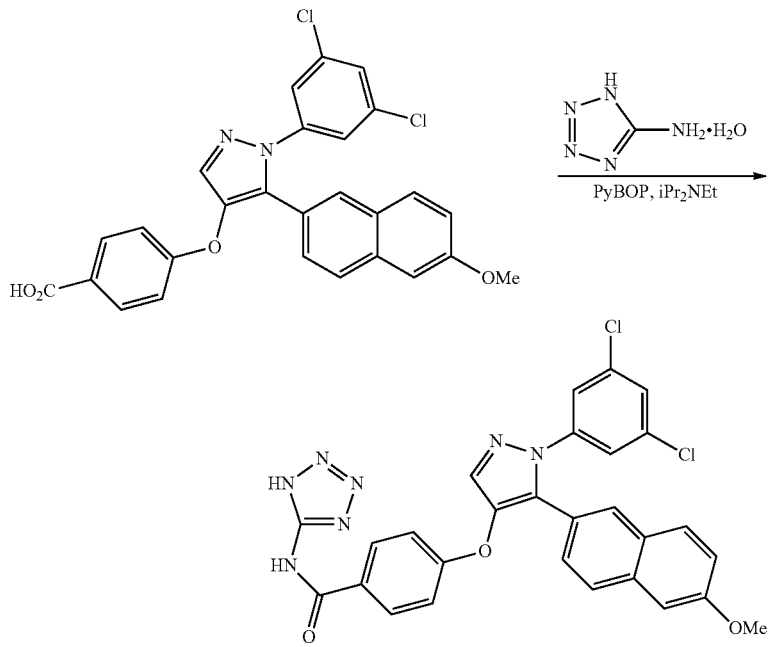

Example 2-1

The benzoic acid prepared in Step 4 (38 mg, 0.075 mmol, 1 eq) was combined with aminotetrazole monohydrate (20 mg, 0.19 mmol, 2.6 eq), PyBOP (50 mg, 0.096 mmol, 1.3 eq), and $iPr_2NEt$ (0.050 mL, 0.29 mmol, 3.8 eq) in DMF (3 mL) and stirred 40 h at room temperature. After removing the volatile components from the reaction under vacuum, MeOH was added to the residue, and the suspension was sonicated. A precipitate formed, which was collected via filtration, washed with MeOH, and dried to afford Example 2-1 (22 mg) as a tan solid.

Scheme 3

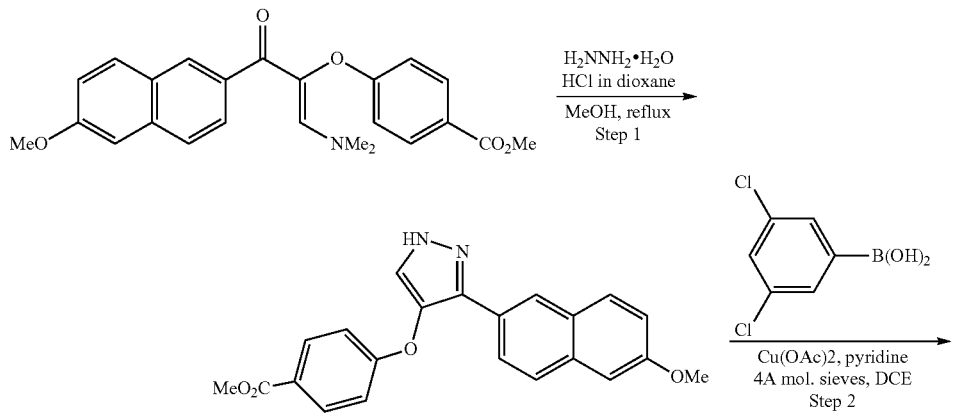

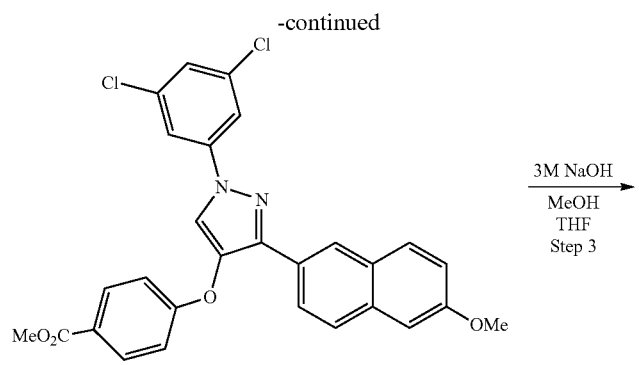

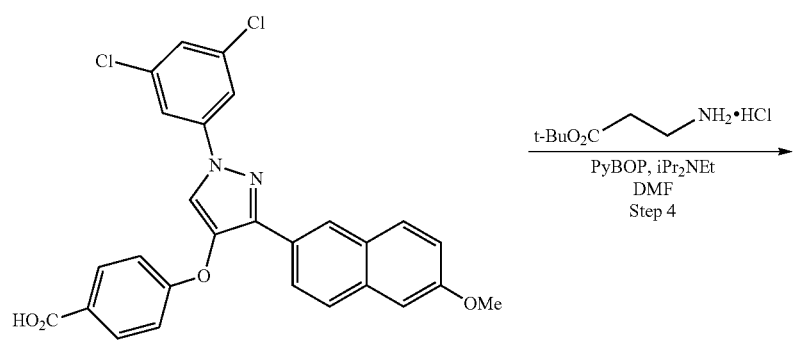

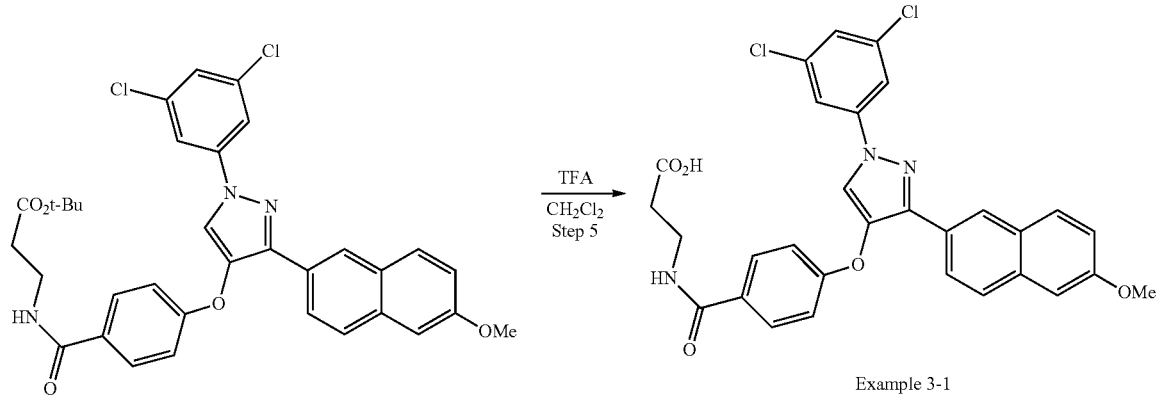

Step 1:

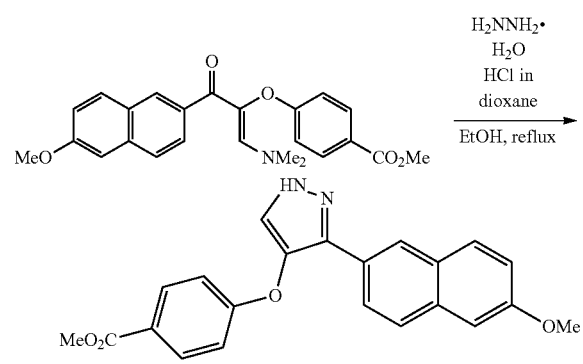

A solution of the enaminoketone prepared in Scheme 2, Step 2 (356 mg, 0.88 mmol, 1 eq), hydrazine hydrate (59 μL, 0.97 mmol, 1.1 eq) and HCl (4N in dioxane, 250 μL, 1.1 eq) in MeOH (10 mL) was heated at reflux 16 h. An additional amount of hydrazine hydrate (50 μL, 0.82 mmol, 0.9 eq) was added and heating at reflux was continued. A final aliquot of hydrazine hydrate (50 μL, 0.82 mmol, 0.9 eq) was added and heating at reflux was continued 1 h more. The reaction was evaporated, and the resulting residue purified via silica gel chromatography (gradient elution: 12% to 100% EtOAc in hexanes) to afford the desired product (276 mg) as a film.

Step 2:

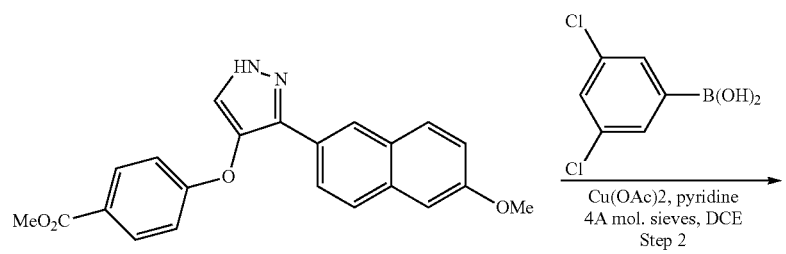

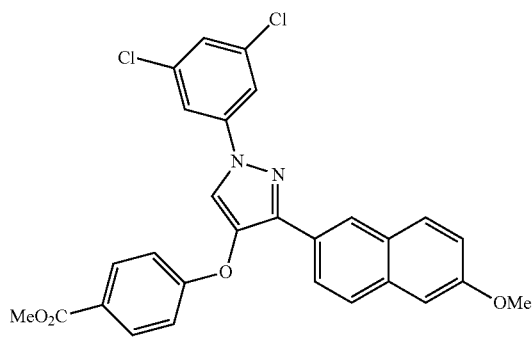

To a solution of the pyrazole prepared in Step 1 (92 mg, 0.25 mmol, 1 eq) in 1,2-dichloroethane (7 mL) was added 3,5-dichloro-phenyl boronic acid (119 mg, 0.63 mmol, 2.5 eq), 4 Å molecular sieves (160 mg), Cu(OAc)$_2$ (68 mg, 0.38 mmol, 1.5 eq), and pyridine (0.04 mL, 0.5 mmol, 2 eq) and the resulting mixture stirred at room temperature open to air for 24 h. The reaction was concentrated to dryness and the residue purified via silica gel chromatography (gradient elution: 8% to 70% EtOAc in hexanes) to afford the desired product (109 mg) as a clear film.

Step 3:

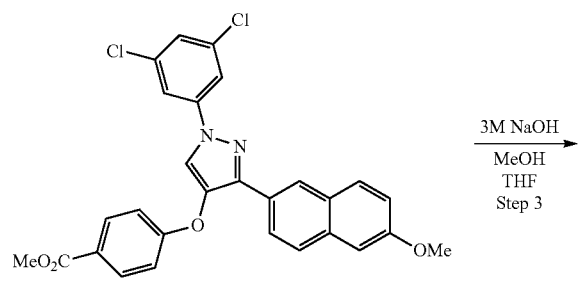

-continued

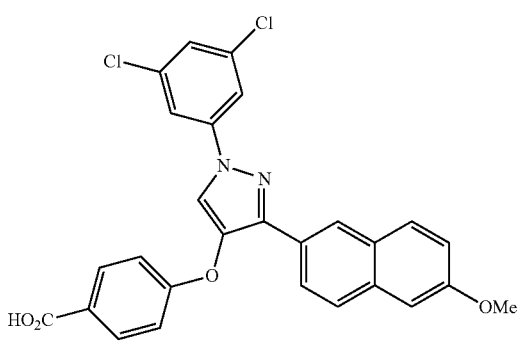

A solution of the product from Step 2 (109 mg, 0.21 mmol, 1 eq) in THF (6 mL) and MeOH (6 mL) was treated with aqueous 3M NaOH (2 mL, 6.0 mmol, 30 eq) and stirred at room temperature for 72 h. The reaction mixture was then partitioned between 1M HCl and EtOAc. The aqueous layer was discarded and the organic layer was washed with brine, dried over anhydrous Na$_2$SO$_4$, filtered and evaporated to afford the desired carboxylic acid which was used in the next step without further purification.

Step 4:

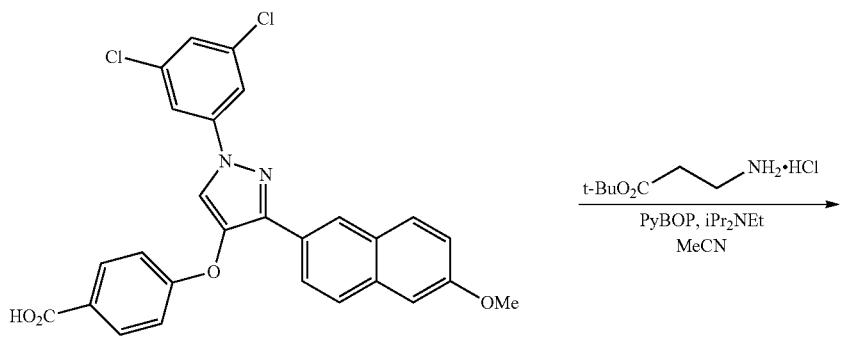

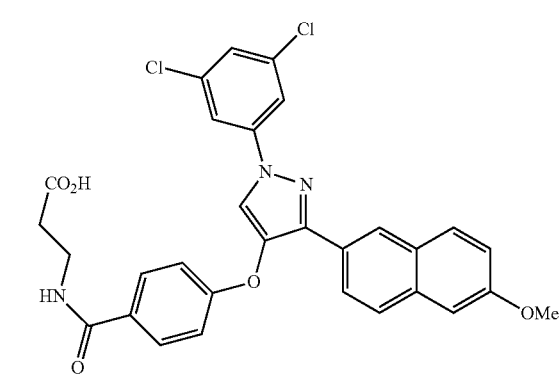

The carboxylic acid prepared in Step 3 (106 mg, 0.21 mmol, 1 eq) was combined with PyBOP (120 mg, 0.23 mmol, 1.1 eq), tert-butyl 3-aminopropanoate, hydrochloride salt (42 mg, 0.23 mmol, 1.1 eq), and iPr$_2$NEt (0.15 mL, 0.84 mmol, 4 eq) in MeCN (2 mL) at room temperature and the resulting solution was stirred for 5 h. Concentration of the reaction mixture afforded a residue which was partitioned between EtOAc and aqueous 0.5M HCl. After disposal of the aqueous layer, the organic layer was washed with brine and saturated sodium bicarbonate, then dried over anhydrous Na$_2$SO$_4$. The solids were removed via filtration and the filtrate evaporated to afford a crude residue which was purified via silica gel chromatography (gradient elution: 0% to 40% EtOAc in hexanes) to afford the coupled product (97 mg) as a clear film.

Step 5:

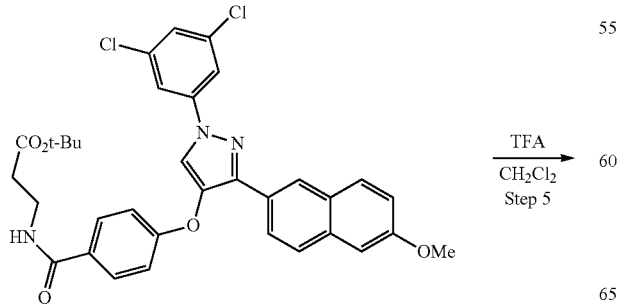

Example 3-1

A solution of the coupled product from Step 4 (97 mg, 0.15 mmol, 1 eq) in CH$_2$Cl$_2$ (3 mL) was treated with TFA (1.5 mL) and the resulting reaction mixture stirred 2 h at room temperature. The reaction was concentrated to dryness and triturated with Et$_2$O to afford Example 3-1 as a tan solid (60 mg).

TABLE 2
Using the conditions described in Scheme 3, and the requisite boronic acid, the following compounds were prepared:
| Boronic Acid | Example Number | Structure |
|---|---|---|
| 3,5-difluorophenylboronic acid | 3-2 | |
| 3-(trifluoromethyl)phenylboronic acid | 3-3 | |
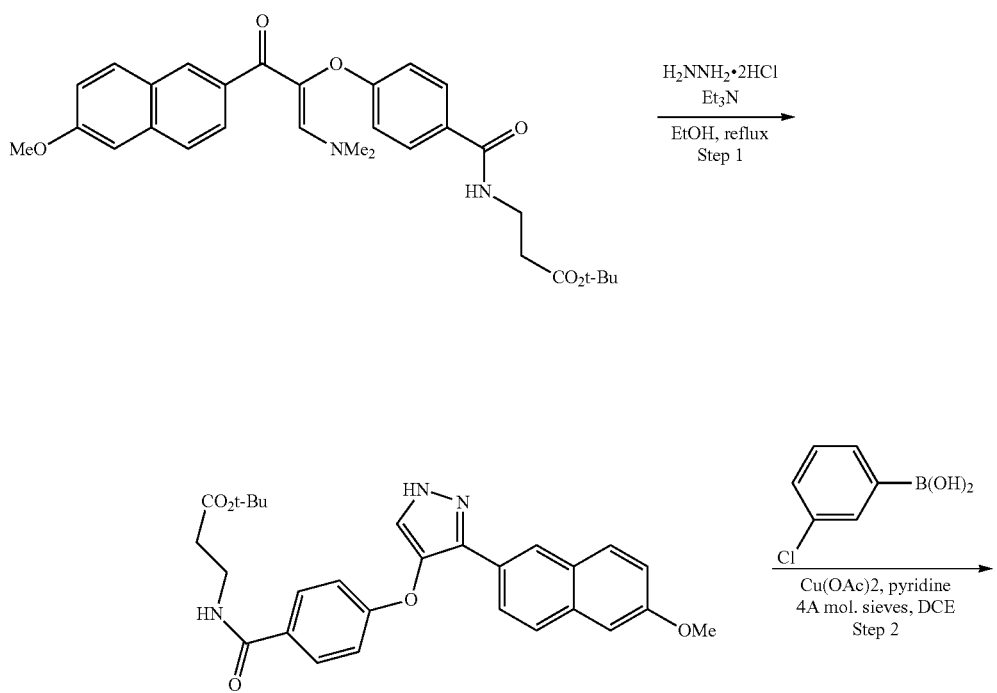
Scheme 4

-continued

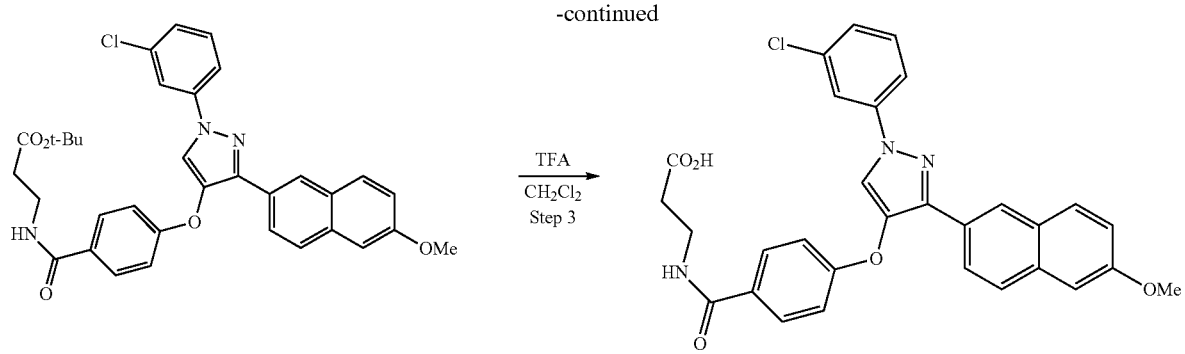

Example 4-1

Step 1:

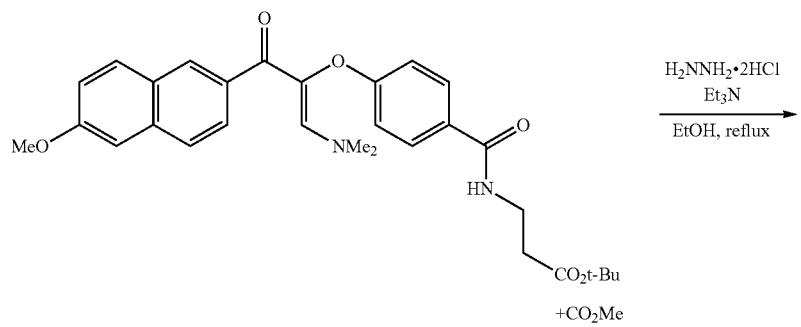

+CO2Me

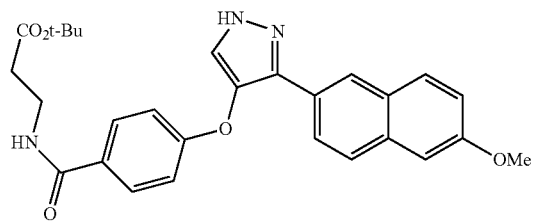

A solution of the product from Scheme 1, Step 3 (1.1 g, 2.12 mmol, 1 eq), hydrazine dihydrochloride (223 mg, 2.12 mmol, 1 eq), and triethylamine (295 μL, 1 eq) in EtOH (10 mL) was heated at reflux 5 h. The reaction was cooled to room temperature, evaporated, and the resulting residue purified via silica gel chromatography (gradient elution: 0% to 100% EtOAc in hexanes) to afford semi-pure material which was then subjected to two additional silica gel purifications (gradient elution: 0% to 15% MeOH in CH$_2$Cl$_2$, then 0% to 100% EtOAc in hexanes) to afford the desired product (100 mg) as a film.

Step 2:

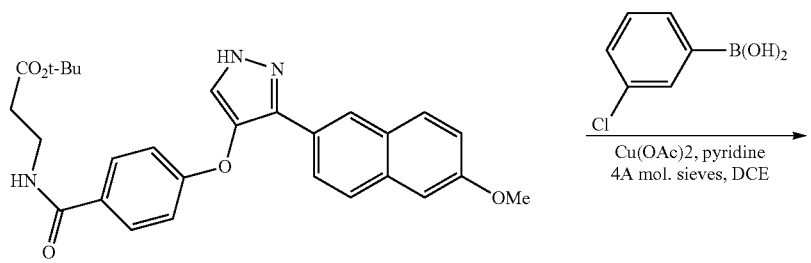

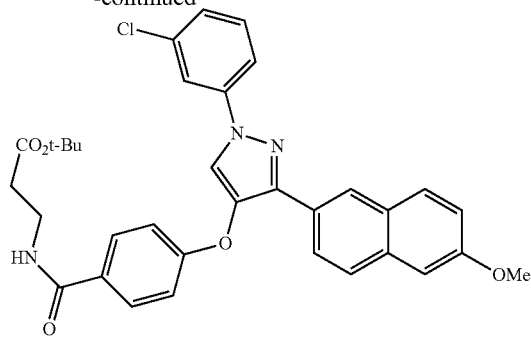

To a solution of the pyrazole prepared in Step 1 (50 mg, 0.10 mmol, 1 eq) in 1,2-dichloroethane (3 mL) was added 3-chlorophenyl boronic acid (39 mg, 0.25 mmol, 2.5 eq), 4 Å molecular sieves (80 mg), Cu(OAc)$_2$ (27 mg, 0.15 mmol, 1.5 eq), and pyridine (0.016 mL, 0.20 mmol, 2 eq) and the resulting mixture stirred at room temperature open to air for 40 h. The reaction was concentrated to dryness and the residue purified via silica gel chromatography (gradient elution: 0% to 100% EtOAc in hexanes) to afford the desired product (47 mg) as a clear film.

Step 3:

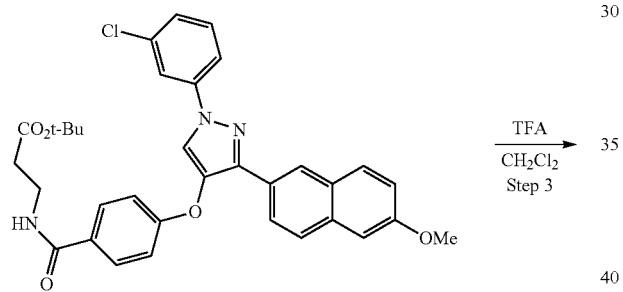

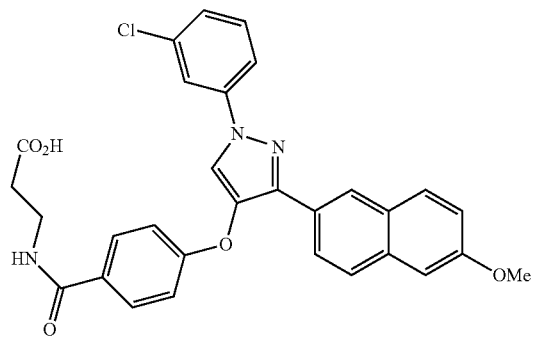

Example 4-1

A solution of the coupled product from Step 2 (47 mg, 0.079 mmol, 1 eq) in CH$_2$Cl$_2$ (4 mL) was treated with TFA (1.5 mL) and the resulting reaction mixture was stirred 3 h at room temperature. The reaction was concentrated to dryness and triturated with cold CHCl$_3$ to afford Example 4-1 as a white solid (20 mg).

TABLE 3

Using the conditions described in Scheme 4, and the requisite boronic acid, the following compound was prepared:

| Boronic Acid | Example Number | Structure |
|---|---|---|
| ![B(OH)2 3,4-dichlorophenyl] | 4-2 | ![3,4-dichloro analog] |

Scheme 5
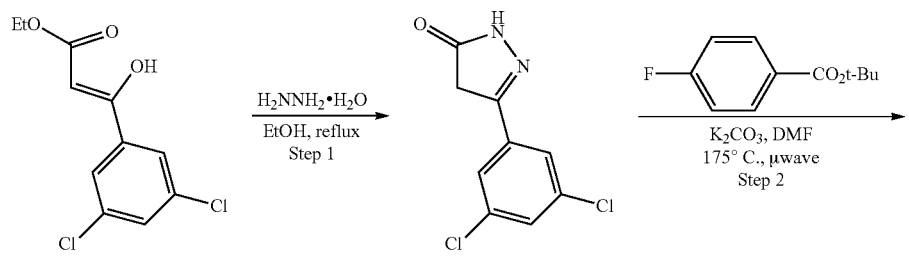
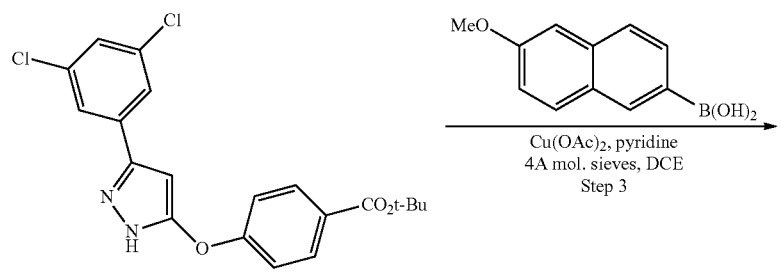
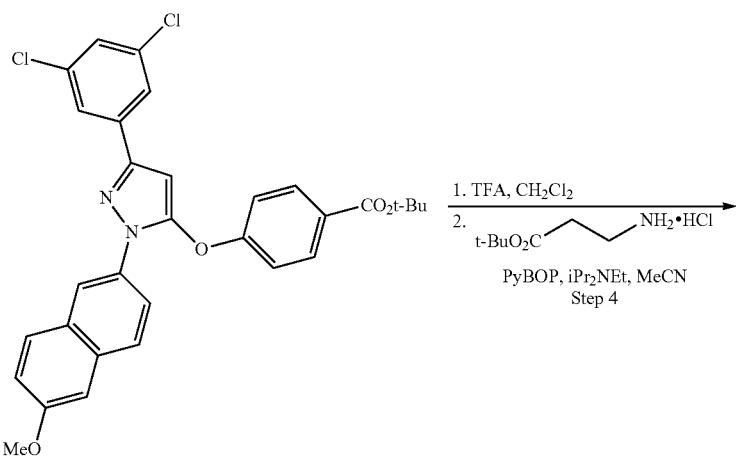
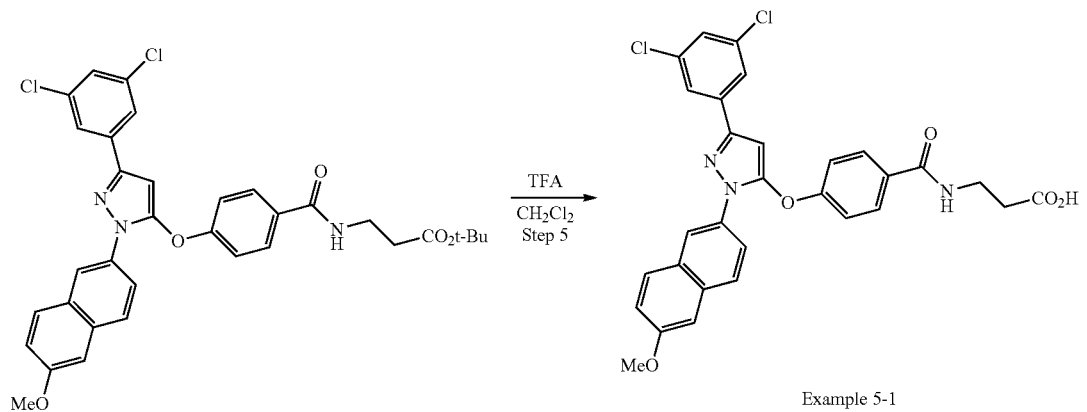
Example 5-1

97

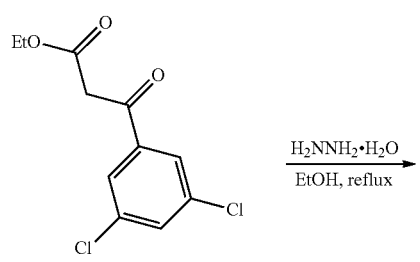

H₂NNH₂·H₂O
EtOH, reflux
→

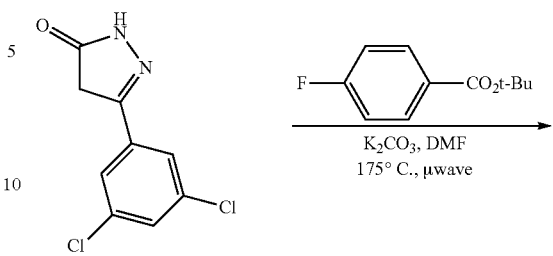

98

Step 2:

Step 1:

A solution of the ketoester (1.6 g, 6.00 mmol, 1 eq) in EtOH (7 mL) was treated with hydrazine hydrate (0.4 mL, 12.0 mmol, 2 eq) and the resulting mixture heated at reflux for 1 h. A large amount of white precipitate formed. An additional amount of EtOH (10 mL) was added, and the mixture refluxed 1 h more. After cooling the reaction to room temperature, a white solid was collected via filtration, washed with EtOH, and dried to afford the desired pyrazolone, which was used without further purification.

The pyrazolone prepared in Scheme 5, Step 1 (500 mg, 2.18 mmol, 1 eq), tert-butyl-4-fluorobenzoate (430 mg, 2.19 mmol, 1 eq), and potassium carbonate (460 mg, 3.33 mmol, 1.5 eq) were combined in DMF (3 mL) in a 2-5 mL Biotage microwave vial. The vial was sealed and heated in an 80° C. oil bath for 2 h. An additional amount of tert-butyl-4-fluorobenzoate (430 mg, 2.19 mmol, 1 eq) was added and the reaction was subjected to microwave heating (175° C., 90 min, very high absorption). The reaction was then cooled to room temperature and adsorbed onto silica gel (10 g). The adsorbed material was purified via silica gel chromatography (Gradient elution: 0% to 15% EtOAc in hexanes) to afford the desired product (30 mg, 3%) as a clear film.

Step 3:

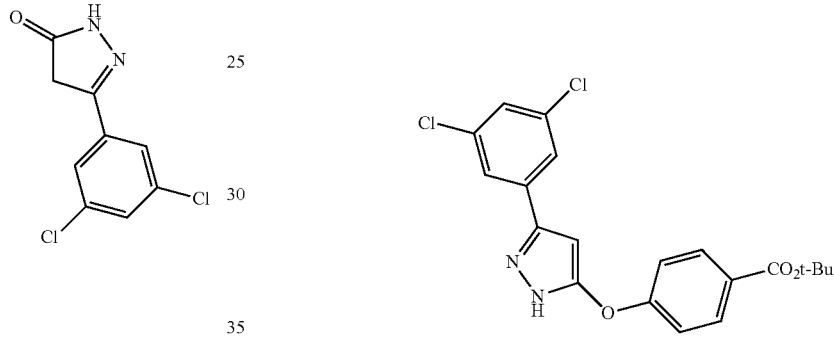

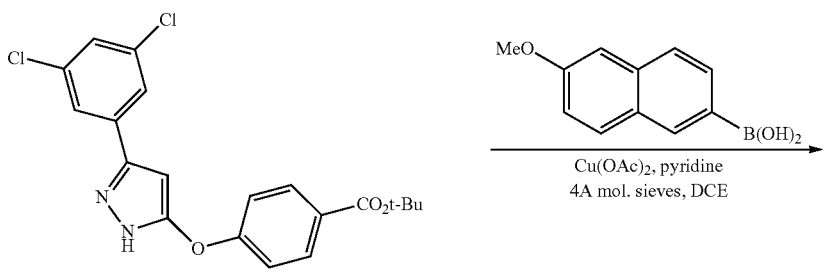

-continued

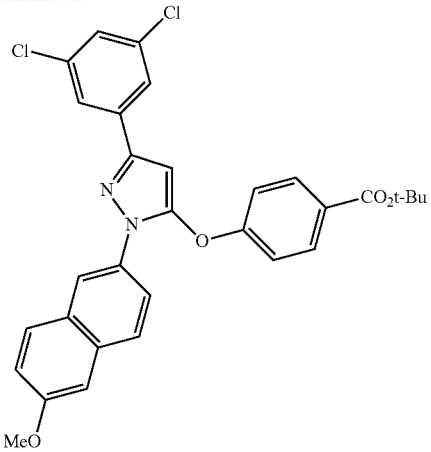

A heterogeneous solution of the product from Step 2 (30 mg, 0.074 mmol, 1 eq), 6-methoxynaphthalen-2-yl boronic acid (37 mg, 0.19 mmol, 2.5 eq), copper (II) acetate (21 mg, 0.12 mmol, 1.6 eq), pyridine (12 μL, 0.15 mmol, 2 eq), and 4 Å molecular sieves (50 mg) in 1,2-dichloroethane (2 mL) was stirred at room temperature open to air for 24 h. The reaction mixture was then concentrated and subjected to silica gel chromatography (Gradient elution 0% to 15% EtOAc in hexanes) to afford the desired product (55 mg, quant.) contaminated with a small amount of the undesired minor N-arylated compound and bis-naphthyl ether. This material was taken to the next step without further purification.

Step 4:

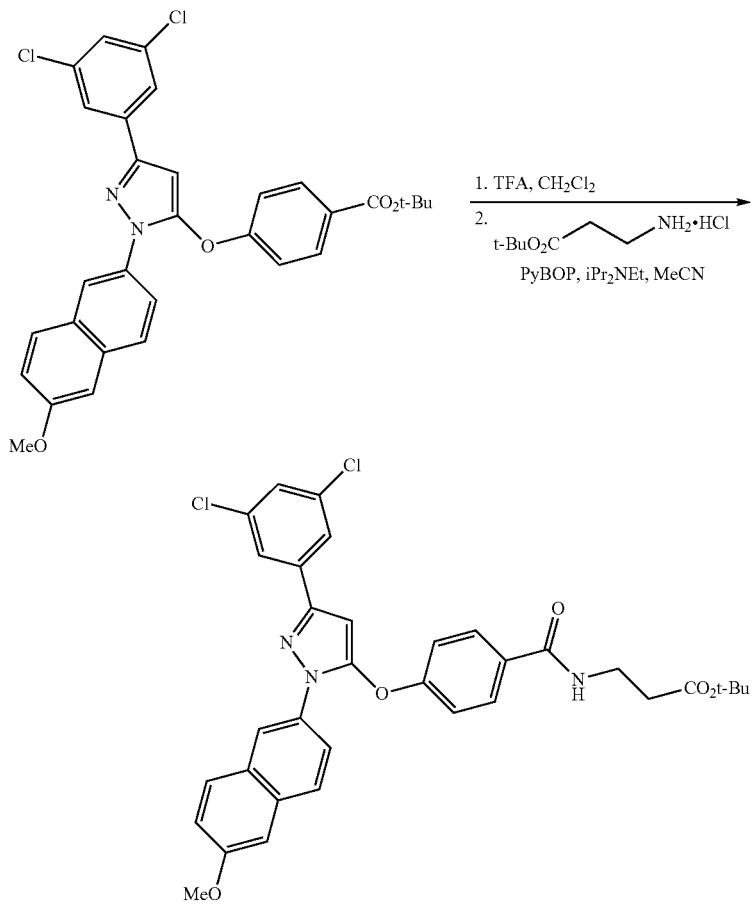

A solution of the N-aryl pyrazole prepared in Step 3 (55 mg, 0.074 mmol, 1 eq) in $CH_2Cl_2$ (4.5 mL) was treated with trifluoroacetic acid (1.5 mL) at room temperature. After stirring for 4 h, the volatiles were removed in vacuo The crude material was combined with PyBOP (51 mg, 0.098 mmol, 1.3 eq), iPr₂NEt (51 µL, 0.29 mmol, 3.9 eq), and tert-butyl 3-aminopropanoate, hydrochloride salt (18 mg, 0.098 mmol, 1.3 eq) in DMF (2 mL) and the resulting solution was stirred at room temperature for 16 h. The volatiles were removed in vacuo, and the residue was purified via silica gel chromatography (gradient elution: 0% to 100% EtOAc in hexanes) to afford the coupled product (37 mg, 79%) as a film.

Step 5:

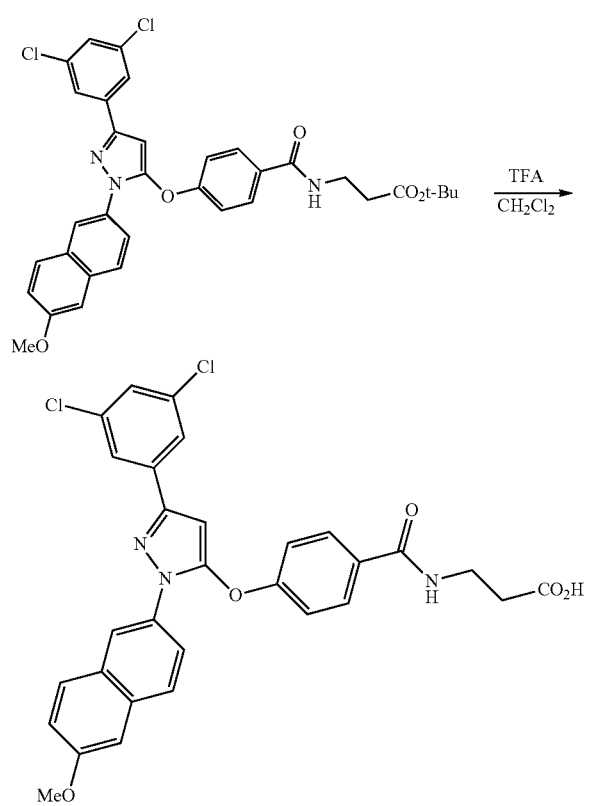

Example 5-1

A solution of the benzamide prepared in Step 4 (37 mg, 0.058 mmol) in CH₂Cl₂ (4 mL) was treated with trifluoroacetic acid (1.5 mL). After stirring for 3 h, the volatiles were removed in vacuo. The crude material was dissolved in MeOH (1.5 mL). After standing for 5 min, a precipitate formed which was collected via filtration and washed with MeOH and Et₂O to afford Example 5-1 (15 mg, 45%) as a dark tan solid.

Scheme 6

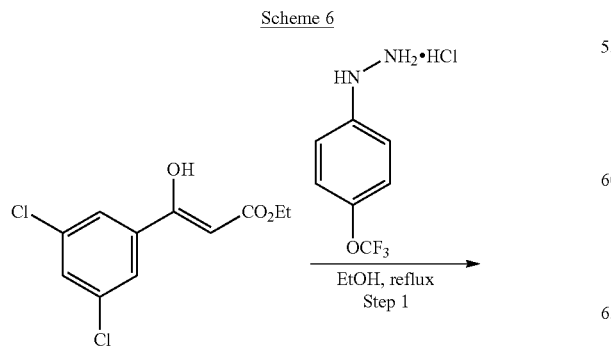

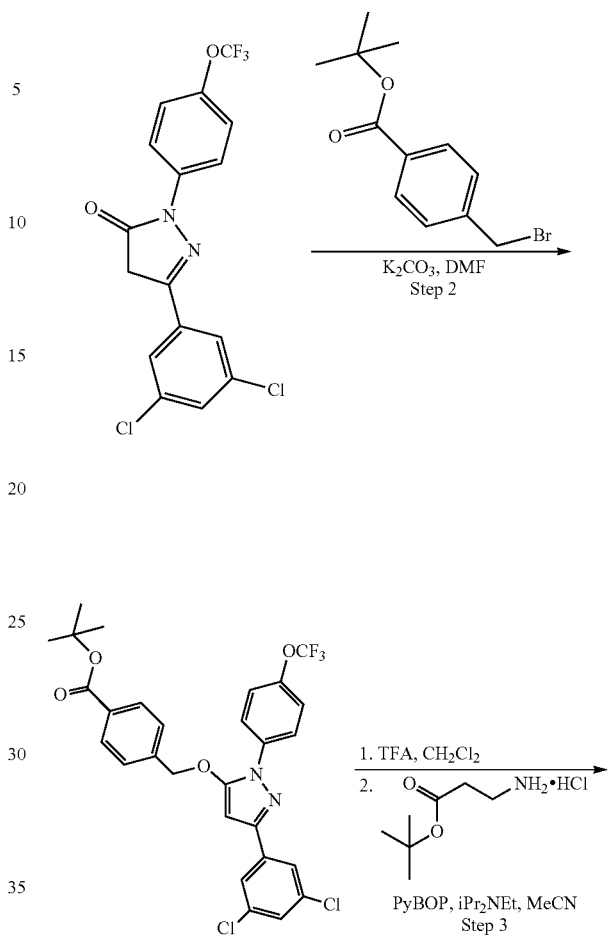

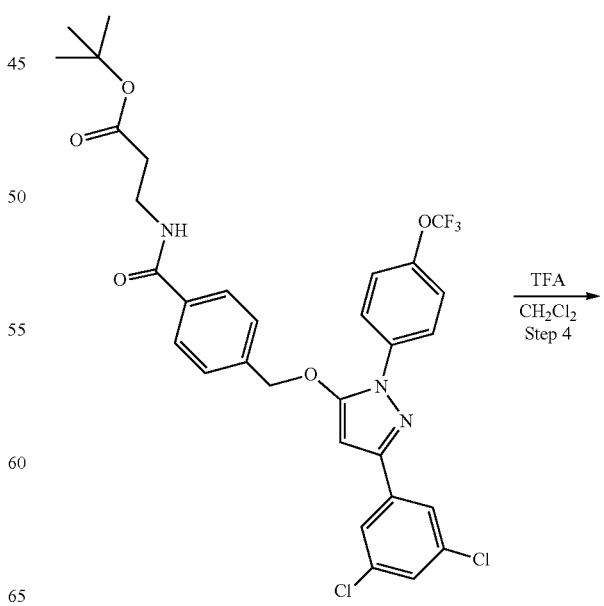

103

-continued

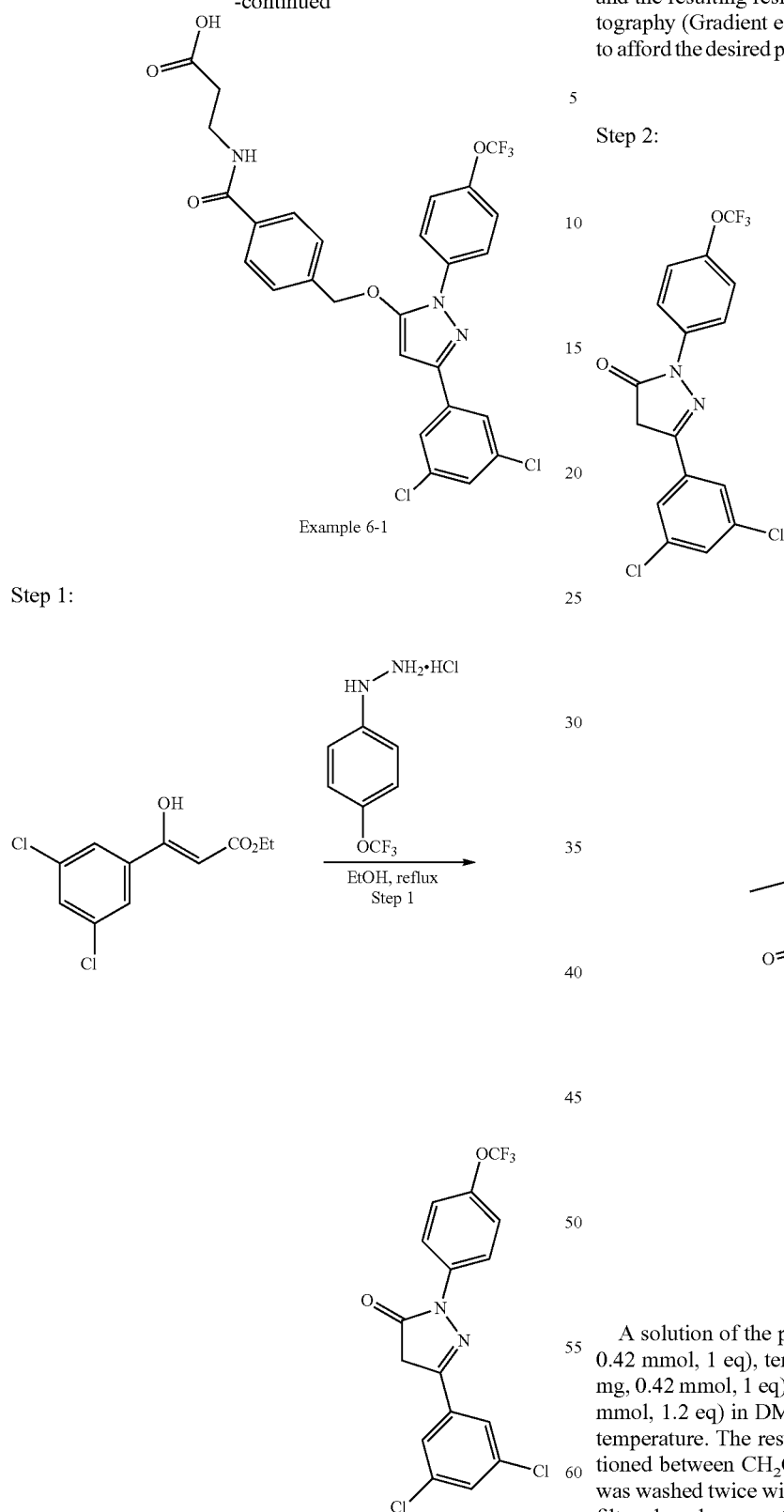

Example 6-1

Step 1:

A solution of the ketoester (206 mg, 0.79 mmol, 1 eq) and (4-(trifluoromethoxy)phenyl)hydrazine hydrochloride (180 mg, 0.79 mmol, 1 eq) in EtOH (3 mL) was heated 30 min at 50° C. then 3 h at reflux. The volatiles were removed in vacuo and the resulting residue was purified via silica gel chromatography (Gradient elution: 0% to 100% EtOAc in hexanes) to afford the desired pyrazolone (181 mg, 60%) as a clear film.

Step 2:

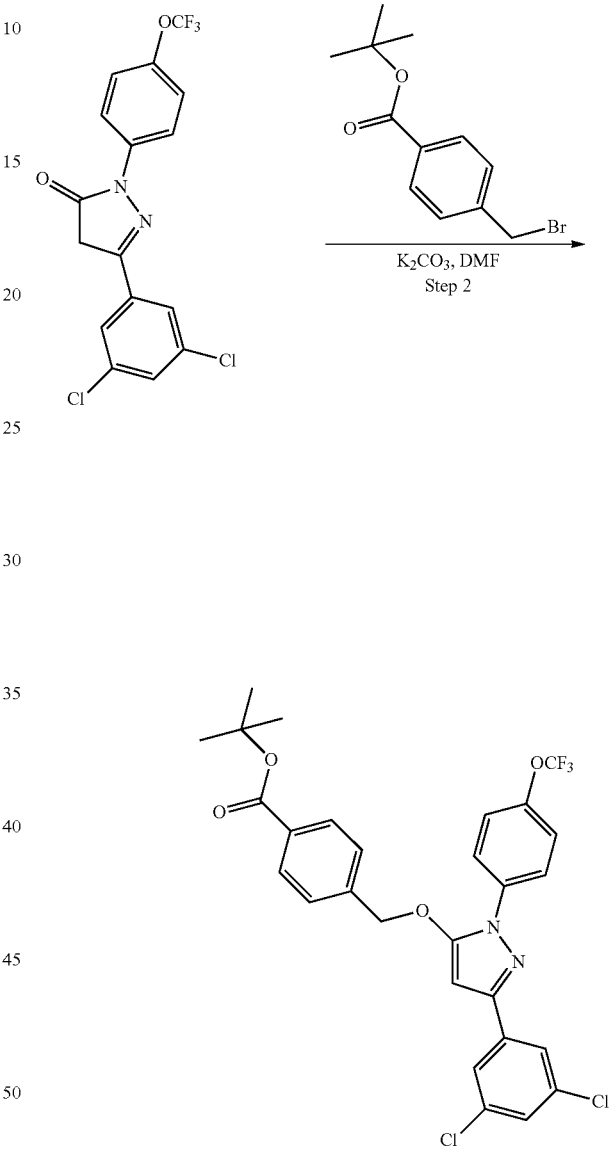

A solution of the pyrazolone prepared in Step 1 (165 mg, 0.42 mmol, 1 eq), tert-butyl 4-(bromomethyl)benzoate (114 mg, 0.42 mmol, 1 eq), and potassium carbonate (70 mg, 0.51 mmol, 1.2 eq) in DMF (5 mL) was stirred for 48 h at room temperature. The resulting reaction mixture was then partitioned between $CH_2Cl_2$ and dilute brine. The organic layer was washed twice with brine, dried over anhydrous $Na_2SO_4$, filtered, and evaporated to afford a crude dark oil. Silica gel chromatography of the crude product (Gradient elution: 0% to 30% EtOAc in hexanes) afforded an inseparable mixture of the desired product and a bis-benzylated product (107 mg) which was taken on to the next step without further purification.

Step 3:

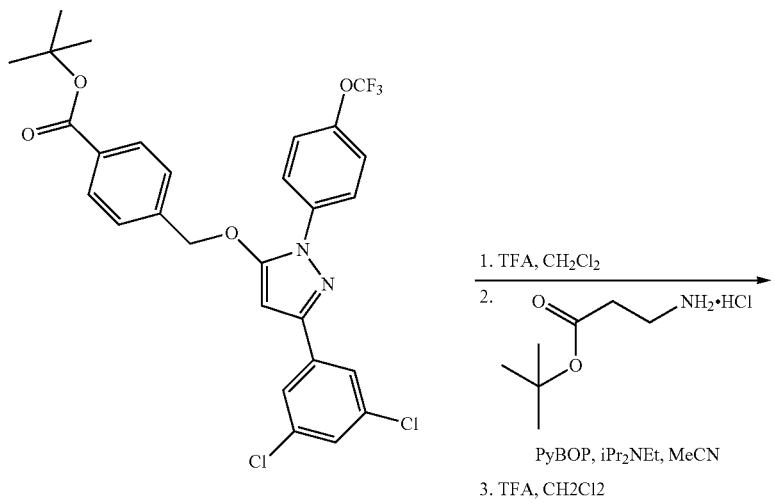

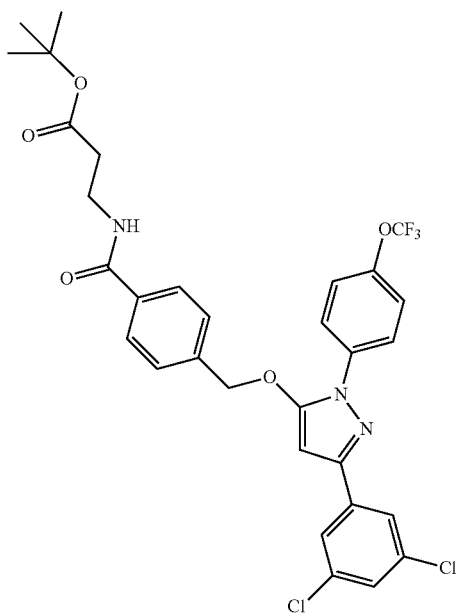

A solution of the tert-butyl ester prepared in Step 2 (107 mg, 0.18 mmol, 1 eq) in CH$_2$Cl$_2$ (5 mL) was treated with trifluoroacetic acid (3 mL) at room temperature. After stirring for 3 h, the volatiles were removed in vacuo. Diethyl ether was added to the residue and the solvent removed in vacuo. The crude material was combined with PyBOP (114 mg, 0.22 mmol, 1.2 eq), iPr$_2$NEt (94 µL, 0.54 mmol, 3 eq), and tert-butyl 3-aminopropanoate, hydrochloride salt (39 mg, 0.22 mmol, 1.2 eq) in CH$_2$Cl$_2$ (2 mL) and the resulting solution was stirred at room temperature for 16 h. The reaction mixture was partitioned between CH$_2$Cl$_2$ and dilute aqueous HCl. The aqueous layer was discarded and the organic layer was washed with brine and saturated aqueous NaHCO$_3$, dried over anhydrous Na$_2$SO$_4$, filtered and evaporated to afford a crude residue which was purified via silica gel chromatography (gradient elution: 0% to 100% EtOAc in hexanes) to afford the coupled product (67 mg, 25% combined yield over Steps 2 and 3) as a film.

Step 4:
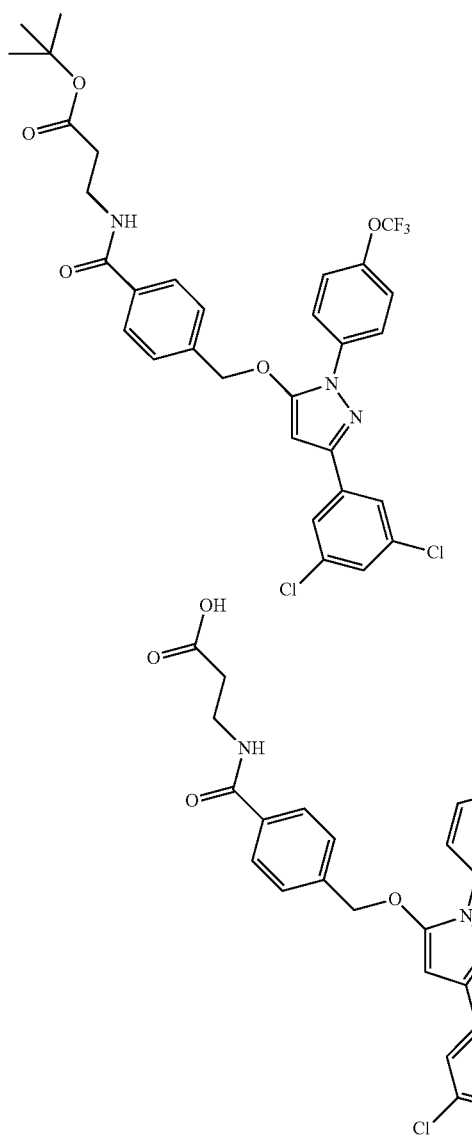
Example 6-1
The product from Step 3 (67 mg, 0.10 mmol, 1 eq) was dissolved in $CH_2Cl_2$ (3 mL) and treated with trifluoroacetic acid (1.5 mL). After stirring for 3 h, the volatiles were removed in vacuo. The crude material was dissolved in acetone and the resulting solution was filtered through a cotton plug. The filtrate was evaporated to afford Example 6-1 (57 mg, 97%) as a tan solid.
Scheme 7
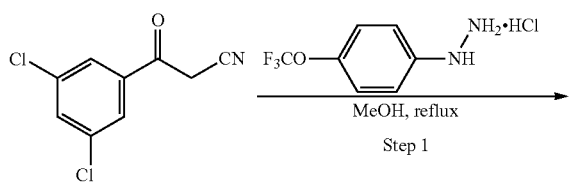
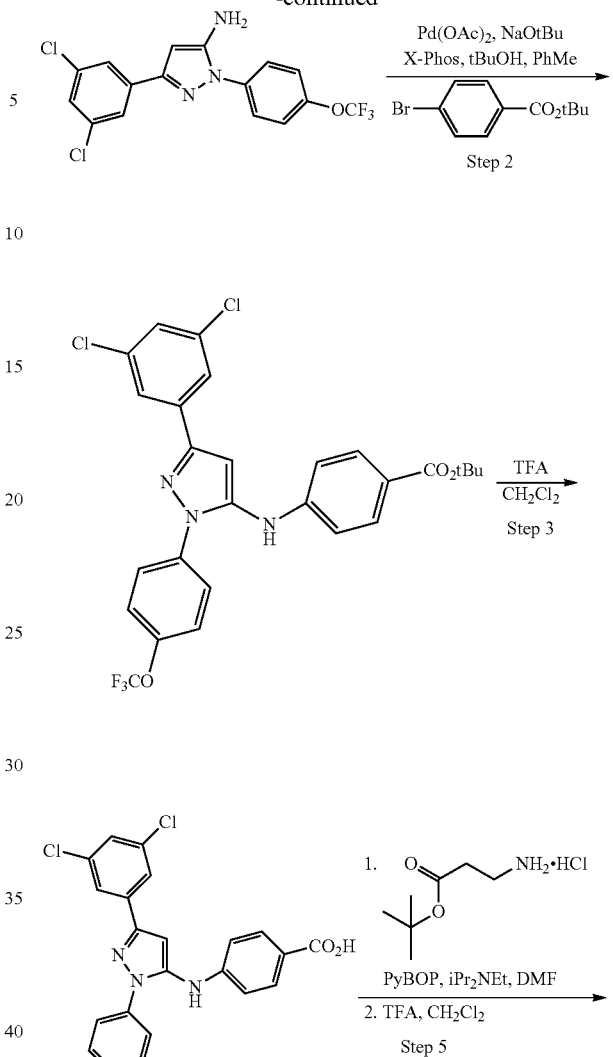
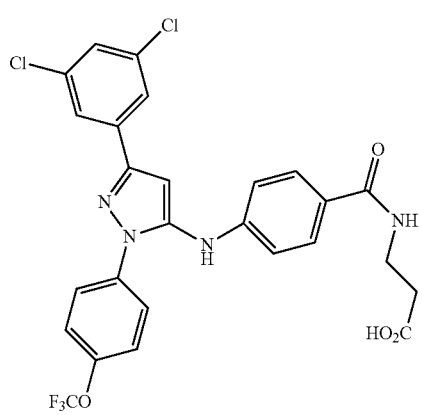
Example 7-1

Step 1:

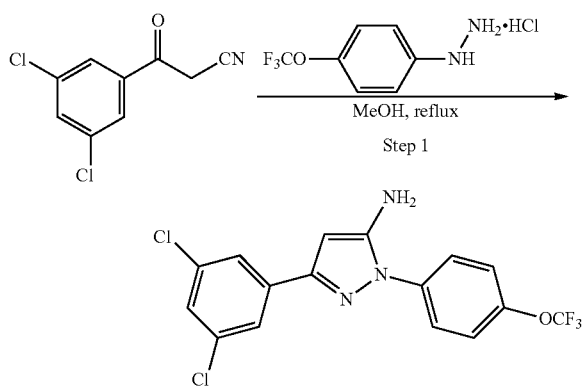

A solution of the cyanoketone (169 mg, 0.79 mmol, 1 eq) and (4-(trifluoromethoxy)phenyl)hydrazine hydrochloride (180 mg, 0.79 mmol, 1 eq) in MeOH (3 mL) was heated at reflux for 4 h. The reaction mixture was then cooled to room temperature and evaporated to afford a residue which was partitioned between $CH_2Cl_2$ and saturated aqueous $NaHCO_3$. The organic layer was saved and the aqueous layer extracted with $CH_2Cl_2$. The organic layers were combined and evaporated to afford a crude residue which was purified via silica gel chromatography (gradient elution: 0% to 50% EtOAc in hexanes) to afford the desired aminopyrazole product (135 mg, 44%) as a white crystalline solid.

Step 2:

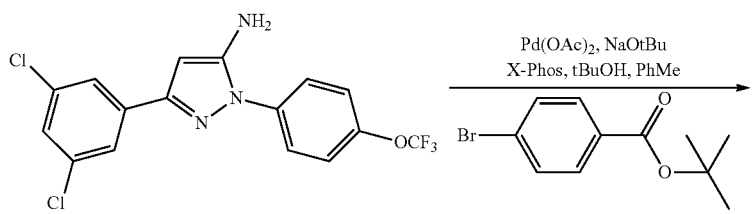

A solution of the product from Step 1 (64 mg, 0.16 mmol, 1 eq) in toluene (1 mL) and tert-BuOH (0.5 mL) in a 0.5-2 mL Biotage microwave vial was charged with tert-butyl 4-bromobenzoate (82 mg, 0.32 mmol, 2 eq), NaOt-Bu (31 mg, 0.32 mmol, 2 eq), Pd(OAc)₂ (4 mg, 0.016 mmol, 0.1 eq) and 2-(dicyclohexylphosphino)-2',4',6'-triisopropyl-1,1'-biphenyl (X-Phos, 8 mg, 0.016 mmol, 0.1 eq). The vial was sealed and subjected to microwave irradiation (Biotage, 130° C., 5 min, normal absorption). The crude reaction mixture was adsorbed onto silica gel and subjected to silica gel chromatography (gradient elution: 0% to 50% EtOAc in hexanes) to afford the desired product (33 mg, 37%) as a clear film.

Step 3:

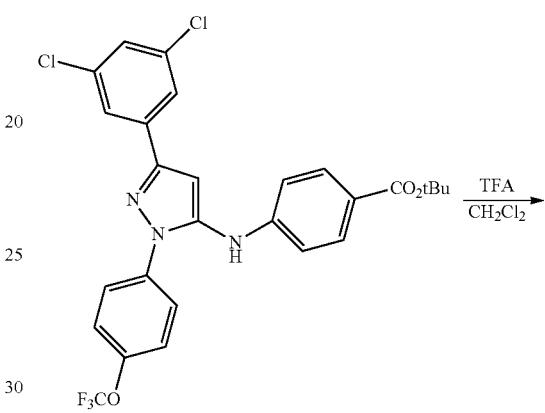

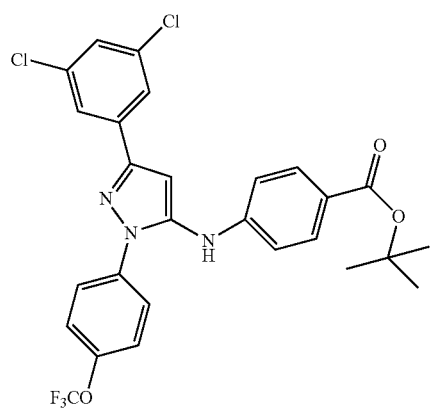

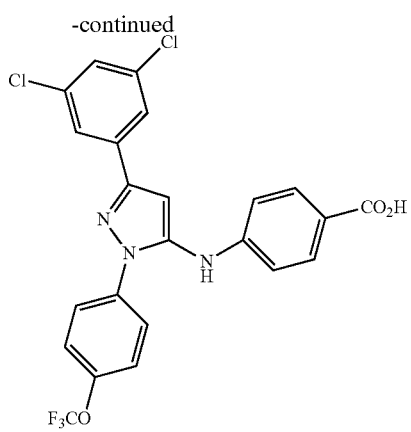

A solution of the product from Step 2 (33 mg, 0.058 mmol, 1 eq) in CH$_2$Cl$_2$ (3 mL) was treated with trifluoroacetic acid (1.5 mL) at room temperature. After stirring for 3 h, the volatiles were removed in vacuo to afford the desired product (29 mg, quant.) as a tan solid which was used without further purification.

Step 4:

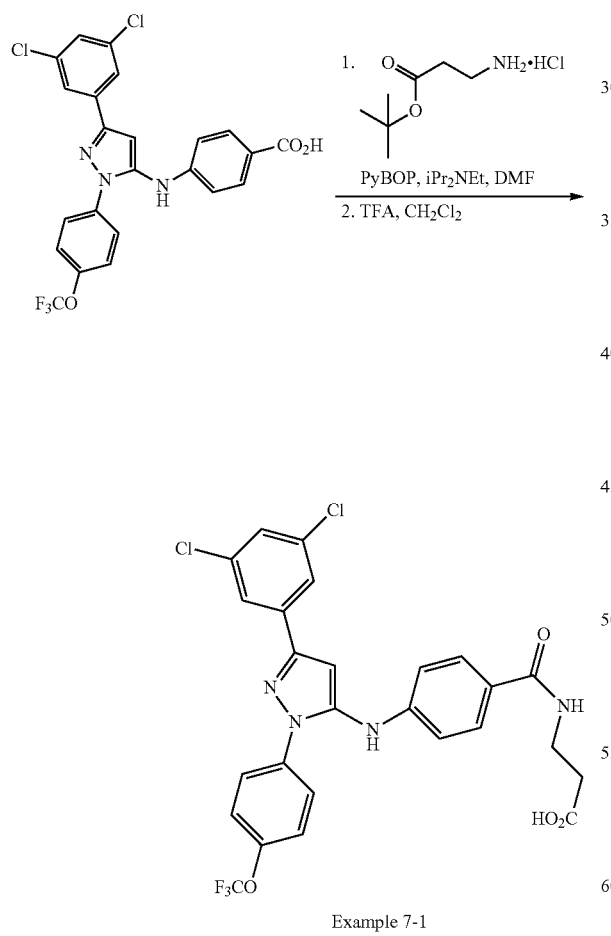

Example 7-1

A solution of the product from Step 3 (17 mg, 0.034 mmol, 1 eq), PyBOP (18 mg, 0.034 mmol, 1 eq), iPr$_2$NEt (18 μL, 0.10 mmol, 3 eq), and Pert-butyl 3-aminopropanoate, hydrochloride salt (6 mg, 0.034 mmol, 1 eq) in DMF (1 mL) was stirred at room temperature for 16 h. The reaction mixture was partitioned between CH$_2$Cl$_2$ and dilute aqueous HCl. The aqueous layer was discarded and the organic layer was washed with saturated aqueous NaHCO$_3$, dried over anhydrous Na$_2$SO$_4$, filtered and evaporated to afford a crude orange oil. The crude product was dissolved in CH$_2$Cl$_2$ (3 mL) and treated with trifluoroacetic acid (1.5 mL). After stirring for 2 h, the volatiles were removed in vacuo. The crude material was dissolved in methanol and subjected to semi-preparative C-18 Reversed Phase HPLC using the method described below. The major peak fractions were evaporated to afford Example 7-1 (9 mg, 45%) as a white solid.

Scheme 8

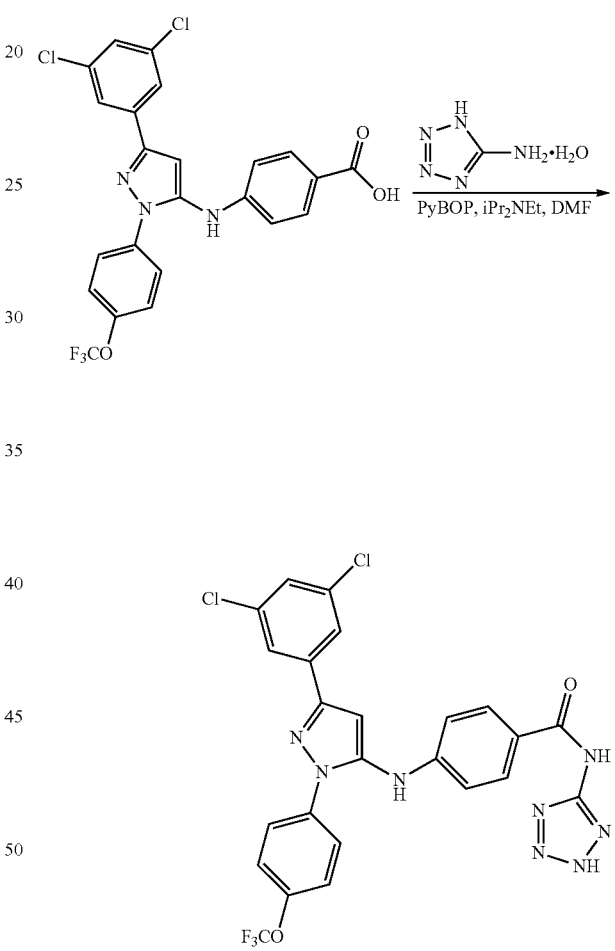

Example 8-1

The product from Scheme 7, Step 3 (22 mg, 0.044 mmol, 1 eq) was combined with aminotetrazole monohydrate (5 mg, 0.044 mmol, 1 eq), PyBOP (23 mg, 0.044 mmol, 1 eq), and iPr$_2$NEt (0.023 mL, 0.13 mmol, 3 eq) in DMF (2 mL) and stirred 72 h at room temperature. The reaction mixture was subjected to semi-preparative C-18 Reversed Phase HPLC (Method A). The major peak fractions were evaporated to afford an off-white solid. The material was then triturated with a 1:1 MeCN:H$_2$O mixture and dried to afford Example 8-1 (12 mg, 48%) as a tan solid.

Scheme 9
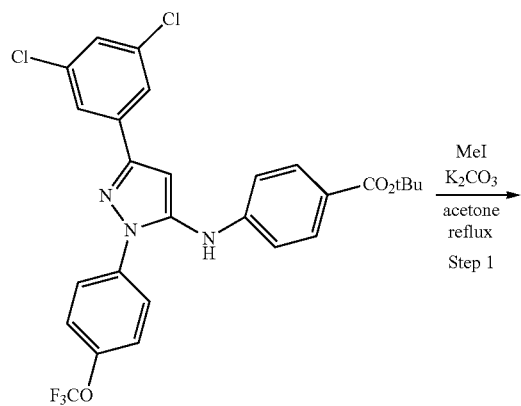
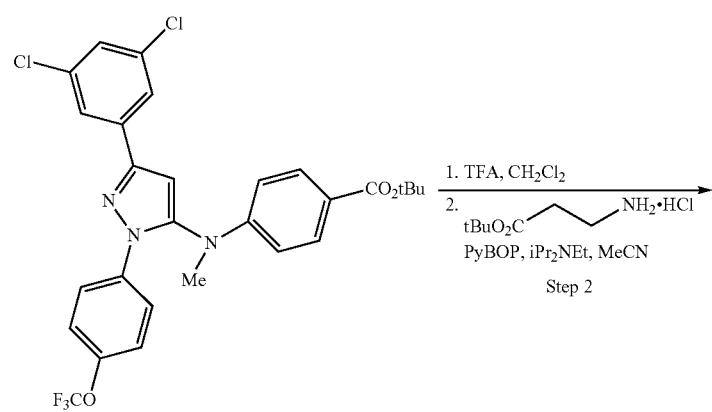
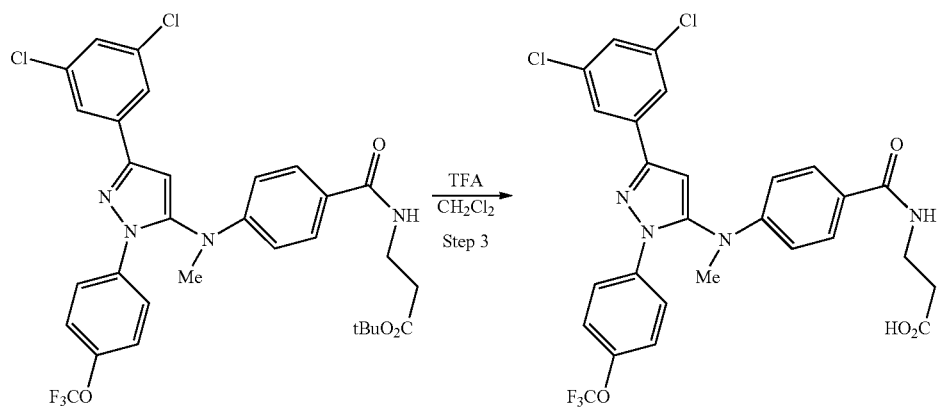
Example 9-1

Step 1:

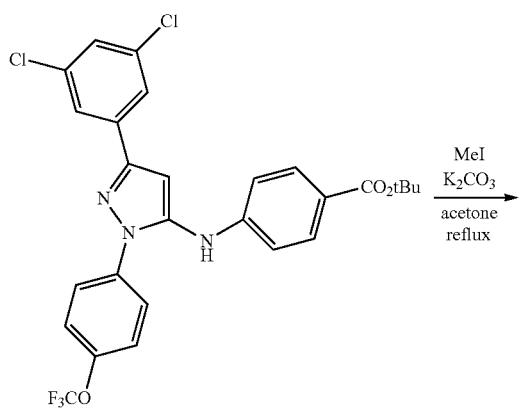

A solution of the material prepared in Scheme 7, Step 2 (100 mg, 0.18 mmol, 1 eq) in acetone (3 mL) was charged with methyl iodide (90 μL, 1.45 mmol, 8 eq) and potassium carbonate (27 mg, 0.20 mmol, 1.1 eq). The resulting heterogeneous mixture was heated in a 60° C. oil bath with stirring for 16 h. Additional amounts of methyl iodide (150 μL) and potassium carbonate (30 mg, 0.22 mmol, 1.2 eq) were added and the reaction was heated at 60° C. for 24 h more. The volatiles were removed in vacuo and the resulting residue purified via silica gel chromatography to afford the desired product (58 mg, 56%) as a clear film.

Step 2:

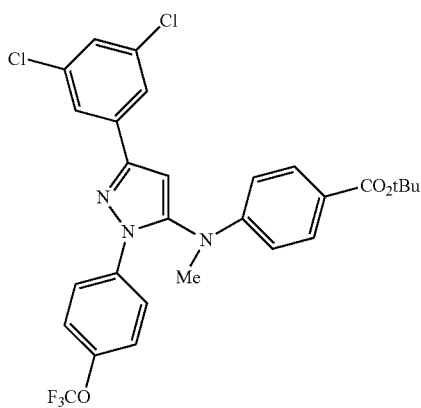

A solution of the product from Step 1 (58 mg, 0.10 mmol, 1 eq) in $CH_2Cl_2$ (3 mL) was treated with trifluoroacetic acid (1.5 mL). After stirring for 2 h, the volatiles were removed in vacuo to afford a crude oil. This oil was then dissolved in MeCN (2 mL) and the resulting solution was charged with PyBOP (57 mg, 0.11 mmol, 1.1 eq), $iPr_2NEt$ (52 μL, 0.30 mmol, 3 eq), and tert-butyl 3-aminopropanoate, hydrochloride salt (20 mg, 0.11 mmol, 1.1 eq). The resulting reaction mixture was stirred for 4 h, at which point the solvent was removed in vacuo to afford a crude residue which was purified via silica gel chromatography (gradient elution: 12% to 100% EtOAc in hexanes). The desired product (53 mg, 82%) was isolated as a viscous oil.

Step 3:

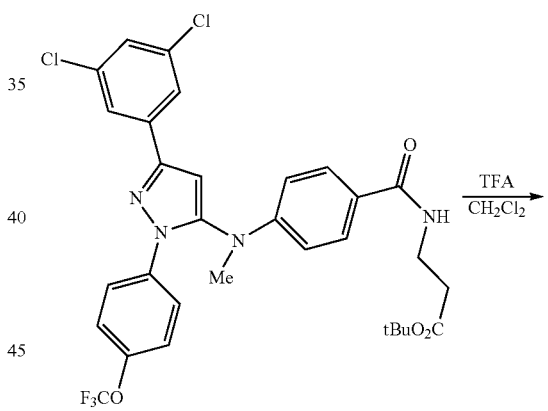

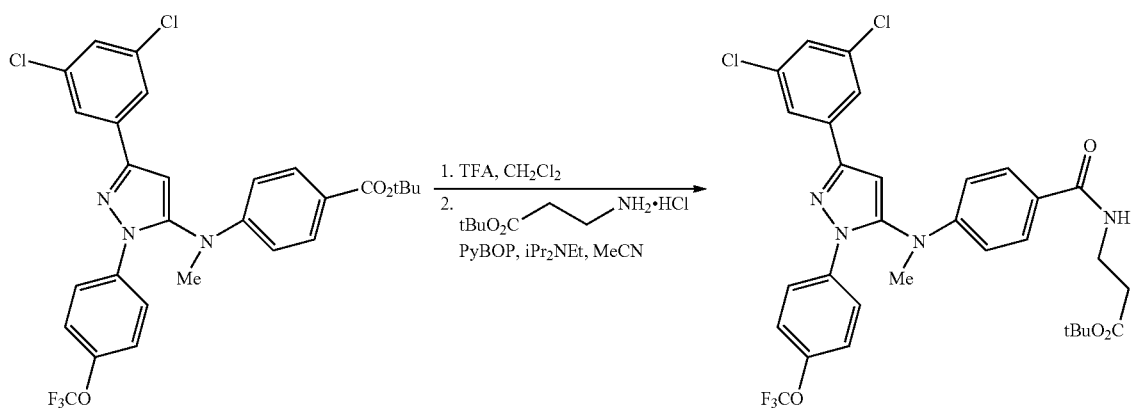

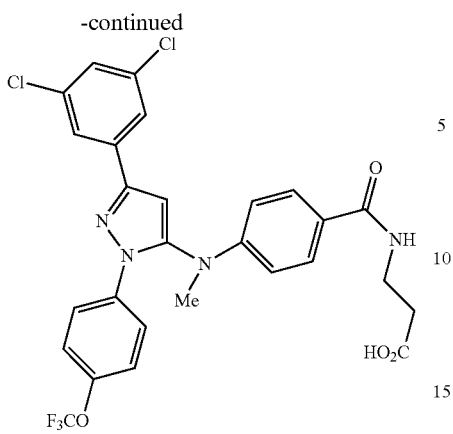

Example 9-1

The product from Step 2 (53 mg, 0.082 mmol, 1 eq) was dissolved in CH$_2$Cl$_2$ (3 mL) and treated with trifluoroacetic acid (1.5 mL). After stirring at room temperature for 3 h, the volatiles were removed in vacuo to afford an oil. The crude product was dissolved in Et$_2$O (5 mL) and allowed to stand 2 h at room temperature. White crystals formed which were collected by filtration, washed with Et$_2$O, and dried to afford Example 9-1 (19 mg, 39%).

Scheme 10

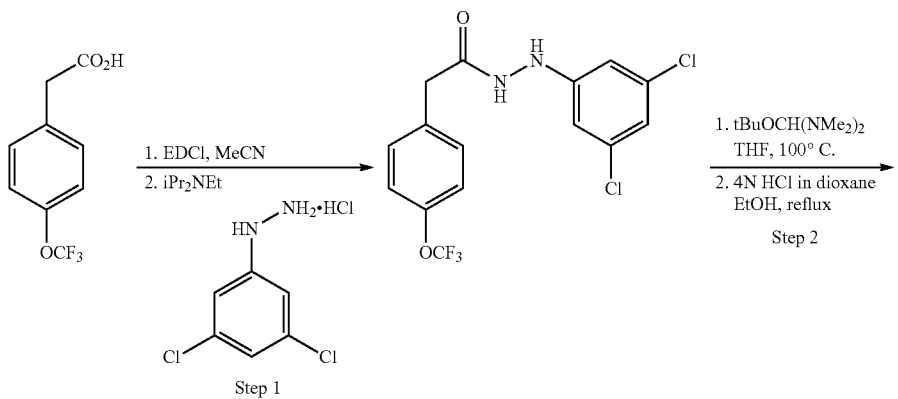

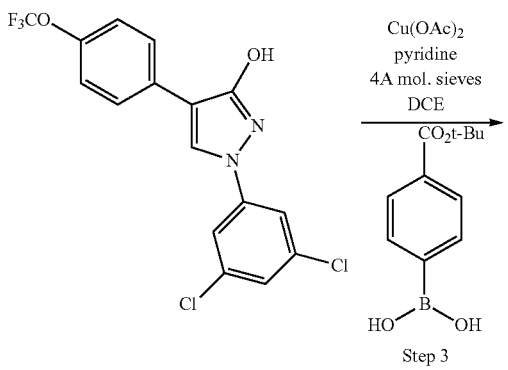

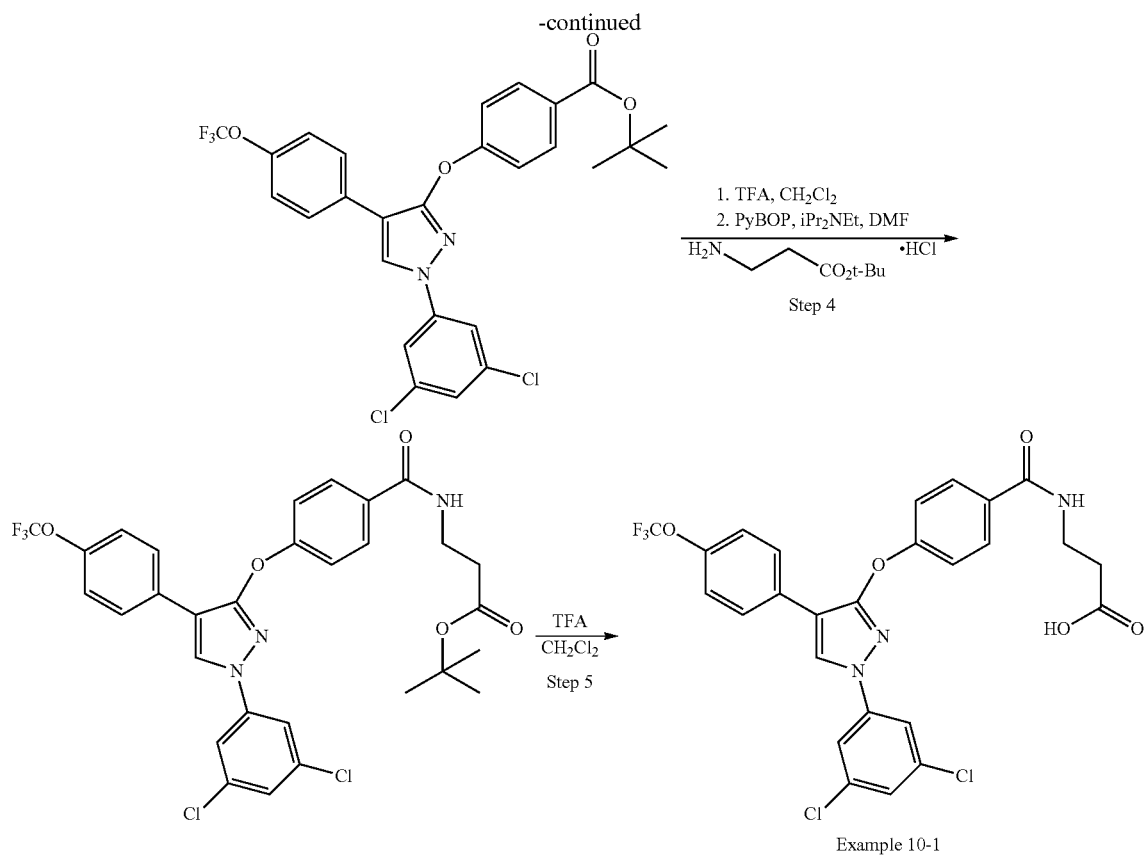

Example 10-1

Step 1:

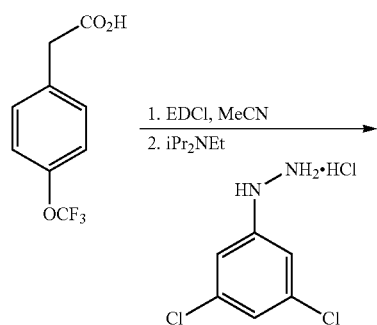

A solution of 4-trifluoromethoxy-phenylacetic acid (1.76 g, 8.0 mmol, 1 eq), EDCI (1.6 g, 8.4 mmol, 1.05 eq), and HOBt.H₂O (1.3 g, 8.4 mmol, 1.05 eq) in MeCN (40 mL) was stirred 16 h at room temperature. 3,5-Dichloro-phenylhydrazine hydrochloride (1.71 g, 8.0 mmol, 1 eq) was added to the reaction mixture and the reaction flask was immersed in an oil bath (60° C.). While stirring at 60° C. iPr₂NEt (2.8 mL, 16.0 mmol, 2 eq) was added dropwise over 1 h. The reaction mixture was poured into water (200 mL) with vigorous stirring. After stirring for 1 h at room temperature, the resulting solids were collected via filtration and washed with water. The solid was slurried with Et₂O then concentrated in vacuo to afford the desired product as a tan solid (2.67 g, 88%).

Step 2:

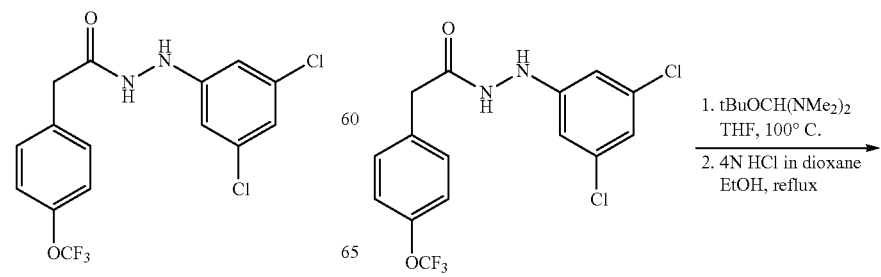

-continued

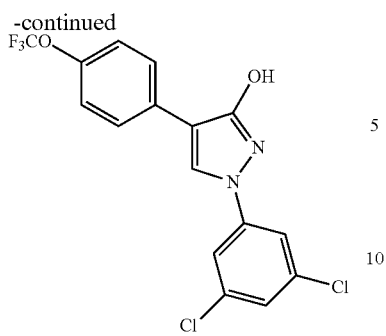

A solution of the product from Step 1 (2.67 g, 7.04 mmol, 1 eq) and tert-butoxy bis(dimethylamino)methane (2.7 mL, 14.1 mmol, 2 eq) in THF (40 mL) was purged with nitrogen and sealed in a glass reaction vessel. The reaction was heated behind a blast shield at 100° C. for 16 h. After cooling the reaction vessel, it was slowly opened and subsequently charged with EtOH (80 mL) and 4N HCl in dioxane (3.7 mL). While uncapped, the reaction vessel was warmed to 60° C., purged with nitrogen, sealed and heated 2 h at 100° C. The reaction vessel was cooled to room temperature, uncapped, and its contents were added to water (400 mL) with stirring. An oily orange solid resulted which was collected via filtration, washed with water, then dried. Methylene chloride was added to the solid, and the resulting suspension was sonicated. The resulting solids were removed via filtration and washed with cold methylene chloride to afford the desired product (1.06 g, 41%) as a white solid.

Step 3:

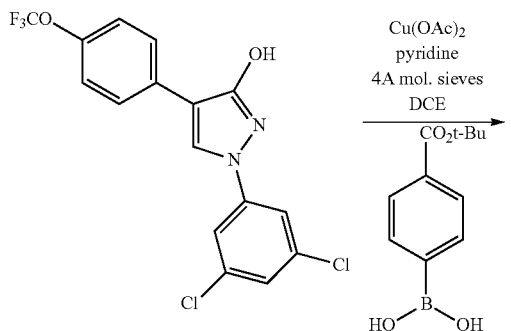

-continued

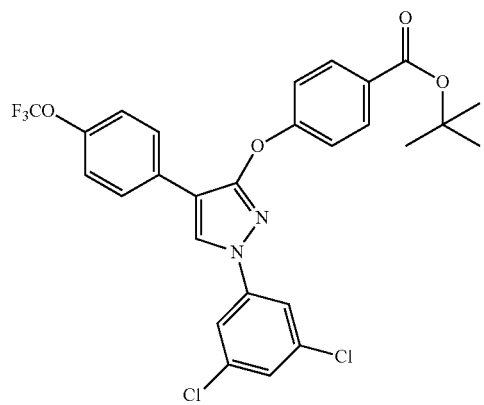

The product from Step 2 (167 mg, 0.43 mmol, 1 eq), 4-(tert-butoxycarbonyl)phenylboronic acid (247 mg, 1.11 mmol, 2.6 eq), Cu(OAc)$_2$ (117 mg, 0.64 mmol, 1.5 eq), pyridine (71 pt, 0.88 mmol, 2.05 eq), and 4 Å molecular sieves (284 mg) were combined in DCE (13 mL). The resulting suspension was stirred at room temperature open to air for 16 h. The reaction was concentrated to dryness and the residue purified via silica gel chromatography (gradient elution: 0% to 30% EtOAc in hexanes) to afford a mixture of the desired product and an inseparable impurity (230 mg) as a clear film. This material was used in the next step without further purification.

Step 4:

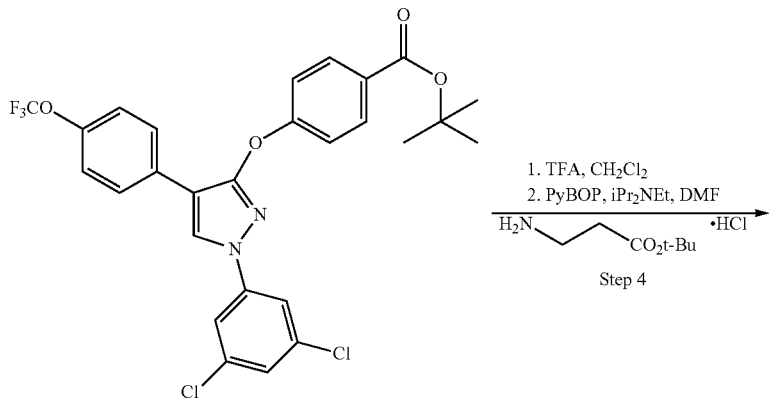

-continued

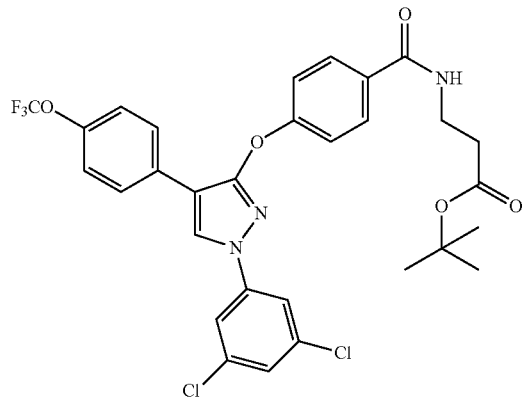

A solution of the product from Step 3 (58 mg, 0.10 mmol, 1 eq) in CH$_2$Cl$_2$ (3 mL) was treated with trifluoroacetic acid (1.5 mL) at room temperature. After stirring for 3 h, the volatiles were removed in vacuo The crude material was combined with PyBOP (78 mg, 0.15 mmol, 1.5 eq), iPr$_2$NEt (52 µL, 0.30 mmol, 3 eq), and tert-butyl 3-aminopropanoate, hydrochloride salt (27 mg, 0.15 mmol, 1.5 eq) in CH$_2$Cl$_2$ (3 mL) and the resulting solution was stirred at room temperature for 16 h. The reaction mixture was partitioned between CH$_2$Cl$_2$ and dilute aqueous HCl. The aqueous layer was discarded and the organic layer was washed with brine and saturated aqueous NaHCO$_3$. Evaporation of the organic layer afforded a residue which was purified via silica gel chromatography (gradient elution: 0% to 75% EtOAc in hexanes) to afford the desired product (33 mg, 52%) as a film.

Step 5:

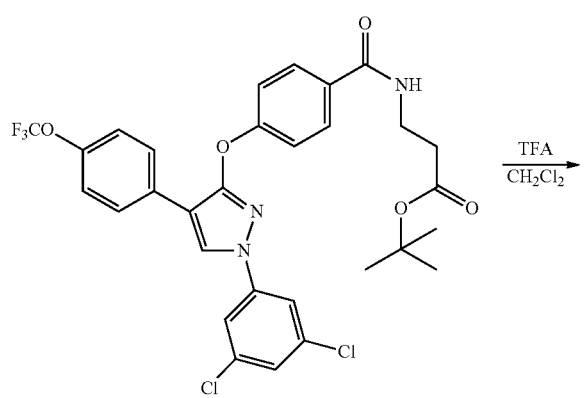

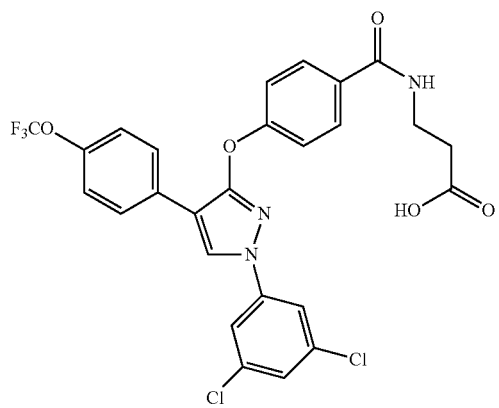

Example 10-1

A solution of the benzamide prepared in Step 4 (33 mg, 0.052 mmol) in CH$_2$Cl$_2$ (3 mL) was treated with trifluoroacetic acid (1.5 mL). After stirring for 3 h, the volatiles were removed in vacuo. The crude material was dissolved in CH$_2$Cl$_2$ (2 mL) and sonicated. The resulting precipitate was collected via filtration and washed with CH$_2$Cl$_2$ to afford Example 10-1 (23 mg, 77%) as a white solid.

TABLE 4
Using the conditions described in Scheme 10, and the requisite arylacetic acid and phenyl hydrazine hydrochloride salt, the following compound was prepared:
| Arylacetic Acid | Phenyl Hydrazine Hydrochloride | Example Number | Structure |
|---|---|---|---|
| | | 10-2 | |
| | | 10-3 | |
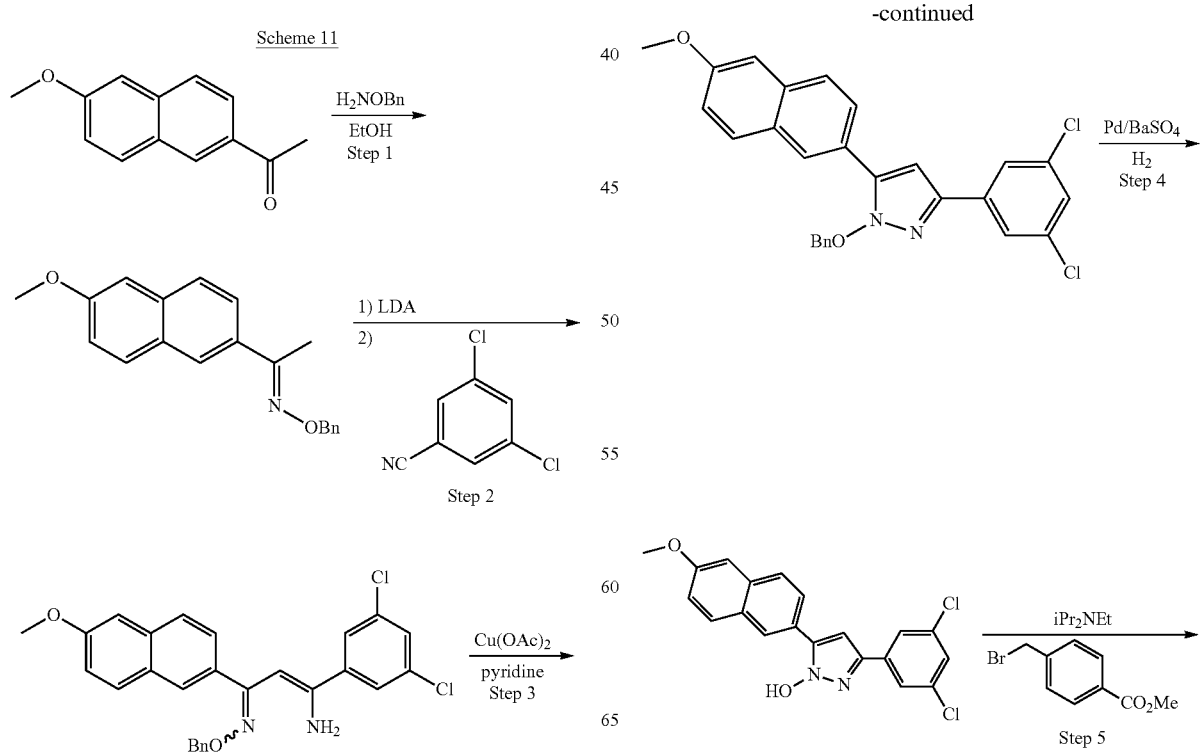

-continued

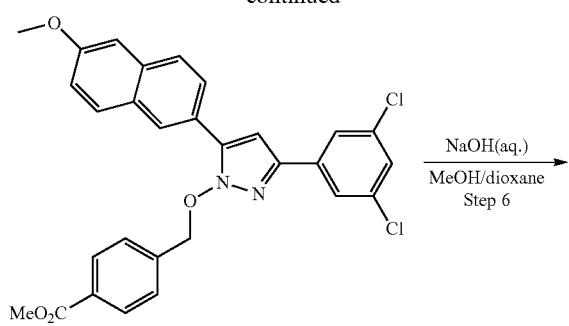

NaOH(aq.)
MeOH/dioxane
Step 6

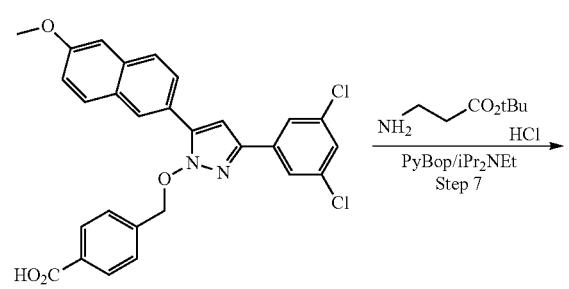

$NH_2$ ~~~ $CO_2tBu$
HCl
PyBop/iPr$_2$NEt
Step 7

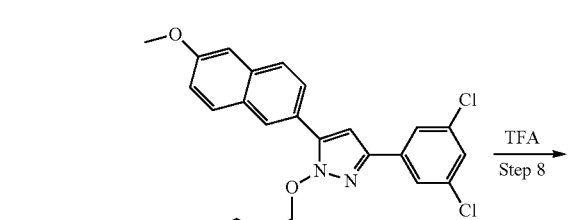

TFA
Step 8

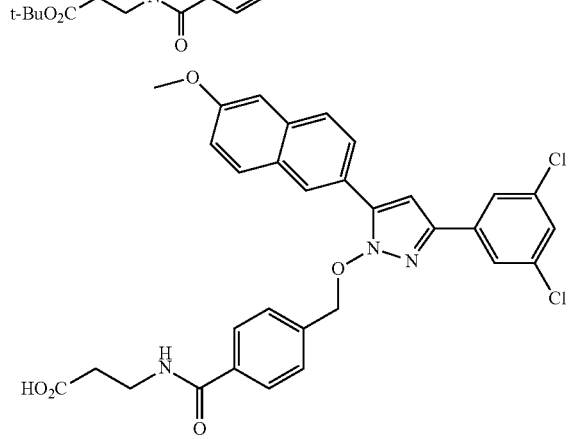

Example 11-1

Step 1:

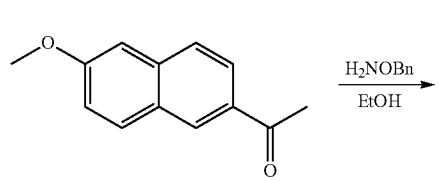

H$_2$NOBn
EtOH

-continued

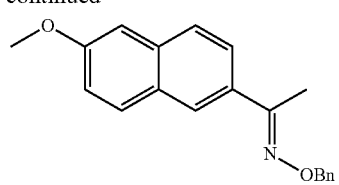

The acetophenone (5 grams, 25 mmol) and O-benzyl hydroxylamine (3.1 g, 25 mmol) were taken up in EtOH (60 mL), and the resulting solution heated at 90° C. for 2 days. The solution was cooled, and hexanes was added to induce crystallization. The solid was recrystallized from EtOH which provided 3.66 g (48%) of the oxime as a white solid.

Step 2:

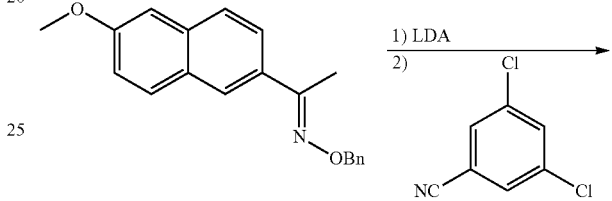

1) LDA
2)

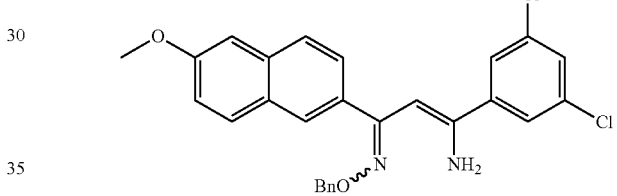

Di-isopropyl amine (2.2 mL) was taken up in THF (15 mL) and cooled to 0° C. N-Butyllithium (5.8 mL of a 2.5 M solution in hexanes) was added dropwise to the solution at 0° C. The LDA/THF solution was stirred at 0° C. for 0.5 h. The solution was cooled to −78° C., and the oxime (3.66 g, 12 mmol) was added as a solution in THF (70 mL) at that temperature. The resulting orange solution was stirred at −78° C. for 2.5 h. The aryl cyanide (2.06 g, 12 mmol) was added as a solution in THF (15 mL) to the solution at −78° C. The resulting solution was stirred at −78° C. for 2.5 h. The solution was poured into a sat. NH$_4$Cl solution. The mixture was extracted with EtOAc. The combined organic layers were washed with brine and dried (MgSO$_4$). Filtration and concentration gave a brown oil. The residue was purified via gradient flash chromatography (0-15% EtOAc in hexanes, SiO$_2$) which furnished 4.26 g (74%) of the ene-amino-oxime as a yellow gum.

Step 3:

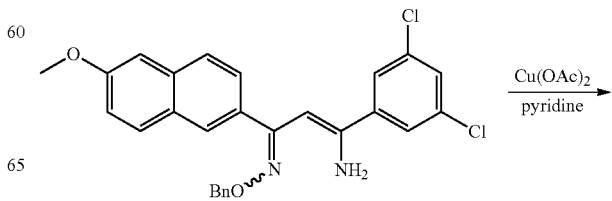

Cu(OAc)$_2$
pyridine

129
-continued

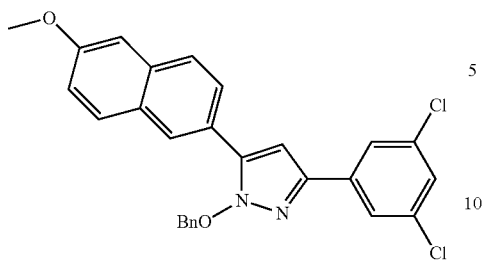

The ene-amino-oxime (3.92 g, 8.2 mmol) and Cu(OAc)₂ (1.8 g, 9.9 mmol) were taken up in pyridine (20 mL), and the solution was heated at 95° C. for 2.5 h. The solution was cooled and partitioned between EtOAc and 10% NH₄OH. The aqueous layer was extracted with EtOAc. The combined organic layers were washed with brine and dried (MgSO₄). Filtration and concentration gave a brown semi-solid. The residue was triturated with CH₂Cl₂/hexanes which provided 1.62 g (42%) of the benzyloxy-pyrazole as an off-white solid.

Step 4:

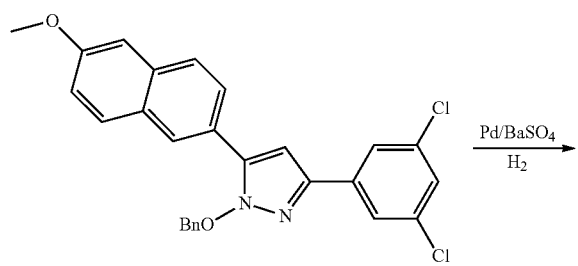

130
-continued

The benzyloxy-pyrazole (700 mg, 1.47 mmol) and Pd/BaSO₄ (200 mg) were taken up in 1/1 CH₂Cl₂/MeOH (80 mL), and stirred at 25° C. under 1 atm H₂ for 2.5 h. The mixture was filtered through Celite. The solution was concentrated which provided 540 mg (95%) of the N-hydroxy pyrazole as a white solid.

Step 5:

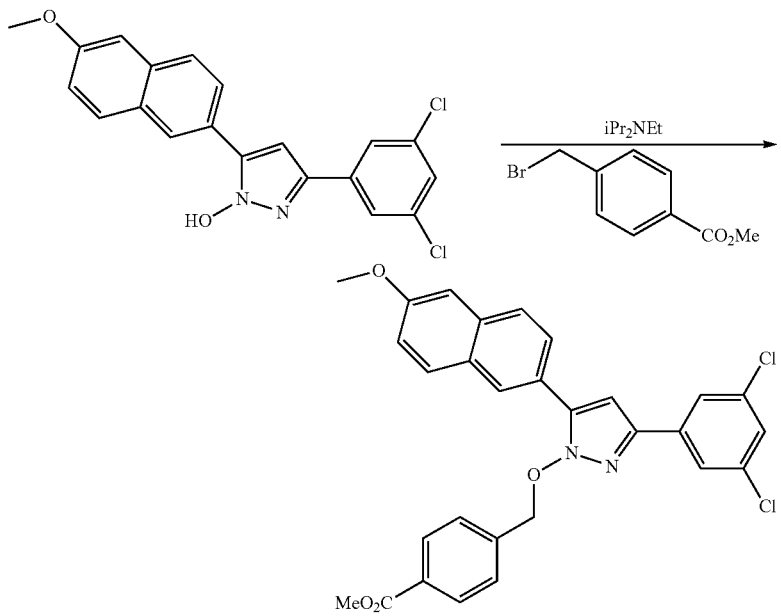

The N-hydroxy pyrazole (240 mg, 0.62 mmol), iPr₂NEt (0.22 mL), and the benzyl bromide (142 mg, 0.62 mmol) were taken up in CH₂Cl₂ (15 mL), and the resulting solution was stirred at 25° C. for 3.5 h. The solution was diluted with CH₂Cl₂ and washed with sat. NaHCO₃(aq.). The aqueous layer was extracted with CH₂Cl₂. The combined organic layers were dried (MgSO₄), filtered, and concentrated which furnished the methyl benzoate. This material was used directly in the next step without further purification.

Step 6:

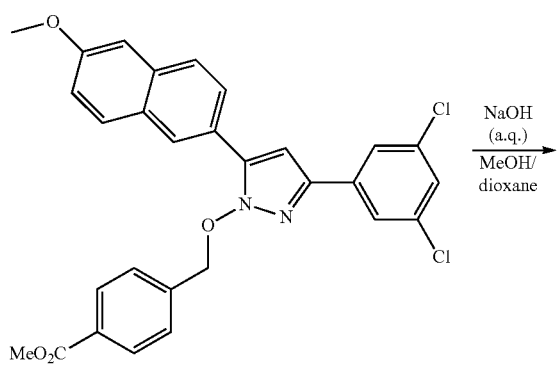

The crude methyl benzoate from Step 5 was taken up in MeOH/dioxane (1/1, 50 mL). Sodium hydroxide (600 mg) in water (5 mL) was added, and the resulting solution was stirred at 25° C. for 18 h. The solution was concentrated, and the residue was partitioned between EtOAc and 1 M HCl (aq.). The aqueous layer was extracted with EtOAc. The combined organic layers were washed with brine and dried (MgSO$_4$). Filtration and concentration provided 91% (327 mg) of the acid as a yellow solid.

Step 7:

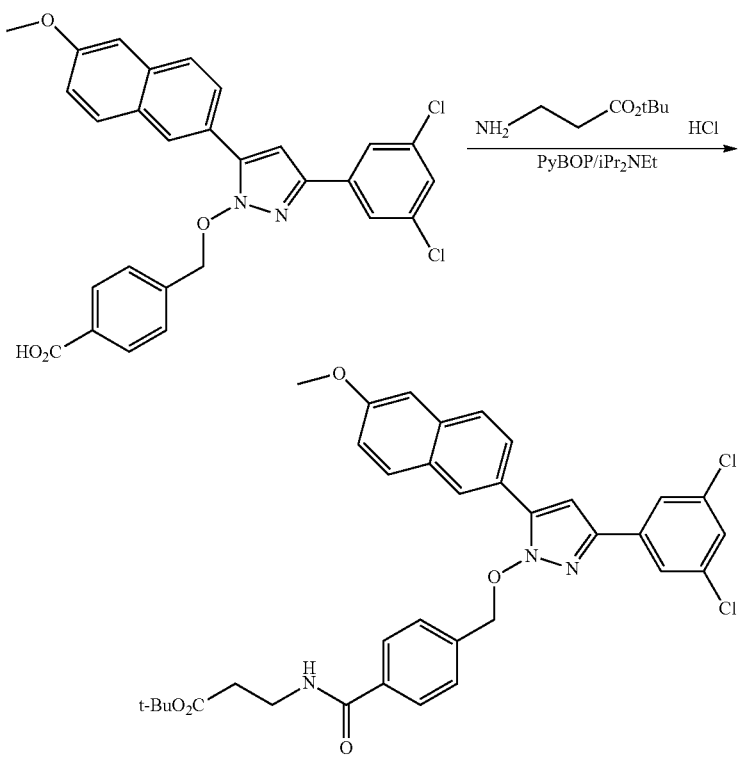

-continued

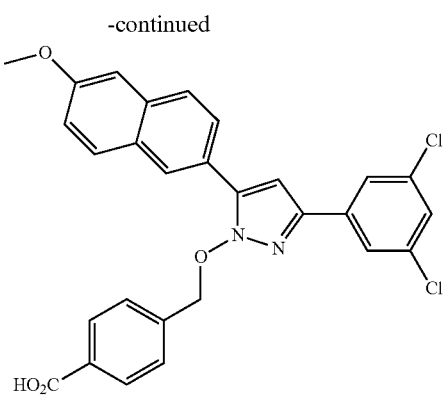

The acid (100 mg, 0.19 mmol), β-alanine tert-Butyl ester HCl (70 mg, 0.39 mmol), PyBOP (120 mg, 0.23 mmol), and iPr$_2$NEt (0.13 mL) were taken up in DMF (2 mL), and the resulting solution was stirred at 25° C. for 18 h. The solution was partitioned between EtOAc and sat. NaHCO$_3$ (aq.). The aqueous layer was extracted with EtOAc. The combined organic layers were washed with brine and dried (MgSO$_4$). Filtration and concentration gave a yellow oil. Purification via gradient flash chromatography (0-25% EtOAc in hexanes, SiO$_2$) gave a white solid. The solid was further purified via thin-layer preparative chromatography (2/1 hexanes/EtOAc, SiO$_2$) which gave 87 mg (70%) of the tert-Butyl ester as a white solid.

Step 8:

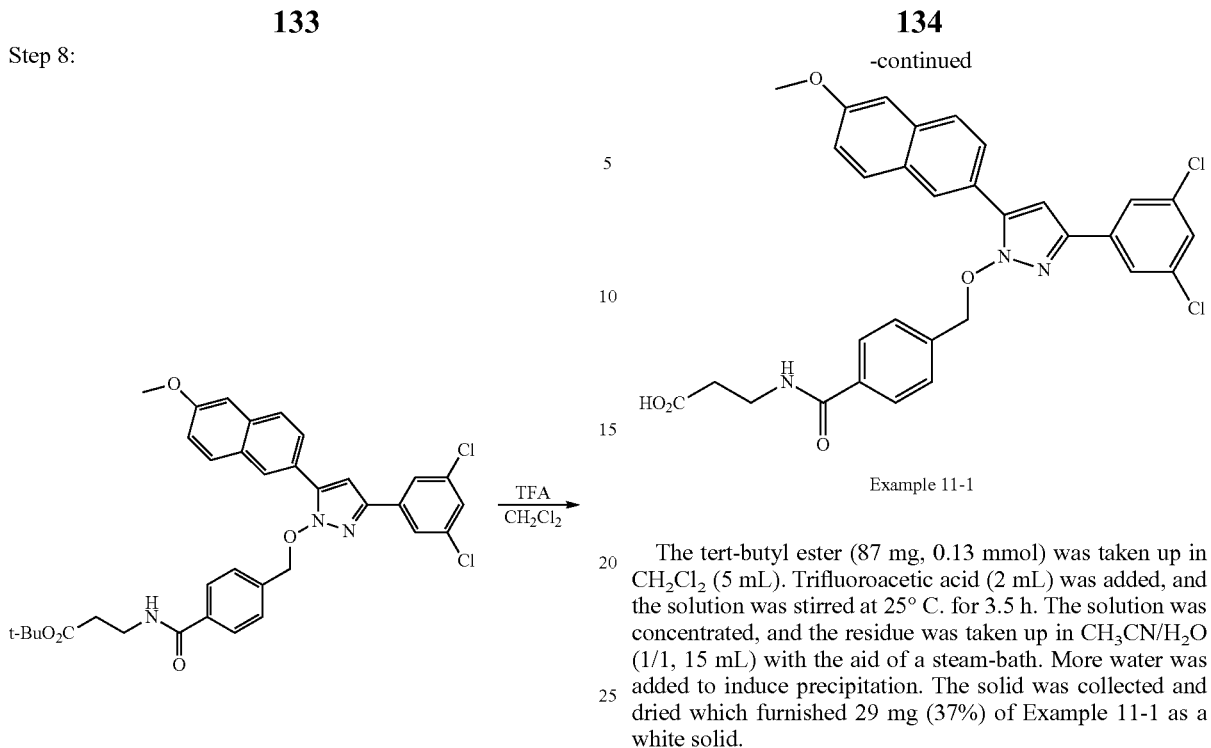

Example 11-1

The tert-butyl ester (87 mg, 0.13 mmol) was taken up in CH$_2$Cl$_2$ (5 mL). Trifluoroacetic acid (2 mL) was added, and the solution was stirred at 25° C. for 3.5 h. The solution was concentrated, and the residue was taken up in CH$_3$CN/H$_2$O (1/1, 15 mL) with the aid of a steam-bath. More water was added to induce precipitation. The solid was collected and dried which furnished 29 mg (37%) of Example 11-1 as a white solid.

Scheme 12

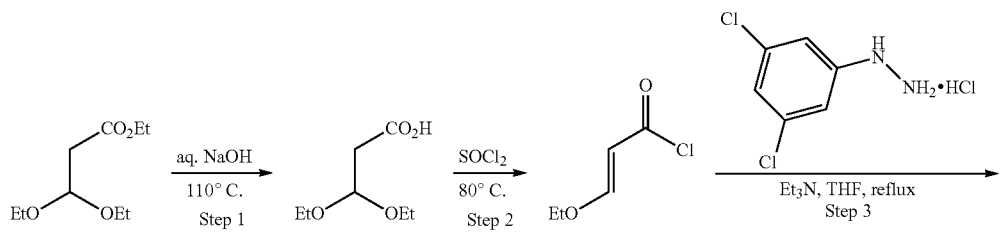

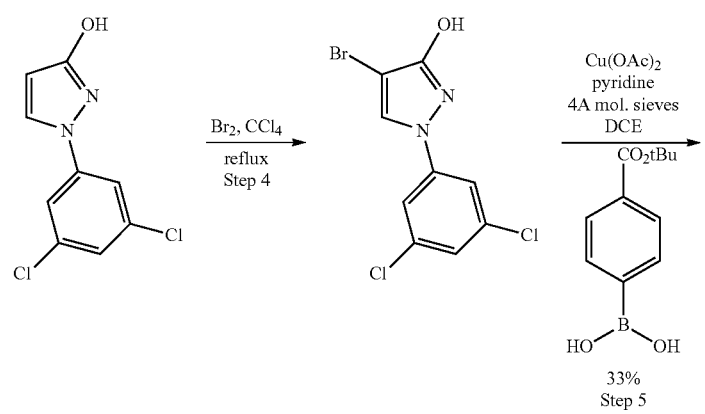

-continued

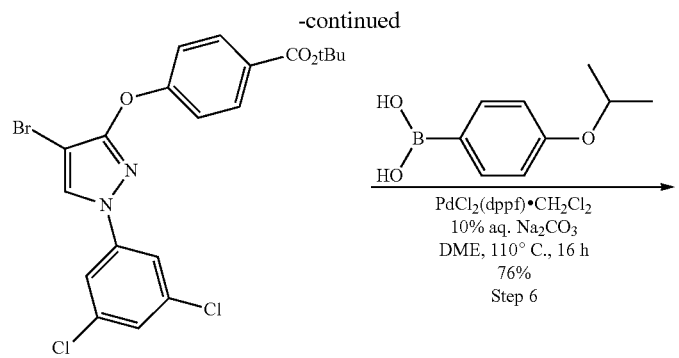

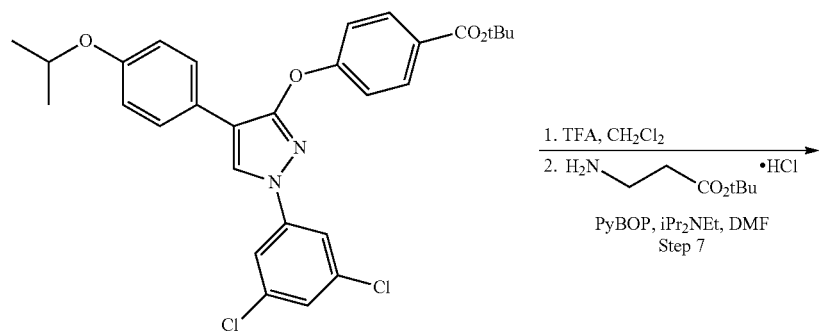

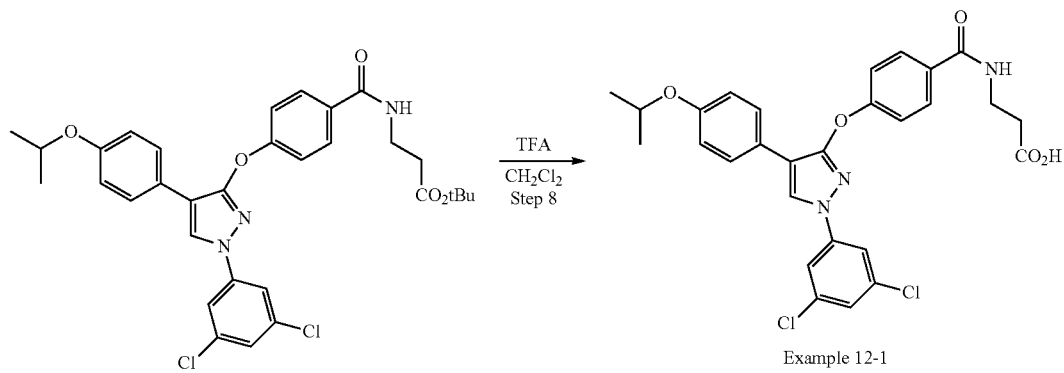

Example 12-1

Step 1:

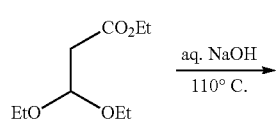

A solution of ethyl 3,3-diethoxypropanoate (4.2 g, 22.0 mmol, 1 eq) and NaOH (1.1 g, 28 mmol, 1.3 eq) in water (8 mL) was heated in a 110° C. oil bath for 1.25 h. The reaction was then cooled to 0° C. and was stirred with concentrated HCl (2.3 mL) and EtOAc (20 mL). The organic layer was saved, and the aqueous layer was extracted with $CH_2Cl_2$. The combined organic layers were dried over $MgSO_4$, filtered, and evaporated to afford 3,3-diethoxypropanoic acid (3.41 g, 96% yield) as an orange oil, which was used in the next step without any further purification.

Step 2:

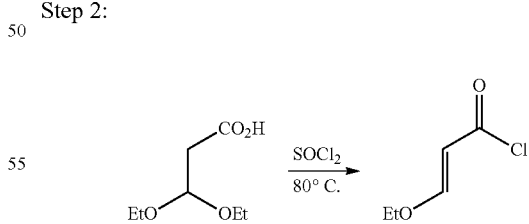

Thionyl chloride (7 mL, 96 mmol, 4.6 eq) was added dropwise to 3,3-diethoxypropanoic acid (3.41 g, 21 mmol, 1 eq) at room temperature. After the gas evolution ceased, the reaction was heated to 80° C. and kept there for 125 h. The reaction was then cooled to room temperature and concentrated to afford (E)-3-ethoxyacryloyl chloride (2.76 g, 98% yield). This crude material was used in the next step without further purification.

Step 3:

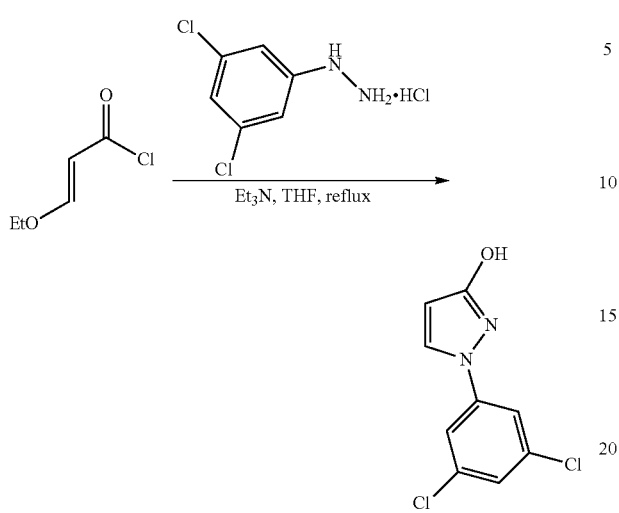

A solution of (E)-3-ethoxyacryloyl chloride (2.76 g, 20.5 mmol, 1 eq), 3,5-dichlorophenylhydrazine hydrochloride (4.82 g, 22.6 mmol, 1.1 eq) and triethylamine (7.2 mL, 51.3 mmol, 2.5 eq) in THF (40 mL) was heated 2 h at reflux. The reaction was then cooled to room temperature and stirred for 72 h. The reaction was then diluted with ethanol and evaporated to afford a crude residue which was then dissolved in 4N HCl in dioxane (20 mL). A precipitate slowly formed, and after stirring 3 h at room temperature, the reaction was concentrated and purified via silica gel chromatography (gradient elution, 0 to 50% EtOAc in hexanes) to afford a mostly pure material. This material was suspended in acetone (5 mL) and hexanes (30 mL). The resulting precipitate was collected via filtration and washed with 6:1 hexanes:acetone to afford the desired product (680 mg) as a yellow solid. The mother liquor was concentrated and subjected to silica gel chromatography (gradient elution, 0 to 50% EtOAc in hexanes) to afford an additional amount of pure product (1.3 g)

Step 4:

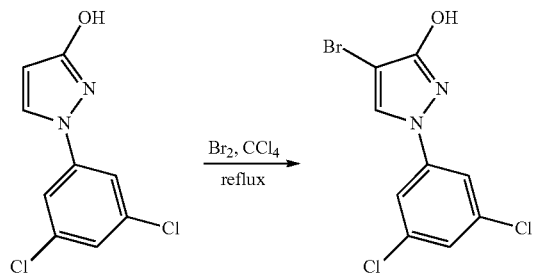 [SMILES: Oc1ccn(-c2cc(Cl)cc(Cl)c2)n1 ; Oc1nn(-c2cc(Cl)cc(Cl)c2)cc1Br]

Bromine (0.16 mL, 3.12 mmol, 1.05 eq) in $CCl_4$ (7.5 mL) was added to a suspension of the product from Step 3 (680 mg, 2.97 mmol, 1 eq) in $CCl_4$ (15 mL) at room temperature. The resulting mixture was stirred at room temperature for 2 h, and at reflux for 30 min. Upon cooling the reaction to room temperature, a precipitate formed, which was collected via flitration and washed with $CCl_4$ to afford the desired product (716 mg, 78% yield) as a tan solid.

Step 5:

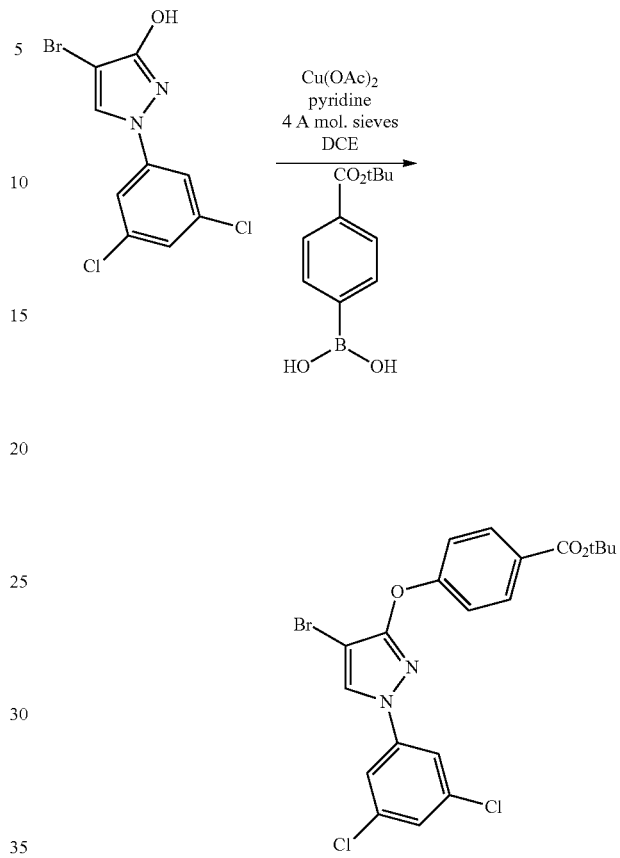

The brominated product from Step 4 (716 mg, 2.32 mmol, 1 eq), 4-(tert-butoxycarbonyl)phenylboronic acid (1.34 g, 6.03 mmol, 2.6 eq), $Cu(OAc)_2$ (632 mg, 3.48 mmol, 1.5 eq), powdered 4 angstrom molecular sieves (1.4 g) and pyridine (0.57 mL, 7.08 mmol, 3.05 eq) were combined in 1,2-dichloroethane (60 mL) and stirred 16 h at room temperature open to air. The reaction was concentrated to afford a residue which was subjected to silica gel chromatography (gradient elution, 0 to 15% EtOAc in hexanes) to afford the desired product with impurities present. The residue was dissolved in diethyl ether (20 mL) and heptane (10 mL) was added. The solution was concentrated to ~½ the volume with a stream of nitrogen and was left to stand. White crystals formed, which were collected via filtration, washed with heptane, and dried to afford the desired product (371 mg, 33%).

Step 6:

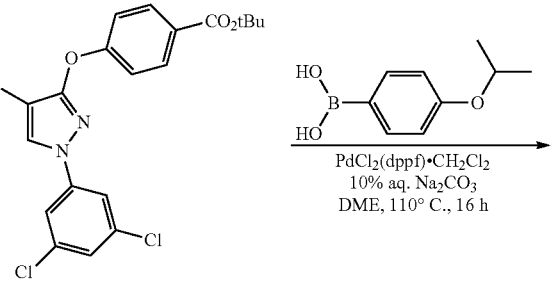

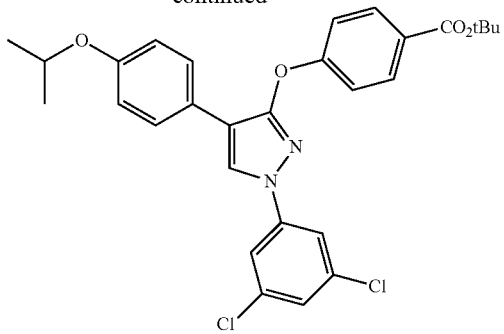

A solution of the product from Step 5 (90 mg, 0.19 mmol, 1 eq), 4-isopropoxyphenylboronic acid (67 mg, 0.37 mmol, 2 eq) and PdCl$_2$(dppf).CH$_2$Cl$_2$ (23 mg, 0.29 mmol, 0.15 eq) were combined with 10% aqueous Na$_2$CO$_3$ (1.5 mL) and DME (3 mL) in a sealed tube. The resulting mixture was heated for 16 h in a 100° C. oil bath. After cooling the vessel, the reaction mixture was partitioned between EtOAc and water. The aqueous layer was discarded, and the organic layer was washed with brine. The organic layer was dried over anhydrous sodium sulfate, was filtered, and was evaporated to afford a crude residue which was subjected to silica gel chromatography (gradient elution, 3% to 50% EtOAc in hexanes) to provide the desired product (78 mg, 76% yield).

Step 7:

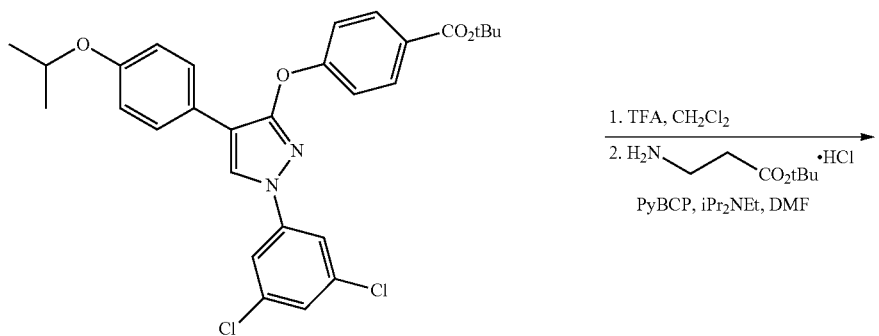

1. TFA, CH$_2$Cl$_2$
2. H$_2$N\~\~\~CO$_2$tBu · HCl

PyBCP, iPr$_2$NEt, DMF

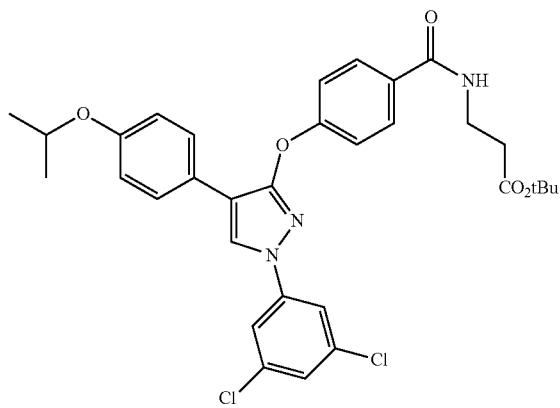

A solution of the product from Step 3 (78 mg, 0.14 mmol, 1 eq) in CH$_2$Cl$_2$ (3 mL) was treated with trifluoroacetic acid (1.5 mL) at room temperature. After stirring for 3 h, the volatiles were removed in vacuo. The crude material was combined with PyBOP (73 mg, 0.14 mmol, 1 eq), iPr$_2$NEt (75 μL, 0.43 mmol, 3 eq), and tert-butyl 3-aminopropanoate, hydrochloride salt (25 mg, 0.14 mmol, 1 eq) in CH$_2$Cl$_2$ (2 mL) and the resulting solution was stirred at room temperature for 16 h. The reaction mixture was partitioned between CH$_2$Cl$_2$ and water. The aqueous layer was discarded and the organic layer was washed with saturated aqueous NaHCO$_3$. Evaporation of the organic layer afforded a residue which was purified via silica gel chromatography (gradient elution, 0% to 100% EtOAc in hexanes) to afford the desired product (77 mg, 91%) as a film.

Step 8:

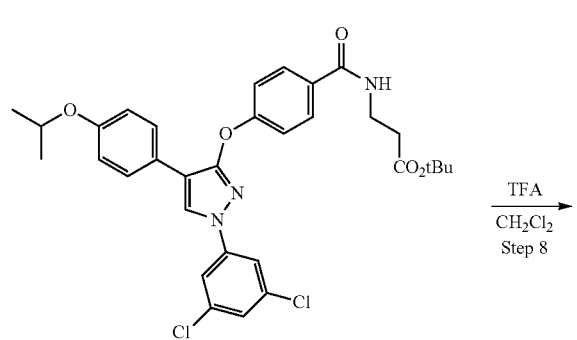

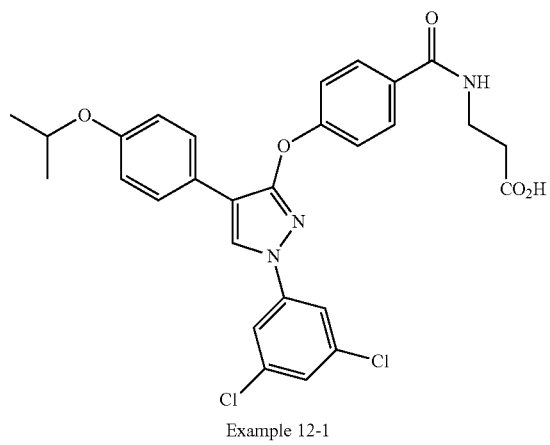

Example 12-1

A solution of the product from Step 7 (77 mg, 0.13 mmol) and 1,3-dimethoxybenzene (10 μL) in CH$_2$Cl$_2$ (6 mL) was treated with TFA (3 mL) and stirred for 3 h at room temperature. The reaction was concentrated and diethyl ether was added to the resulting residue. A white solid formed, which was collected via filtration, washed with diethyl ether, and dried to afford Example 12-1 (55 mg, 76%).

TABLE 5

Using the conditions described in Scheme 12, and the requisite boronic acid, the following compounds were prepared:

| Boronic Acid | Example Number | Structure |
|---|---|---|
|  | 12-2 |  |

TABLE 5-continued

Using the conditions described in Scheme 12, and the requisite boronic acid, the following compounds were prepared:

| Boronic Acid | Example Number | Structure |
|---|---|---|
| 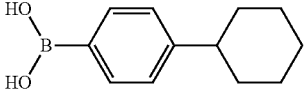 [SMILES: OB(O)c1ccc(C2CCCCC2)cc1] | 12-3 | 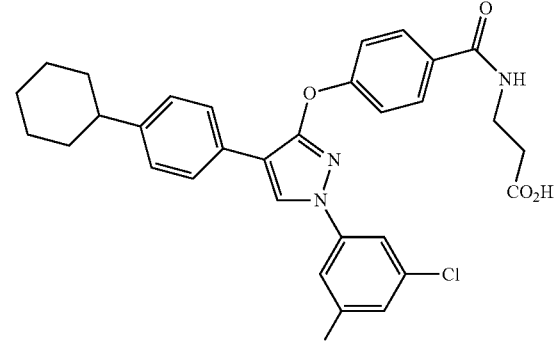 |
| 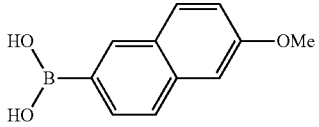 [SMILES: COc1ccc2cc(B(O)O)ccc2c1] | 12-4 | 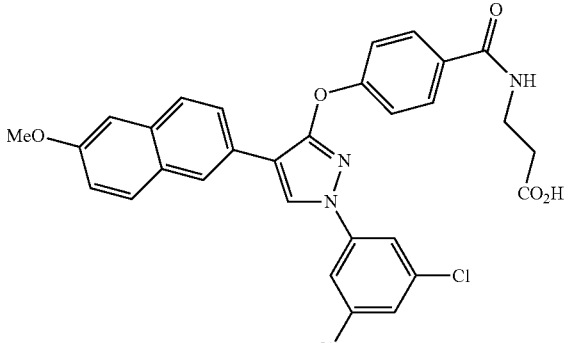 |

Scheme 13

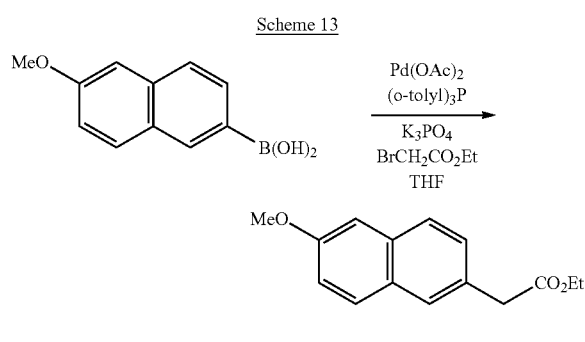

Into a 1 L round bottomed flask containing THF (335 mL) was added 6-methoxynaphthalen-2-ylboronic acid (20.15 g, 99.7 mmol, 1.2 eq), Pd(OAc)$_2$ (563 mg, 2.51 mmol, 0.03 eq), tri-o-tolylphosphine (2.3 g, 7.56 mmol, 0.09 eq), K$_3$PO$_4$ (89 g, 419 mmol, 5 eq), and ethylbromoacetate (9.2 mL, 82.6 mmol, 1 eq). The resulting mixture was stirred for 24 h at room temperature. Water and EtOAc were added to the reaction and the mixture was stirred for 1 h. The layers were separated and both were saved. The aqueous layer was extracted with EtOAc. The organic layers were combined, washed with brine, dried over anhydrous sodium sulfate, filtered, and evaporated to afford a crude material, which was subjected to silica gel chromatography (gradient elution 0% to 20% EtOAc in hexanes) to afford ethyl 2-(6-methoxynaphthalen-2-yl)acetate (15.4 g, 76%) as a white, crystalline solid.

Scheme 14

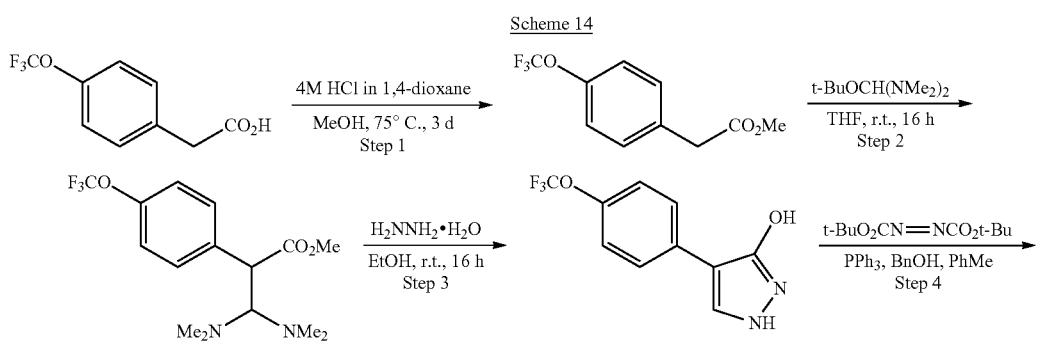

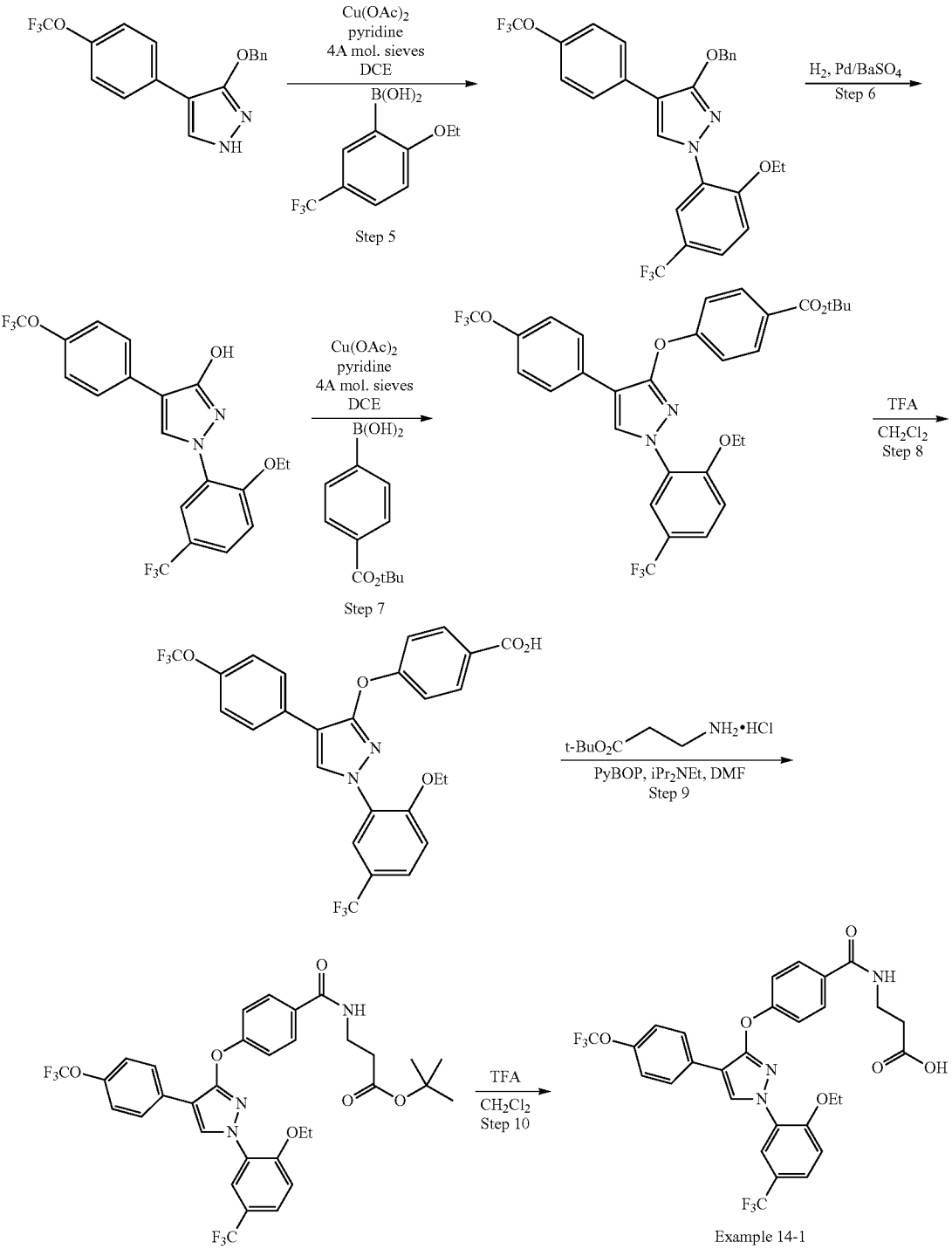
Example 14-1
Step 1:
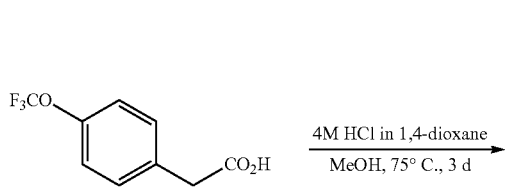
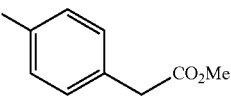
A solution of 2-(4-(trifluoromethoxy)phenyl)acetic acid (15 g, 68.1 mmol) in methanol (100 mL) was treated with 4N HCl in 1,4-dioxane (40 mL). The resulting mixture was heated at 75° C. for 3 days. The reaction was cooled and the volatiles were removed in vacuo to afford the desired methyl ester (15.5 g).

Step 2:

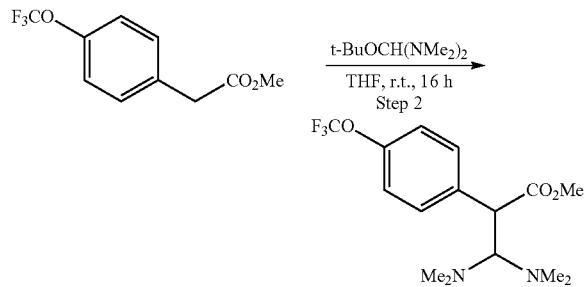

1-tert-Butoxy-N,N,N',N'-tetramethylmethanediamine (16 g, 92.7 mmol, 1.4 eq) was added to a solution of the methyl ester from Step 1 (15.5 g, 66.23 mmol, 1 eq) in THF (20 mL). The resulting mixture was stirred overnight at room temperature. The volatiles were removed in vacuo to afford the desired product as a solid (22 g).

Step 3:

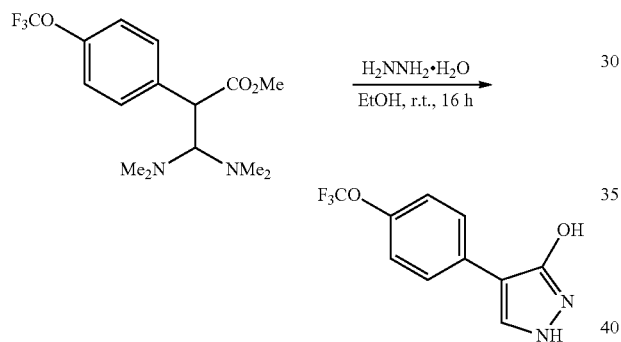

A solution of the product from Step 2 (2 g, 5.9 mmol, 1 eq) in ethanol (8 mL) was treated with hydrazine hydrate (0.46 mL, 5.9 mmol, 1 eq). The reaction mixture was then stirred for 2 days at room temperature. The volatiles were removed in vacuo and the residue was suspended in hexanes/Et$_2$O. The solids were removed via filtration. The resulting filtrate was concentrated to afford the desired product (1.1 g) which was used in the next step without further purification.

Step 4:

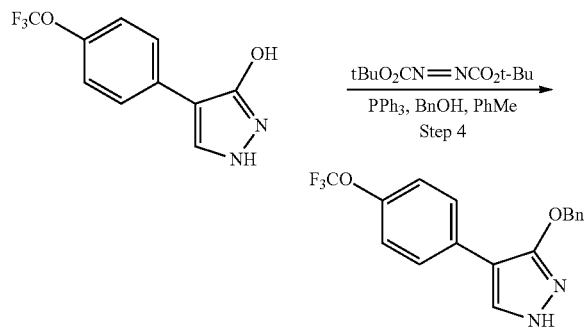

The crude product from Step 3 (1.1 g, 4.5 mmol, 1 eq), triphenylphosphine (1.3 g, 4.95 mmol, 1.1 eq), and benzyl alcohol (0.54 g, 4.95 mmol, 1.1 eq) were dissolved in THF (10 mL). Di-tert-butylazodicarboxylate (1.14 g, 4.95 mmol, 1.1 eq) was added, and the resulting reaction was stirred overnight at room temperature. At room temperature, 4N HCl in 1,4-dioxane was added, and the mixture was stirred for 10 min. The volatiles were removed in vacuo, and the resulting residue was partitioned between aqueous 1M NaOH and ethyl acetate. The organic layer was dried over anhydrous sodium sulfate, was filtered, and was concentrated to afford a crude residue which was subjected to silica gel chromatography (gradient elution, hexanes/ethyl acetate) to provide the desired product (0.45 g).

Step 5:

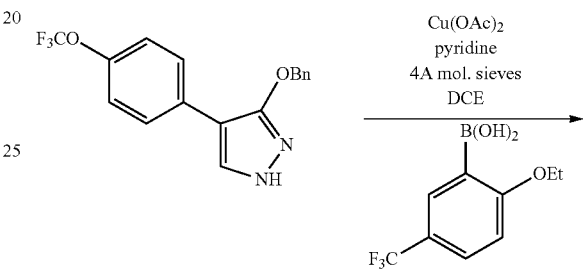

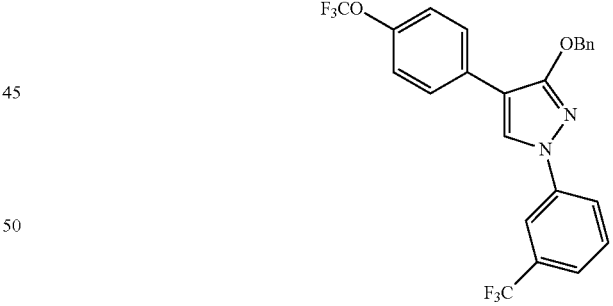

The product from Step 4 (0.35 g, 1.50 mmol, 1 eq), 2-ethoxy-5-(trifluoromethyl)phenylboronic acid (0.87 g, 3.75 mmol, 2.5 eq), pyridine (0.473 g, 6.00 mmol, 4 eq), Cu(OAc)$_2$ (0.407 g, 2.25 mmol, 1.5 eq), and powdered 4 angstrom molecular sieves (1.9 g) were combined in 1,2-dichloroethane (4 mL). The resulting mixture was stirred at room temperature for 2 days. Diethyl ether was added to the reaction and the mixture was filtered through Celite. The filtrate was concentrated to afford a crude residue which was purified via preparative thin layer silica gel chromatography (20 cm×20 cm, 1000 μm, developed with 10% EtOAc in hexanes) to afford the desired product (114 mg).

Step 6:

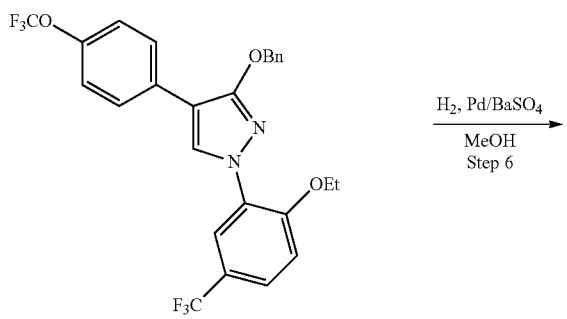

The product from Step 5 (114 mg, 0.218 mmol) was dissolved in methanol (15 mL) and 10% palladium on BaSO₄ (30 mg) was added. The solution was stirred under a hydrogen atmosphere (1 atm) for 18 h. The reaction was then purged with nitrogen, filtered through Celite and the filtrate was concentrated to afford the desired product (90 mg) which was used in the next step without further purification.

Step 7:

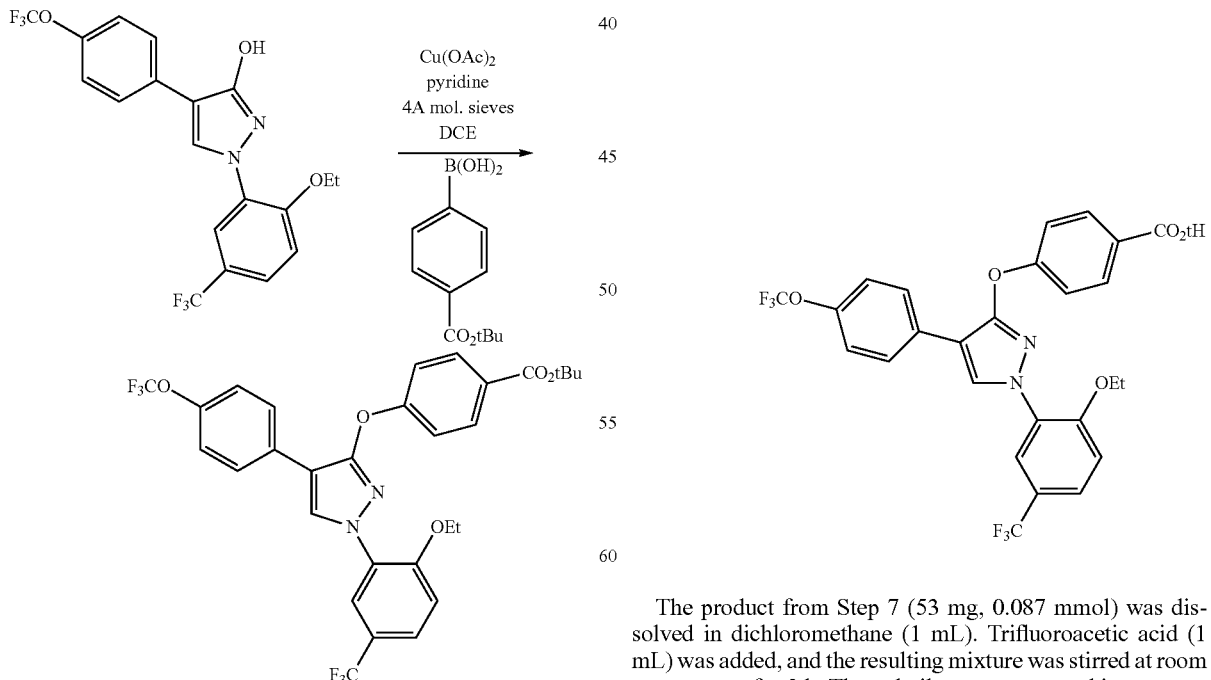

The product from Step 6 (90 mg, 0.21 mmol, 1 eq), 4-(tert-butoxycarbonyl)phenylboronic acid (120 mg, 0.53 mmol, 2.5 eq), pyridine (82 mg, 1.05 mmol, 5 eq), Cu(OAc)₂ (57 mg, 0.31 mmol, 1.5 eq) and 4 angstrom molecular sieves (200 mg) were combined in dichloromethane (2 mL) and stirred overnight. Diethyl ether (20 mL) was added, and the mixture was filtered through Celite. The resulting filtrate was evaporated to afford a crude residue which was purified via preparative thin layer silica gel chromatography (20 cm×20 cm, 1000 μm, developed with 10% EtOAc in hexanes) to afford the desired product (53 mg).

Step 8:

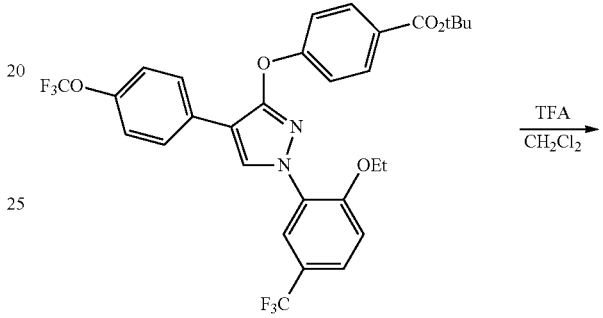

The product from Step 7 (53 mg, 0.087 mmol) was dissolved in dichloromethane (1 mL). Trifluoroacetic acid (1 mL) was added, and the resulting mixture was stirred at room temperature for 2 h. The volatiles were removed in vacuo to afford the desired benzoic acid (49 mg) which was used in the subsequent step without further purification.

Step 9:

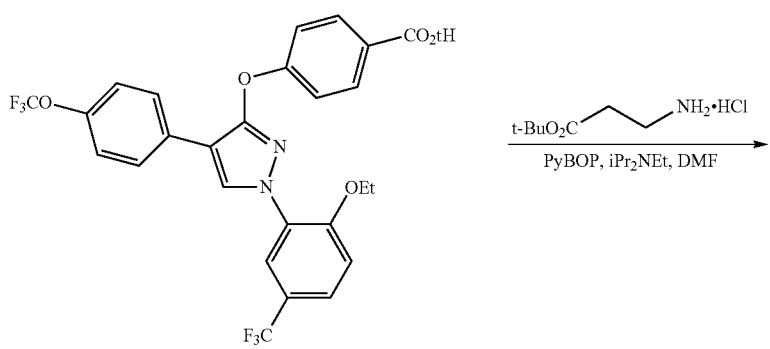

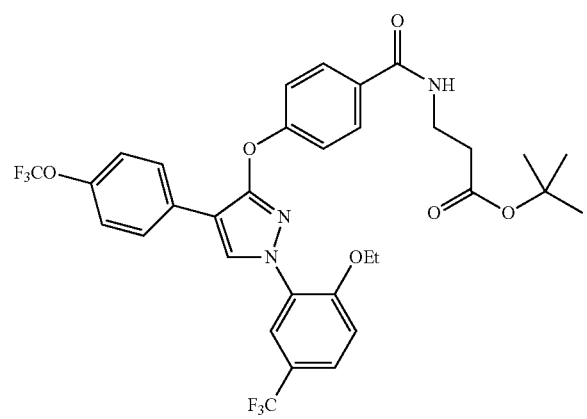

The crude material from Step 8 (49 mg, 0.089 mmol) was combined with PyBOP (60 mg, 0.107 mmol, 1.2 eq), iPr$_2$NEt (34 mg, 0.27 mmol, 3 eq), and tert-butyl 3-aminopropanoate, hydrochloride salt (24 mg, 0.13 mmol, 1.5 eq) in MeCN (2 mL) and the resulting solution was stirred at room temperature for 72 h. Evaporation of the solvent afforded a residue which was purified via preparative thin layer silica gel chromatography (20 cm×20 cm, 1000 μm developed with 1:1.5 EtOAc:hexanes) to afford the desired product (49 mg).

Step 10:

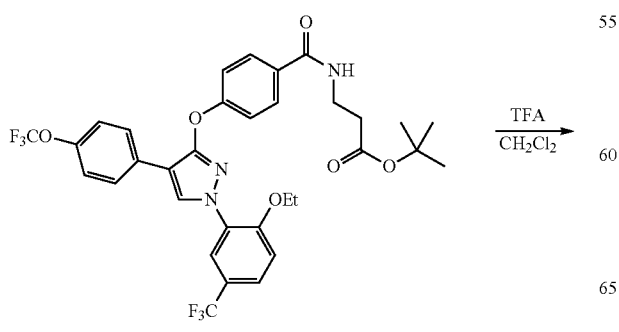

-continued

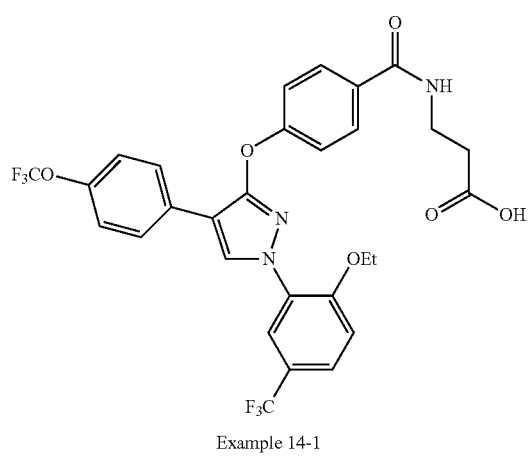

Example 14-1

A solution of the product from Step 9 (49 mg, 0.072 mmol) was dissolved in dichloromethane (1 mL). Trifluoroacetic acid (1 mL) was added and the reaction was stirred for 2 h. The reaction was concentrated to afford Example 14-1 (46 mg).

TABLE 6

Using the conditions described in Scheme 14 and the requisite boronic acid, the following compounds were prepared:

| Boronic Acid | Example Number | Structure |
|---|---|---|
| 2-isopropoxy-5-(trifluoromethyl)phenylboronic acid | 14-2 | |
| 2-methoxy-5-(trifluoromethyl)phenylboronic acid | 14-3 | |
| 2-fluoro-5-(trifluoromethyl)phenylboronic acid | 14-4 | |

TABLE 6-continued

Using the conditions described in Scheme 14 and the requisite boronic acid, the following compounds were prepared:

| Boronic Acid | Example Number | Structure |
|---|---|---|
| B(OH)₂, Cl, F (3-chloro-5-fluorophenyl) | 14-5 | [structure shown] |

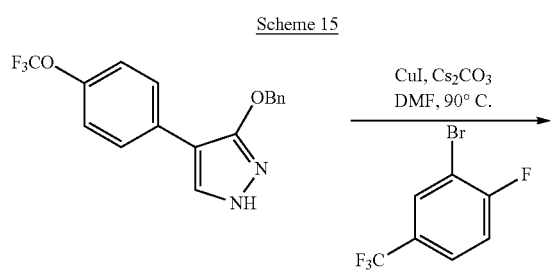

Scheme 15

The product from Scheme 14, Step 4 (136 mg, 0.407 mmol, 1 eq), 2-bromo-1-fluoro-4-(trifluoromethyl)benzene (148 mg, 0.61 mmol, 1.5 eq), CuI (16 mg, 0.084 mmol, 0.2 eq), and Cs₂CO₃ (265 mg, 0.82 mmol, 2 eq) were combined in DMF (1.5 mL) and heated for 3 h at 90° C. The reaction was filtered and the filtrate was partitioned between EtOAc and water. The aqueous layer was discarded, and the organic layer was washed three times more with water, was dried over anhydrous sodium sulfate, was filtered, and was evaporated to afford a crude residue. Preparative thin layer silica gel chromatography (20 cm×20 cm, 1000 μm, developed with 3% EtOAc in hexanes) afforded the desired product (145 mg).

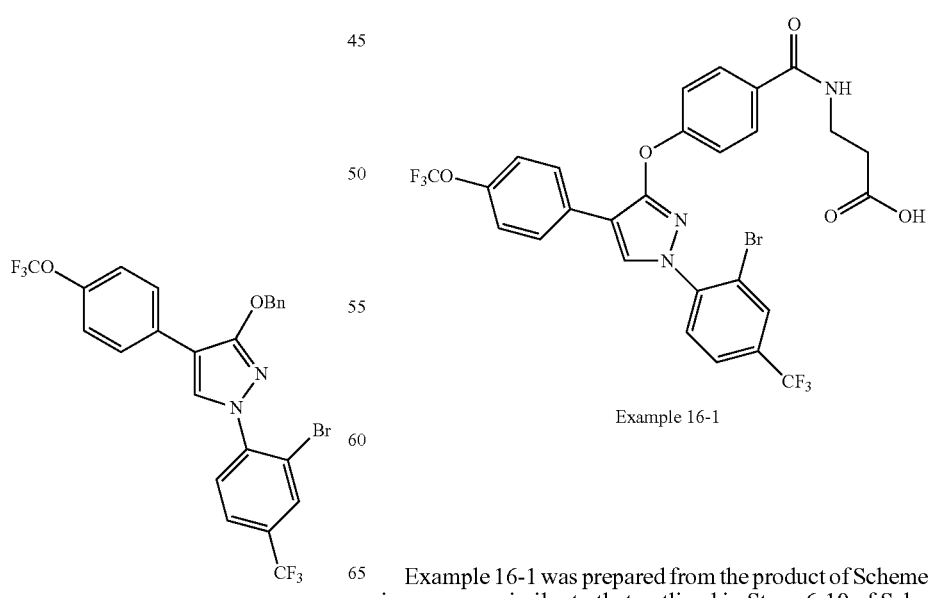

Scheme 16

Example 16-1

Example 16-1 was prepared from the product of Scheme 15 in a manner similar to that outlined in Steps 6-10 of Scheme 14.

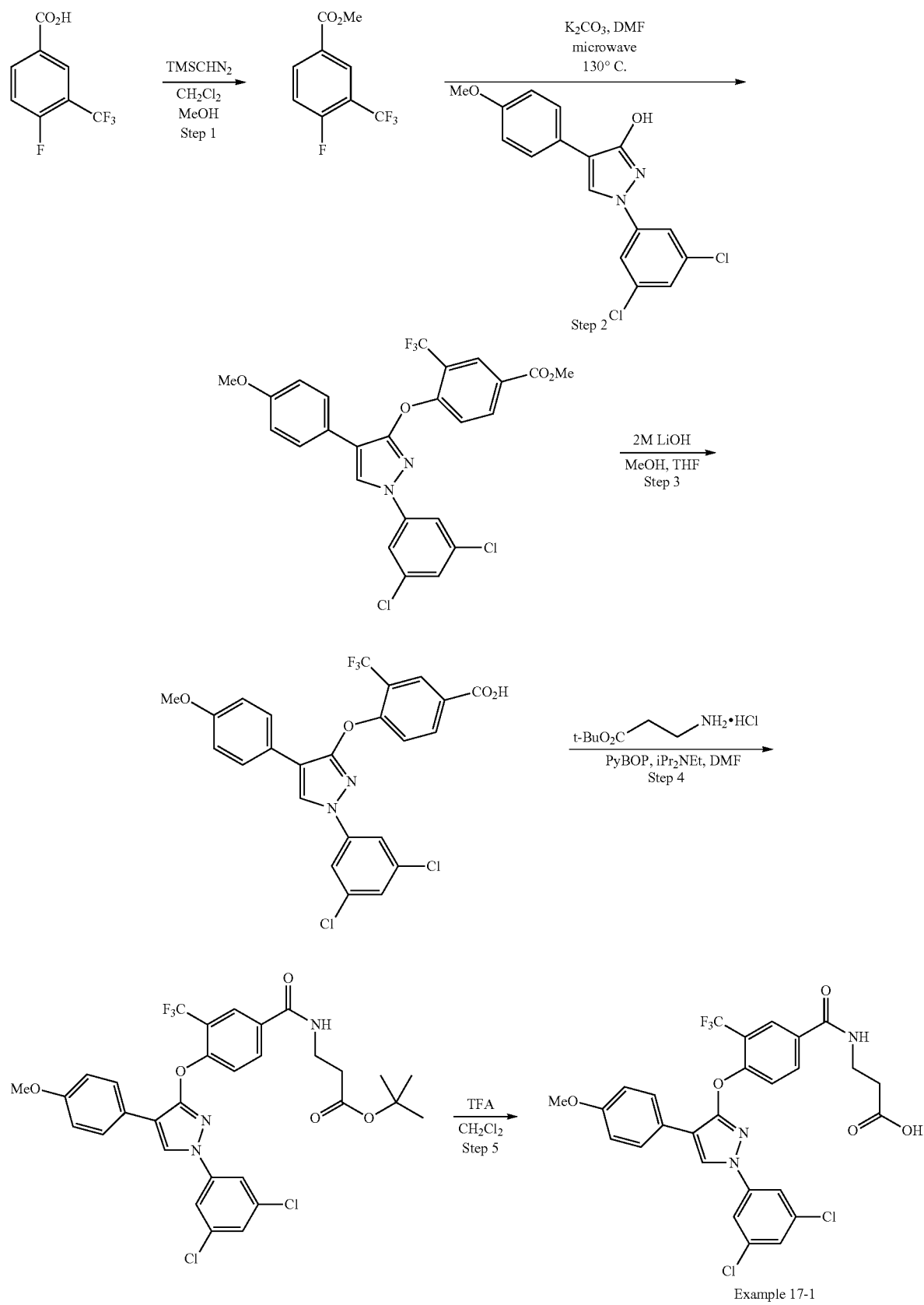
Scheme 17
Example 17-1

Step 1:

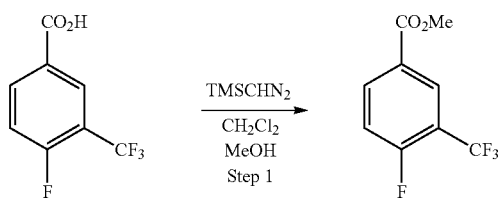 [SMILES: O=C(O)c1ccc(F)c(C(F)(F)F)c1 ; COC(=O)c1ccc(F)c(C(F)(F)F)c1]

A solution of 4-fluoro-3-(trifluoromethyl)benzoic acid (260 mg, 1.25 mmol, 1 eq) in MeOH (0.5 mL) and $CH_2Cl_2$ (2 mL) was treated with $TMSCHN_2$ (2M in hexanes, 0.85 mL, 1.70 mmol, 1A eq) dropwise with stirring at room temperature. After the reaction was stirred for 10 min, acetic acid was added until the yellow color disappeared. The mixture was concentrated to afford methyl 4-fluoro-3-(trifluoromethyl)benzoate, which was used in the next step without further purification.

Step 2:

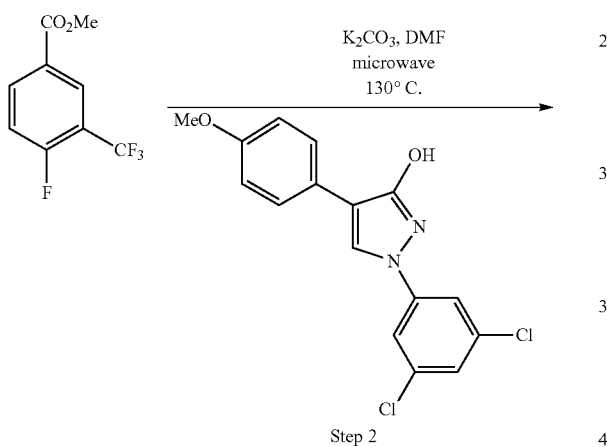

A solution of the pyrazole (Intermediate produced in Step 2 of the synthesis of Example 10-3), (70 mg, 0.21 mmol, 1 eq), methyl 4-fluoro-3-(trifluoromethyl)benzoate (55 mg, 0.25 mmol, 1.2 eq) and $K_2CO_3$ (165 mg, 1.19 mmol, 5.7 eq) in DMF (2 mL) were transferred to a microwave tube. The tube was sealed and subjected to microwave irradiation (130° C., very high absorption, 20 min). The reaction was then partitioned between EtOAc and brine. The aqueous layer was discarded, and the organic layer was washed twice with brine. The organic layer was dried over anhydrous magnesium sulfate, filtered, and evaporated to afford a crude residue which was purified via silica gel chromatography (gradient elution, 0% to 25% EtOAc in hexanes) to provide the desired product (89 mg, 79%) as a white solid.

Step 3:

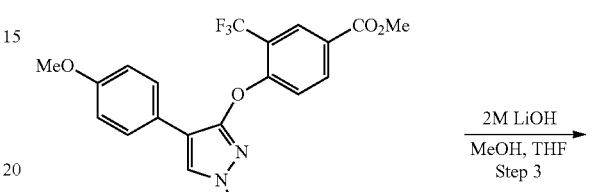

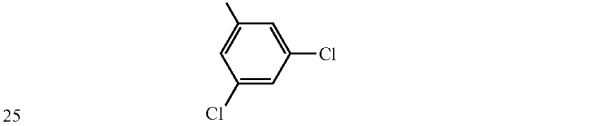

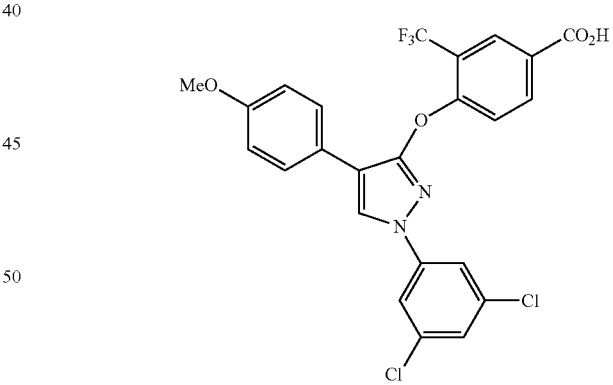

The product from Step 2 (116 mg, 0.22 mmol, 1 eq) was dissolved in a mixture of MeOH (2 mL) and THF (4 mL). An aqueous 2M LiOH solution (2 mL, 4.00 mmol, 18.2 eq) was added and the resulting mixture was stirred at room temperature for 4 h. The reaction mixture was adjusted to pH 1-2 with 1M HCl and was then partitioned between EtOAc and brine. The organic layer was saved and the aqueous layer was extracted with EtOAc. The combined organic extracts were washed with brine three times, were dried over anhydrous sodium sulfate, were filtered, and were evaporated to afford the desired product (112 mg, 97%) as a white solid.

Step 4:

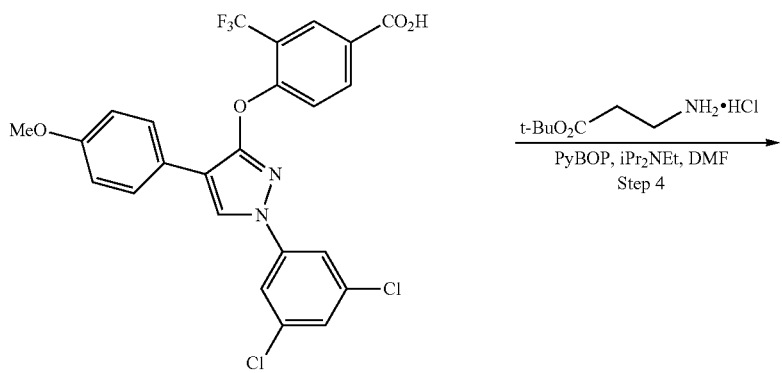

The crude material from Step 3 (112 mg, 0.21 mmol, 1 eq) was combined with PyBOP (109 mg, 0.21 mmol, 1 eq), iPr$_2$NEt (0.15 mL, 0.84 mmol, 4 eq), and tert-butyl 3-aminopropanoate, hydrochloride salt (38 mg, 0.213 mmol, 1 eq) in DMF (2 mL) and the resulting solution was stirred at room temperature for 16 h. The reaction was partitioned between EtOAc and acidified brine. The aqueous layer was discarded and the organic layer was washed with brine, saturated aqueous sodium bicarbonate, and brine. After drying the organic layer over anhydrous Na$_2$SO$_4$, subsequent filtration and evaporation of the filtrate afforded a residue which was purified via silica gel chromatography (gradient elution, 5% to 75% EtOAc in hexanes) to afford the desired product (134 mg, 94%) as a clear, colorless film.

Step 5:

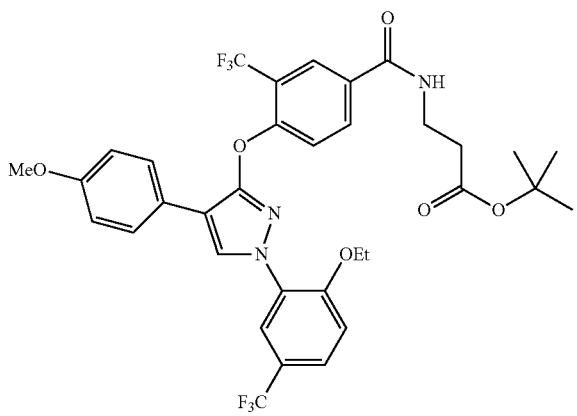

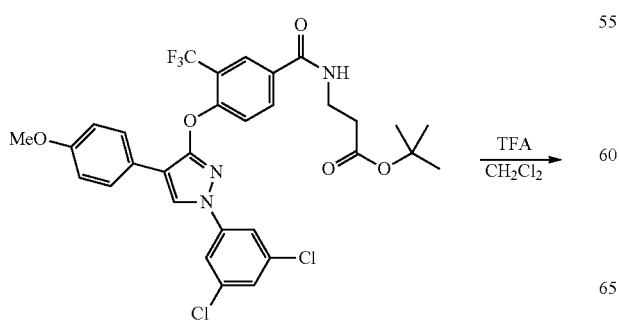

-continued

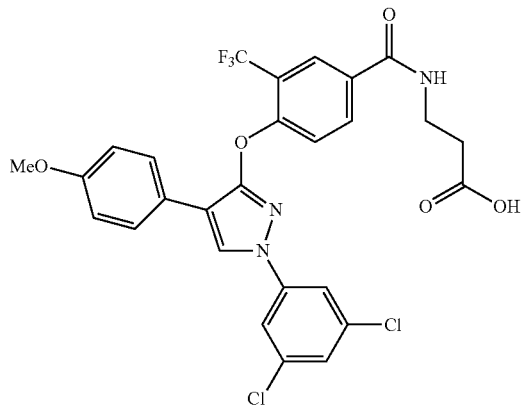

Example 17-1

The product from Step 4 (134 mg,) was dissolved in CH$_2$Cl$_2$ (5 mL). Trifluoroacetic acid (3 mL) was added, and the reaction was stirred for 3 h at room temperature. The volatile materials were removed in vacuo to afford an off white residue. The residue was suspended in MeOH (5 mL) via sonication. The remaining solid was collected by filtration, washed with MeOH and dried to afford Example 17-1 (110 mg) as a white solid.

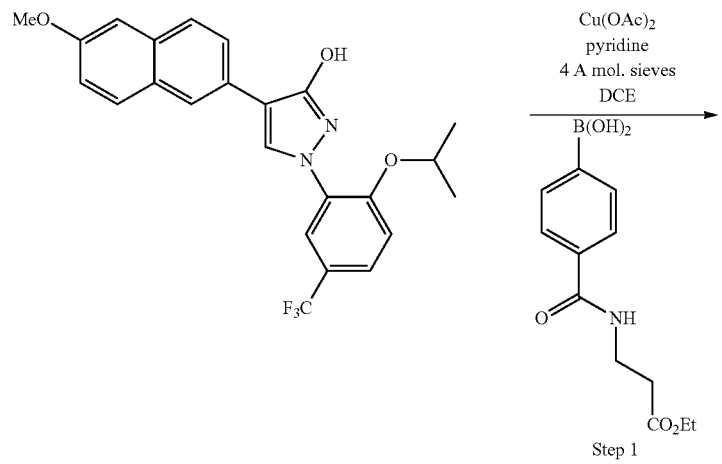
Scheme 18
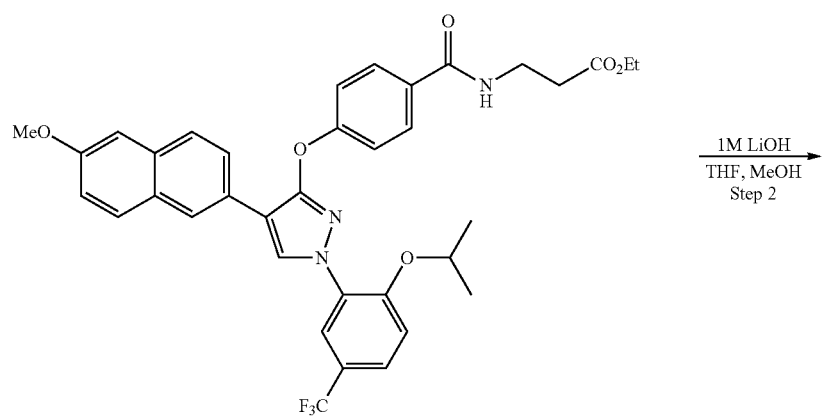
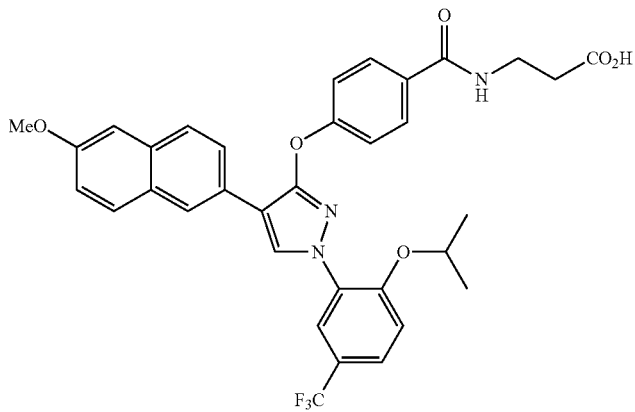
Example 18-1

Step 1:

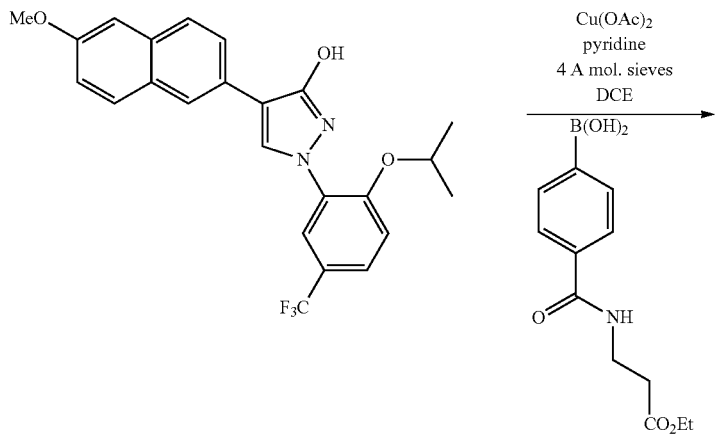

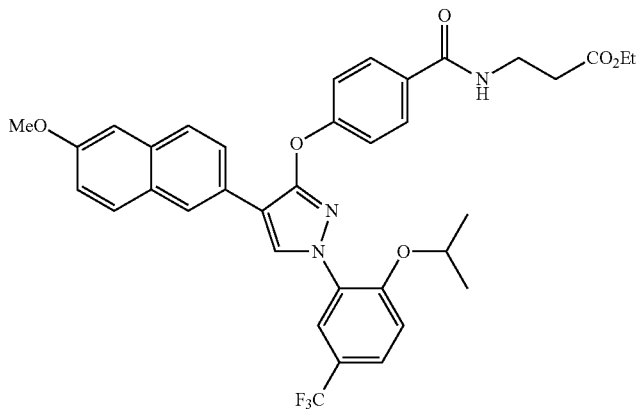

The pyrazole starting material (prepared from ethyl 2-(6-methoxynaphthalen-2-yl)acetate, in a manner similar to that outlined in Steps 2-6 of Scheme 14, 114 mg, 0.26 mmol, 1 eq), 4-(3-ethoxy-3-oxopropylcarbamoyl)phenylboronic acid (205 mg, 0.77 mmol, 3 eq), pyridine (0.17 mL, 2.08 mmol, 8 eq) and 4 angstrom molecular sieves (139 mg) were combined in methylene chloride (7 mL) and sonicated to create a fine suspension. Cu(OAc)$_2$ (53 mg, 0.29 mmol, 1.1 eq) was added, and the reaction was stirred 16 h at room temperature with the flask open to air. An additional amount of methylene chloride (10 mL) was added and the stirring was continued for 24 h. The reaction was partitioned between methylene chloride and saturated aqueous NaHCO$_3$. The organic layer was saved and the aqueous layer was extracted with methylene chloride. The organic layers were combined, washed with brine, dried over anhydrous Na$_2$SO$_4$, filtered and evaporated to afford a crude residue which was subjected to silica gel chromatography (gradient elution, 15% to 100% EtOAc in hexanes) to afford the desired product (55 mg).

Step 2:

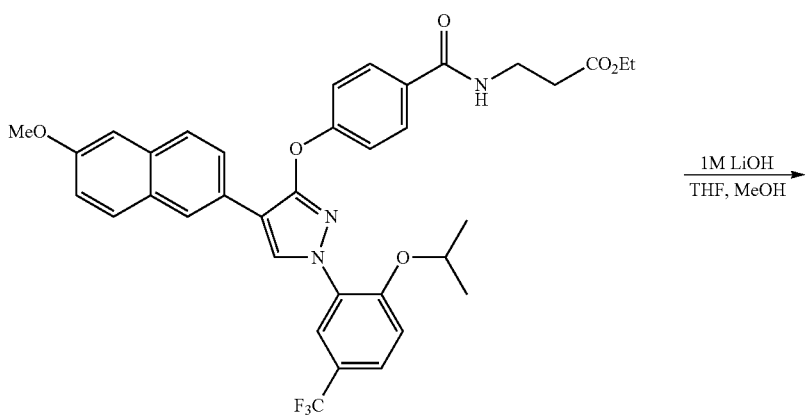

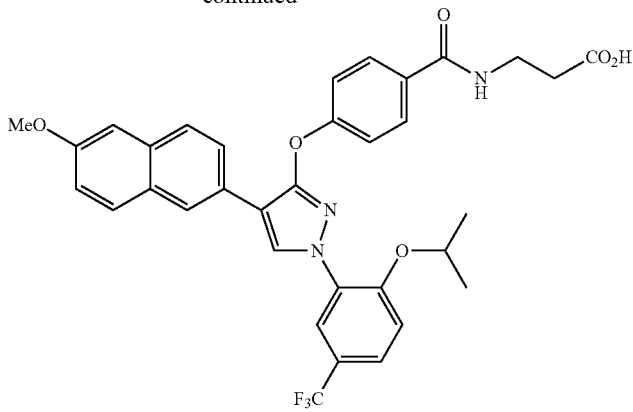

Example 18-1

The product from Step 1 (55 mg, 0.083 mmol, 1 eq) was dissolved in MeOH (1.5 mL) and THF (1.5 mL). An aqueous 1M LiOH solution (0.42 mL, 0.42 mmol, 5 eq) was added and the reaction was stirred for 4 h. The reaction mixture was adjusted to pH 7 with aqueous HCl. The solvents were removed in vacuo to afford a residue which was subjected to silica gel chromatography (gradient elution, 0% to 75% MeOH in EtOAc) to afford a mostly pure product. This material was subjected to reversed-phase C18 chromatography (isocratic elution for one column volume with 10% MeCN in water with 0.1% HCOOH, then gradient to 95% MeCN over six column volumes, then isocratic elution at 95% MeCN for eight column volumes) to afford Example 18-1 (36 mg, 68%) as a yellow foam.

Scheme 19

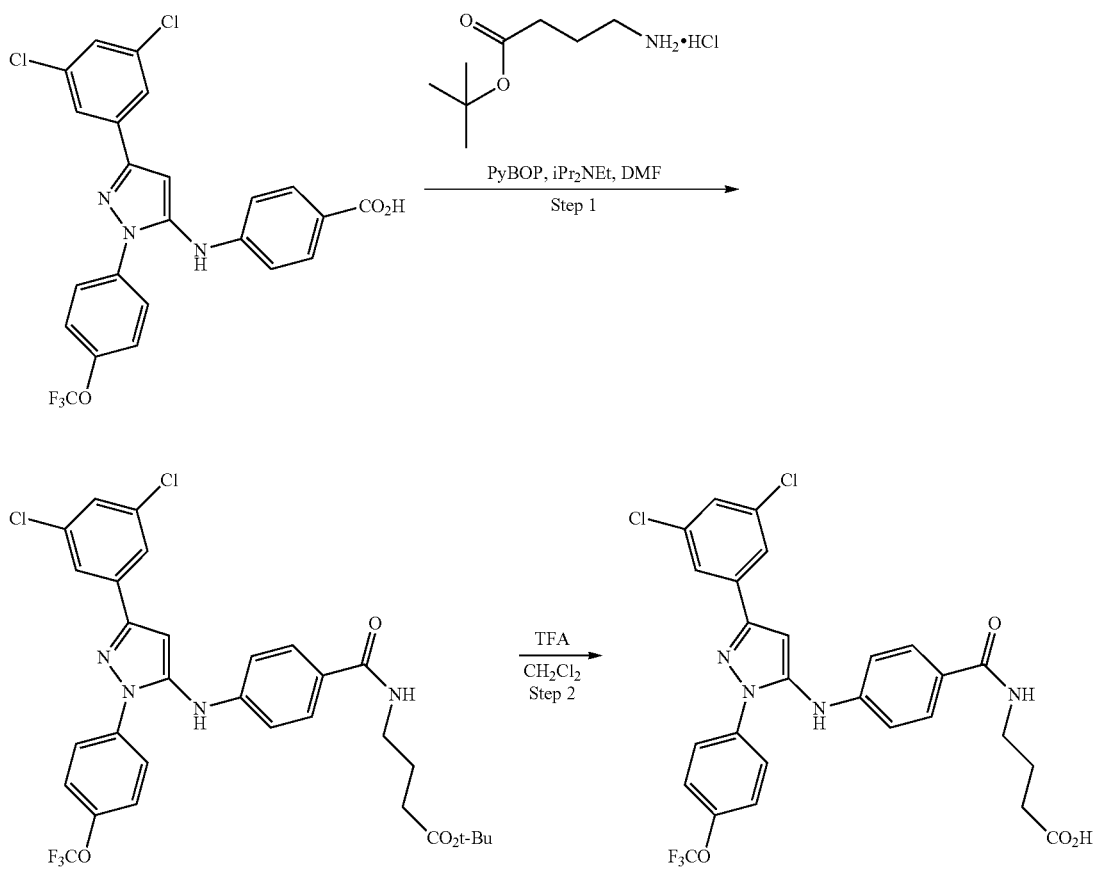

Example 19-1

Step 1:

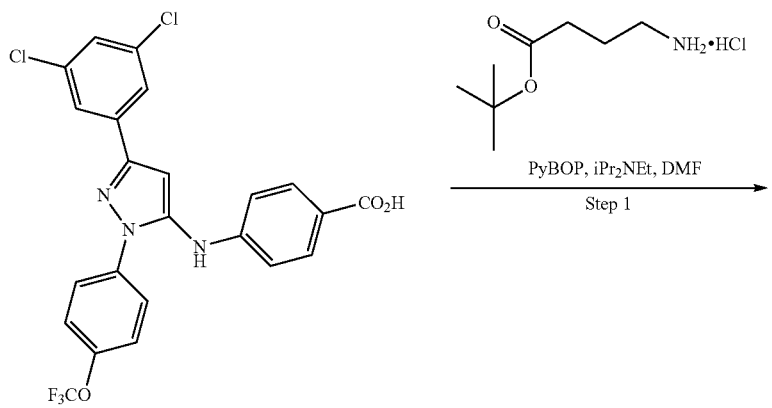

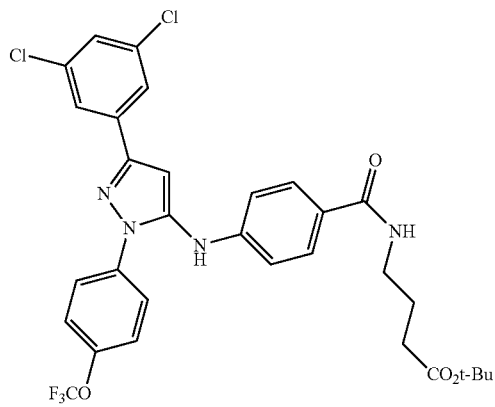

The product from Scheme 7, Step 3 (51 mg, 0.10 mmol, 1 eq) was combined with tert-butyl 4-aminobutanoate hydrochloride (22 mg, 0.11 mmol, 1.1 eq), PyBOP (54 mg, 0.11 mmol, 1.1 eq), and iPr$_2$NEt (0.066 mL, 0.40 mmol, 4 eq) in DMF (2 mL) and stirred 16 h at room temperature. Additional amounts of tert-butyl 4-aminobutanoate hydrochloride (22 mg, 0.11 mmol, 1.1 eq) and PyBOP (50 mg, 0.10 mmol, 1 eq) were added and the reaction stirred for 72 h. The reaction was concentrated to afford a crude residue which was partitioned between EtOAc and dilute aqueous HCl. The aqueous layer was discarded and the organic layer was washed with saturated aqueous sodium bicarbonate. After drying the organic layer over anhydrous Na$_2$SO$_4$, subsequent filtration and evaporation of the filtrate afforded a residue which was purified via silica gel chromatography (gradient elution, 0% to 80% EtOAc in hexanes) to afford the desired product (52 mg, 80%) as a clear, colorless film.

Step 2:

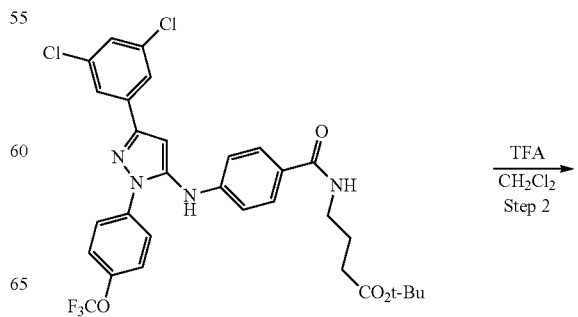

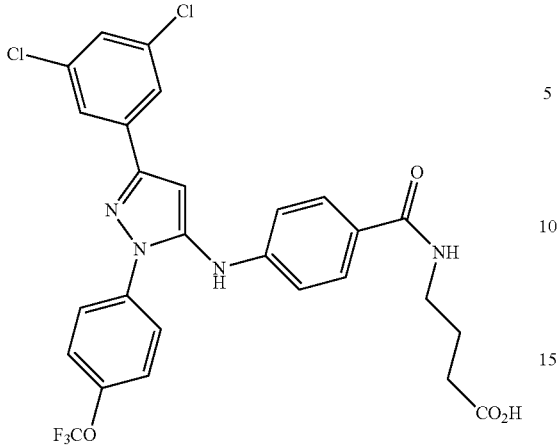

Example 19-1

The product from Step 1 (52 mg,) was dissolved in CH$_2$Cl$_2$ (6 mL). Trifluoroacetic acid (3 mL) was added, and the reaction was stirred for 3 h at room temperature. The volatile materials were removed in vacuo to afford an off white residue which was purified by preparative thin layer silica gel chromatography (20 cm×20 cm, 1000 μm, developed with 8% MeOH in CH$_2$Cl$_2$) to afford Example 19-1 (9 mg) as a white solid.

Scheme 20

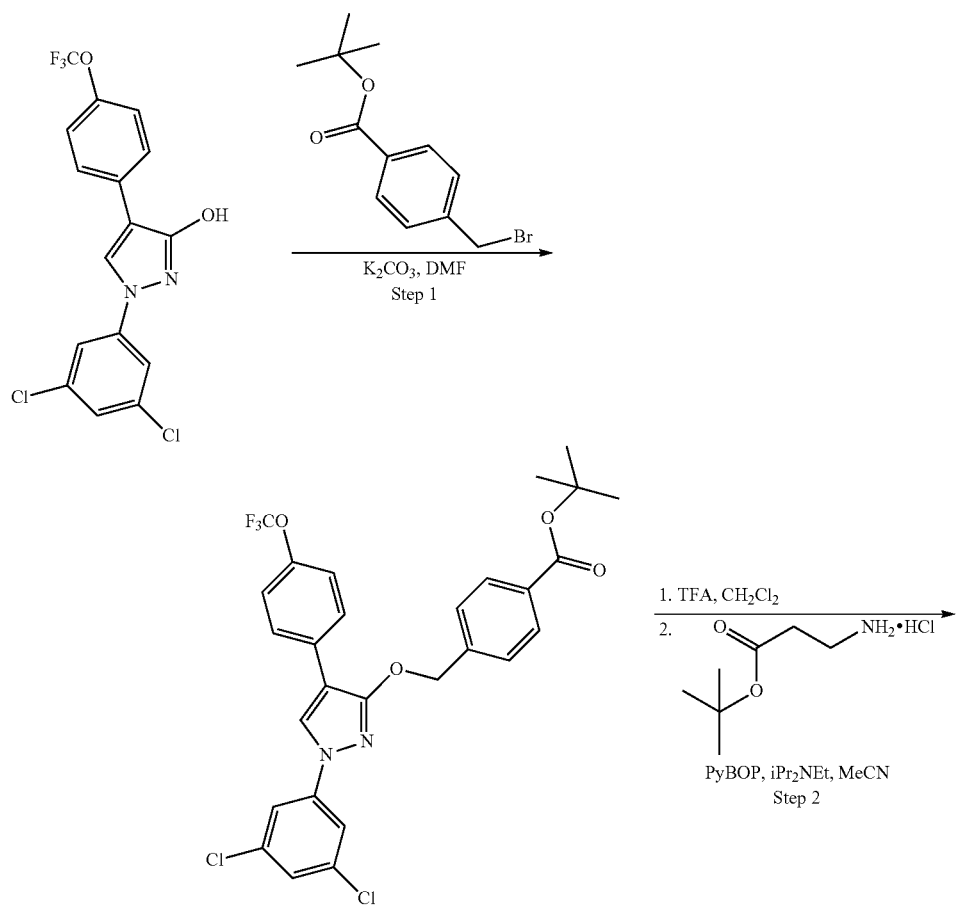

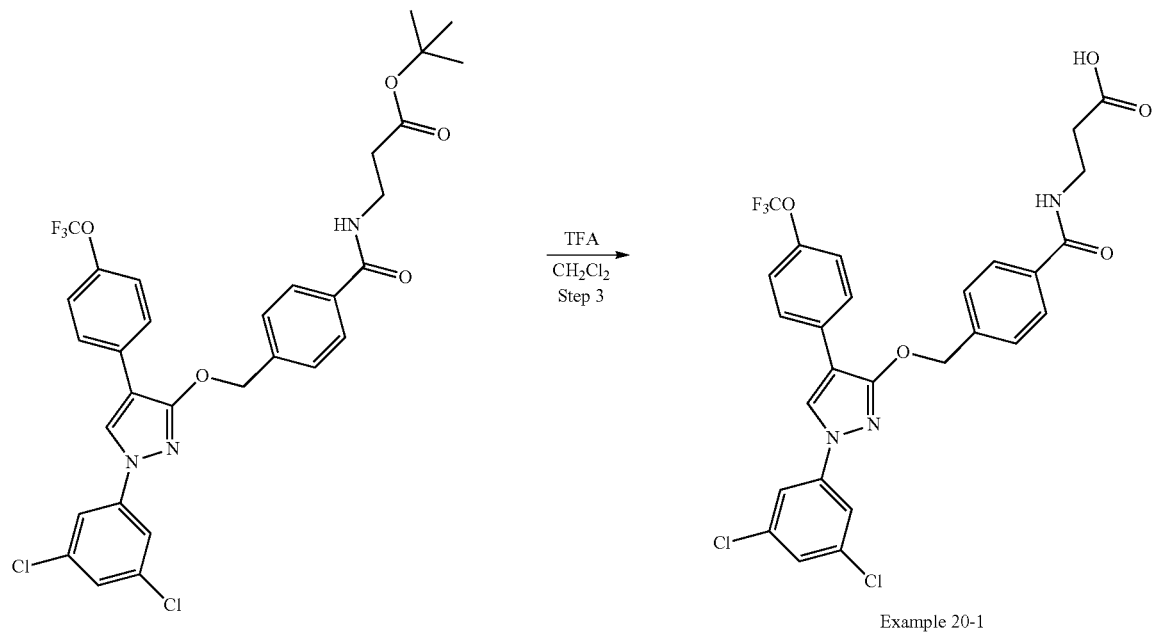

Example 20-1

Step 1:

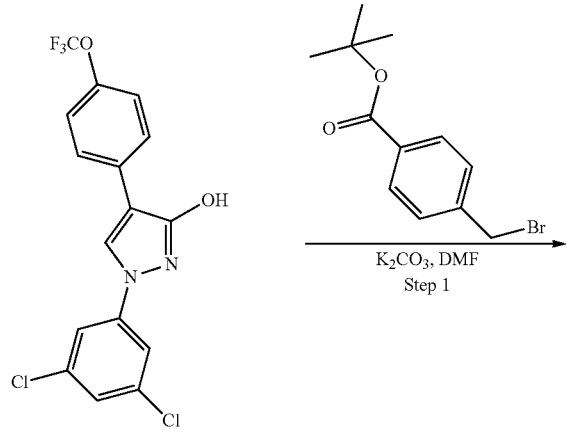

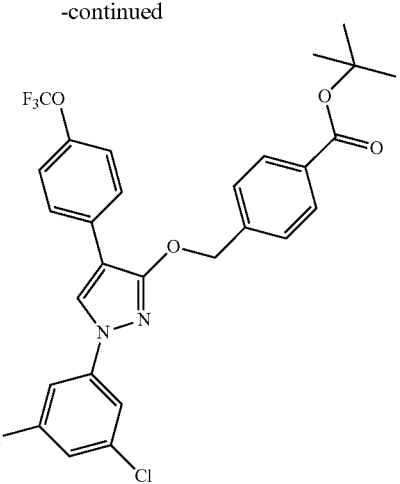

A solution of the pyrazolone prepared in Scheme 10, Step 2 (21 mg, 0.054 mmol, 1 eq), tert-butyl 4-(bromomethyl) benzoate (15 mg, 0.054 mmol, 1 eq), and potassium carbonate (9 mg, 0.065 mmol, 1.2 eq) in DMF (2 mL) was stirred for 16 h at room temperature. The reaction mixture was then partitioned between EtOAc and dilute aqueous HCl. The organic layer was washed with brine and saturated aqueous NaHCO$_3$, dried over anhydrous Na$_2$SO$_4$, filtered, and evaporated to afford a crude residue. Silica gel chromatography of the crude product (Gradient elution: 0% to 40% EtOAc in hexanes) afforded the desired product (26 mg) which was taken on to the next step without further purification.

Step 2:

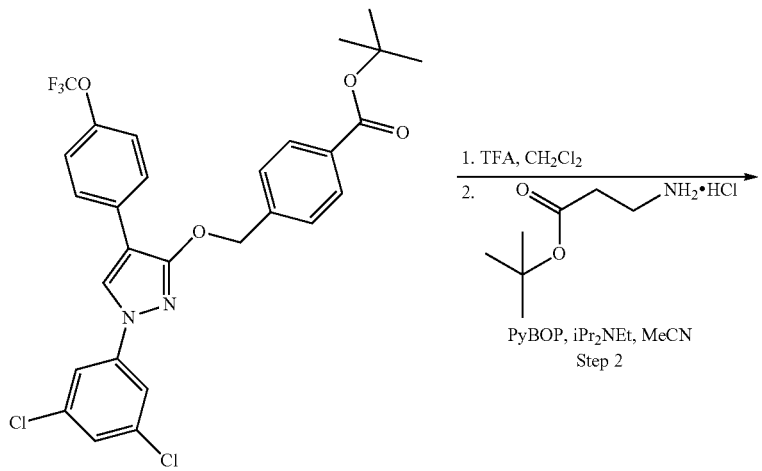

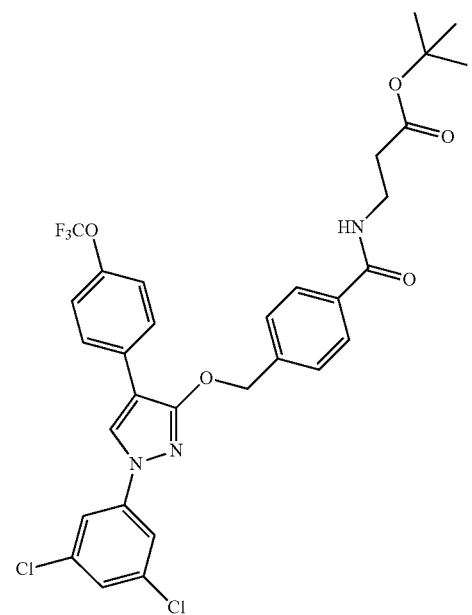

A solution of the tert-butyl ester prepared in Step 1 (26 mg, 0.045 mmol, 1 eq) in CH$_2$Cl$_2$ (3 mL) was treated with trifluoroacetic acid (1.5 mL) at room temperature. After stirring for 2 h, the volatiles were removed in vacuo. The crude material was combined with PyBOP (26 mg, 0.050 mmol, 1.1 eq), iPr$_2$NEt (16 μL, 0.090 mmol, 2 eq), and tert-butyl 3-aminopropanoate, hydrochloride salt (9 mg, 0.050 mmol, 1.1 eq) in CH$_2$Cl$_2$ (2 mL) and the resulting solution was stirred at room temperature for 16 h. The reaction mixture was purified via silica gel chromatography (gradient elution: 0% to 75% EtOAc in hexanes) to afford the coupled product (25 mg) as a film.

Step 3:

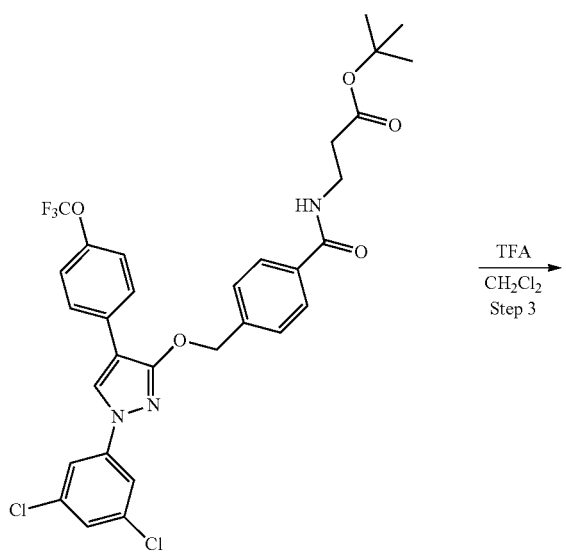

The product from Step 2 (25 mg, 0.038 mmol, 1 eq) was dissolved in CH₂Cl₂ (3 mL) and treated with trifluoroacetic acid (1.5 mL). After stirring for 2 h, the volatiles were removed in vacuo. The crude material was dissolved in Et₂O (3 mL) and the resulting solution was sonicated. A white solid resulted, which was collected via filtration, washed with Et₂O and dried to afford Example 20-1 (10 mg).

Microwave Reactions

All microwave reactions were performed using a Biotage Initiator Sixty microwave reactor.

Analytical Chromatography Conditions

The conditions utilized for the Electro Spray Ionization Liquid Chromatography-Mass Spectrometry (ESI-LC/MS) analysis of all examples described is as follows:

Column: Phenomenex Gemini C-18, 50×4.6 mm, 5 micron.

Mobile phase:

A: 0.05% Trifluoacetic acid in water

B: 0.05% Trifluoacetic acid in acetonitrile

Gradient: 90% A and 10% B to 5% A and 95% B over 5 minutes

Flow rate: 1.0 ml/min

UV detection: 254 nm

Spectrometer: PE SCIEX API-150EX, single quadrupole mass spectrometer.

High Resolution Mass Spectrometry Conditions

The conditions utilized for the High Resolution Mass Spectrometry (HRMS) analysis of all examples described is as follows:

Mobile phase:

A: 0.1% Trifluoacetic acid in water

B: 0.1% Trifluoacetic acid in acetonitrile

Elution: Isocratic, 5% A and 95% B

Flow rate: 0.1 mL/min

Method: direct infusion with NaCsI external standard calibrant.

HPLC System: Agilent 1110

Spectrometer: JEOL Accu-ToF model: JMS-T110LC

Preparative Chromatography Conditions

The conditions utilized for Preparative 018 Reversed-Phase Liquid Chromatography purification is as follows:

Column: Waters Prep LC 25 mm Module.

25 mm×100 mm Nova Pak® HR, C18, 6 µm, 60 Å column.

Mobile phase:

A: 0.1% formic acid in water

B: 0.1% formic acid in acetonitrile

Elution: Hold at 90% A and 10% B for 1 minute

Gradient from 10% B to 100% B over 10 minutes

Hold at 100% B for 6 minutes

Flow rate: 30 mL/min

UV detection: 254 nm

Example Compounds of the Invention

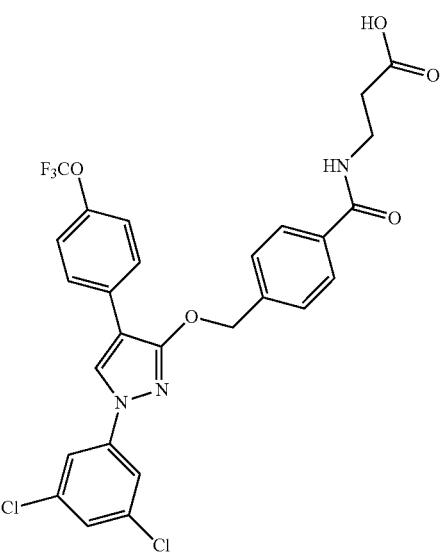

Example 20-1

TABLE A

The compounds of Formula (I) shown in the following table were prepared according to one or more of the methods reported above. The example numbers in Table A below correspond to the numbers of the examples described above. The observed ESI-LC/MS [M + H]⁺ is the observed mass spectrometry reading for the compound indicated. The retention time value refers to the retention time (in minutes) of the compound indicated when subjected to the LCMS conditions described above. The observed High Resolution Mass Spectrometry (HRMS) reading is the observed reading (as either [M + H]⁺ or [M + Na]⁺) for the compound indicated when subjected to the HRMS conditions described above. "—" in the table below means not measured.

| Example | Compound | ESI-LC/MS [M + H]$^+$ | Retention Time (min) | HRMS |
|---|---|---|---|---|
| 1-1 | | 576.3 | 4.97 | [M + Na]$^+$ $C_{30}H_{23}Cl_2N_3NaO_5$ calc: 598.09125 found: 598.08917 |
| 1-2 | | 542.3 | 4.52 | [M + Na]$^+$ $C_{30}H_{24}Cl_1N_3NaO_5$ calc: 564.13022 found: 564.13081 |
| 1-3 | | 592.3 | 4.80 | [M + Na]$^+$ $C_{31}H_{24}F_3N_3NaO_6$ calc: 614.15149 found: 614.15214 |
| 1-4 | | 576.3 | 4.42 | — |

TABLE A-continued

The compounds of Formula (I) shown in the following table were prepared according to one or more of the methods reported above. The example numbers in Table A below correspond to the numbers of the examples described above. The observed ESI-LC/MS [M + H]⁺ is the observed mass spectrometry reading for the compound indicated. The retention time value refers to the retention time (in minutes) of the compound indicated when subjected to the LCMS conditions described above. The observed High Resolution Mass Spectrometry (HRMS) reading is the observed reading (as either [M + H]⁺ or [M + Na]⁺) for the compound indicated when subjected to the HRMS conditions described above. "—" in the table below means not measured.

| Example | Compound | ESI-LC/MS [M + H]$^+$ | Retention Time (min) | HRMS |
|---|---|---|---|---|
| 2-1 | | 572.3 | 4.97 | [M + Na]$^+$ $C_{28}H_{19}Cl_2N_7NaO_3$ calc: 594.08241 found: 594.08413 |
| 3-1 | | 576.3 | 5.79 | — |
| 3-2 | | 544.3 | 4.99 | [M + Na]$^+$ $C_{30}H_{23}F_2N_3NaO_5$ calc: 566.15035 found: 566.15300 |
| 3-3 | | 576.3 | 5.23 | [M + Na]$^+$ $C_{31}H_{24}F_3N_3NaO_5$ calc: 598.15657 found: 598.15831 |

TABLE A-continued

The compounds of Formula (I) shown in the following table were prepared according to one or more of the methods reported above. The example numbers in Table A below correspond to the numbers of the examples described above. The observed ESI-LC/MS [M + H]+ is the observed mass spectrometry reading for the compound indicated. The retention time value refers to the retention time (in minutes) of the compound indicated when subjected to the LCMS conditions described above. The observed High Resolution Mass Spectrometry (HRMS) reading is the observed reading (as either [M + H]+ or [M + Na]+) for the compound indicated when subjected to the HRMS conditions described above. "—" in the table below means not measured.

| Example | Compound | ESI-LC/MS [M + H]+ | Retention Time (min) | HRMS |
|---|---|---|---|---|
| 4-1 | | 542.3 | 5.20 | — |
| 4-2 | | 576.3 | 5.57 | [M + H]+ $C_{30}H_{24}Cl_2N_3O_5$ calc: 576.10930 found: 576.10908 |
| 5-1 | | 576.3 | 5.72 | — |

TABLE A-continued

The compounds of Formula (I) shown in the following table were prepared according to one or more of the methods reported above. The example numbers in Table A below correspond to the numbers of the examples described above. The observed ESI-LC/MS [M + H]$^+$ is the observed mass spectrometry reading for the compound indicated. The retention time value refers to the retention time (in minutes) of the compound indicated when subjected to the LCMS conditions described above.
The observed High Resolution Mass Spectrometry (HRMS) reading is the observed reading (as either [M + H]$^+$ or [M + Na]$^+$) for the compound indicated when subjected to the HRMS conditions described above. "—" in the table below means not measured.

| Example | Compound | ESI-LC/MS [M + H]$^+$ | Retention Time (min) | HRMS |
|---|---|---|---|---|
| 6-1 | 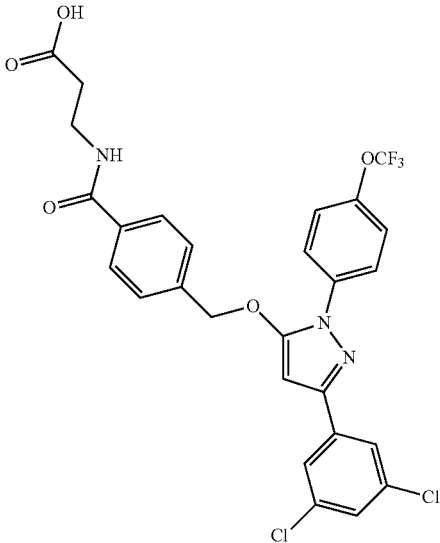 [SMILES: O=C(O)CCNC(=O)c1ccc(COc2cc(-c3cc(Cl)cc(Cl)c3)nn2-c2ccc(OC(F)(F)F)cc2)cc1] | 594.3 | 5.91 | — |
| 7-1 | 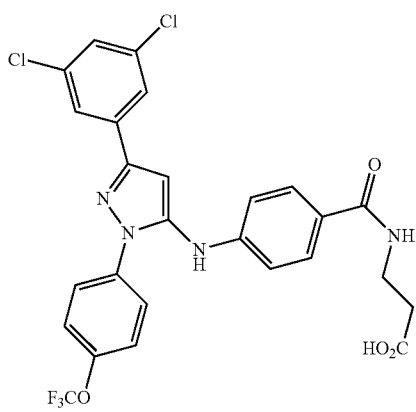 [SMILES: O=C(O)CCNC(=O)c1ccc(Nc2cc(-c3cc(Cl)cc(Cl)c3)nn2-c2ccc(OC(F)(F)F)cc2)cc1] | 579.3 | 5.23 | [M + Na]$^+$ C$_{26}$H$_{19}$Cl$_2$F$_3$N$_4$NaO$_4$ calc: 601.06331 found: 601.06422 |
| 8-1 | 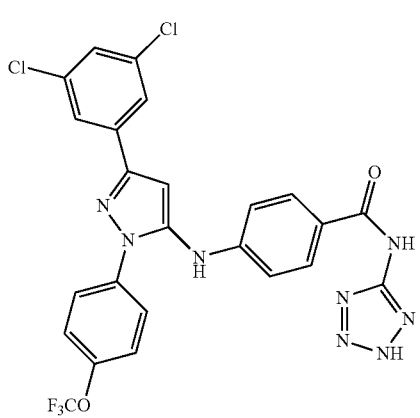 [SMILES: O=C(Nc1nn[nH]n1)c1ccc(Nc2cc(-c3cc(Cl)cc(Cl)c3)nn2-c2ccc(OC(F)(F)F)cc2)cc1] | 575.3 | 5.36 | — |

TABLE A-continued

The compounds of Formula (I) shown in the following table were prepared according to one or more of the methods reported above. The example numbers in Table A below correspond to the numbers of the examples described above. The observed ESI-LC/MS [M + H]⁺ is the observed mass spectrometry reading for the compound indicated. The retention time value refers to the retention time (in minutes) of the compound indicated when subjected to the LCMS conditions described above.
The observed High Resolution Mass Spectrometry (HRMS) reading is the observed reading (as either [M + H]⁺ or [M + Na]⁺) for the compound indicated when subjected to the HRMS conditions described above. "—" in the table below means not measured.

| Example | Compound | ESI-LC/MS [M + H]$^+$ | Retention Time (min) | HRMS |
|---|---|---|---|---|
| 9-1 | | 593.3 | 5.35 | — |
| 10-1 | | 580.3 | 5.36 | [M + Na]$^+$<br>C$_{26}$H$_{18}$Cl$_2$F$_3$N$_3$NaO$_5$<br>calc: 602.04733<br>found: 601.04978 |
| 10-2 | | 546.3 | 5.09 | [M + Na]$^+$<br>C$_{26}$H$_{19}$Cl$_1$F$_3$N$_3$NaO$_5$<br>calc: 568.08630<br>found: 568.08852 |

TABLE A-continued

The compounds of Formula (I) shown in the following table were prepared according to one or more of the methods reported above. The example numbers in Table A below correspond to the numbers of the examples described above. The observed ESI-LC/MS [M + H]⁺ is the observed mass spectrometry reading for the compound indicated. The retention time value refers to the retention time (in minutes) of the compound indicated when subjected to the LCMS conditions described above. The observed High Resolution Mass Spectrometry (HRMS) reading is the observed reading (as either [M + H]⁺ or [M + Na]⁺) for the compound indicated when subjected to the HRMS conditions described above. "—" in the table below means not measured.

| Example | Compound | ESI-LC/MS [M + H]$^+$ | Retention Time (min) | HRMS |
|---|---|---|---|---|
| 10-3 | | 526.3 | 5.10 | [M + H]$^+$ $C_{26}H_{22}Cl_2N_3O_5$ calc: 526.09365 found: 526.09511 |
| 11-1 | | 590 | 5.57 | [M + H]$^+$ $C_{31}H_{25}Cl_2N_3O_5$ calc: 590.12495 found: 590.12404 |
| 12-1 | | 554.3 | 5.35 | [M + H]$^+$ $C_{28}H_{26}Cl_2N_3O_5$ calc: 554.12495 found: 554.12492 |

TABLE A-continued

The compounds of Formula (I) shown in the following table were prepared according to one or more of the methods reported above. The example numbers in Table A below correspond to the numbers of the examples described above. The observed ESI-LC/MS [M + H]⁺ is the observed mass spectrometry reading for the compound indicated. The retention time value refers to the retention time (in minutes) of the compound indicated when subjected to the LCMS conditions described above. The observed High Resolution Mass Spectrometry (HRMS) reading is the observed reading (as either [M + H]⁺ or [M + Na]⁺) for the compound indicated when subjected to the HRMS conditions described above. "—" in the table below means not measured.

| Example | Compound | ESI-LC/MS [M + H]⁺ | Retention Time (min) | HRMS |
|---|---|---|---|---|
| 12-2 | 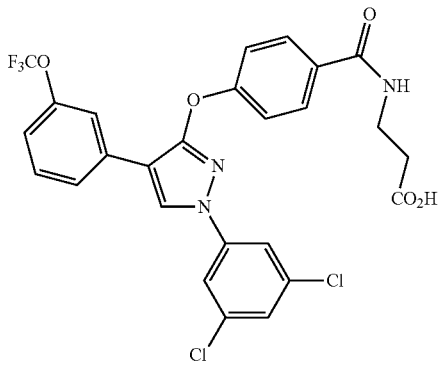 [SMILES: O=C(O)CCNC(=O)c1ccc(Oc2nn(-c3cc(Cl)cc(Cl)c3)cc2-c2cccc(OC(F)(F)F)c2)cc1] | 580.3 | 5.50 | [M + H]⁺ $C_{26}H_{19}Cl_2F_3N_3O_5$ calc: 580.06539 found: 580.06424 |
| 12-3 | 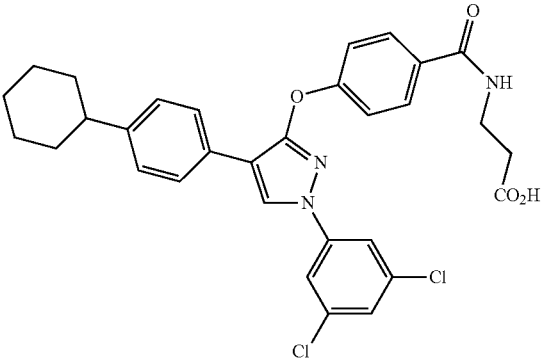 [SMILES: O=C(O)CCNC(=O)c1ccc(Oc2nn(-c3cc(Cl)cc(Cl)c3)cc2-c2ccc(C3CCCCC3)cc2)cc1] | 578.3 | 6.28 | [M + H]⁺ $C_{31}H_{30}Cl_2N_3O_4$ calc: 578.16134 found: 578.16160 |
| 12-4 | 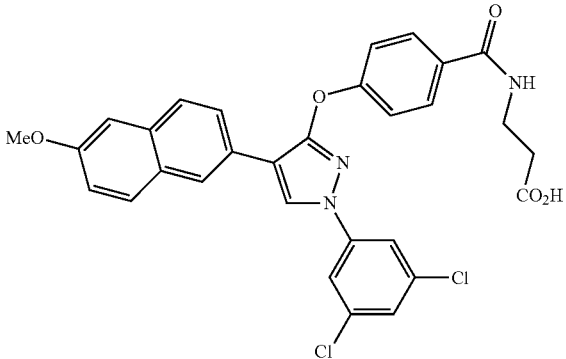 [SMILES: COc1ccc2cc(-c3cn(-c4cc(Cl)cc(Cl)c4)nc3Oc3ccc(C(=O)NCCC(=O)O)cc3)ccc2c1] | 576.3 | 5.63 | — |

TABLE A-continued

The compounds of Formula (I) shown in the following table were prepared according to one or more of the methods reported above. The example numbers in Table A below correspond to the numbers of the examples described above. The observed ESI-LC/MS [M + H]⁺ is the observed mass spectrometry reading for the compound indicated. The retention time value refers to the retention time (in minutes) of the compound indicated when subjected to the LCMS conditions described above.
The observed High Resolution Mass Spectrometry (HRMS) reading is the observed reading (as either [M + H]⁺ or [M + Na]⁺) for the compound indicated when subjected to the HRMS conditions described above. "—" in the table below means not measured.

| Example | Compound | ESI-LC/MS [M + H]$^+$ | Retention Time (min) | HRMS |
|---|---|---|---|---|
| 14-1 | | 624.3 | 5.18 | — |
| 14-2 | | 638.4 | 5.23 | — |
| 14-3 | | 610.3 | 5.11 | — |

TABLE A-continued

The compounds of Formula (I) shown in the following table were prepared according to one or more of the methods reported above. The example numbers in Table A below correspond to the numbers of the examples described above. The observed ESI-LC/MS [M + H]⁺ is the observed mass spectrometry reading for the compound indicated. The retention time value refers to the retention time (in minutes) of the compound indicated when subjected to the LCMS conditions described above. The observed High Resolution Mass Spectrometry (HRMS) reading is the observed reading (as either [M + H]⁺ or [M + Na]⁺) for the compound indicated when subjected to the HRMS conditions described above. "—" in the table below means not measured.

| Example | Compound | ESI-LC/MS [M + H]$^+$ | Retention Time (min) | HRMS |
|---|---|---|---|---|
| 14-4 | | 598.3 | 5.03 | — |
| 14-5 | | 564.3 | 5.08 | — |
| 16-1 | | 658.4 | 4.63 | — |

TABLE A-continued

The compounds of Formula (I) shown in the following table were prepared according to one or more of the methods reported above. The example numbers in Table A below correspond to the numbers of the examples described above. The observed ESI-LC/MS [M + H]⁺ is the observed mass spectrometry reading for the compound indicated. The retention time value refers to the retention time (in minutes) of the compound indicated when subjected to the LCMS conditions described above. The observed High Resolution Mass Spectrometry (HRMS) reading is the observed reading (as either [M + H]⁺ or [M + Na]⁺) for the compound indicated when subjected to the HRMS conditions described above. "—" in the table below means not measured.

| Example | Compound | ESI-LC/MS [M + H]⁺ | Retention Time (min) | HRMS |
|---|---|---|---|---|
| 17-1 | | 594.3 | 5.46 | [M + H]⁺ $C_{27}H_{21}Cl_2F_3N_3O_5$ calc: 594.08104 found: 594.08020 |
| 18-1 | | 5.31 | 634.3 | [M + H]⁺ $C_{34}H_{31}F_3N_3O_6$ calc: 634.21649 found: 634.21496 |
| 19-1 | | 5.39 | 593.3 | — |

TABLE A-continued

The compounds of Formula (I) shown in the following table were prepared according to one or more of the methods reported above. The example numbers in Table A below correspond to the numbers of the examples described above. The observed ESI-LC/MS [M + H]⁺ is the observed mass spectrometry reading for the compound indicated. The retention time value refers to the retention time (in minutes) of the compound indicated when subjected to the LCMS conditions described above. The observed High Resolution Mass Spectrometry (HRMS) reading is the observed reading (as either [M + H]⁺ or [M + Na]⁺) for the compound indicated when subjected to the HRMS conditions described above. "—" in the table below means not measured.

| Example | Compound | ESI-LC/MS [M + H]⁺ | Retention Time (min) | HRMS |
| --- | --- | --- | --- | --- |
| 20-1 | 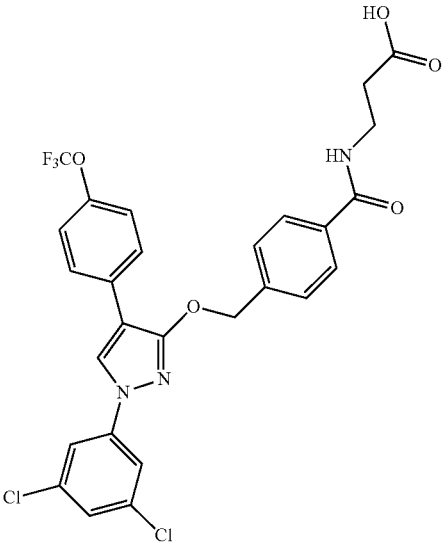 [SMILES: O=C(O)CCNC(=O)c1ccc(COc2nn(-c3cc(Cl)cc(Cl)c3)cc2-c2ccc(OC(F)(F)F)cc2)cc1] | 594.3 | 5.81 | — |

ABBREVIATION LIST

| Abbreviation | Reagent |
| --- | --- |
| EDCl | 1,3-Propanediamine, N3-(ethylcarbonimidoyl)-N1,N1-dimethyl-, hydrochloride |
| iPr₂NEt | diisopropylethylamine |
| HOBt | 1-hydroxybenzotriazole |
| MeCN | acetonitrile |
| Et₂O | diethyl ether |
| Cu(OAc)₂ | copper (II) acetate |
| EtOH | ethanol |
| DCE | 1,2-dichloroethane |
| DMF | N,N-dimethylformamide |
| MeOH | methanol |
| PyBOP | benzotriazol-1-yloxy tris(pyrrolidino)phosphonium hexafluorophosphate |
| DMF·DMA | N,N-dimethylformamide, dimethyl acetal |
| THF | tetrahydrofuran |
| TFA | trifluoroacetic acid |
| Pd/BaSO₄ | palladium on barium sulfate |
| LDA | lithium diisopropylamide |
| NaOH | sodium hydroxide |
| EtOAc | ethyl acetate |
| Na₂SO₄ | sodium sulfate |
| MgSO₄ | magnesium sulfate |
| Et₃N | triethylamine |
| Pd(OAc)₂ | palladium (II) acetate |
| NaOt-Bu | sodium tert-butoxide |
| X-Phos | 2-(dicyclohexylphosphino)-2',4',6'-triisopropyl-1,1'-biphenyl |
| NaHCO₃ | sodium bicarbonate |
| NH₄Cl | ammonium chloride |
| NH₄OH | ammonium hydroxide |
| CCl₄ | carbon tetrachloride |

Biological Assays

The ability of the compounds of the invention to inhibit the binding of glucagon and their utility in treating or preventing type 2 diabetes mellitus and related conditions can be demonstrated by the following in vitro assays.

Glucagon Receptor Binding Assay

Recombinant human glucagon receptor (huGlucR) membranes and mouse glucagon receptor (mGlucR) membranes were prepared in-house from huGlucR/clone 103c/CHO and mouse liver tissue, respectively. 0.03 ug/li huGluR membranes (or 0.5 ug/ml mGlucR) was incubated in assay buffer containing 0.05 nM $^{125}$I-Glucagon (Perkin Elmer, NEX 207) and varying concentrations of antagonist at room temperature for 60 to 90 (assay buffer: 50 mM HEPES, 1 mM MgCl₂, 1 mM CaCl₂, 1 mg/ml BSA, COMPLETE protease inhibitor cocktail, pH 7.4). The total volume of the assay was 200 ul. The assay was performed at room temperature using 96-deep well plate. Compound 4c, racemic diastereomer 1 (D1), (1.0 µM final concentration), described by G. H. Ladouceur et al. in Bioorganic and Medicinal Chemistry Letters, 12 (2002), 3421-3424, was used to determine non-specific binding. Following incubation, the reaction was stopped by rapid filtration through Unfilter-96 GF/C glass fiber filter plates (Perkin Elmer) pre-soaked in 0.5% polyethyleneimine. The filtrate was washed using 50 mM Tris-HCl, pH 7.4. Dried filter plates containing bound radioactivity were counted in the presence of scintillation fluid (Microscint 0, Perkin-Elmer) using a Topcount scintillation counter. Data was analyzed using the software program Prism (GraphPad). $IC_{50}$ values were calculated using non-linear regression analysis assuming single site competition.

Inhibition of Glucagon-Stimulated Intracellular cAMP Assay

Recombinant human glucagon receptor-expressing CHO cells were harvested using a non-enzymatic cell dissociation solution (GIBCO 2672), pelleted and resuspended in stimulation buffer (1×HBSS, 5 mM Hepes, 0.1% BSA, pH7.4 in the presence of proteinase inhibitor and phosphodiesterase inhibitors). The adenylate cyclase assay was constructed following the LANCE cAMP Kit (Perkin Elmer, AD0264) instructions. Briefly, cells were preincubated with anti-cAMP antibody and 12 points series diluted compound in stimulation buffer with a final concentration of 3% DMSO for 30 minutes prior to stimulation with 300 pM glucagon for 45 minutes. The reaction was stopped by incubating with the supplied detection buffer containing Europium chelate of the Eu-SA/Biotin-cAMP tracer for 20 hours. The assay was done as triplicates in a 384 well plate. Fluorescence at 665 nm was measured using PheraStar instruments. Basal activity (100% inhibition) was determined using the DMSO control and 0% inhibition was defined as cAMP stimulation produced by 300 pM glucagon. Standard cAMP concentrations were assayed concurrently for conversion of fluorescence signal to cAMP level. Data was analyzed using the software program Prism from GraphPad. $IC_{50}$ values were calculated using non-linear regression analysis assuming single site competition. $IC_{50}$ values for the compounds of the invention shown in the examples measured less than about 10 μM, in preferred embodiments less than about 1 μM, in more preferred embodiments less than about 500 nM.

In another embodiment, the present invention provides a pharmaceutical composition comprising a compound of the invention described above in combination with a pharmaceutically acceptable carrier.

In another embodiment, the present invention provides a method for inhibiting glucagon receptors comprising exposing an effective amount of a compound or a composition comprising a compound of the invention to glucagon receptors. In one embodiment, said glucagon receptors are part of a glucagon receptor assay. Non-limiting examples of such assays include glucagon receptor assays and glucagon-strimuloated intracellular cAMP formation assays such as those described above. In one embodiment, said glucagon receptors are expressed in a population of cells. In one embodiment, the population of cells is in in vitro. In one embodiment, the population of cells is in ex viva In one embodiment, the population of cells is in a patient.

Methods of Treatment, Compositions, and Combination Therapy

In another embodiment, the present invention provides a method of treating type 2 diabetes mellitus in a patient in need of such treatment comprising administering to said patient a compound of the invention or a composition comprising a compound of the invention in an amount effective to treat type 2 diabetes mellitus.

In another embodiment, the present invention provides a method of delaying the onset of type 2 diabetes mellitus in a patient in need of such treatment comprising administering to said patient a compound of the invention or a composition comprising a compound of the invention in an amount effective to delay the onset of type 2 diabetes mellitus.

In another embodiment, the present invention provides a method of treating hyperglycemia, diabetes, or insulin resistance in a patient in need of such treatment comprising administering to said patient a compound of the invention, or a composition comprising a compound of the invention, in an amount that is effective to treat hyperglycemia, diabetes, or insulin resistance.

In another embodiment, the present invention provides a method of treating non-insulin dependent diabetes mellitus in a patient in need of such treatment comprising administering to said patient an anti-diabetic effective amount of a compound of the invention or a composition comprising an effective amount of a compound of the invention.

In another embodiment, the present invention provides a method of treating obesity in a patient in need of such treatment comprising administering to said patient a compound of the invention or a composition comprising a compound of the invention in an amount that is effective to treat obesity.

In another embodiment, the present invention provides a method of treating one or more conditions associated with Syndrome X (also known as metabolic syndrome, metabolic syndrome X, insulin resistance syndome, Reaven's syndrome) in a patient in need of such treatment comprising administering to said patient a compound of the invention or a composition comprising an effective amount of a compound of the invention in an amount that is effective to treat Syndrome X.

In another embodiment, the present invention provides a method of treating a lipid disorder in a patient in need of such treatment comprising administering to said patient a compound of the invention, or a composition comprising a compound of the invention, in an amount that is effective to treat said lipid disorder. Non-limiting examples of such lipid disorders include: dyslipidemia, hyperlipidemia, hypertriglyceridemia, hypercholesterolemia, low HDL and high LDL, and metabolic syndrome.

In another embodiment, the present invention provides a method of treating atherosclerosis in a patient in need of such treatment comprising administering to said patient a compound of the invention or a composition comprising a compound of the invention, in an amount effective to treat atherosclerosis.

In another embodiment, the present invention provides a method of delaying the onset of, or reducing the risk of developing, atherosclerosis in a patient in need of such treatment comprising administering to said patient a compound of the invention or a composition comprising a compound of the invention, in an amount effective to delay the onset of, or reduce the risk of developing, atherosclerosis.

In another embodiment, the present invention provides a method of treating a condition or a combination of conditions selected from hyperglycemia, low glucose tolerance, insulin resistance, obesity, abdominal obesity, lipid disorders, dyslipidemia, hyperlipidemia, hypertriglyceridemia, hypercholesterolemia, low HDL levels, high LDL levels, atherosclerosis, atherosclerosis and its sequelae, vascular restenosis, pancreatitis, neurodegenerative disease, retinopathy, nephropathy, neuropathy, Syndrome X and other conditions where insulin resistance is a component, in a patient in need thereof, comprising administering to said patient a compound of the invention, or a composition comprising a compound of the invention, in an amount that is effective to treat said condition or conditions.

In another embodiment, the present invention provides a method of delaying the onset of a condition or a combination of conditions selected from hyperglycemia, low glucose tolerance, insulin resistance, obesity, abdominal obesity, lipid disorders, dyslipidemia, hyperlipidemia, hypertriglyceridemia, hypercholesterolemia, low HDL levels, high LDL levels, atherosclerosis, atherosclerosis and its sequelae, vascular restenosis, pancreatitis, neurodegenerative disease, retinopathy, nephropathy, neuropathy, Syndrome X and other conditions where insulin resistance is a component, in a patient in need thereof, comprising administering to said patient a compound of the invention, or a composition comprising a compound of the invention, in an amount that is effective to delay the onset said condition or conditions.

In another embodiment, the present invention provides a method of reducing the risk of developing a condition or a combination of conditions selected from hyperglycemia, low glucose tolerance, insulin resistance, obesity, abdominal obesity, lipid disorders, dyslipidemia, hyperlipidemia, hypertriglyceridemia, hypercholesterolemia, low HDL levels, high LDL levels, atherosclerosis, atherosclerosis and its sequelae, vascular restenosis, pancreatitis, neurodegenerative disease, retinopathy, nephropathy, neuropathy, Syndrome X and other conditions where insulin resistance or hyperglycemia is a component, in a patient in need thereof, comprising administering to said patient a compound of the invention, or a composition comprising a compound of the invention, in an amount that is effective to reduce the risk of developing said condition or conditions.

In another embodiment, the present invention provides a method of treating a condition selected from type 2 diabetes mellitus, hyperglycemia, low glucose tolerance, insulin resistance, obesity, abdominal obesity, lipid disorders, dyslipidemia, hyperlipidemia, hypertriglyceridemia, hypercholesterolemia, low HDL levels, high LDL levels, atherosclerosis, atherosclerosis and its sequelae, vascular restenosis, pancreatitis, neurodegenerative disease, retinopathy, nephropathy, neuropathy, Syndrome X and other conditions where insulin resistance is a component, in a patient in need thereof, comprising administering to said patient effective amounts of a compound of the invention and one or more additional active agents.

Non-limiting examples of such additional active agents include the following:

DPP-IV inhibitors. Non-limiting examples of DPP-IV inhibitors include alogliptin (Takeda), saxagliptin (Brystol-Myers Squibb), sitagliptin (Januvia™ Merck), vildagliptin (Galvus™, Novartis), denagliptin (GlaxoSmithKline), ABT-279 and ABT-341 (Abbott), ALS-2-0426 (Alantos), ARI-2243 (Arisaph), BI-A and BI-B (Boehringer Ingelheim), SYR-322 (Takeda), compounds disclosed in U.S. Pat. No. 6,699,871, MP-513 (Mitsubishi), DP-893 (Pfizer), RO-0730699 (Roche) and combinations thereof. Non-limiting examples of such combinations include Janumet™, a combination of sitagliptin/metformin HCl (Merck).

Insulin sensitizers. Non-limiting examples of insulin sensitizers include PPAR agonists and biguanides. Non-limiting examples of PPAR agonists include glitazone and thiaglitazone agents such as rosiglitazone, rosiglitazone maleate (AVANDIA™, GlaxoSmithKline), pioglitazone, pioglitazone hydrochloride (ACTOS™, Takeda), ciglitazone and MCC-555 (Mitstubishi Chemical Co.), troglitazone and englitazone. Non-limiting example of biguanides include phenformin, metformin, metformin hydrochloride (such as GLUCOPHAGE®, Bristol-Myers Squibb), metformin hydrochloride with glyburide (such as GLUCOVANCE™, Bristol-Myers Squibb) and buformin. Other non-limiting examples of insulin sensitizers include PTP-1B inhibitors; and glucokinase activators, such as miglitol, acarbose, and voglibose.

Insulin and insulin mimetics. Non-limiting examples of orally administrable insulin and insulin containing compositions include AL-401 (Autoimmune), and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

Sulfonylureas and other insulin secretagogues. Non-limiting examples of sulfonylureas and other secretagogues include glipizide, tolbutamide, glyburide, glimepiride, chlorpropamide, acetohexamide, gliamilide, gliclazide, glibenclamide, tolazamide, GLP-1, GLP-1 mimetics, exendin, GIP, secretin, nateglinide, meglitinide, glibenclamide, and repaglinide. Non-limiting examples of GLP-1 mimetics include Byetta™ (exenatide), Liraglutinide, CJC-1131 (ConjuChem), exenatide-LAR (Amylin), BIM-51077 (Ipsen/LaRoche), ZP-10 (Zealand Pharmaceuticals), and compounds disclosed in International Publication No. WO 00/07617.

Glucosidase inhibitors and alpha glucosidase inhibitors.

Glucagon receptor antagonists other than compounds of the invention.

Hepatic glucose output lowering agents other than a glucagon receptor antagonist. Non-limiting examples of hepatic glucose output lowering agents include Glucophage and Glucophage XR.

An antihypertensive agent. Non-limiting examples of antihypertensive agents include beta-blockers and calcium channel blockers (for example diltiazem, verapamil, nifedipine, amlopidine, and mybefradil), ACE inhibitors (for example captopril, lisinopril, enalapril, spirapril, ceranopril, zefenopril, fosinopril, cilazopril, and quinapril), AT-1 receptor antagonists (for example losartan, irbesartan, and valsartan), renin inhibitors and endothelin receptor antagonists (for example sitaxsentan).

A meglitinide. Non-limiting examples of meglitinides useful in the present methods for treating diabetes include repaglinide and nateglinide.

An agent that blocks or slows the breakdown of starches or sugars in vivo. Non-limiting examples of antidiabetic agents that slow or block the breakdown of starches and sugars in vivo include alpha-glucosidase inhibitors and certain peptides for increasing insulin production; Alpha-glucosidase inhibitors (which help the body to lower blood sugar by delaying the digestion of ingested carbohydrates, thereby resulting in a smaller rise in blood glucose concentration following meals). Non-limiting examples of alpha-glucosidase inhibitors include acarbose; miglitol; camiglibose; certain polyamines as disclosed in WO 01/47528 (incorporated herein by reference); and voglibose.

Peptides for increasing insulin production. Non-limiting examples of suitable peptides for increasing insulin production including amlintide (CAS Reg. No. 122384-88-7, Amylin); pramlintide, exendin, certain compounds having Glucagon-like peptide-1 (GLP-1) agonistic activity as disclosed in WO 00/07617 (incorporated herein by reference).

A histamine $H_3$ receptor antagonist. Non-limiting examples of histamine $H_3$ receptor antagonist agents include the following compound:

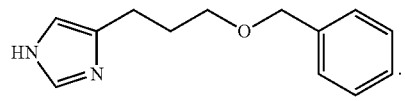 [SMILES: c1ccc(COCCCc2c[nH]cn2)cc1]

A sodium glucose uptake transporter 2 (SGLT-2) inhibitor. Non-limiting examples of SGLT-2 inhibitors useful in the present methods include dapagliflozin and sergliflozin, AVE2268 (Sanofi-Aventis) and T-1095 (Tanabe Seiyaku).

PACAP (pituitary adenylate cyclase activating polypeptide agonists) and PACAP mimetics.

Cholesterol lowering agents. Non-limiting examples of cholesterol lowering agents include HMG-CoA reducatase inhibitors, sequestrants, nicotinyl alcohol, nicotinic acid and salts thereof, PPAR alpha agonists, PPAR alpha/gamma dual agonists, inhibitors of cholesterol absorption (such as ezetimibe (Zetia®)), combinations of HMG-CoA reductase inhibitors and cholesterol absorption agents (such as Vytorin®), acyl CoA:cholesterol acyltransferase inhibitors, anti-oxidants, LXR modulators, and CETP (cholesterolester transfer protein) inhibitors such as Torcetrapib™ (Pfizer) and Anacetrapib™ (Merck).

Agents capable of raising serum HDL cholesterol levels. Non-limiting examples include niacin (vitamin B-3), such as Niaspan™ (Kos). Niacin may be administered alone or optionally combined with one or more additional active agents such as: niacin/lovastatin (Advicor™, Abbott), niacin/simvastatin (Simcor™, Abbott), and/or niacin/aspirin.

PPAR delta agonists.

Antiobesity agents. Non-limiting examples of anti-obesity agents useful in the present methods for treating diabetes include a 5-HT2C agonist, such as lorcaserin; a neuropeptide γ antagonist; an MCR4 agonist; an MCH receptor antagonist; a protein hormone, such as leptin or adiponectin; an AMP kinase activator; and a lipase inhibitor, such as orlistat.

Ileal bile acid transporter inhibitors.

Anti-inflammatory agents, such as NSAIDs. Non-limiting examples of NSAIDS include a salicylate, such as aspirin, amoxiprin, benorilate or diflunisal; an arylalkanoic acid, such as diclofenac, etodolac, indometacin, ketorolac, nabumetone, sulindac or tolmetin; a 2-arylpropionic acid (a "profen"), such as ibuprofen, carprofen, fenoprofen, flurbiprofen, loxoprofen, naproxen, tiaprofenic acid or suprofen; a fenamic acid, such as mefenamic acid or meclofenamic acid; a pyrazolidine derivative, such as phenylbutazone, azapropazone, metamizole or oxyphenbutazone; a coxib, such as celecoxib, etoricoxib, lumiracoxib or parecoxib; an oxicam, such as piroxicam, lornoxicam, meloxicam or tenoxicam; or a sulfonanilide, such as nimesulide.

Anti-pain medications, including NSAIDs as discussed above, and opiates. Non-limiting examples of opiates include an anilidopiperidine, a phenylpiperidine, a diphenylpropylamine derivative, a benzomorphane derivative, an oripavine derivative and a morphinane derivative. Additional illustrative examples of opiates include morphine, diamorphine, heroin, buprenorphine, dipipanone, pethidine, dextromoramide, alfentanil, fentanyl, remifentanil, methadone, codeine, dihydrocodeine, tramadol, pentazocine, vicodin, oxycodone, hydrocodone, percocet, percodan, norco, dilaudid, darvocet or lorcet.

Antidepressants. Non-limiting examples of tricyclic antidepressants useful in the present methods for treating pain include amitryptyline, carbamazepine, gabapentin or pregabalin.

Protein tyrosine phosphatase-1B (PTP-1B) inhibitors.

CB1 antagonists/inverse agonists. Non-limiting examples of CB1 receptor antagonists and inverse agonists include rimonabant and those disclosed in WO03/077847A2, published Sep. 25, 2003, WO05/000809, published Jan. 6, 2005, and WO2006/060461, published Jun. 8, 2006.

In another embodiment, the present invention provides a method of treating a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor.

In another embodiment, the present invention provides a method of treating a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor, wherein the HMG-CoA reductase inhibitor is a statin.

In another embodiment, the present invention provides a method of treating a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor, wherein the HMG-CoA reductase inhibitor is a statin selected from lovastatin, simvastatin, pravastatin, fluvastatin, atorvastatin, itavastatin, ZD-4522, and rivastatin.

In another embodiment, the present invention provides a method of reducing the risk of developing, or delaying the onset of, a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor.

In another embodiment, the present invention provides a method of reducing the risk of developing, or delaying the onset of, a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor, wherein the HMG-CoA reductase inhibitor is a statin.

In another embodiment, the present invention provides a method of reducing the risk of developing, or delaying the onset of, a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor, wherein the HMG-CoA reductase inhibitor is a statin selected from lovastatin, simvastatin, pravastatin, fluvastatin, atorvastatin, itavastatin, ZD-4522, and rivastatin.

In another embodiment, the present invention provides a method of reducing the risk of developing, or delaying the onset of atherosclerosis, high LDL levels, hyperlipidemia, and dyslipidemia, in a patient in need of such treatment, comprising administering to the patient a therapeutically effective amount or amounts of a compound of the invention, or a composition comprising a compound of the invention, and a cholesterol absorption inhibitor, optionally in further combination with a statin.

In another embodiment, the present invention provides a method of reducing the risk of developing, or delaying the onset of atherosclerosis, high LDL levels, hyperlipidemia, and dyslipidemia, in a patient in need of such treatment, comprising administering to the patient a therapeutically effective amount or amounts of a compound of the invention, or a composition comprising a compound of the invention, and a cholesterol absorption inhibitor, optionally in further combination with one or more statins, wherein the cholesterol absorption inhibitor is selected from ezetimibe, ezetimibe/simvastatin combination (Vytorin®), and a stanol.

In another embodiment, the present invention provides a pharmaceutical composition comprising (1) a compound according to the invention; (2) one or more compounds or agents selected from DPP-IV inhibitors, insulin sensitizers, insulin and insulin mimetics, a sulfonylurea, an insulin secretagogue, a glucosidase inhibitor, an alpha glucosidase inhibitor, a glucagon receptor antagonists other than a compound of the invention, a hepatic glucose output lowering agent other than a glucagon receptor antagonist, an antihypertensive agent, a meglitinide, an agent that blocks or slows the breakdown of starches or sugars in vivo, an alpha-glucosidase inhibitor, a peptide capable of increasing insulin production, a histamine $H_3$ receptor antagonist, a sodium glucose uptake transporter 2 (SGLT-2) inhibitor, a peptide that increases insulin production, a GIP cholesterol lowering agent, a PACAP, a PACAP mimetic, a PACAP receptor agonist, a cholesterol lowering agent, a PPAR delta agonist, an antiobesity agent, an ileal bile acid transporter inhibitor, an anti-inflammatory agent, an anti-pain medication, an antidepressant, a protein tyrosine phosphatase-1B (PTP-1B) inhibitor, a CB1 antagonist, and a CB1 inverse agonist; and (3) one or more pharmaceutically acceptable carriers.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts).

In one embodiment, the one or more compounds of the invention is administered during at time when the additional therapeutic agent(s) exert their prophylactic or therapeutic effect, or vice versa.

In another embodiment, the one or more compounds of the invention and the additional therapeutic agent(s) are administered in doses commonly employed when such agents are used as monotherapy for treating a condition.

In another embodiment, the one or more compounds of the invention and the additional therapeutic agent(s) are administered in doses lower than the doses commonly employed when such agents are used as monotherapy for treating a condition.

In still another embodiment, the one or more compounds of the invention and the additional therapeutic agent(s) act synergistically and are administered in doses lower than the doses commonly employed when such agents are used as monotherapy for treating a condition.

In one embodiment, the one or more compounds of the invention and the additional therapeutic agent(s) are present in the same composition. In one embodiment, this composition is suitable for oral administration. In another embodiment, this composition is suitable for intravenous administration.

The one or more compounds of the invention and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of one or more compounds of the invention and the additional therapeutic agent(s) may inhibit the resistance of a condition to the agent(s).

In one embodiment, when the patient is treated for diabetes, a diabetic complication, impaired glucose tolerance or impaired fasting glucose, the other therapeutic is an antidiabetic agent which is not a compound of the invention. In another embodiment, when the patient is treated for pain, the other therapeutic agent is an analgesic agent which is not a compound of the invention.

In another embodiment, the other therapeutic agent is an agent useful for reducing any potential side effect of a compound of the invention. Non-limiting examples of such potential side effects include nausea, vomiting, headache, fever, lethargy, muscle aches, diarrhea, general pain, and pain at an injection site.

In one embodiment, the other therapeutic agent is used at its known therapeutically effective dose. In another embodiment, the other therapeutic agent is used at its normally prescribed dosage. In another embodiment, the other therapeutic agent is used at less than its normally prescribed dosage or its known therapeutically effective dose.

The doses and dosage regimen of the other agents used in the combination therapies of the present invention for the treatment or prevention of a condition described herein can be determined by the attending clinician, taking into consideration the approved doses and dosage regimen in the package insert; the age, sex and general health of the patient; and the type and severity of the viral infection or related disease or disorder. When administered in combination, the compound(s) of the invention and the other agent(s) for treating diseases or conditions listed above can be administered simultaneously or sequentially. This is particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the one or more compounds of the invention and the additional therapeutic agent(s) can, when administered as combination therapy, range from about 0.1 to about 2000 mg per day, although variations will necessarily occur depending on the target of the therapy, the patient and the route of administration. In one embodiment, the dosage is from about $O_2$ to about 100 mg/day, administered in a single dose or in 2-4 divided doses. In another embodiment, the dosage is from about 1 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses.

As indicated above, in one embodiment, the invention provides compositions comprising an effective amount of one or more compounds of the invention or a pharmaceutically acceptable salt, solvate, ester or prodrug thereof, and a pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

In one embodiment, the compound of the invention is administered orally.

In another embodiment, the compound of the invention is administered parenterally.

In another embodiment, the compound of the invention is administered intravenously.

In one embodiment, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation is from about 0.1 to about 2000 mg. Variations will necessarily occur depending on the target of the therapy, the patient and the route of administration. In one embodiment, the unit dose dosage is from about 0.2 to about 1000 mg. In another embodiment, the unit dose dosage is from about 1 to about 500 mg. In another embodiment, the unit dose dosage is from about 1 to about 100 mg/day. In still another embodiment, the unit dose dosage is from about 1 to about 50 mg. In yet another embodiment, the unit dose dosage is from about 1 to about 10 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

When the invention comprises a combination of at least one compound of the invention and an additional therapeutic agent, the two active components may be co-administered simultaneously or sequentially, or a single pharmaceutical composition comprising at least one compound of the invention and an additional therapeutic agent in a pharmaceutically acceptable carrier can be administered. The components of the combination can be administered individually or together in any conventional dosage form such as capsule, tablet, powder, cachet, suspension, solution, suppository, nasal spray, etc. The dosage of the additional therapeutic agent can be determined from published material, and may range from about 1 to about 1000 mg per dose. In one embodiment, when used in combination, the dosage levels of the individual components are lower than the recommended individual dosages because of the advantageous effect of the combination.

Thus, the term "pharmaceutical composition" is also intended to encompass both the bulk composition and individual dosage units comprised of more than one (e.g., two) pharmaceutically active agents such as, for example, a compound of the present invention and an additional agent selected from the various the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

In one embodiment, the components of a combination therapy regime are to be administered simultaneously, they can be administered in a single composition with a pharmaceutically acceptable carrier.

In another embodiment, when the components of a combination therapy regime are to be administered separately or sequentially, they can be administered in separate compositions, each containing a pharmaceutically acceptable carrier.

The components of the combination therapy can be administered individually or together in any conventional dosage form such as capsule, tablet, powder, cachet, suspension, solution, suppository, nasal spray, etc.

Kits

In one embodiment, the present invention provides a kit comprising a effective amount of one or more compounds of the invention, or a pharmaceutically acceptable salt or solvate thereof, and a pharmaceutically acceptable carrier, vehicle or diluent.

In another aspect the present invention provides a kit comprising an amount of one or more compounds of the invention, or a pharmaceutically acceptable salt or solvate thereof, and an amount of at least one additional therapeutic agent described above, wherein the combined amounts are effective for treating or preventing a condition described herein in a patient.

When the components of a combination therapy regime are to are to be administered in more than one composition, they can be provided in a kit comprising in a single package, one container comprising a compound of the invention in pharmaceutically acceptable carrier, and one or more separate containers, each comprising one or more additional therapeutic agents in a pharmaceutically acceptable carrier, with the active components of each composition being present in amounts such that the combination is therapeutically effective.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparant to those skilled in the art and are intended to fall within the scope of the appended claims.

A number of references have been cited herein, the entire disclosures of which are incorporated herein by reference.

We claim:
1. A compound, or a tautomer or isomer thereof, or a pharmaceutically acceptable salt of said compound, tautomer, or isomer, said compound having the general structure shown in Formula (VI):

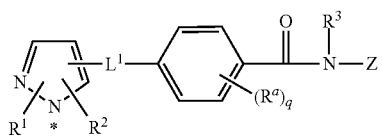

(VI)

wherein $R^1$, $R^2$, $R^3$, $L^1$, and Z are selected independently of each other and wherein:
q is 0 to 1;
$L^1$ is selected from the group consisting of —NH—, —N(CH$_3$)—, —O(CH$_2$)—, and —O—;
$R^1$ is selected from the group consisting of:
phenyl and naphthyl,
   wherein said phenyl and said naphthyl are each substituted with at least one group each independently selected from:
   halo, alkyl, haloalkyl, alkoxy, haloalkoxy, and cycloalkyl;
$R^2$ is selected from the group consisting of:
phenyl and naphthyl,
   wherein said phenyl and said naphthyl are each substituted with at least one group each independently selected from:
   halo, alkyl, haloalkyl, alkoxy, haloalkoxy, and cycloalkyl;
Z is selected from the group consisting of —(CH$_2$)—(CH (CH$_3$))—C(O)OH, —(CH$_2$)—(CH$_2$)—(CH$_2$)—C(O) OH, —(CH$_2$)—C(CH$_3$)$_2$—C(O)OH, —(CH$_2$)—C (CH$_3$)(OH)—C(O)OH, —CH$_2$—CH$_2$—C(O)OH, —CH$_2$—CH(OH)—C(O)OH, —CH(CH$_3$)—CH$_2$—C (O)OH, —CH$_2$—CH(F)—C(O)OH, —CH$_2$—CF$_2$—C (O)OH, —CH(CH$_3$)—CF$_2$—C(O)OH, —CH$_2$—CH$_2$—CF$_2$—C(O)OH,

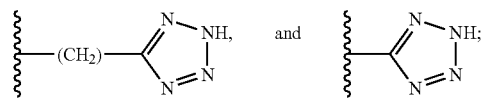

and $R^3$ is selected from H and alkyl.
2. A compound of claim 1, or a tautomer or isomer thereof, or a pharmaceutically acceptable salt of said compound, tautomer, or isomer, wherein:
$R^1$ is selected from phenyl and naphthyl,
   wherein said phenyl and said naphthyl are substituted with from 1 to 2 groups each independently selected from:
   halo, alkyl, haloalkyl, alkoxy, haloalkoxy, and cycloalkyl; and
$R^2$ is selected from the group consisting of:
phenyl and naphthyl,
   wherein said phenyl and said naphthyl are substituted with from 1 to 2 groups each independently selected from:
   halo, alkyl, haloalkyl, alkoxy, haloalkoxy, and cycloalkyl.
3. A compound of claim 1, or a tautomer or isomer thereof, or a pharmaceutically acceptable salt of said compound, tautomer, or isomer, wherein:
$R^1$ is phenyl,
   wherein said phenyl is substituted with from 1 to 2 groups each independently selected from:
   halo, alkyl, haloalkyl, alkoxy, haloalkoxy, and cycloalkyl; and
$R^2$ is phenyl,
   wherein said phenyl is substituted with from 1 to 2 groups each independently selected from:
   halo, alkyl, haloalkyl, alkoxy, haloalkoxy, and cycloalkyl.
4. A compound of claim 1, or a tautomer or isomer thereof, or a pharmaceutically acceptable salt of said compound, tautomer, or isomer, wherein:
$R^1$ is naphthyl,
   wherein said naphthyl is substituted with from 1 to 2 groups each independently selected from:
   halo, alkyl, haloalkyl, alkoxy, haloalkoxy, and cycloalkyl; and
$R^2$ is phenyl,
   wherein said phenyl is substituted with from 1 to 2 groups each independently selected from:
   halo, alkyl, haloalkyl, alkoxy, haloalkoxy, and cycloalkyl.
5. A compound of claim 1, or a tautomer or isomer thereof, or a pharmaceutically acceptable salt of said compound, tautomer, or isomer, wherein:
Z is selected from the group consisting of —(CH$_2$)—(CH (CH$_3$))—C(O)OH, —(CH$_2$)—(CH$_2$)—(CH$_2$)—C(O) OH, —(CH$_2$)—C(CH$_3$)$_2$—C(O)OH, —(CH$_2$)—C (CH$_3$)(OH)—C(O)OH, —CH$_2$—CH$_2$—C(O)OH, —CH$_2$—CH(OH)—C(O)OH, —CH(CH$_3$)—CH$_2$—C (O)OH, —CH$_2$—CH(F)—C(O)OH, —CH$_2$—CF$_2$—C (O)OH, —CH(CH$_3$)—CF$_2$—C(O)OH, and —CH$_2$—CH$_2$—CF$_2$—C(O)OH.
6. A compound of claim 1, or a tautomer or isomer thereof, or a pharmaceutically acceptable salt of said compound, tautomer, or isomer, wherein:
Z is selected from the group consisting of —(CH$_2$)—(CH (CH$_3$))—C(O)OH, —(CH$_2$)—(CH$_2$)—(CH$_2$)—C(O) OH, —(CH$_2$)—C(CH$_3$)$_2$—C(O)OH, —(CH$_2$)—C (CH₃)(OH)—C(O)OH, —CH₂—CH₂—C(O)OH, —CH₂—CH(OH)—C(O)OH, —CH(CH₃)—CH₂—C(O)OH, —CH₂—CH(F)—C(O)OH, —CH₂—CF₂—C(O)OH, —CH(CH₃)—CF₂—C(O)OH, and —CH₂—CH₂—CF₂—C(O)OH, and R³ is H.

7. A compound of claim 1, or a tautomer or isomer thereof, or a pharmaceutically acceptable salt of said compound, tautomer, or isomer, wherein:

Z is selected from

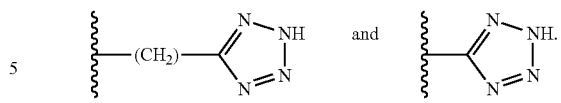

8. A compound, or a tautomer or isomer thereof, or a pharmaceutically acceptable salt of said compound, tautomer, or isomer, said compound being selected from the group consisting of:

| Example | Compound |
|---|---|
| 1-1 | |
| 1-2 | |
| 1-3 | |
| 1-4 | |

-continued
| Example | Compound |
|---------|----------|
| 2-1 | 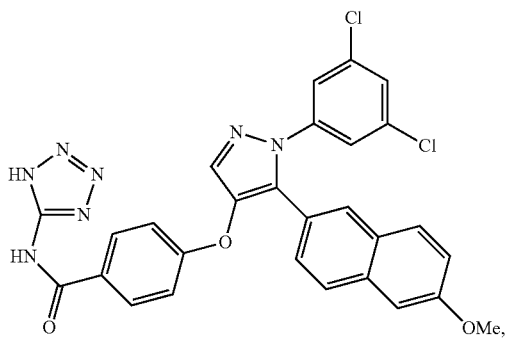 [SMILES: COc1ccc2cc(-c3c(Oc4ccc(C(=O)Nc5nnn[nH]5)cc4)cnn3-c3cc(Cl)cc(Cl)c3)ccc2c1] |
| 3-1 | 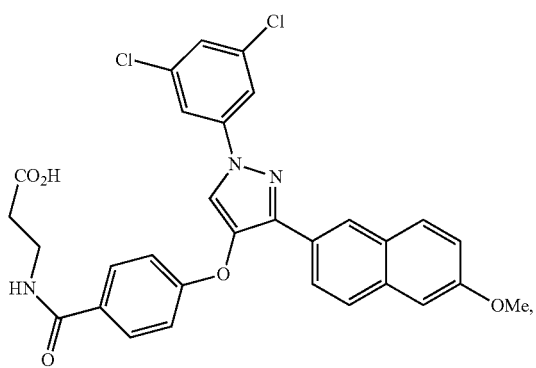 [SMILES: COc1ccc2cc(-c3nn(-c4cc(Cl)cc(Cl)c4)cc3Oc3ccc(C(=O)NCCC(=O)O)cc3)ccc2c1] |
| 3-2 | 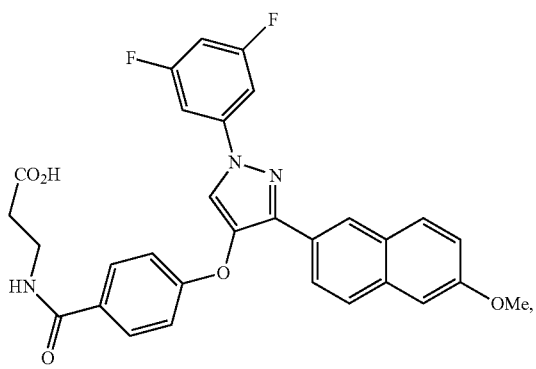 [SMILES: COc1ccc2cc(-c3nn(-c4cc(F)cc(F)c4)cc3Oc3ccc(C(=O)NCCC(=O)O)cc3)ccc2c1] |
| 3-3 | 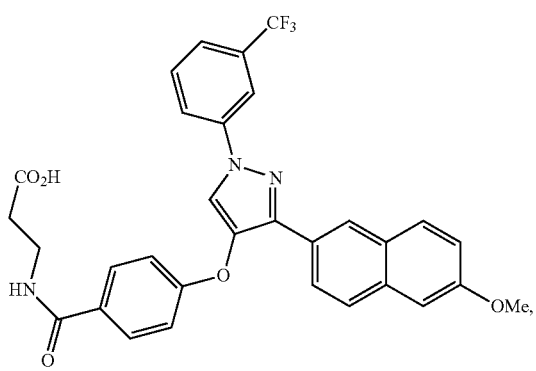 [SMILES: COc1ccc2cc(-c3nn(-c4cccc(C(F)(F)F)c4)cc3Oc3ccc(C(=O)NCCC(=O)O)cc3)ccc2c1] |

| Example | Compound |
|---|---|
| 4-1 | 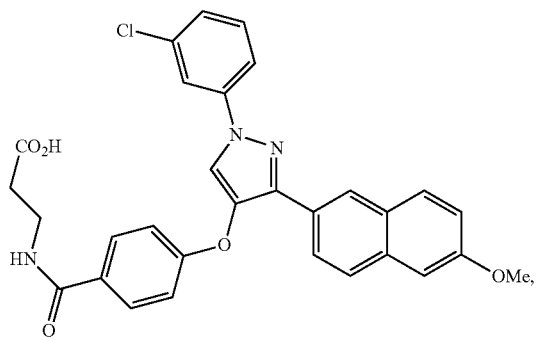 [SMILES: COc1ccc2cc(-c3nn(-c4cccc(Cl)c4)cc3Oc3ccc(C(=O)NCCC(=O)O)cc3)ccc2c1] |
| 4-2 | 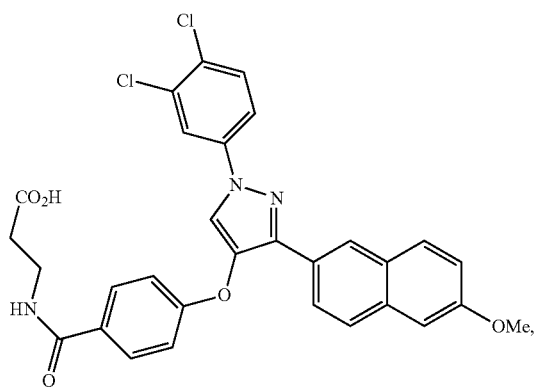 [SMILES: COc1ccc2cc(-c3nn(-c4ccc(Cl)c(Cl)c4)cc3Oc3ccc(C(=O)NCCC(=O)O)cc3)ccc2c1] |
| 5-1 | 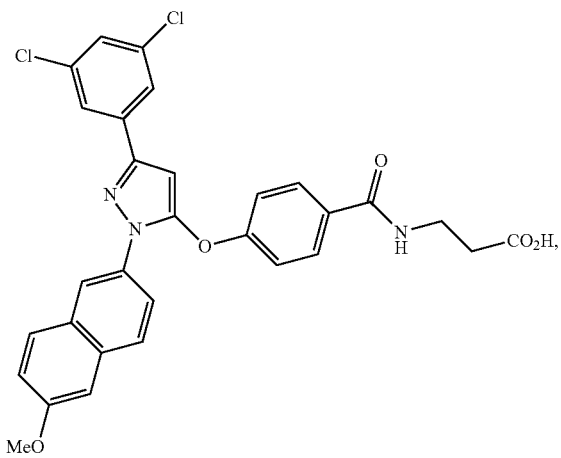 [SMILES: COc1ccc2cc(-n3nc(-c4cc(Cl)cc(Cl)c4)cc3Oc3ccc(C(=O)NCCC(=O)O)cc3)ccc2c1] |

| Example | Compound |
|---|---|
| 6-1 | 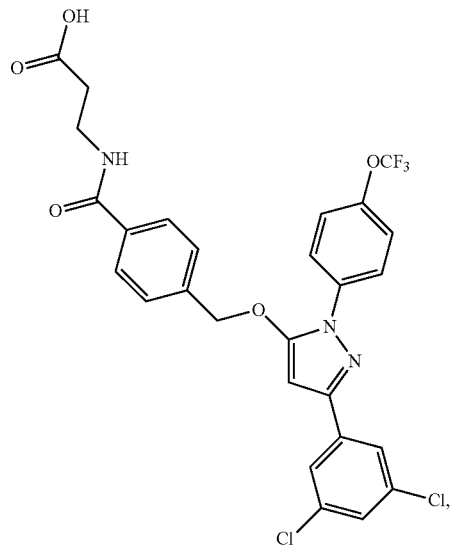 [SMILES: O=C(O)CCNC(=O)c1ccc(COc2cc(-c3cc(Cl)cc(Cl)c3)nn2-c2ccc(OC(F)(F)F)cc2)cc1] |
| 7-1 | 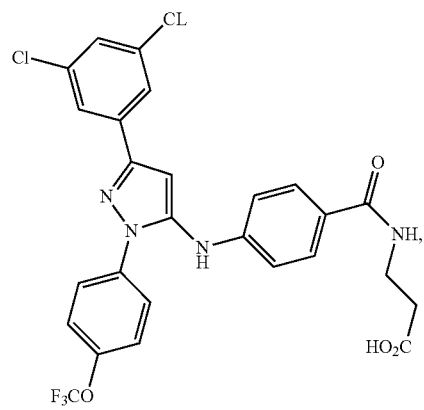 |
| 8-1 | 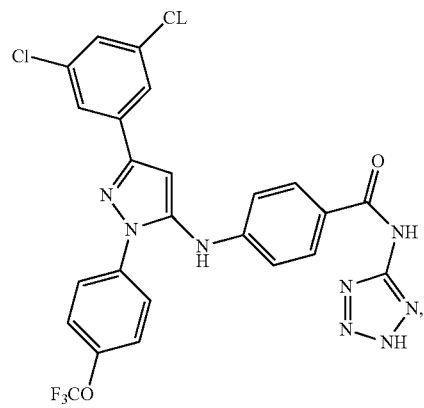 |

-continued
| Example | Compound |
|---|---|
| 9-1 | 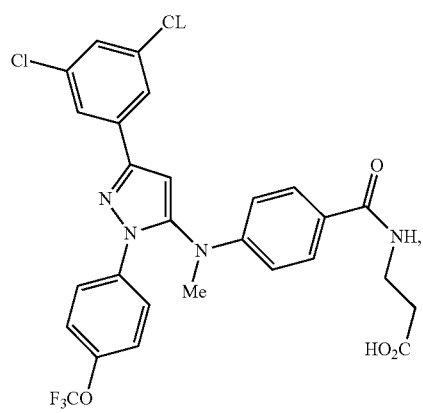 |
| 10-1 | 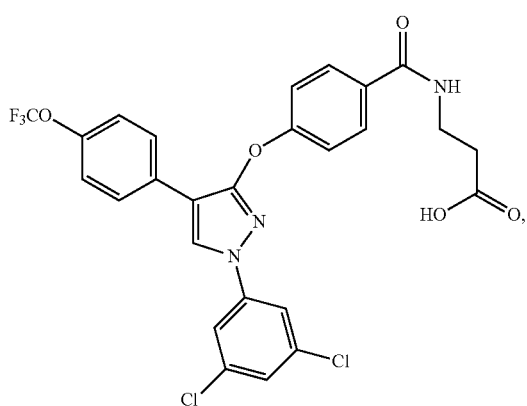 [SMILES: O=C(O)CCNC(=O)c1ccc(Oc2nn(-c3cc(Cl)cc(Cl)c3)cc2-c2ccc(OC(F)(F)F)cc2)cc1] |
| 10-2 | 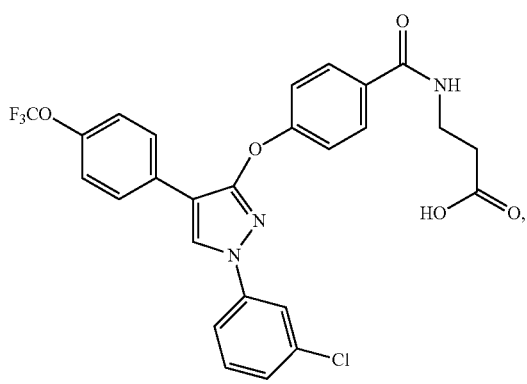 [SMILES: O=C(O)CCNC(=O)c1ccc(Oc2nn(-c3cccc(Cl)c3)cc2-c2ccc(OC(F)(F)F)cc2)cc1] |
| 10-3 | 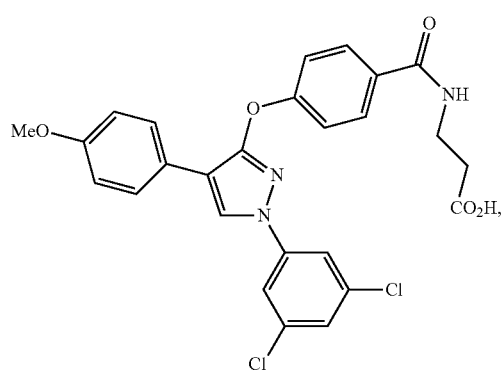 [SMILES: COc1ccc(-c2cn(-c3cc(Cl)cc(Cl)c3)nc2Oc2ccc(C(=O)NCCC(=O)O)cc2)cc1] |

-continued

| Example | Compound |
|---------|----------|
| 11-1 | |
| 12-1 | |
| 12-2 | |
| 12-3 | |

-continued
| Example | Compound |
|---|---|
| 12-4 | 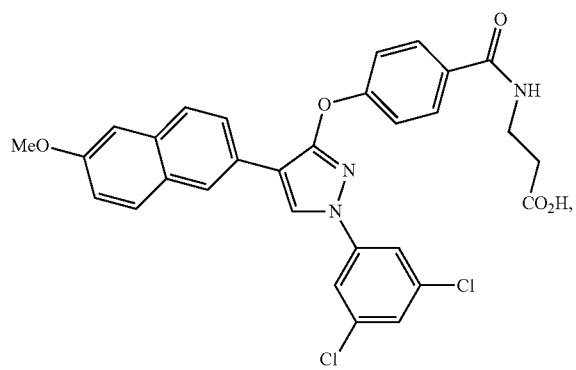 [SMILES: COc1ccc2cc(-c3cn(-c4cc(Cl)cc(Cl)c4)nc3Oc3ccc(C(=O)NCCC(=O)O)cc3)ccc2c1] |
| 14-1 | 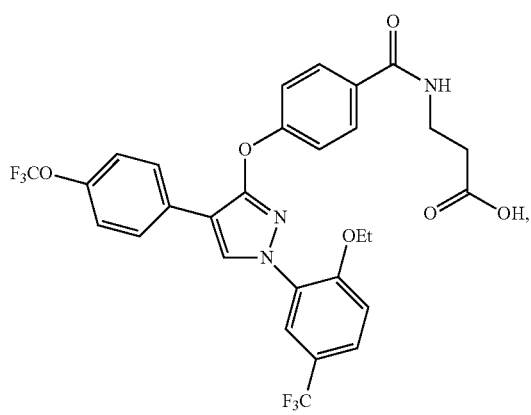 [SMILES: CCOc1ccc(C(F)(F)F)cc1-n1cc(-c2ccc(OC(F)(F)F)cc2)c(Oc2ccc(C(=O)NCCC(=O)O)cc2)n1] |
| 14-2 | 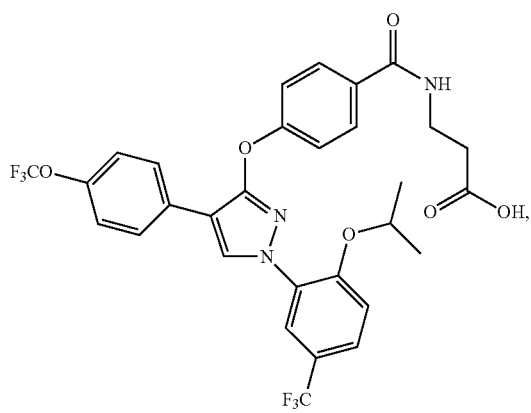 [SMILES: CC(C)Oc1ccc(C(F)(F)F)cc1-n1cc(-c2ccc(OC(F)(F)F)cc2)c(Oc2ccc(C(=O)NCCC(=O)O)cc2)n1] |
| 14-3 | 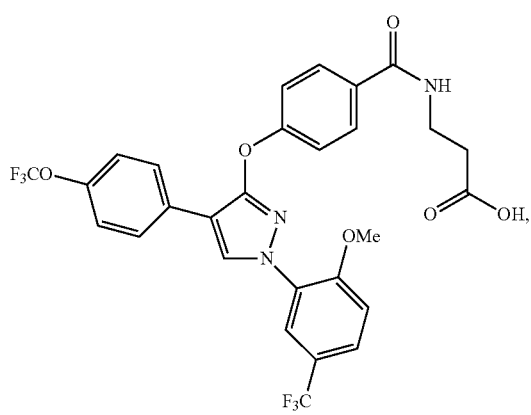 [SMILES: COc1ccc(C(F)(F)F)cc1-n1cc(-c2ccc(OC(F)(F)F)cc2)c(Oc2ccc(C(=O)NCCC(=O)O)cc2)n1] |

| Example | Compound |
|---|---|
| 14-4 | 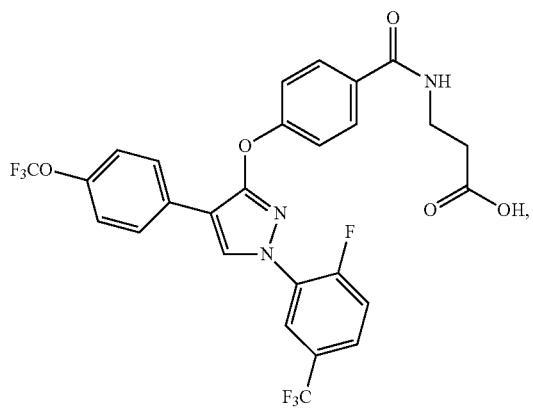 [SMILES: O=C(O)CCNC(=O)c1ccc(Oc2nn(-c3cc(C(F)(F)F)ccc3F)cc2-c2ccc(OC(F)(F)F)cc2)cc1] |
| 14-5 | 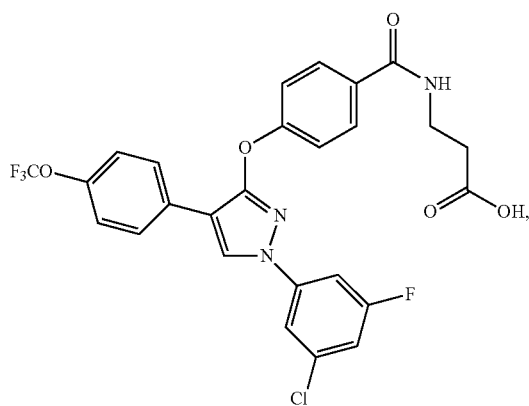 [SMILES: O=C(O)CCNC(=O)c1ccc(Oc2nn(-c3cc(F)cc(Cl)c3)cc2-c2ccc(OC(F)(F)F)cc2)cc1] |
| 16-1 | 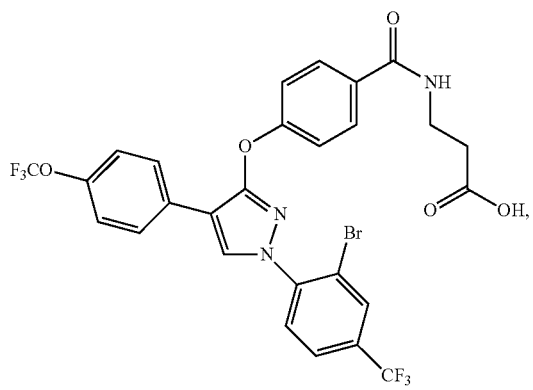 [SMILES: O=C(O)CCNC(=O)c1ccc(Oc2nn(-c3ccc(C(F)(F)F)cc3Br)cc2-c2ccc(OC(F)(F)F)cc2)cc1] |
| 17-1 | 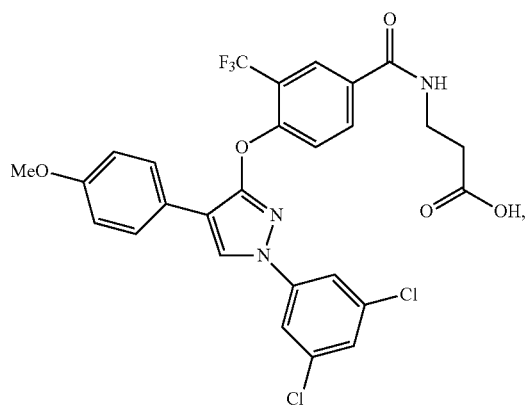 [SMILES: COc1ccc(-c2cn(-c3cc(Cl)cc(Cl)c3)nc2Oc2ccc(C(=O)NCCC(=O)O)cc2C(F)(F)F)cc1] |

| Example | Compound |
|---|---|
| 18-1 | 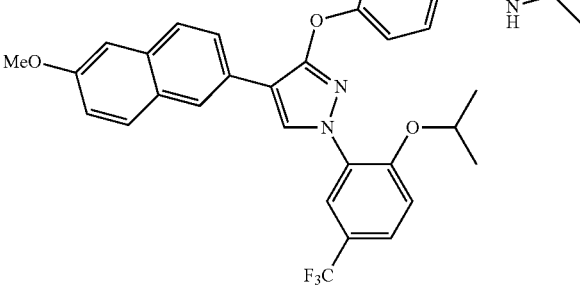 |
| 19-1 | 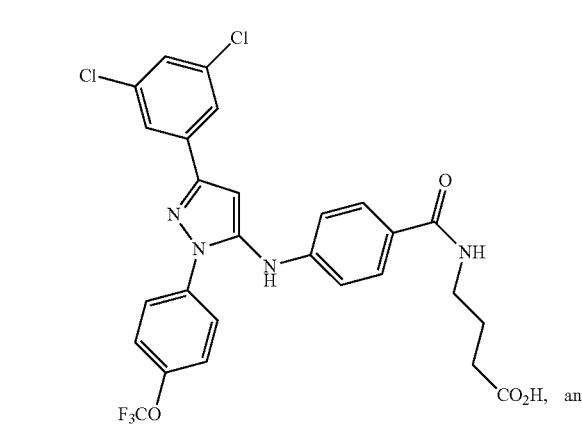 |
| 20-1 | 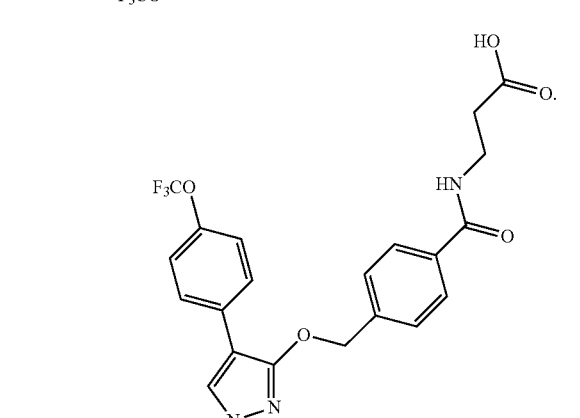 |

9. A pharmaceutical composition comprising a compound of claim 1, or a tautomer or isomer thereof, or a pharmaceutically acceptable salt of said compound, tautomer, or isomer, and a pharmaceutically acceptable carrier.

10. A pharmaceutical composition according to claim 9, further comprising a at least one antidiabetic agent other than a compound of claim 1.

11. A pharmaceutical composition according to claim 10, wherein said at least one antidiabetic agent other than a compound of claim 1 is selected from: a DPP-IV inhibitor, an insulin sensitizer, insulin, an insulin mimetic, an insulin secretagogue, a glucosidase inhibitor, an alpha glucosidase inhibitor, a glucagon receptor antagonist other than a compound of claim 6, glucophage, glucophage XR, an antihypertensive agent, a meglitinide, an alpha-glucosidase inhibitor, amlintide, pramlintide, exendin, a histamine $H_3$ receptor antagonist, dapagliflozin, sergliflozin, AVE2268 (Sanofi-Aventis) and T-1095 (Tanabe Seiyaku), a cholesterol lowering agent, a PACAP, a PACAP mimetic, a PACAP receptor 3 agonist, a PPAR delta agonist, an antiobesity agent, an ileal bile acid transporter inhibitor, an NSAID, and a CB1 receptor antagonist, and a CB 1 receptor inverse agonist.

12. A method for treating or delaying the onset of type 2 diabetes mellitus in a patient in need thereof comprising administering to said patient a compound of claim 1 in an amount that is effective to treat type 2 diabetes mellitus.

* * * * *

UNITED STATES PATENT AND TRADEMARK OFFICE
CERTIFICATE OF CORRECTION

Page 1 of 1

PATENT NO. : 8,623,818 B2
APPLICATION NO. : 12/992771
DATED : January 7, 2014
INVENTOR(S) : Greenlee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 519 days.

Signed and Sealed this
Sixteenth Day of June, 2015

Michelle K. Lee
*Director of the United States Patent and Trademark Office*